(12) United States Patent
Thatcher et al.

(10) Patent No.: US 11,332,466 B2
(45) Date of Patent: May 17, 2022

(54) PYRIDINONE-BASED EPIGENETIC MODIFIERS AND USES THEREOF

(71) Applicant: THE BOARD OF TRUSTEES OF THE UNIVERSITY OF ILLINOIS, Urbana, IL (US)

(72) Inventors: Gregory R. Thatcher, Chicago, IL (US); Rui Xiong, Chicago, IL (US); Jiong Zhao, Chicago, IL (US); Yangfeng Li, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 16/767,977

(22) PCT Filed: Dec. 1, 2018

(86) PCT No.: PCT/US2018/063521
§ 371 (c)(1),
(2) Date: May 28, 2020

(87) PCT Pub. No.: WO2019/109057
PCT Pub. Date: Jun. 6, 2019

(65) Prior Publication Data
US 2021/0002272 A1 Jan. 7, 2021

Related U.S. Application Data

(60) Provisional application No. 62/593,302, filed on Dec. 1, 2017, provisional application No. 62/666,806, filed on May 4, 2018.

(51) Int. Cl.
*C07D 471/04* (2006.01)
(52) U.S. Cl.
CPC .................. *C07D 471/04* (2013.01)
(58) Field of Classification Search
CPC .................................................. C07D 471/04

USPC .......................................................... 514/300
See application file for complete search history.

(56) References Cited

U.S. PATENT DOCUMENTS

| 7,049,312 B1 * | 5/2006 | Rafferty ................. A61P 17/02 514/224.2 |
| 2014/0256710 A1 | 9/2014 | Dachun et al. |
| 2014/0275026 A1 | 9/2014 | Wang et al. |

OTHER PUBLICATIONS

Vidler et al., Discovery of Novel Small-Molecule Inhibitors of BRD4 Using Structure-Based Virtual Screening, Journal of Medicinal Chemisrty, vol. 56, No. 20, 8073-8088, 2018.
Hasvold et al., Methylpyrrole inhibitors of BET bromodomains, Bioorganic & Medicinal Chemistry Letters, vol. 27, No. 10, p. 2225-2233, 2017.
Nechayev et al., Microwave-assisted acid-catalyzed nucleophilic heteroaromatic substitution: the synthesis of 7-amino-6-azaindoles. Tetrahedron, vol. 71, No. 8, 1311-1321, 2015.
Nechayev et al., The synthesis of low molecular weight pyrrolo[2,3-] pyridine-7-one scaffold, Molecular Diversity, Kluwer Academic Publishers, DO, vol. 16, No. 4, p. 749-757, 2012.
International Search Report issued for application PCT/US2018/063521, dated Mar. 6, 2019.
International Preliminary Report on Patentability for application PCT/US2018/063521, dated Jun. 2, 2020.

\* cited by examiner

*Primary Examiner* — Niloofar Rahmani
(74) *Attorney, Agent, or Firm* — Thomas | Horstemeyer, LLP

(57) ABSTRACT

Described herein are pyridinone-based compounds, derivatives thereof, and pharmaceutical formulations thereof. In some aspects, the pyridinone-based compounds, derivatives thereof, and/or pharmaceutical formulations thereof can be administered to a subject in need thereof. In some aspects, pyridinone-based compounds, derivatives thereof, and/or pharmaceutical formulations thereof can modulate an activity and/or a function of a BRD protein and/or BET protein.

13 Claims, 8 Drawing Sheets

Example 70

PYRIDINONE-BASED EPIGENETIC MODIFIERS AND USES THEREOF

CROSS-REFERENCE TO RELATED APPLICATIONS

This application is a National Stage of International Application No. PCT/US2018/063521, filed Dec. 1, 2018, which claims the benefit of and priority to U.S. Provisional Patent Application No. 62/593,302, filed on Dec. 1, 2017, entitled "Pyridinone-Based Epigenetic Modulators," the contents of which is incorporated by reference herein in its entirety.

This application also claims the benefit of and priority to U.S. Provisional Patent Application No. 62/666,806, filed on May 4, 2018, entitled "Pyridinone-Based Epigenetic Modulators," the contents of which is incorporated by reference herein in its entirety.

BACKGROUND

Cancer and other diseases, such as arthritis, lupus, and neurodegenerative disorders, for example, are associated with significant mortality and/or morbidity and remain major health concerns worldwide. Despite advances in the understanding of these diseases and disorders, there still exists a need for additional and/or improved treatments.

SUMMARY

In aspects, described herein are compounds according to Formula XXV

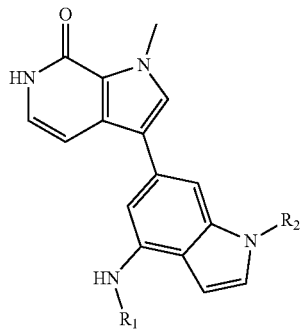
Formula XXV wherein $R_1$ is

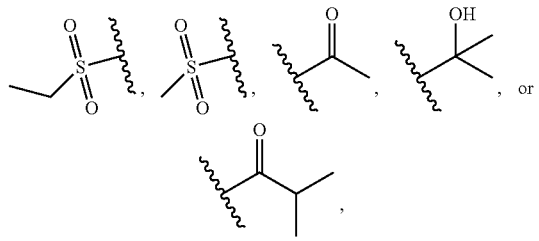

wherein $R_2$ is

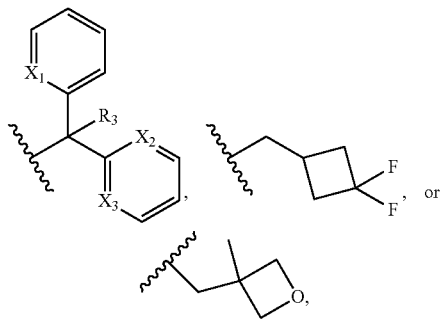

wherein $R_3$ is H, $CH_3$, or $CH_2CH_3$, and
wherein $X_1$, $X_2$, and $X_3$, are each independently selected from the group of: C or N.

In aspects, the compound is selected from the group of: (70), (71), (72), (73), (74), (126), (130), (131), and (132).

In aspects, described herein are compounds according to Formula XXIV

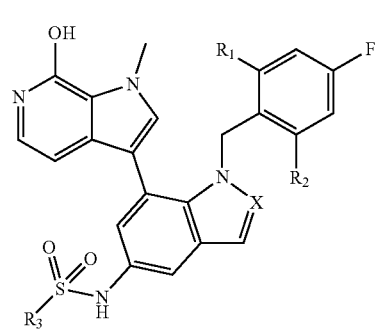
Formula XXIV wherein $R_1$ and $R_2$ are each independently selected from $CH_3$ or H,
wherein $R_3$ is $CH_3$ or $CH_2CH_3$, and
wherein X is C or N.

In some aspects, the compound is selected from the group of: (22), (23), (30), and (31).

In aspects, described herein are compounds according to Formula XXVI

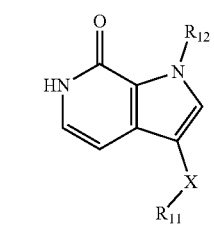
Formula XXVI wherein $R_{12}$ is a $C_1$-$C_3$ alkyl, a $C_1$-$C_3$ haloalkyl, propylenyl, —$CH_2(CO)CH$=$CH_2$, oxiran-2-ylmethyl, or $CH_2(CO)CH_2Cl$, wherein $R_{11}$ is a nitrogen-containing bicyclic or tricyclic heteroaryl, an aryl, or a biaryl, each of which is optionally substituted with 1, 2, or 3 substituents each independently selected from the group of: —$N(R^a)S(O)_2R^b$, —$S(O)_2NR^aR^b$, —$C(O)NR^aR^b$ —$N(R^a)C(O)R^b$ —$NR^aR^b$, —$(C_1$-$C_6$ alkylenyl)$R^c$, —$(C_1$-$C_3$ cycloalkylenyl)$R^c$, an aryl, a heteroaryl, and —(C₁-C₆ alkylenyl)R$^c$R$^{c'}$, —H, a halogen, —CN, a propylenyl, a C₁-C₃ alkyl, a C₁-C₃ haloalkyl, —OR$_{70}$, —NR$_{70}$R$_{70}$, —C(O)OR$_{70}$, —C(O)NR$_{70}$R$_{70}$, —S(O)₂R$_{70}$, —S(O)₂NR$_{70}$R$_{70}$, —CH₂(CO)CH=CH₂, oxiran-2-ylmethyl, and CH₂(CO)CH₂Cl, and R$_{70}$, wherein X is optionally present, and when present, is selected from —O—, —C(O)—, —N(R$_{77}$)—, and —CH(R$_{70}$)—, R$_{77}$ is selected from the group of: —H, a halogen, —CN, a C₁-C₃ haloalkyl, —OR$_{70}$, —NR$_{70}$R$_{70}$, —C(O)OR$_{70}$, —C(O)NR$_{70}$R$_{70}$, —S(O)₂R$_{70}$, —S(O)₂NR$_{70}$R$_{70}$, and R$_{70}$, wherein R$_{70}$, at each occurrence, are each independently selected from the group of: a C₁-C₆ alkyl, a C₂-C₆ alkenyl, a C₂-C₆ alkynyl, a halogen, a C₁-C₆ haloalkyl, —CN, NO₂, —OR$^e$, —S(O)₂NR$^e$R$^f$, —C(O)R$^e$, —C(O)NR$^e$R$^f$, —NR$^e$R$^f$, —N(R$^e$)C(O)R$^f$, a —(C₁-C₆ alkylenyl)-OR$^e$, a —(C₁-C₆ alkylenyl)-C(O)NR$^e$R$^f$, a —(C₁-C₆ alkylenyl)-NR$^e$R$^f$, and a —(C₁-C₆ alkylenyl)-N(R$^e$)C(O)R$^f$, wherein R$^a$ and R$^b$, at each occurrence, are independently selected from the group of: H, a C₁-C₆ alkenyl, a C₁-C₆ alkynyl, a C₁-C₆ haloalkyl, R$^c$, and a C₁-C₆ alkyl, wherein the C₁-C₆ alkyl is optionally substituted with one substituent selected from the group of: —OR$^e$, —NR$^e$R$^f$, —C(O)OR$^e$, —C(O)NR$^e$R$^f$, —S(O)₂R$^e$, —S(O)₂NR$^e$R$^f$, and R$^c$, wherein R$^c$ and R$^{c'}$, at each occurrence, are each independently selected from the group of: an aryl, a heteroaryl, a heterocycle, a cycloalkyl, and a cycloalkenyl, and wherein each R$^c$ group is optionally substituted with 1, 2, 3, 4, or 5 R$^d$ groups, wherein R$^d$, at each occurrence, are each independently selected from the group of: a C₁-C₆ alkyl, a C₂-C₆ alkenyl, a C₂-C₆ alkynyl, a halogen, a C₁-C₆ haloalkyl, —CN, NO₂, —OR$^e$, —S(O)₂NR$^e$R$^f$, —C(O)R$^e$, —C(O)NR$^e$R$^f$, —NR$^e$R$^f$, —N(R$^e$)C(O)R$^f$, a —(C₁-C₆ alkylenyl)-OR$^e$, a —(C₁-C₆ alkylenyl)-C(O)NR$^e$R$^f$, a —(C₁-C₆ alkylenyl)-NR$^e$R$^f$, and a —(C₁-C₆ alkylenyl)-N(R$^e$)C(O)R$^f$, and wherein R$^e$ and R$^f$, at each occurrence, are each independently selected from the group of: H, a C₁-C₆ alkyl, a C₁-C₆ cycloalkyl, a aryl, a heteroaryl and a C₁-C₆ haloalkyl.

In some aspects, the compound is according to Formula I

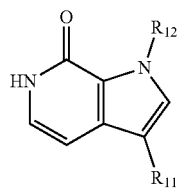

Formula I wherein R$_{12}$ is a C₁-C₃ alkyl, a C₁-C₃ haloalkyl, propylenyl, —CH₂(CO)CH=CH₂, oxiran-2-ylmethyl, or CH₂(CO)CH₂Cl, wherein R$_{11}$ is a nitrogen-containing bicyclic or tricyclic heteroaryl, each of which is optionally substituted with 1, 2, or 3 substituents each independently selected from the group of: —N(R$^a$)S(O)₂R$^b$, —S(O)₂NR$^a$R$^b$, —C(O)NR$^a$R$^b$ —N(R$^a$)C(O)R$^b$ —NR$^a$R$^b$, —(C₁-C₆ alkylenyl)R$^c$, —(C₁-C₃ cycloalkylenyl)R$^c$, an aryl, a heteroaryl, and —(C₁-C₆ alkylenyl)R$^c$R$^{c'}$, wherein R$^a$ and R$^b$, at each occurrence, are each independently selected from the group of: H, a C₁-C₆ alkenyl, a C₁-C₆ alkynyl, a C₁-C₆ haloalkyl, R$^c$, and a C₁-C₆ alkyl, wherein the C₁-C₆ alkyl is optionally substituted with one substituent selected from the group of: —OR$^e$, —NR$^e$R$^f$, —C(O)OR$^e$, —C(O)NR$^e$R$^f$, —S(O)₂R$^e$, —S(O)₂NR$^e$R$^f$, and R$^c$, wherein R$^c$ and R$^{c'}$, at each occurrence, are each independently selected from the group of: an aryl, a heteroaryl, a heterocycle, a cycloalkyl, and a cycloalkenyl, and wherein each R$^c$ group is optionally substituted with 1, 2, 3, 4, or 5 R$^d$ groups, wherein R$^d$, at each occurrence, are each independently selected from the group of: a C₁-C₆ alkyl, a C₂-C₆ alkenyl, a C₂-C₆ alkynyl, a halogen, a C₁-C₆ haloalkyl, —CN, NO₂, —OR$^e$, —S(O)₂NR$^e$R$^f$, —C(O)R$^e$, —C(O)NR$^e$R$^f$, —NR$^e$R$^f$, —N(R$^e$)C(O)R$^f$, a —(C₁-C₆ alkylenyl)-OR$^e$, a —(C₁-C₆ alkylenyl)-C(O)NR$^e$R$^f$, a —(C₁-C₆ alkylenyl)-NR$^e$R$^f$, and a —(C₁-C₆ alkylenyl)-N(R$^e$)C(O)R$^f$, and wherein R$^e$ and R$^f$, at each occurrence, are each independently selected from the group of: H, a C₁-C₆ alkyl, a C₁-C₆ cycloalkyl, an aryl, a heteroaryl and a C₁-C₆ haloalkyl.

In aspects, the compound is according to Formula II

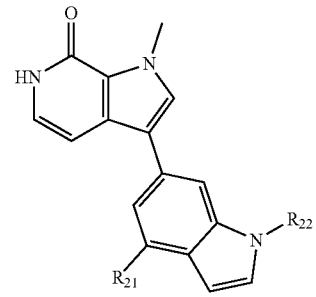

Formula II wherein R$^{21}$ is —N(R$^a$)S(O)₂R$^b$, —S(O)₂NR$^a$R$^b$, S(O)₂R$^a$, —C(O)NR$^a$R$^b$ —N(R$^a$)C(O)R$^b$ —NR$^a$R$^b$, or a —(C₁-C₆ alkylenyl)R$^c$, wherein R$^a$ and R$^b$, at each occurrence, are each independently selected from the group of: H, a C₁-C₆ alkyl, a C₁-C₆ alkenyl, a C₁-C₆ alkynyl, a C₁-C₆ haloalkyl, R$^c$, and a C₁-C₆ alkyl, wherein the C₁-C₆ alkyl is optionally substituted with one substituent selected from the group of: —OR$^{y1}$, —NR$^{y3}$R$^{y4}$, —C(O)OR$^{y2}$, —C(O)NR$^{y3}$R$^{y4}$, —S(O)₂R$^{y1}$, —S(O)₂NR$^{y3}$R$^{y4}$, and R$^c$, wherein R$^{y1}$, at each occurrence, can each be independently selected from the group of: H, a C₁-C₆ alkyl, a C₁-C₆ cycloalkyl, a aryl, a heteroaryl and a C₁-C₆ haloalkyl, wherein R$^{y2}$, at each occurrence, can each be independently selected from the group of: H, a C₁-C₆ alkyl, a C₁-C₆ cycloalkyl, a aryl, a heteroaryl and a C₁-C₆ haloalkyl, wherein R$^{y3}$, at each occurrence, can each be independently selected from the group of: H, a C₁-C₆ alkyl, a C₁-C₆ cycloalkyl, a aryl, a heteroaryl and a C₁-C₆ haloalkyl, wherein R$^{y4}$, at each occurrence, can each be independently selected from the group of: H, a C₁-C₆ alkyl, a C₁-C₆ cycloalkyl, a aryl, a heteroaryl and a C₁-C₆ haloalkyl, wherein R$^{22}$ is selected from the group of: a —(C₁-C₆ alkylenyl)R$^c$, a —(C₁-C₃ cycloalkylenyl)R$^c$, and a —(C₁-C₆ alkylenyl)R$^c$R$^{c'}$, wherein R$^c$ and R$^{c'}$, at each occurrence, are each independently selected from the group of: an aryl, a heteroaryl, a heterocycle, a cycloalkyl, and a cycloalkenyl; and each R$^c$ group is optionally substituted with 1, 2, 3, 4, or 5 R$^d$ groups, where R$^d$, at each occurrence, are each independently selected from the group of: a C₁-C₆ alkyl, a C₂-C₆ alkenyl, a $C_2$-$C_6$ alkynyl, a halogen, a $C_1$-$C_6$ haloalkyl, —CN, $NO_2$, —$OR^e$, —$S(O)_2NR^eR^f$, —$C(O)R^e$, —$C(O)NR^eR^f$, —$NR^eR^f$, —$N(R^e)C(O)R^f$, a —($C_1$-$C_6$ alkylenyl)-$OR^e$, —($C_1$-$C_6$ alkylenyl)-$C(O)NR^eR^f$, a —($C_1$-$C_6$ alkylenyl)-$NR^eR^f$, and a —($C_1$-$C_6$ alkylenyl)-$N(R^e)C(O)R^f$, and wherein $R^e$ and $R^f$, at each occurrence, are each independently selected from the group of: H, a $C_1$-$C_6$ alkyl, and a $C_1$-$C_6$ haloalkyl.

In aspects, the compound is according to Formula III

Formula III

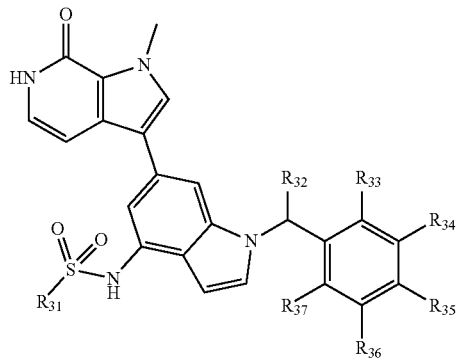

wherein $R_{31}$ is selected from the group of: a $C_1$-$C_6$ alkenyl, a $C_1$-$C_6$ cycloalkyl, and a $C_1$-$C_6$ haloalkyl, wherein $R_{32}$ is selected from the group of: a $C_1$-$C_6$ alkenyl, a $C_1$-$C_8$ cycloalkyl, —H, -D, a $C_1$-$C_8$ substituted cycloalkylenyl, a substituted aryl, and a substituted heteroaryl, and wherein $R_{33}$, $R_{34}$, $R_{35}$, $R_{36}$, and $R_{37}$ are each independently selected from the group of: —H, a halogen, —CN, and a $C_1$-$C_3$ haloalkyl.

In aspects, the compound is according to Formula IV

Formula IV

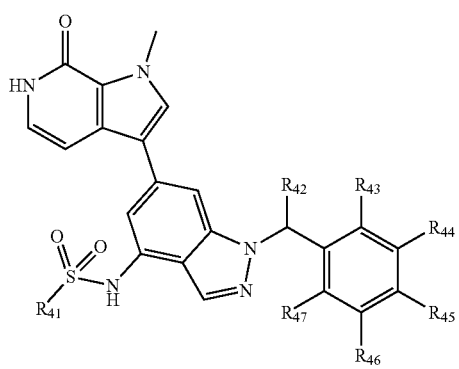

wherein $R_{41}$ is selected from the group of: a $C_1$-$C_6$ alkylenyl, a $C_1$-$C_6$ cycloalkyl, and a $C_1$-$C_6$ haloalkyl, wherein $R_{42}$ is selected from the group of: $C_1$-$C_6$ alkenyl, a $C_1$-$C_8$ cycloalkyl, —H, -D, a $C_1$-$C_8$ substituted cycloalkylenyl, a substituted aryl, a substituted heteroaryl, and wherein $R_{43}$, $R_{44}$, $R_{45}$, $R_{46}$, and $R_{47}$ are each independently selected from the group of: —H, a halogen, —CN, and a $C_1$-$C_3$ haloalkyl.

In aspects, the compound is according to Formula V

Formula V

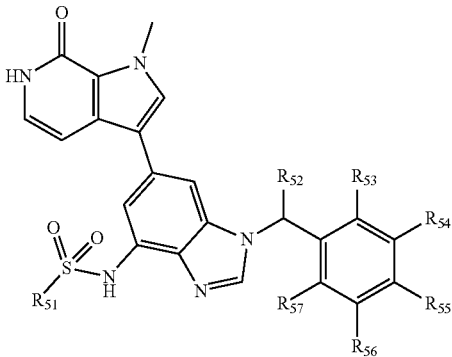

wherein $R_{51}$ is selected from the group of: a $C_1$-$C_6$ alkenyl, a $C_1$-$C_6$ cycloalkyl, and a $C_1$-$C_6$ haloalkyl, wherein $R_{52}$ is selected from the group of: a $C_1$-$C_6$ alkenyl, a $C_1$-$C_8$ cycloalkyl, —H, -D, a $C_1$-$C_8$ substituted cycloalkylenyl, a substituted aryl, and a substituted heteroaryl, and wherein $R_{53}$, $R_{54}$, $R_{55}$, $R_{56}$, and $R_{57}$ are each independently selected from the group of: —H, a halogen, —CN, and a $C_1$-$C_3$ haloalkyl.

In aspects, the compound is according to Formula VI

Formula VI

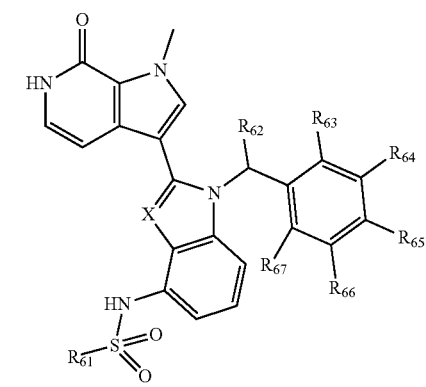

wherein X is C or N, wherein $R_{61}$ is selected from the group of: a $C_1$-$C_6$ alkenyl, a $C_1$-$C_6$ cycloalkyl, and a $C_1$-$C_6$ haloalkyl, wherein $R_{62}$ is selected from the group of: a $C_1$-$C_6$ alkenyl, a $C_1$-$C_8$ cycloalkyl, —H, -D, a $C_1$-$C_8$ substituted cycloalkylenyl, a substituted aryl, and a substituted heteroaryl, and wherein $R_{63}$, $R_{64}$, $R_{65}$, $R_{66}$, and $R_{67}$ are each independently selected from the group of: —H, a halogen, —CN, and a $C_1$-$C_3$ haloalkyl.

In aspects, the compound is according to Formula IX,

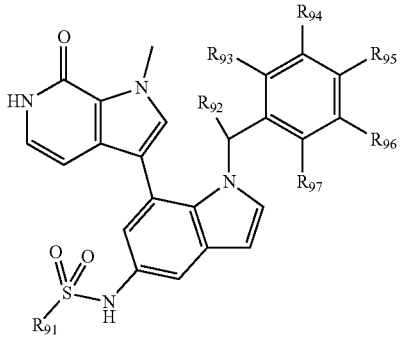

Formula IX wherein X is C or N, wherein $R_{91}$ is selected from the group of: a $C_1$-$C_6$ alkenyl, a $C_1$-$C_6$ cycloalkyl, and a $C_1$-$C_6$ haloalkyl, wherein $R_{92}$ is selected from the group of: a $C_1$-$C_6$ alkenyl, a $C_1$-$C_8$ cycloalkyl, —H, -D, a $C_1$-$C_8$ substituted cycloalkylenyl, a substituted aryl, and a substituted heteroaryl, and wherein $R_{93}$, $R_{94}$, $R_{95}$, $R_{96}$, and $R_{97}$ are each independently selected from the group of: —H, a halogen, —CN, and a $C_1$-$C_3$ haloalkyl.

In aspects, the compound is according to Formula XVI

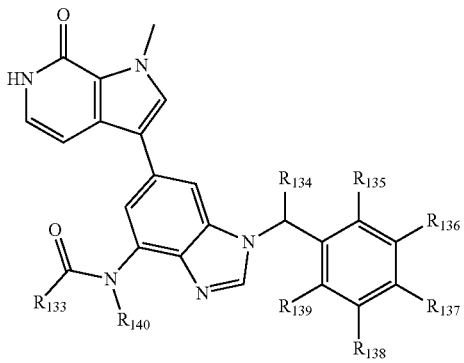

Formula XVI wherein $R_{133}$ is selected from the group of: a $C_1$-$C_6$ alkenyl, a $C_1$-$C_6$ cycloalkyl, and a $C_1$-$C_6$ haloalkyl, wherein $R_{134}$ is selected from the group of: a $C_1$-$C_6$ alkenyl, $C_1$-$C_8$ cycloalkyl, —H, -D, a $C_1$-$C_8$ substituted cycloalkylenyl, a substituted aryl, and a substituted heteroaryl, wherein $R_{135}$, $R_{136}$, $R_{137}$, $R_{138}$, and $R_{139}$ are each independently selected from the group of: —H, a halogen, —CN, and a $C_1$-$C_3$ haloalkyl, In aspects, the compound is according to Formula XVII

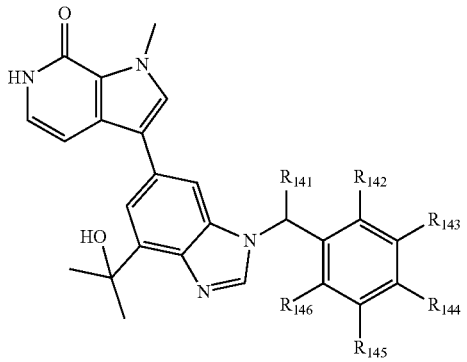

Formula XVII wherein $R_{141}$ is selected from the group of: a $C_1$-$C_6$ alkenyl, a $C_1$-$C_8$ cycloalkyl, —H, -D, a $C_1$-$C_8$ substituted cycloalkylenyl, a substituted aryl, and a substituted heteroaryl, and wherein $R_{142}$, $R_{143}$, $R_{144}$, $R_{145}$, and $R_{146}$ are each independently selected from the group of: —H, a halogen, —CN, and a $C_1$-$C_3$ haloalkyl.

and wherein $R_{140}$ is selected from the group of: a $C_1$-$C_6$ alkenyl, a $C_1$-$C_8$ cycloalkyl, —H, -D, a $C_1$-$C_8$ substituted cycloalkylenyl, a substituted aryl, and a substituted heteroaryl.

In aspects, the compound is according to Formula XIX

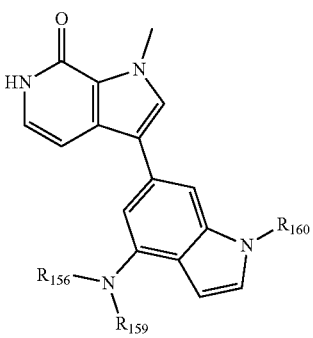

Formula XIX wherein $R_{156}$ is

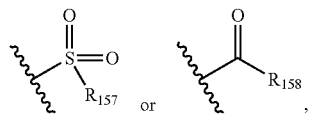

wherein $R_{157}$ is Me or $CH_2CH_3$,
wherein $R_{158}$ is Me, $CH_2CH_3$, or

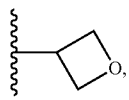

wherein $R_{159}$ is H, $CH_2CH_3$, or wherein $R_{160}$ is wherein $R_{161}$ is H, Me, or Cl,
wherein $R_{162}$ is H or F,
wherein $R_{163}$ is H or F,
and wherein $R_{164}$ is H or Me.
In aspects, the compound is according to Formula XX Formula XX wherein $R^{165}$ is wherein $R_{166}$ is H, Me, or Cl,
wherein $R_{167}$ is H or F,
wherein $R_{168}$ is H or F,
and wherein $R_{169}$ is H or Me.
In aspects, the compound is according to Formula XXI Formula XXI wherein $R_{31}$ is wherein $R_{157}$ is Me or $CH_2CH_3$, $CH(CH3)_2$ where $R_{158}$ can be Me, $CH_2CH_3$, $CH(CH3)_2$ or wherein $R_{31}$ is selected from the group of: a $C_1$-$C_6$ alkyl, a $C_1$-$C_6$ alkenyl, a $C_1$-$C_6$ cycloalkyl, and a $C_1$-$C_6$ haloalkyl, wherein $R_{32}$ is selected from the group of: a $C_1$-$C_6$ alkyl, a $C_1$-$C_6$ alkenyl, a $C_1$-$C_8$ cycloalkyl, —H, -D, a $C_1$-$C_8$ substituted cycloalkylenyl, a substituted aryl, and a substituted heteroaryl, and wherein $R_{33}$, $R_{34}$, $R_{35}$, $R_{36}$, $R_{37}$, $R_{33}'$, $R_{34}'$, $R_{35}'$, $R_{36}'$, and $R_{37}'$ are each independently selected from the group of: —H, a halogen, —CN, a $C_1$-$C_3$ haloalkyl, a $C_1$-C6 cycloalkyl, a $C_1$-$C_6$ alkylamine, a $C_1$-$C_6$ cycloalkylamine, a $C_1$-$C_6$ alkylester and a $C_1$-$C_6$ alkylamide.

In aspects, the compound is according to Formula XXII,

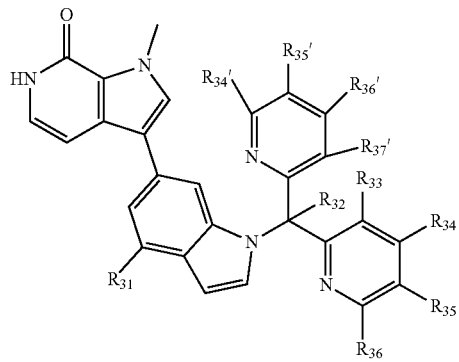

wherein $R_{31}$ is

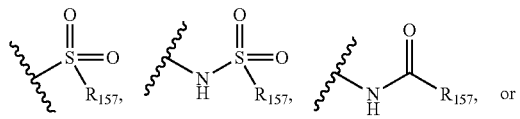

wherein $R_{157}$ is Me, $CH_2CH_3$, or $CH(CH3)_2$ wherein $R_{32}$ is selected from the group of: a $C_1$-$C_6$ alkyl, a $C_1$-$C_6$ alkenyl, a $C_1$-$C_8$ cycloalkyl, —H, -D, a $C_1$-$C_8$ substituted cycloalkylenyl, a substituted aryl, and a substituted heteroaryl, and wherein $R_{33}$, $R_{34}$, $R_{35}$, $R_{36}$, $R_{37}$, R34', R35', R36' R37' are each independently selected from the group of: —H, a halogen, —CN, $C_1$-$C_3$ haloalkyl, a $C_1$-$C_6$ cycloalkyl, a $C_1$-a $C_6$ alkylamine, a $C_1$-$C_6$ cycloalkylamine, a $C_1$-$C_6$ alkylester and a $C_1$-$C_6$ alkylamides.

In aspects, the compound is according to Formula XXIII,

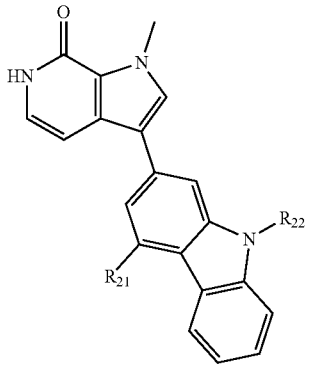

Formula XXIII wherein $R^{21}$ is —$N(R^a)S(O)_2R^b$, —$S(O)_2NR^aR^b$, $S(O)_2R^a$ —$C(O)NR^aR^b$ —$N(R^a)C(O)R^b$ —$NR^aR^b$, or a —($C_1$-$C_6$ alkylenyl)$R^c$, wherein $R^a$ and $R^b$, at each occurrence, are each independently selected from the group of: H, $C_1$-$C_6$ alkyl, $C_1$-$C_6$ alkenyl, C1-$C_6$ alkynyl, $C_1$-$C_6$ haloalkyl, $R^c$, and $C_1$-$C_6$ alkyl where the $C_1$-$C_6$ alkyl can be substituted with one substituent selected from the group of: —$OR^{y1}$, —$NR^{y3}R^{y4}$, —$C(O)OR^{y2}$, —$C(O)NR^{y3}R^{y4}$, —$S(O)_2R^{y1}$, —$S(O)_2NR^{y3}R^{y4}$, and $R^c$, wherein $R^{y1}$, at each occurrence, are each independently selected from the group of: H, Me or $CH_2CH_3$, $CH(CH_3)_2$, wherein $R^{y2}$, at each occurrence, are each independently selected from the group of: H, Me or $CH_2CH_3$, $CH(CH_3)_2$, wherein $R^{y3}$, at each occurrence, are each independently selected from the group of: H, Me or $CH_2CH_3$, $CH(CH_3)_2$, wherein $R^{y4}$, at each occurrence, are each independently selected from the group of: H, Me or $CH_2CH_3$, $CH(CH_3)_2$, wherein $R^{22}$ is selected from the group of: a —($C_1$-$C_6$ alkylenyl)$R^c$, a —($C_1$-$C_3$ cycloalkylenyl)$R^c$, and a —($C_1$-$C_6$ alkylenyl)$R^cR^{c'}$, wherein $R^c$ and $R^{c'}$, at each occurrence, are each independently selected from the group of: an aryl, a heteroaryl, a heterocycle, a cycloalkyl, and a cycloalkenyl; and each $R^c$ group can be optionally substituted with 1, 2, 3, 4, or 5 $R^d$ groups, where $R^d$, at each occurrence, are each independently selected from the group of: a $C_1$-$C_6$ alkyl, a $C_2$-$C_6$ alkenyl, a $C_2$-$C_6$ alkynyl, a halogen, a $C_1$-$C_6$ haloalkyl, —CN, $NO_2$, —$OR^e$, —$S(O)_2NR^eR^f$, —$C(O)R^e$, —$C(O)NR^eR^f$, —$NR^eR^f$, —$N(R^e)C(O)R^f$, a —($C_1$-$C_6$ alkylenyl)-$OR^e$, a —($C_1$-$C_6$ alkylenyl)-$C(O)NR^eR^f$, a —($C_1$-$C_6$ alkylenyl)-$NR^eR^f$, and a —($C_1$-$C_6$ alkylenyl)-$N(R^e)C(O)R^f$, and wherein $R^e$ and $R^f$, at each occurrence, can each be independently selected from the group of: H, a $C_1$-$C_6$ alkyl, and a $C_1$-$C_6$ haloalkyl.

In aspects, the compound is according to Formula VII

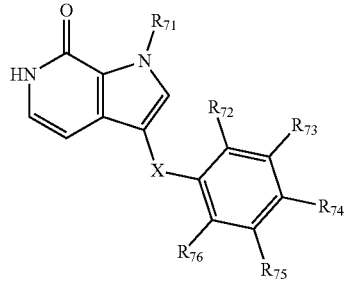

Formula VII wherein X is selected from the group of: —O—, —C(O)—, —N($R_{77}$)—, and —CH($R_{70}$)—, wherein $R_{71}$ is selected from the group of: a $C_1$-$C_3$ alkyl, a $C_1$-$C_3$ haloalkyl, a propylenyl, —$CH_2$(CO)CH=$CH_2$, oxiran-2-ylmethyl, and $CH_2$(CO)$CH_2$Cl, wherein $R_{72}$, $R_{73}$, $R_{74}$, $R_{75}$, $R_{76}$, and $R_{77}$ are each independently selected from the group of: —H, a halogen, —CN, a $C_1$-$C_3$ haloalkyl, —$OR_{70}$, —$NR_{70}R_{70}$, —C(O)$OR_{70}$, —C(O)$NR_{70}R_{70}$, —S(O)$_2R_{70}$, —S(O)$_2NR_{70}R_{70}$, and $R_{70}$, wherein $R_{70}$, at each occurrence, are each independently selected from the group of: a $C_1$-$C_6$ alkyl, a $C_2$-$C_6$ alkenyl, a $C_2$-$C_6$ alkynyl, a halogen, a $C_1$-$C_6$ haloalkyl, —CN, $NO_2$, —$OR^e$, —S(O)$_2NR^eR^f$, —C(O)$R^e$, —C(O)$NR^eR^f$, —$NR^eR^f$, —N($R^e$)C(O)$R^f$, a —($C_1$-$C_6$ alkylenyl)-$OR^e$, a —($C_1$-$C_6$ alkylenyl)-C(O)$NR^eR^f$, a —($C_1$-$C_6$ alkylenyl)-$NR^eR^f$, and a —($C_1$-$C_6$ alkylenyl)-N($R^e$)C(O)$R^f$, and wherein $R^e$ and $R^f$, at each occurrence, are each independently selected from the group of: H, a $C_1$-$C_6$ alkyl, and a $C_1$-$C_6$ haloalkyl.

In aspects, the compound is according to Formula VIII

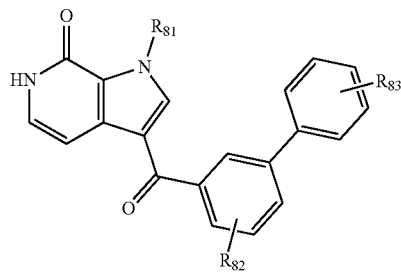

Formula VIII wherein $R_{81}$, $R_{82}$, and $R_{83}$ are each independently selected from the group of: a $C_1$-$C_3$ alkyl, a $C_1$-$C_3$ haloalkyl, a propylenyl, —$CH_2$(CO)CH=$CH_2$, oxiran-2-ylmethyl, and $CH_2$(CO)$CH_2$Cl.

In aspects, also described herein are compounds according to Formula X

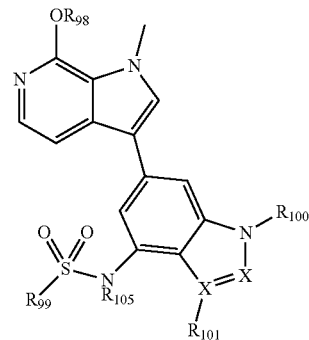

Formula X wherein each X, at each occurrence, is C or N,
wherein $R_{98}$ is H or Me,
wherein $R_{99}$ is selected from the group of: Me, Et, and CH($CH_2$)$_2$,
wherein $R_{100}$ is selected from the group of:

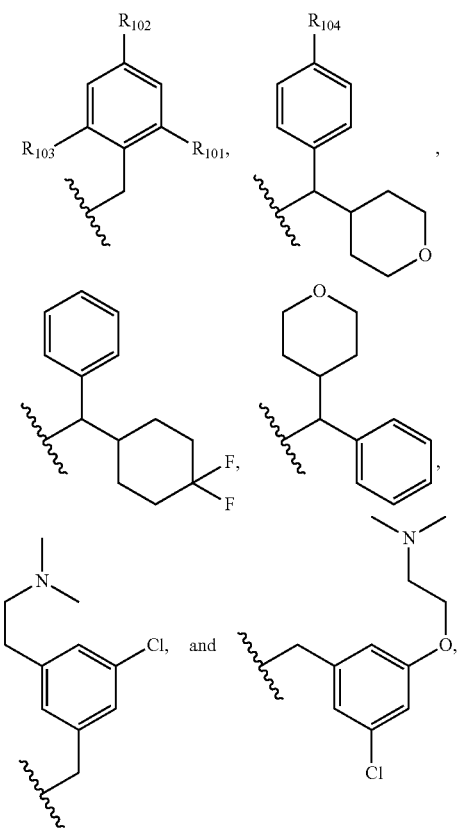

wherein $R_{101}$ is selected from the group of: Cl, F, H, Me, a cycloheteroalkyl, and

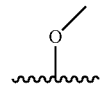

wherein $R_{102}$ is selected from the group of: H, Cl, F, OH, CF$_3$ and CN, wherein $R_{103}$ is selected from the group of: Cl, F, H,

and Me, wherein $R_{104}$ is H or F, and wherein $R_{105}$ is H or

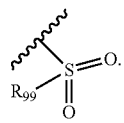

In aspects, also described herein are compounds according to Formula XII

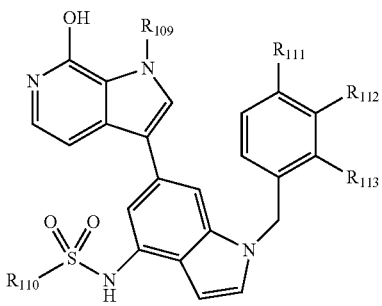

Formula XII wherein $R_{109}$ is

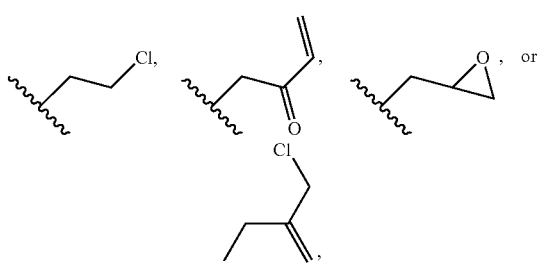

wherein $R_{110}$ is Me or CH$_2$CH$_3$,
wherein $R_{111}$ is F, H, Cl, or CN,
wherein $R_{112}$ is H, Cl, or F,
and wherein $R_{113}$ is H, Me, Cl, or F.

In aspects, also described herein are compounds according to Formula XIII

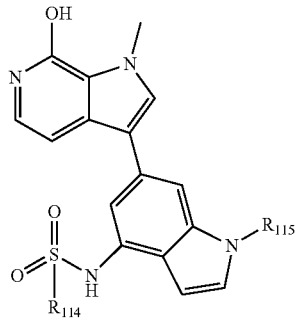

Formula XIII wherein $R_{114}$ is Me or CH$_2$CH$_3$,
wherein $R_{115}$ is selected from the group of:

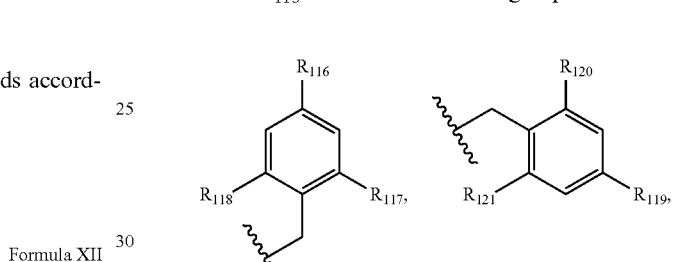

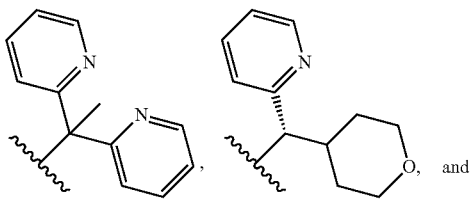

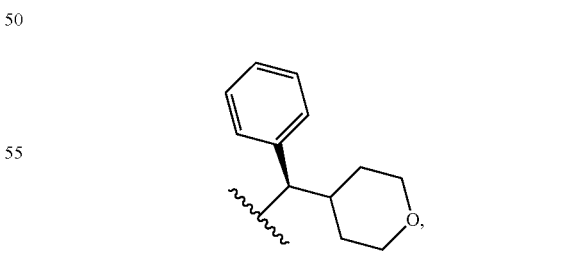

wherein $R_{116}$ is H, F, or N(CH$_3$)$_2$,
wherein $R_{117}$ is H, Cl, F, CF$_3$, or Me,
wherein $R_{118}$ is H, Me, or CF$_3$,
wherein $R_{119}$ is H, F, or N(CH$_3$)$_2$,
wherein $R_{120}$ is H, Me, or CF$_3$,
and wherein $R_{121}$ is H or Me.

In aspects, also described herein are compounds according to Formula XIV

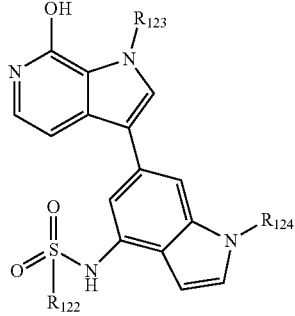
Formula XIV wherein $R_{122}$ is Me or $CH_2CH_3$,
wherein $R_{123}$ is

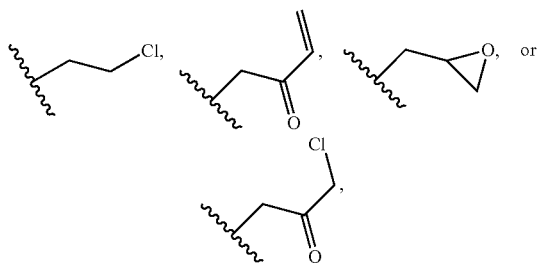

wherein $R_{124}$ is

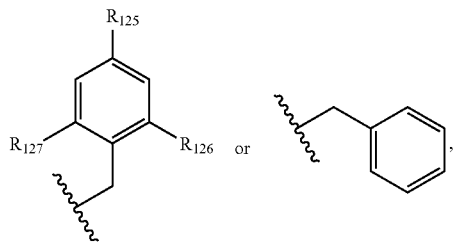

wherein $R_{125}$ is H or F,
wherein $R_{126}$ is H or Me,
and wherein $R_{127}$ is H or Me.

In aspects, also described herein are compounds according to Formula XV

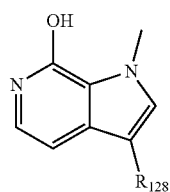
Formula XV wherein $R_{128}$ is

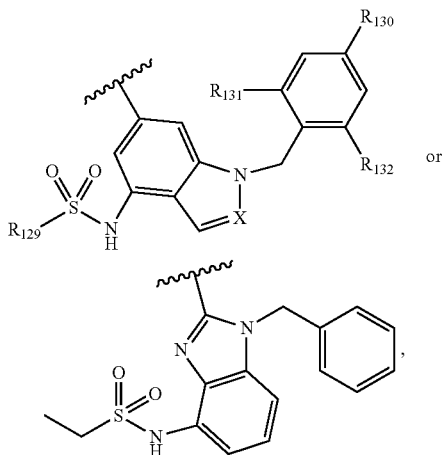

wherein $R_{129}$ is Me or $CH_2CH_3$,
wherein $R_{130}$ is H or F,
wherein $R_{131}$ is H or Me,
wherein $R_{132}$ is H or Me,
and wherein X is C or N.

In aspects, also described herein are compounds according to Formula XVIII

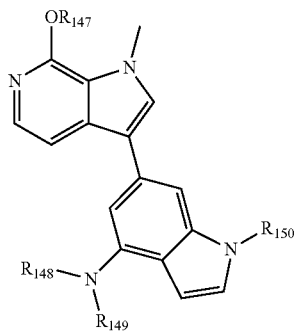
Formula XVIII wherein $R_{147}$ is H or Me,
wherein $R_{148}$ is

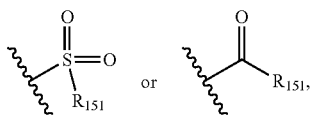

wherein $R_{149}$ is H, $CH_2CH_3$, or

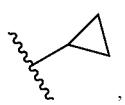

wherein R$_{150}$ is

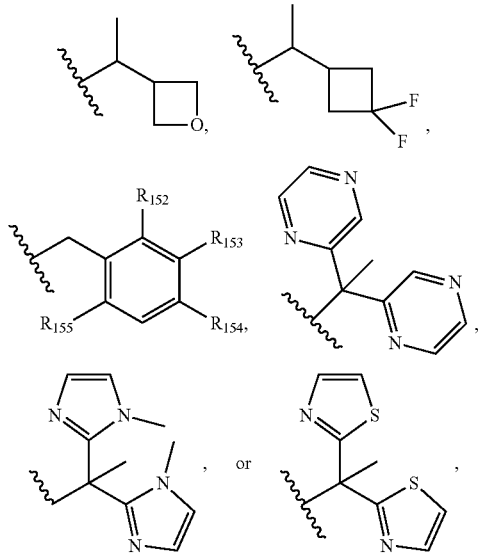

wherein R$_{151}$ is Me, Et, or CH(CH$_2$)$_2$,
wherein R$_{152}$ is H, Me, or Cl, where R$_{153}$ can be H or F,
wherein R$_{154}$ is H or F,
and wherein R$_{155}$ is H or Me.

In aspects, also described herein are compounds according to Formula XI

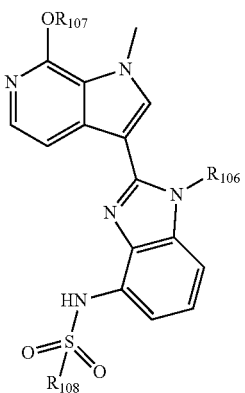

wherein R$_{107}$ is H or Me,
wherein R$_{108}$ is selected from the group of: Me, Et, and CH(CH$_2$)$_2$,
and wherein R$_{106}$ is selected from the group of:

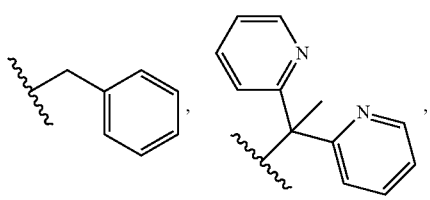

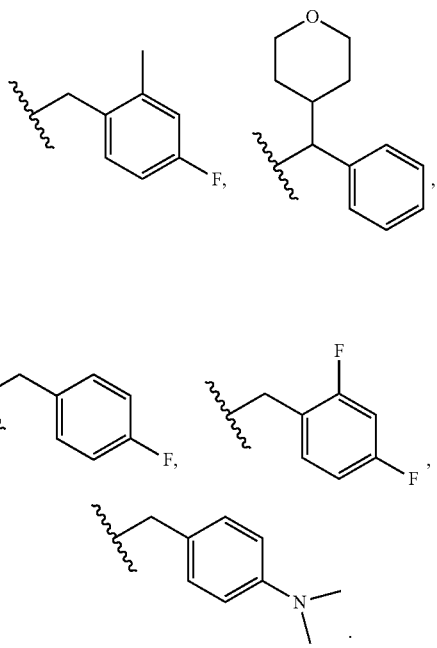

In aspects, also described herein are compounds according to Formula VII

Formula VII

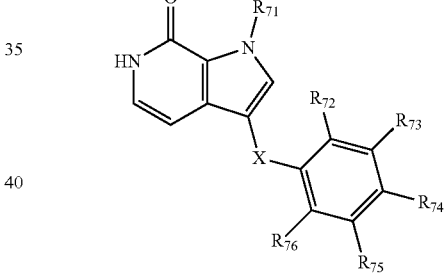

wherein X is selected from the group of: —O—, —C(O)—, —N(R$_{77}$)—, and —CH(R$_{70}$)—, wherein R$_{71}$ is selected from the group of: a C$_1$-C$_3$ alkyl, a C$_1$-C$_3$ haloalkyl, a propylenyl, —CH$_2$(CO)CH═CH$_2$, oxiran-2-ylmethyl, and CH$_2$(CO)CH$_2$Cl, wherein R$_{72}$, R$_{73}$, R$_{74}$, R$_{75}$, R$_{76}$, and R$_{77}$ are each independently selected from the group of: —H, a halogen, —CN, a C$_1$-C$_3$ haloalkyl, —OR$_{70}$, —NR$_{70}$R$_{70}$, —C(O)OR$_{70}$, —C(O)NR$_{70}$R$_{70}$, —S(O)$_2$R$_{70}$, —S(O)$_2$NR$_{70}$R$_{70}$, and R$_{70}$, wherein R$_{70}$, at each occurrence, are each independently selected from the group of: a C$_1$-C$_6$ alkyl, a C$_2$-C$_6$ alkenyl, a C$_2$-C$_6$ alkynyl, a halogen, a C$_1$-C$_6$ haloalkyl, —CN, NO$_2$, —OR$^e$, —S(O)$_2$NR$^e$R$^f$, —C(O)R$^e$, —C(O)NR$^e$R$^f$, —NR$^e$R$^f$, —N(R$^e$)C(O)R$^f$, a —(C$_1$-C$_6$ alkylenyl)-OR$^e$, a —(C$_1$-C$_6$ alkylenyl)-C(O)NR$^e$R$^f$, a —(C$_1$-C$_6$ alkylenyl)-NR$^e$R$^f$, and a —(C$_1$-C$_6$ alkylenyl)-N(R$^e$)C(O)R$^f$, and where R$^e$ and R$^f$, at each occurrence, are each independently selected from the group of: H, a C$_1$-C$_6$ alkyl, and a C$_1$-C$_6$ haloalkyl.

In aspects, also described herein are compounds according to Formula VIII

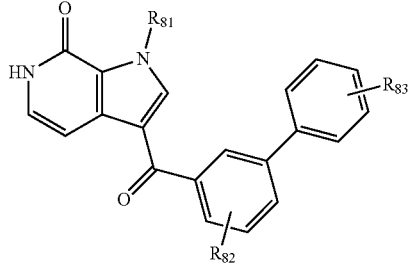

Formula VIII wherein $R_{81}$, $R_{82}$, and $R_{83}$ are each independently selected from the group of: a $C_1$-$C_3$ alkyl, a $C_1$-$C_3$ haloalkyl, a propylenyl, —$CH_2(CO)CH$=$CH_2$, oxiran-2-ylmethyl, and $CH_2(CO)CH_2Cl$.

In aspects, a compound described herein is any one of compounds (1)-(132). In aspects, a compound described herein is any one of compounds (2), (10), (22), (23), (30), (31), (70), (71), (72), (73), (74), (126), (130), (131), (132), or any combination thereof. In aspects, a compound described herein is any one of compounds (22), (23), (30), (31), or any combination thereof. In aspects, a compound described herein is any one of compounds (70), (71), (72), (73), (74), (126), (130), (131), (132), or any combination thereof. In aspects, a compound described herein is any one of compounds (70), (71), (72), or any combination thereof. In aspects, a compound described herein is any one of compounds (126), (130), (131), (132), or any combination thereof. In aspects, a compound described herein is any one of compounds (70), (71), (72), (73), (74), or any combination thereof.

In aspects, a compound described herein has an $IC_{50}$ against a cell of less than 0.001, less than 0.01, less than 0.1, less than 1 μM, less than 3 μM, and/or less than 5 μM. In aspects, a compound described herein has an $IC_{50}$ against a cell ranging from 0.0001 μM to 0.001 μM, from 0.001 to 0.01 μM, from 0.01 μM to 0.1 μM, 0.1 μM to 1 μM, 1 μM to 2 μM, 2 μM to 3 μM, 3 μM to 4 μM, or 4 μM to 5 μM. In aspects, the cell is a cancer cell and/or a resistant cancer cell.

In aspects, a compound described herein is capable of specifically binding a bromodomain, a BRD protein, a BET protein, or any combination thereof. In aspects, a compound described herein capable of modulating an activity or a functionality of a BRD protein, a BET protein, or a BRD protein and a BET protein. In aspects, a compound described herein is capable of reducing, inhibiting, or eliminating an activity or a functionality of a BRD protein, a BET protein, or a BRD protein and a BET protein.

In aspects, also described herein are pharmaceutical formulations that contain a compound as described herein and a pharmaceutically acceptable carrier.

In aspects, also described herein is the use of a compound as described herein in the manufacture of a medicament to treat or prevent a cancer or other disease that histone modifications can be modulated to treat and/or prevent a disease and/or a symptom thereof, which can include, but is not limited to, arthritis, lupus, pulmonary arterial hypertension, heart remodeling, a neurodegenerative disease and or combination thereof.

In aspects, also described herein is the use of a compound as described herein or a pharmaceutical formulation thereof for the treatment or prevention of a cancer or other disease that histone modifications can be modulated to treat and/or prevent a disease and/or a symptom thereof, which can include, but is not limited to, arthritis, lupus, pulmonary arterial hypertension, heart remodeling, a neurodegenerative disease or any combination thereof.

In aspects, described herein are methods that can include the step of administering a compound as described herein or a pharmaceutical formulation thereof to a subject. In aspects, the subject has or is suspected of having a cancer or other disease that histone modifications can be modulated to treat and/or prevent a disease and/or a symptom thereof, which can include, but is not limited to, arthritis, lupus, pulmonary arterial hypertension, heart remodeling, a neurodegenerative disease or any combination thereof.

In aspects, also described herein are methods of treating or preventing a disease or disorder in a subject in need thereof that can include the step of administering a compound as described herein or a pharmaceutical formulation thereof to the subject in need thereof and wherein the disease or disorder is a cancer or other disease that histone modifications can be modulated to treat and/or prevent a disease and/or a symptom thereof, which can include, but is not limited to, arthritis, lupus, pulmonary arterial hypertension, heart remodeling, a neurodegenerative disease or any combination thereof.

In aspects, also described herein are kits that can include a a compound as described herein or a pharmaceutical formulation thereof; and instructions fixed in a tangible medium of expression, wherein the instructions direct administration of the compound or pharmaceutical formulation to a subject in need thereof, wherein the subject in need thereof has or is suspected of having a cancer or other disease that histone modifications can be modulated to treat and/or prevent a disease and/or a symptom thereof, which can include, but is not limited to, arthritis, lupus, pulmonary arterial hypertension, heart remodeling, a neurodegenerative disease or any combination thereof. In aspects, the kit further contains an auxiliary agent. In aspects, the auxiliary agent is a chemotherapeutic agent.

In aspects, described herein are methods that can include the step of contacting a cell with a compound as described herein or a pharmaceutical formulation thereof. In aspects, the cell is a cancer cell and/or a resistant cancer cell. In aspects, the method can further include the step of specifically binding the compound to a bromodomain of a protein within the cell. In aspects, the method can further include the step of specifically binding the compound to a BRD protein, a BET protein, or a BRD protein and a BET protein within the cell.

In aspects, also described herein are methods of modulating an activity or a functionality a BRD protein, a BET protein, or a BRD protein and a BET protein in a cell, that can include the step of contacting the cell with a compound as described herein or a pharmaceutical formulation thereof. In aspects, the cell can be a cancer cell and/or a resistant cancer cell.

BRIEF DESCRIPTION OF THE DRAWINGS

Further aspects of the present disclosure will be readily appreciated upon review of the detailed description of its various aspects, described below, when taken in conjunction with the accompanying drawings.

DETAILED DESCRIPTION

Figure 1:
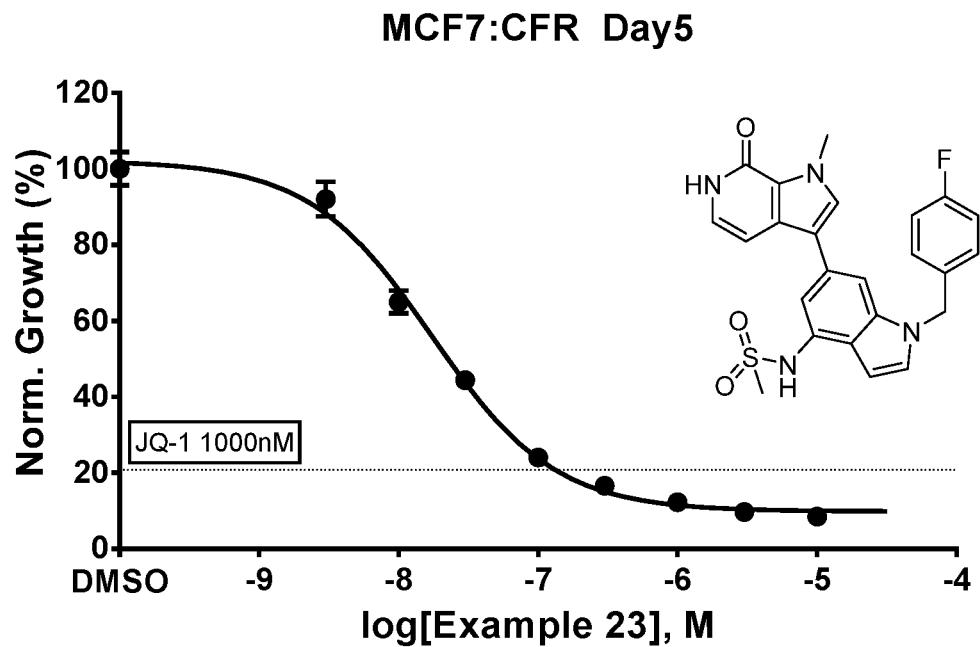
FIG. 1 shows a graph that can demonstrate growth inhibition of Compound (23) in fulvestrant-resistant MCF-7:CFR breast cancer cell model.

Before the present disclosure is described in greater detail, it is to be understood that this disclosure is not limited to particular aspects described, and as such may, of course, vary. It is also to be understood that the terminology used herein is for the purpose of describing particular aspects only, and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual aspects described and illustrated herein has discrete components and features which may be readily separated from or combined with the features of any of the other several aspects without departing from the scope or spirit of the present disclosure. Any recited method can be carried out in the order of events recited or in any other order that is logically possible.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used in the specification and the appended claims, the singular forms "a," "an," and "the" include plural referents unless the context clearly dictates otherwise.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

Aspects of the present disclosure will employ, unless otherwise indicated, techniques of molecular biology, microbiology, organic chemistry, biochemistry, physiology, cell biology, cancer biology, and the like, which are within the skill of the art. Such techniques are explained fully in the literature.

Before the aspects of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular aspects only, and is not intended to be limiting. It is also possible in the present disclosure that steps can be executed in different sequence where this is logically possible unless the context clearly dictates otherwise.

Definitions

As used herein, "active agent" or "active ingredient" refers to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed. An active agent can be a primary active agent, or in other words, the component(s) of a composition to which the whole or part of the effect of the composition is attributed. An active agent can be a secondary agent, or in other words, the component(s) of a composition to which an additional part and/or other effect of the composition is attributed.

As used herein, "administering" and the like refers to an administration that is oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravitreal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" includes subcutaneous, intravenous, intramuscular, intra-articular, intra-synovial, intrasternal, intrathecal, intrahepatic, intralesional, and intracranial injections or infusion techniques.

As used herein, "anti-infective" refers to compounds or molecules that can either kill an infectious agent or inhibit it from spreading. Anti-infectives include, but are not limited to, antibiotics, antibacterials, antifungals, antivirals, and antiprotozoans.

The term "biocompatible", as used herein, refers to a material that along with any metabolites or degradation products thereof that are generally non-toxic to the recipient and do not cause any significant adverse effects to the recipient. Generally speaking, biocompatible materials are materials that do not elicit a significant inflammatory or immune response when administered to a patient.

The term "biodegradable" as used herein, generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

As used herein "cancer" can refer to one or more types of cancer including, but not limited to, acute lymphoblastic leukemia, acute myeloid leukemia, adrenocortical carcinoma, Kaposi Sarcoma, AIDS-related lymphoma, primary central nervous system (CNS) lymphoma, anal cancer, appendix cancer, astrocytomas, atypical teratoid/Rhabdoid tumors, basal cell carcinoma of the skin, bile duct cancer, bladder cancer, bone cancer (including but not limited to Ewing Sarcoma, osteosarcomas, and malignant fibrous histiocytoma), brain tumors, breast cancer, bronchial tumors, Burkitt lymphoma, carcinoid tumor, cardiac tumors, germ cell tumors, embryonal tumors, cervical cancer, cholangiocarcinoma, chordoma, chronic lymphocytic leukemia, chronic myelogenous leukemia, chronic myeloproliferative neoplasms, colorectal cancer, craniopharyngioma, cutaneous T-Cell lymphoma, ductal carcinoma in situ, endometrial cancer, ependymoma, esophageal cancer, esthesioneuroblastoma, extracranial germ cell tumor, extragonadal germ cell tumor, eye cancer (including, but not limited to, intraocular melanoma and retinoblastoma), fallopian tube cancer, gallbladder cancer, kidney cancer, gastric cancer, gastrointestinal carcinoid tumor, gastrointestinal stromal tumors, central nervous system germ cell tumors, extracranial germ cell tumors, extragonadal germ cell tumors, ovarian germ cell tumors, ovarian cancer, testicular cancer, gestational trophoblastic disease, hairy cell leukemia, head and neck cancers, hepatocellular (liver) cancer, Langerhans cell histiocytosis, Hodgkin lymphoma, hypopharyngeal cancer, islet cell tumors, pancreatic neuroendocrine tumors, kidney (renal cell) cancer, laryngeal cancer, leukemia, lip cancer, oral cancer, lung cancer (non-small cell and small cell), lymphoma, melanoma, Merkel cell carcinoma, mesothelioma, metastatic squamous cell neck cancer, midline tract carcinoma with and without NUT gene changes (includes NUT-midline carcinoma), multiple endocrine neoplasia syndromes, multiple myeloma, plasma cell neoplasms, mycosis fungoides, myelodyspastic syndromes, myelodysplastic/myeloproliferative neoplasms, chronic myelogenous leukemia, nasal cancer, sinus cancer, non-Hodgkin lymphoma, pancreatic cancer, paraganglioma, paranasal sinus cancer, parathyroid cancer, penile cancer, pharyngeal cancer, pheochromocytoma, pituitary cancer, peritoneal cancer, prostate cancer, rectal cancer, Rhabdomyosarcoma, salivary gland cancer, uterine sarcoma, Sezary syndrome, skin cancer, small intestine cancer, large intestine cancer (colon cancer), soft tissue sarcoma, T-cell lymphoma, throat cancer, oropharyngeal cancer, nasopharyngeal cancer, hypopharyngeal cancer, thymoma, thymic carcinoma, thyroid cancer, transitional cell cancer of the renal pelvis and ureter, urethral cancer, uterine cancer, vaginal cancer, cervical cancer, vascular tumors and cancer, vulvar cancer, and Wilms Tumor. The cancer can be breast cancer, endocrine resistant breast cancer, CDK4/6 resistant breast cancer, prostate cancer, castrate-resistant prostate cancer, myelofibrosis, acute myeloid leukemia, diffuse large B-cell lymphoma. The cancer can be a cancer that is resistant to traditional or conventional therapies. The cancer can be resistant to an endocrine therapy, a kinase inhibitor therapy, a cell cycle inhibitor therapy. The caner can be a cancer that is resistant to a CDK4/6 inhibitor, aromatase inhibitor, fulvestrant, tamoxifen, or any combination thereof.

As used herein, "chemotherapeutic agent" or "chemotherapeutic" refers to a therapeutic agent utilized to prevent or treat cancer.

As used herein, "concentrated" refers to a molecule or population thereof, including but not limited to a polynucleotide, peptide, polypeptide, protein, antibody, or fragments thereof, that is distinguishable from its naturally occurring counterpart in that the concentration or number of molecules per volume is greater than that of its naturally occurring counterpart.

As used herein, "control" refers to an alternative subject or sample used in an experiment for comparison purpose and included to minimize or distinguish the effect of variables other than an independent variable.

The term "copolymer" as used herein, generally refers to a single polymeric material that is comprised of two or more different monomers. The copolymer can be of any form, such as random, block, graft, etc. The copolymers can have any end-group, including capped or acid end groups.

As used herein, "deoxyribonucleic acid (DNA)" and "ribonucleic acid (RNA)" can generally refer to any polyribonucleotide or polydeoxyribonucleotide, which may be unmodified RNA or DNA or modified RNA or DNA. RNA can be in the form of non-coding RNA such as tRNA (transfer RNA), snRNA (small nuclear RNA), rRNA (ribosomal RNA), anti-sense RNA, RNAi (RNA interference construct), siRNA (short interfering RNA), microRNA (miRNA), or ribozymes, aptamers, guide RNA (gRNA) or coding mRNA (messenger RNA).

As used herein, "derivative" can refer to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this may be the case. The term "derivative" can include prodrugs, or metabolites of the parent compound. Derivatives include compounds in which free amino groups in the parent compound have been derivatized to form amine hydrochlorides, p-toluene sulfoamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form methyl and ethyl esters, or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides. "Derivatives" also includes extensions of the replacement of the cyclopentane ring with saturated or unsaturated cyclohexane or other more complex, e.g., nitrogen-containing rings, and extensions of these rings with side various groups. Derivatives can also include the salt forms, such as pharmaceutically acceptable salt forms of a parent compound or derivative thereof.

As used herein, "diluted" refers to an amount of a molecule, compound, or composition including but not limited to, a chemical compound, polynucleotide, peptide, polypeptide, protein, antibody, or fragments thereof, that indicates that the sample is distinguishable from its naturally occurring counterpart in that the concentration or number of molecules per volume is less than that of its naturally occurring counterpart.

As used herein, "dose," "unit dose," or "dosage" can refer to physically discrete units suitable for use in a subject, each unit containing a predetermined quantity of a pyridinone-based compound described herein, derivative thereof, and/or a pharmaceutical formulation thereof calculated to produce the desired response or responses in association with its administration.

As used herein, "hydrate" refers to a compound formed by the addition of water. Typically, but not always, this will be crystalline lattice structures that incorporate water molecules. Hydrates include stoichiometric hydrates, as well as compositions containing variable amounts of water.

The term "hydrophilic", as used herein, refers to substances that have strongly polar groups that are readily soluble in water.

The term "hydrophobic", as used herein, refers to substances that lack an affinity for water; tending to repel and not absorb water as well as not dissolve in or mix with water.

As used herein, "immunomodulator," refers to an agent, such as a therapeutic agent, which is capable of modulating or regulating one or more immune function or response.

As used herein, "isolated" means separated from constituents, cellular and otherwise, in which the polynucleotide, peptide, polypeptide, protein, antibody, or fragments thereof, are normally associated with in nature. A non-naturally occurring polynucleotide, peptide, polypeptide, protein, antibody, or fragments thereof, do not require "isolation" to distinguish it from its naturally occurring counterpart.

The term "lipophilic", as used herein, refers to compounds having an affinity for lipids.

As used herein, "mammal," for the purposes of treatments, can refer to any animal classified as a mammal, including human, domestic and farm animals, nonhuman primates, and zoo, sports, or pet animals, such as, but not limited to, dogs, horses, cats, and cows.

As used herein, "modulate" refers to changing a behavior, characteristic, action, and/or activity of something, such as, but not limited to, a polynucleotide, protein, enzymatic or other cellular process, cell function, tissue function, organ functions, and/or or subject function or disease causing entity (e.g. a tumor, bacteria, virus, etc.).

The term "molecular weight", as used herein, can generally refer to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein, "negative control" refers to a "control" that is designed to produce no effect or result, provided that all reagents are functioning properly and that the experiment is properly conducted. Other terms that are interchangeable with "negative control" include "sham," "placebo," and "mock."

As used herein, "neurodegenerative disease" refers to diseases that result in and/or are characterized by a degeneration of one or more components of the brain and/or nervous system. Neurodegenerative diseases include, but are not limited to, Alzheimer's disease and related dementia, Parkinson's disease, and frontotemporal lobe dementia.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable" can refer to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" refers to any acid or base addition salt whose counter-ions are non-toxic to the subject to which they are administered in pharmaceutical doses of the salts.

As used herein, "positive control" refers to a "control" that is designed to produce the desired result, provided that all reagents are functioning properly and that the experiment is properly conducted.

As used herein, "preventative" and "prevent" refers to hindering, slowing the progression of, or stopping a disease or condition before it occurs, even if undiagnosed, or while the disease or condition is still in the sub-clinical phase. "Preventative" and "prevent" also refers to partially or completely delaying or precluding the recurrence of a disease, disorder, condition, or symptom thereof or reacquiring a disease, disorder, condition, or symptom thereof. "Preventative" and "prevent" also refers to reducing a subject's risk of acquiring or reacquiring a disease, disorder condition, or symptom thereof.

As used herein, "solvate" refers to a complex of variable stoichiometry formed by a solute (e.g. formulas (I)-(XX) (A), (B), (C), (D) etc., or any other compound or derivative thereof described herein) and a solvent. Pharmaceutically acceptable solvates may be formed for crystalline compounds wherein solvent molecules are incorporated into the crystalline lattice during crystallization. The incorporated solvent molecules can be water molecules or non-aqueous molecules, such as but not limited to, ethanol, isopropanol, dimethyl sulfoxide, acetic acid, ethanolamine, and ethyl acetate molecules.

As used herein, the term "specific binding" can refer to non-covalent physical association of a first and a second moiety wherein the association between the first and second moieties is at least 2 times as strong, at least 5 times as strong as, at least 10 times as strong as, at least 50 times as strong as, at least 100 times as strong as, or stronger than the association of either moiety with most or all other moieties present in the environment in which binding occurs. Binding of two or more entities may be considered specific if the equilibrium dissociation constant, Kd, is $10^{-3}$ M or less, $10^{-4}$ M or less, $10^{-5}$ M or less, $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less under the conditions employed, e.g., under physiological conditions such as those inside a cell or consistent with cell survival. In some embodiments, specific binding can be accomplished by a plurality of weaker interactions (e.g., a plurality of individual interactions, wherein each individual interaction is characterized by a Kd of greater than $10^{-3}$ M). In some embodiments, specific binding, which can be referred to as "molecular recognition," is a saturable binding interaction between two entities that is dependent on complementary orientation of functional groups on each entity. Examples of specific binding interactions include primer-polynucleotide interaction, aptamer-aptamer target interactions, antibody-antigen interactions, avidin-biotin interactions, ligand-receptor interactions, metal-chelate interactions, hybridization between complementary nucleic acids, molecule-protein interactions, etc.

As used interchangeably herein, "subject," "individual," or "patient" can refer to a vertebrate organism, such as a mammal (e.g. human). "Subject" can also refer to a cell, a population of cells, a tissue, an organ, or an organism, preferably to human and constituents thereof.

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used interchangeably herein, the terms "sufficient" and "effective," can refer to an amount (e.g. mass, volume, dosage, concentration, and/or time period) needed to achieve one or more desired result(s). For example, a "therapeutically effective amount" refers to an amount needed to achieve one or more therapeutic effects. As another example, an "effective amount" refers to the amount needed to achieve one or more desired effects. An "effective amount" can be, in some aspects, a "therapeutically effective amount." Desired effects can include, specific binding of a bromodomain, BRD protein, and/or a BET protein, modulating an activity or function of a BRD protein and/or a BET protein, inhibiting an activity or function of a BRD protein and/or a BET protein, treating and or preventing a cancer or other disease that histone modifications can be modulated to treat and/or prevent a disease and/or a symptom thereof, which can include, but is not limited to, arthritis, lupus, pulmonary arterial hypertension, heart remodeling, and/or a neurodegenerative disease in a subject.

As used herein, "tangible medium of expression" can refer to a medium that is physically tangible and is not a mere abstract thought or an unrecorded spoken word. Tangible medium of expression includes, but is not limited to, words on a cellulosic or plastic material or data stored on a suitable device such as a flash memory or CD-ROM.

As used herein, "therapeutic" can refer to treating, healing, and/or ameliorating a disease, disorder, condition, or side effect, or to decreasing in the rate of advancement of a disease, disorder, condition, or side effect.

As used herein, the terms "treating" and "treatment" refers generally to obtaining a desired pharmacological and/or physiological effect. The effect can be, but does not necessarily have to be, prophylactic in terms of preventing or partially preventing a disease, symptom or condition thereof, such as a cancer or other disease that histone modifications can be modulated to treat and/or prevent a disease and/or a symptom thereof, which can include, but is not limited to, arthritis, lupus, pulmonary arterial hypertension, heart remodeling, and/or a neurodegenerative disease. The effect can be therapeutic in terms of a partial or complete cure of a disease, condition, symptom or adverse effect attributed to the disease, disorder, or condition. The term "treatment" as used herein covers any treatment of a cancer or other disease that histone modifications can be modulated to treat and/or prevent a disease and/or a symptom thereof, which can include, but is not limited to, arthritis, lupus, pulmonary arterial hypertension, heart remodeling, and/or a neurodegenerative disease in a subject, particularly a human, and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

As used herein, "alkyl" and "alkylene" refer to a saturated hydrocarbon chain having the specified number of member atoms. The term "alkyl" can also refer to the radical of saturated aliphatic groups (i.e., an alkane with one hydrogen atom removed), including straight-chain alkyl groups, branched-chain alkyl groups, cycloalkyl (alicyclic) groups, alkyl-substituted cycloalkyl groups, and cycloalkyl-substituted alkyl groups. "Alkyl" also refers to a saturated hydrocarbon chain having the specified number of atoms.

The term "alkyl" (or "lower alkyl") as used herein can include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein can refer to an alkyl group, as defined above, but having from one to ten carbons in its backbone structure. Likewise, "lower alkenyl" and "lower alkynyl" have similar chain lengths.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls can be substituted in the same manner.

As used herein, "$C_{1-6}$ alkyl" can refer to an alkyl group having any number of member atoms from 1 to 6 member atoms, such as for example 1 to 4 atoms. Other alkyl groups may have any number of member atoms as indicated by the numbers given in the formula, which, like the previous example, can refer to an alkyl group having any number of member atoms within the specified range of member atoms. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl.

As used herein, "heterocyclic group" can refer to a non-aromatic ring and having the specified number of member atoms being saturated or having one or more degrees of unsaturation and, unless otherwise specified, containing one or more heteroatoms.

As used herein, "heteroaryl" can refer to an aromatic ring having the specified number of member atoms and, unless otherwise specified, containing one or more heteroatoms. Bicyclic and other polycyclic ring systems having a heteroaryl ring are described as fused systems.

The term "heteroalkyl," as used herein, can refer to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "heteroalkyl," as used herein, can refer to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

As used herein, "alkoxyl" or "alkoxy," as used herein, can refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl is an ether or resembles an alkoxyl, such as can be represented by one of —O-alkyl, —O-alkenyl, and —O-alkynyl. The terms "aroxy" and "aryloxy", as used interchangeably herein, can be represented by —O-aryl or O-heteroaryl, wherein aryl and heteroaryl are as defined below. The alkoxy and aroxy groups can be substituted as described above for alkyl.

As used herein, "amine" and "amino" (and its protonated form) are art-recognized and refer to both unsubstituted and substituted amines, e.g., a moiety that can be represented by the general formula:

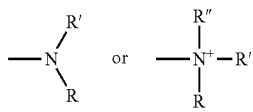

wherein R, R', and R" each independently represent a hydrogen, an alkyl, an alkenyl, —(CH$_2$)$_m$—R$_c$ or R and R' taken together with the N atom to which they are attached complete a heterocycle having from 4 to 8 atoms in the ring structure; R$_c$ represents an aryl, a cycloalkyl, a cycloalkenyl, a heterocycle or a polycycle; and m is zero or an integer in the range of 1 to 8. In some embodiments, only one of R or R' can be a carbonyl, e.g., R, R' and the nitrogen together do not form an imide. In other embodiments, the term "amine" does not encompass amides, e.g., wherein one of R and R' represents a carbonyl. In further embodiments, R and R' (and optionally R") each independently represent a hydrogen, an alkyl or cycloakyl, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R and R' is an alkyl group.

As used herein, "amido" is art-recognized as an amino-substituted carbonyl and includes a moiety that can be represented by the general formula:

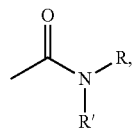

wherein R and R' are as defined above.

As used herein, "Aryl" can refer to $C_5$-$C_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics." The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, and combinations thereof.

The term "aryl" can also include polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. One or more of the rings can be substituted as defined above for "aryl."

As used herein, "aralkyl," can refer to an alkyl group substituted with an aryl group (e.g., an aromatic or heteroaromatic group).

As used herein, "aralkyloxy" can be represented by —O-aralkyl, wherein aralkyl is as defined above.

As used herein, "carbocycle," can refer to an aromatic or non-aromatic ring(s) in which each atom of the ring(s) is carbon.

As used herein, "heterocycle" or "heterocyclic" can refer to a monocyclic or bicyclic structure containing 3-10 ring atoms, and in some embodiments, containing from 5-6 ring atoms, wherein the ring atoms are carbon and one to four heteroatoms each selected from the following group of non-peroxide oxygen, sulfur, and N(Y) wherein Y is absent or is H, O, ($C_1$-$C_{10}$) alkyl, phenyl or benzyl, and optionally containing 1-3 double bonds and optionally substituted with one or more substituents. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbonyl" is art-recognized and includes such moieties as can be represented by the general formula:

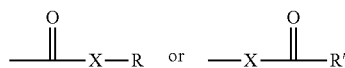

wherein X is a bond or represents an oxygen or a sulfur, and R and R' are as defined above. Where X is an oxygen and R or R' is not hydrogen, the formula represents an "ester". Where X is an oxygen and R is as defined above, the moiety is referred to herein as a carboxyl group, and particularly when R is a hydrogen, the formula represents a "carboxylic acid." Where X is an oxygen and R' is hydrogen, the formula represents a "formate." In general, where the oxygen atom of the above formula is replaced by sulfur, the formula represents a "thiocarbonyl" group. Where X is a sulfur and R or R' is not hydrogen, the formula represents a "thioester." Where X is a sulfur and R is hydrogen, the formula represents a "thiocarboxylic acid." Where X is a sulfur and R' is hydrogen, the formula represents a "thioformate." On the other hand, where X is a bond, and R is not hydrogen, the above formula represents a "ketone" group. Where X is a bond, and R is hydrogen, the above formula represents an "aldehyde" group.

As used herein, "heteroatom" as used herein can refer to an atom of any element other than carbon or hydrogen. Exemplary heteroatoms include, but are not limited to, boron, nitrogen, oxygen, phosphorus, sulfur, silicon, arsenic, and selenium.

As used herein, "nitro" can refer to —$NO_2$; the term "halogen" designates —F, —Cl, —Br, or —I; the term "sulfhydryl" refers to —SH; the term "hydroxyl" refers to —OH; and the term "sulfonyl" refers to —$SO_2$—.

The term "substituted" as used herein, can refer to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, e.g. 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

Heteroatoms, such as nitrogen, can have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc.

As used herein, "suitable substituent" can refer to a chemically and pharmaceutically acceptable group, i.e., a moiety that does not significantly interfere with the preparation of or negate the efficacy of the inventive compounds. Such suitable substituents may be routinely chosen by those skilled in the art. Suitable substituents include but are not limited to the following: a halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, $C_2$-$C_6$ alkynyl, $C_3$-$C_8$ cycloalkenyl, ($C_3$-$C_8$ cycloalkyl)$C_1$-$C_6$ alkyl, ($C_3$-$C_8$ cycloalkyl)$C_2$-$C_6$ alkenyl, ($C_3$-$C_8$ cycloalkyl) $C_1$-$C_6$ alkoxy, $C_3$-$C_7$ heterocycloalkyl, ($C_3$-$C_7$ heterocycloalkyl) $C_1$-$C_6$ alkyl, ($C_3$-$C_7$ heterocycloalkyl)$C_2$-$C_6$ alkenyl, ($C_3$-$C_7$ heterocycloalkyl)$C_1$-$C_6$ alkoxyl, hydroxy, carboxy, oxo, sulfanyl, $C_1$-$C_6$ alkylsulfanyl, aryl, heteroaryl, aryloxy, heteroaryloxy, arylalkyl, heteroaralkyl, arylalkoxy, heteroaralkoxy, nitro, cyano, amino, $C_1$-$C_6$ alkylamino, di-($C_1$-$C_6$ alkyl)amino, carbamoyl, ($C_1$-$C_6$ alkyl)carbonyl, ($C_1$-$C_6$ alkoxy)carbonyl, ($C_1$-$C_6$ alkyl)aminocarbonyl, di-($C_1$-$C_6$ alkyl)aminocarbonyl, arylcarbonyl, aryloxycarbonyl, ($C_1$-$C_6$ alkyl)sulfonyl, and arylsulfonyl. The groups listed above as suitable substituents are as defined hereinafter except that a suitable substituent may not be further optionally substituted.

As used herein, "optionally substituted" can indicate that a group may be unsubstituted or substituted with one or more substituents as defined herein.

It will be appreciated that as used herein, the following structures are equivalent as tautomers.

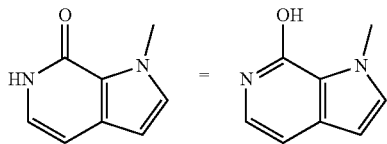

Unless otherwise defined herein, all technical and scientific terms used herein have the same meaning as commonly understood by one of ordinary skill in the art.

Discussion

Cancer and other diseases, such as arthritis, lupus, and neurodegenerative disorders, for example, are associated with significant mortality and/or morbidity and remain major health concerns worldwide. Despite advances in the understanding of these diseases and disorders, there still exists a need for additional and/or improved treatments.

Histone modifications are modifications to histones, e.g. acetylation or methylation, which can result in alteration in gene expression. Gene expression can be altered by the reorganization of the genome as a result of the histone modification. Reorganization changes which areas of the genome are active (referred to as euchromatin), where the DNA is accessible for transcription, and inactive (referred to as heterochromatin), where the DNA is more compact and less accessible for transcription.

The major types of histones are H1, which is the linker histone and is responsible for stabilization, H2A, H2B, H3 and H4, which are known as the core histones. Histones pack and order the DNA into structures known as nucleosomes. Each nucleosome contains two subunits each being a core histone. Histones can be modified by methylation at lysine and/or arginine residues, acetylation at lysine residues, ubiquitylation, and/or phosphorylation. Histones can be acetylated on lysines. Histone acetylation is often associated with an open chromatin structure, which makes the chromatin accessible to transcription factors and is thus associated with an increase in gene expression. Histone acetylation is typically in promoter regions of the DNA.

Histone modification is a dynamic process and is regulated by a specific set of enzymes. These epigenetic regulators can be divided into writers, readers, and erasers. Epigenetic writers include enzymes such as histone acetyltransferases (HATs), histone methyltransferases (HMTs/KMTs), protein arginine methyltransferases (PRMTs) and kinases, which add epigenetic marks on histones. Epigenetic erasers include enzymes such as histone deacetylases (HDACs), lysine demethylases (KDMs) and phosphatases, which catalyze the reversal of epigenetic marks. Epigenetic readers include enzymes that recognize and bind to the epigenetic marks laid down by the epigenetic writers, thereby determining their functional outcome and include proteins containing bromodomains, chromodomains, and Tudor.

A bromodomain is about a 110 amino acid protein domain that recognizes acetylated lysine residues. As discussed above, bromodomains are epigenetic readers of lysine acetylation that transduce the signal carried by acetylated lysine residues and translates it into phenotypes. Bromodomains have been implicated in having a role in various diseases including, but not limited to, cancers and multiple sclerosis.

With that said, described herein are compounds and formulations thereof that can modulate the activity of the bromodomain and extraterminal (BET) family of bromodomains and bromodomain proteins (e.g. BRD2, BRD3, MRD4, and BRDT). Also described herein are methods of using the compounds and formulations thereof described herein to treat and/or prevent a disease or disorder. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Pyridinone-Based Compounds

Described herein are pyridinone-based compounds that can, in some aspects, modulate the activity of a bromodomain protein (BRD) and/or bromodomain and extraterminal (BET) family of bromodomains. In some aspects, the pyridinone-based compounds and/or derivatives thereof described herein can inhibit or decrease the activity of a BRD protein and/or BET protein.

In some aspects, the compound can be according to Formula I

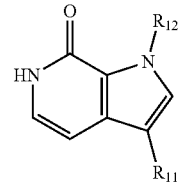

Formula I where $R_{12}$ can be a $C_1$-$C_3$ alkyl, a $C_1$-$C_3$ haloalkyl, propylenyl, —$CH_2$(CO)CH=$CH_2$, oxiran-2-ylmethyl, or $CH_2$(CO)$CH_2$Cl, where $R_{11}$ can be a nitrogen-containing bicyclic or tricyclic heteroaryl, each of which can be substituted with 1, 2, or 3 substituents each can be independently selected from the group of: —N($R^a$)S(O)$_2R^b$, —S(O)$_2$N$R^aR^b$, —C(O)N$R^aR^b$ —N($R^a$)C(O)$R^b$ —N$R^aR^b$ —($C_1$-$C_6$ alkylenyl)$R^c$, —($C_1$-$C_3$ cycloalkylenyl)$R^c$, and —($C_1$-$C_6$ alkylenyl)$R^cR^{c'}$, where $R^a$ and $R^b$, at each occurrence, can each be independently selected from the group of: H, a $C_1$-$C_6$ alkenyl, a $C_1$-$C_6$ alkynyl, a $C_1$-$C_6$ haloalkyl, $R^c$, or a $C_1$-$C_6$ alkyl, where the $C_1$-$C_6$ alkyl can be substituted with one substituent selected from the group of: —$OR^e$, —$NR^eR^f$, —C(O)$OR^e$, —C(O)$NR^eR^f$, —S(O)$_2R^e$, —S(O)$_2NR^eR^f$, and $R^c$, where $R^c$ and $R^{c'}$, at each occurrence, can each be independently selected from the group of: an aryl, a heteroaryl, a heterocycle, a cycloalkyl, or a cycloalkenyl, and where each $R^c$ group can be substituted with 1, 2, 3, 4, or 5 $R^d$ groups, where $R^d$, at each occurrence, can be independently selected from the group of: a $C_1$-$C_6$ alkyl, a $C_2$-$C_6$ alkenyl, a $C_2$-$C_6$ alkynyl, a halogen, a $C_1$-$C_6$ haloalkyl, —CN, $NO_2$, —$OR^e$, —$S(O)_2NR^eR^f$, —$C(O)R^e$, —$C(O)NR^eR^f$, —$NR^eR^f$, —$N(R^e)C(O)R^f$, a —($C_1$-$C_6$ alkylenyl)-$OR^e$, a —($C_1$-$C_6$ alkylenyl)-$C(O)NR^eR^f$, a —($C_1$-$C_6$ alkylenyl)-$NR^eR^f$, and a —($C_1$-$C_6$ alkylenyl)-$N(R^e)C(O)R^f$, and where $R^e$ and $R^f$, at each occurrence, can each be independently selected from the group of: H, a $C_1$-$C_6$ alkyl, a $C_1$-$C_6$ cycloalkyl, a aryl, a heteroaryl and a $C_1$-$C_6$ haloalkyl.

In some aspects, the compound can be according to Formula II:

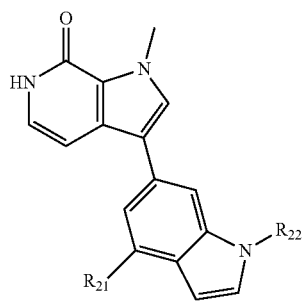

Formula II where $R^{21}$ can be —$N(R^a)S(O)_2R^b$, —$S(O)_2NR^aR^b$, $S(O)_2R^a$, —$C(O)NR^aR^b$ —$N(R^a)C(O)R^b$ —$NR^aR^b$, or a —($C_1$-$C_6$ alkylenyl)$R^c$, where $R^a$ and $R^b$, at each occurrence, can each be independently selected from the group of: H, $C_1$-$C_6$ alkyl, $C_1$-$C_6$ alkenyl, $C_1$-$C_6$ alkynyl, $C_1$-$C_6$ haloalkyl, $R^c$, and $C_1$-$C_6$ alkyl where the $C_1$-$C_6$ alkyl can be substituted with one substituent selected from the group of: —$OR^{y1}$, —$NR^{y3}R^{y4}$, —$C(O)OR^{y2}$, —$C(O)NR^{y3}R^{y4}$, —$S(O)_2R^{y1}$, —$S(O)_2NR^{y3}R^{y4}$, and $R^c$, where $R^{y1}$, at each occurrence, can each be independently selected from the group of: H, a $C_1$-$C_6$ alkyl, a $C_1$-$C_6$ cycloalkyl, a aryl, a heteroaryl and a $C_1$-$C_6$ haloalkyl, where $R^{y2}$, at each occurrence, can each be independently selected from the group of: H, a $C_1$-$C_6$ alkyl, a $C_1$-$C_6$ cycloalkyl, a aryl, a heteroaryl and a $C_1$-$C_6$ haloalkyl, where $R^{y3}$, at each occurrence, can each be independently selected from the group of: H, a $C_1$-$C_6$ alkyl, a $C_1$-$C_6$ cycloalkyl, a aryl, a heteroaryl and a $C_1$-$C_6$ haloalkyl, where $R^{y4}$, at each occurrence, can each be independently selected from the group of: H, a $C_1$-$C_6$ alkyl, a $C_1$-$C_6$ cycloalkyl, a aryl, a heteroaryl and a $C_1$-$C_6$ haloalkyl, where $R^{22}$ can be selected from the group of: a —($C_1$-$C_6$ alkylenyl)$R^c$, a —($C_1$-$C_3$ cycloalkylenyl)$R^c$, and a —($C_1$-$C_6$ alkylenyl)$R^cR^{c'}$, where $R^c$ and $R^{c'}$, at each occurrence, can each be independently selected from the group of: an aryl, a heteroaryl, a heterocycle, a cycloalkyl, and a cycloalkenyl; and each $R^c$ group can be substituted with 1, 2, 3, 4, or 5 $R^d$ groups, where $R^d$, at each occurrence, can be independently selected from the group of: a $C_1$-$C_6$ alkyl, a $C_2$-$C_6$ alkenyl, a $C_2$-$C_6$ alkynyl, a halogen, a $C_1$-$C_6$ haloalkyl, —CN, $NO_2$, —$OR^e$, —$S(O)_2NR^eR^f$, —$C(O)R^e$, —$C(O)NR^eR^f$, —$NR^eR^f$, —$N(R^e)C(O)R^f$, a —($C_1$-$C_6$ alkylenyl)-$OR^e$, a —($C_1$-$C_6$ alkylenyl)-$C(O)NR^eR^f$, a —($C_1$-$C_6$ alkylenyl)-$NR^eR^f$, and a —($C_1$-$C_6$ alkylenyl)-$N(R^e)C(O)R^f$, and where $R^e$ and $R^f$, at each occurrence, can each be independently selected from the group of: H, a $C_1$-$C_6$ alkyl, and a $C_1$-$C_6$ haloalkyl.

In some aspects, the compound can be according to Formula III

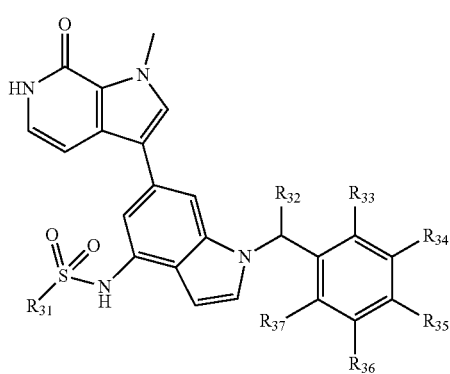

Formula III where $R_{31}$ can be selected from the group of: a $C_1$-$C_6$ alkenyl, a $C_1$-$C_6$ cycloalkyl, and a $C_1$-$C_6$ haloalkyl, where $R_{32}$ can be selected from the group of: a $C_1$-$C_6$ alkenyl, a $C_1$-$C_8$ cycloalkyl, —H, -D, a $C_1$-$C_8$ substituted cycloalkylenyl, a substituted aryl, and a substituted heteroaryl, which can include the pure enantiomer if the molecule contains chiral center, and where $R_{33}$, $R_{34}$, $R_{35}$, $R_{36}$, and $R_{37}$ can each be independently selected from the group of: —H, a halogen, —CN, and a $C_1$-$C_3$ haloalkyl.

In some aspects, the compound can be according to Formula IV

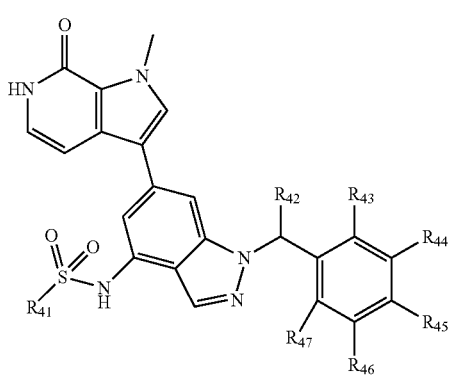

Formula IV where $R_{41}$ can be selected from the group of: a $C_1$-$C_6$ alkylenyl, a $C_1$-$C_6$ cycloalkyl, and a $C_1$-$C_6$ haloalkyl, where $R_{42}$ can be selected from the group of: a $C_1$-$C_6$ alkenyl, a $C_1$-$C_8$ cycloalkyl, —H, -D, a $C_1$-$C_8$ substituted cycloalkylenyl, a substituted aryl, a substituted heteroaryl, which can include a pure enantiomer if the molecule contains chiral center, and where $R_{43}$, $R_{44}$, $R_{45}$, $R_{46}$, and $R_{47}$ can each be independently selected from the group of: —H, a halogen, —CN, and a $C_1$-$C_3$ haloalkyl.

In some aspects, the compound can be according to Formula V

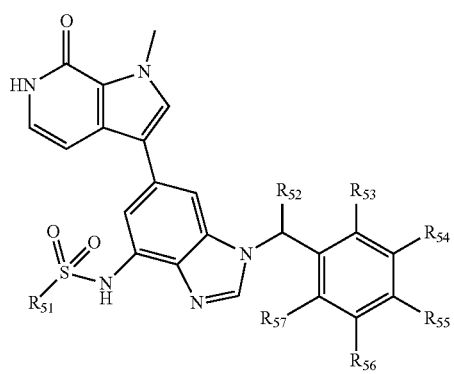

Formula V where $R_{51}$ can be selected from the group of: a $C_1$-$C_6$ alkenyl, a $C_1$-$C_6$ cycloalkyl, and a $C_1$-$C_6$ haloalkyl, where $R_{52}$ can be selected from the group of: a $C_1$-$C_6$ alkenyl, a $C_1$-$C_8$ cycloalkyl, —H, -D, a $C_1$-$C_8$ substituted cycloalkylenyl, a substituted aryl, and a substituted heteroaryl, which can include a pure enantiomer if the molecule contains chiral center, and where $R_{53}$, $R_{54}$, $R_{55}$, $R_{56}$, and $R_{57}$ can each be independently selected from the group of: —H, a halogen, —CN, and a $C_1$-$C_3$ haloalkyl.

In some aspects, the compound can be according to Formula VI

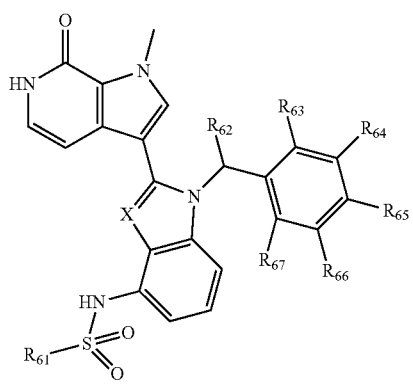

Formula VI where X can be selected from C or N, where $R_{61}$ can be selected from the group of: a $C_1$-$C_6$ alkenyl, a $C_1$-$C_6$ cycloalkyl, and a $C_1$-$C_6$ haloalkyl, where $R_{62}$ can be selected from the group of: a $C_1$-$C_6$ alkenyl, a $C_1$-$C_8$ cycloalkyl, —H, -D, a $C_1$-$C_8$ substituted cycloalkylenyl, a substituted aryl, and a substituted heteroaryl, which can include a pure enantiomer if the molecule contains chiral center, and where $R_{63}$, $R_{64}$, $R_{65}$, $R_{66}$, and $R_{67}$ can each be independently selected from the group of: —H, a halogen, —CN, and a $C_1$-$C_3$ haloalkyl.

In some aspects, the compound can be according to Formula VII

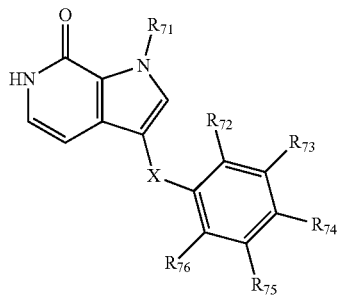

Formula VII where X can be selected from the group of: —O—, —C(O)—, —N($R_{77}$)—, and —CH($R_{70}$)—, where $R_{71}$ can be selected from the group of: a $C_1$-$C_3$ alkyl, a $C_1$-$C_3$ haloalkyl, a propylenyl, —$CH_2$(CO)CH=$CH_2$, oxiran-2-ylmethyl, and $CH_2$(CO)$CH_2$Cl, where $R_{72}$, $R_{73}$, $R_{74}$, $R_{75}$, $R_{76}$, and $R_{77}$ can each be independently selected from the group of: —H, a halogen, —CN, a $C_1$-$C_3$ haloalkyl, —$OR_{70}$, —$NR_{70}R_{70}$, —C(O)$OR_{70}$, —C(O)$NR_{70}R_{70}$, —S(O)$_2R_{70}$, —S(O)$_2NR_{70}R_{70}$, and $R_{70}$, where $R_{70}$, at each occurrence, can be each independently selected from the group of: a $C_1$-$C_6$ alkyl, a $C_2$-$C_6$ alkenyl, a $C_2$-$C_6$ alkynyl, a halogen, a $C_1$-$C_6$ haloalkyl, —CN, $NO_2$, —$OR^e$, —S(O)$_2NR^eR^f$, —C(O)$R^e$, —C(O)$NR^eR^f$, —$NR^eR^f$, —N($R^e$)C(O)$R^f$, a —($C_1$-$C_6$ alkylenyl)-$OR^e$, a —($C_1$-$C_6$ alkylenyl)-C(O)$NR^eR^f$, a —($C_1$-$C_6$ alkylenyl)-$NR^eR^f$, and a —($C_1$-$C_6$ alkylenyl)-N($R^e$)C(O)$R^f$, and where $R^e$ and $R^f$, at each occurrence, can each be independently selected from the group of: H, a $C_1$-$C_6$ alkyl, and a $C_1$-$C_6$ haloalkyl.

In some aspects, the compound can be according to Formula VIII

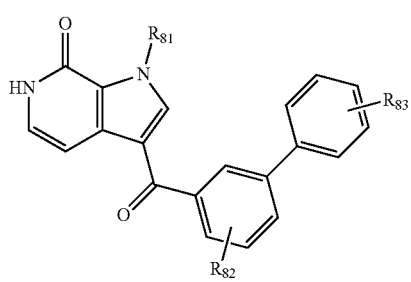

Formula VIII where $R_{81}$, $R_{82}$, $R_{83}$ can each be independently selected from the group of: a $C_1$-$C_3$ alkyl, a $C_1$-$C_3$ haloalkyl, a propylenyl, —$CH_2$(CO)CH=$CH_2$, oxiran-2-ylmethyl, and $CH_2$(CO)$CH_2$Cl.

In some aspects, the compound can be according to Formula IX,

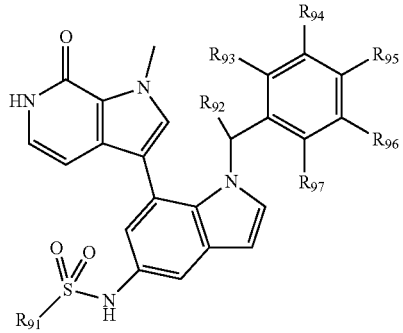

Formula IX where $R_{91}$ can be selected from the group of: a $C_1$-$C_6$ alkenyl, a $C_1$-$C_6$ cycloalkyl, and a $C_1$-$C_6$ haloalkyl, where $R_{92}$ can be selected from the group of: a $C_1$-$C_6$ alkenyl, a $C_1$-$C_8$ cycloalkyl, —H, -D, a $C_1$-$C_8$ substituted cycloalkylenyl, a substituted aryl, and a substituted heteroaryl, which can include a pure enantiomer if the molecule contains chiral center, and where $R_{93}$, $R_{94}$, $R_{95}$, $R_{96}$, and $R_{97}$ can each be independently selected from the group of: —H, a halogen, —CN, and a $C_1$-$C_3$ haloalkyl.

In some aspects, the compound can be according to Formula X

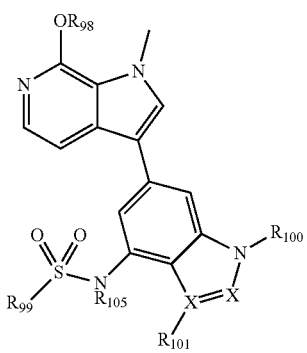

Formula X where each X can each be independently selected from C or N, where $R_{98}$ can be selected from the group of: H or Me, where $R_{99}$ can each be selected from the group of: Me, Et, and $CH(CH_2)_2$, where $R_{100}$ can be selected from the group of:

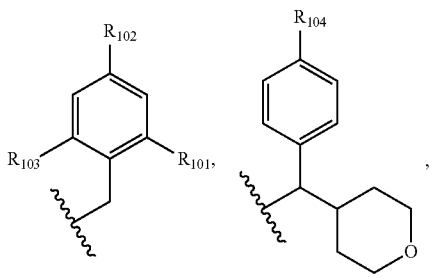

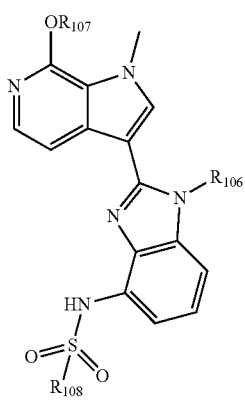

where $R_{101}$ can be Cl, F, H, Me, a cycloheteroalkyl, or

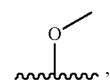

where $R_{102}$ can be H, Cl, F, OH, $CF_3$ or CN,
where $R_{103}$ can be Cl, F, H,

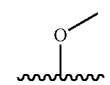

or Me, and where $R_{104}$ can be H or F, and where $R_{105}$ can be H or

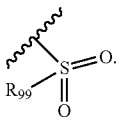

In some aspects, the compound can be according to Formula XI

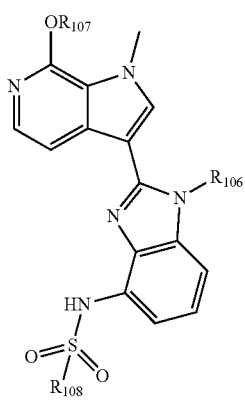

where $R_{107}$ can be selected from the group of: H or a Me, where $R_{108}$ can each be selected from the group of: Me, Et, and $CH(CH_2)_2$, where $R_{106}$ can be selected from the group of:

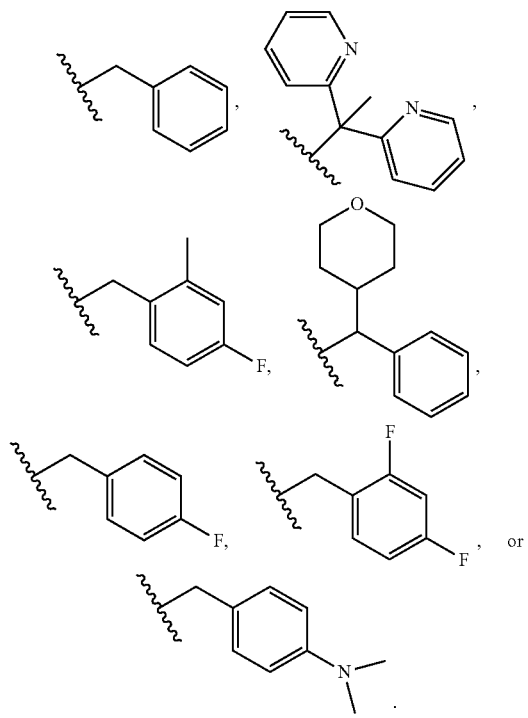

In some aspects, the compound can be according to Formula XII

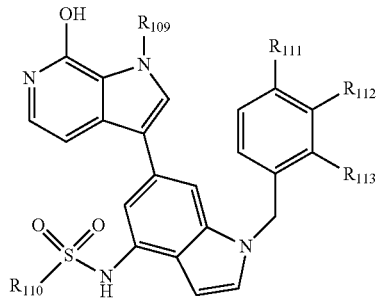

where $R_{109}$ can be

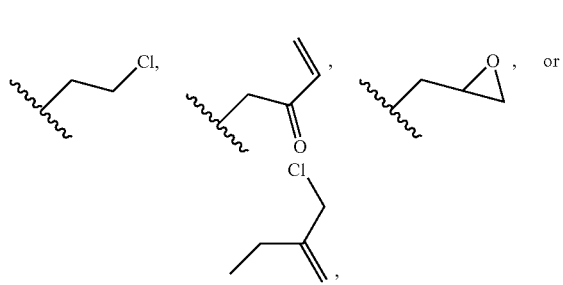

where $R_{110}$ can be a Me or $CH_2CH_3$, where $R_{111}$ can be F, H, Cl, or CN, where $R_{112}$ can be H, Cl, or F, and where $R_{113}$ can be H, Me, Cl, or F.

In some aspects, the compound can be according to Formula XIII

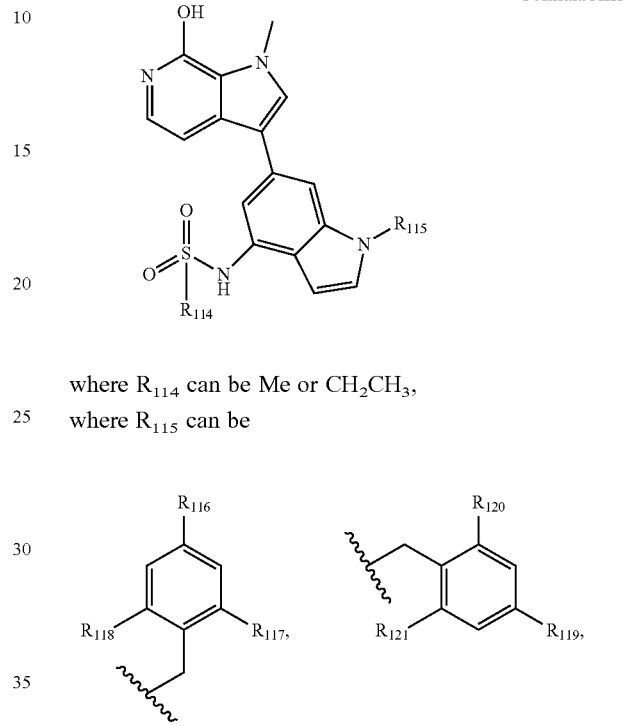

where $R_{114}$ can be Me or $CH_2CH_3$, where $R_{115}$ can be where $R_{116}$ can be H, F, or $N(CH_3)_2$, where $R_{117}$ can be H, Cl, F, $CF_3$, or Me, where $R_{118}$ can be H, Me, or $CF_3$, where $R_{119}$ can be H, F, or $N(CH_3)_2$, where $R_{120}$ can be H, Me, or $CF_3$, and where $R_{121}$ can be H or Me.

In some aspects, the compound can be according to Formula XIV

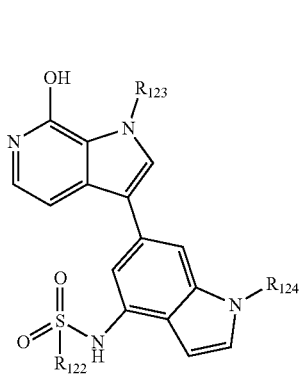

Formula XIV where $R_{122}$ can be Me or $CH_2CH_3$,
where $R_{123}$ can be

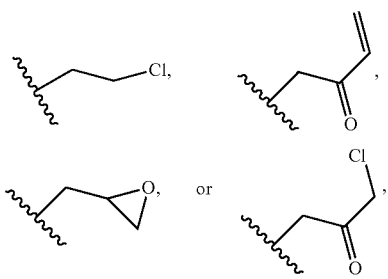

where $R_{124}$ can be

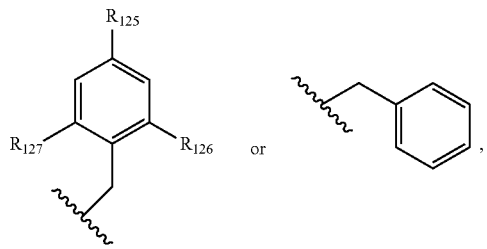

where $R_{125}$ can be H or F, $R_{126}$ can be H or Me, and where $R_{127}$ can be H or Me.

In some aspects, the compound can be according to Formula XV

Formula XV

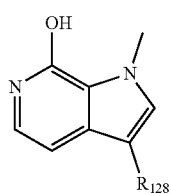

where $R_{128}$ can be

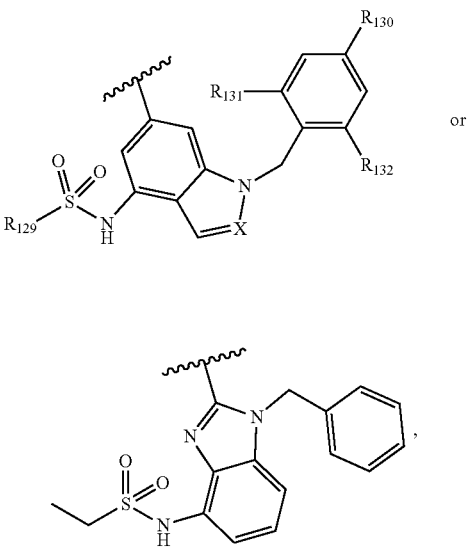

where $R_{129}$ can be a Me or $CH_2CH_3$, where $R_{130}$ can be H or F, where $R_{131}$ can be H or a Me, where $R_{132}$ can be H or a Me, and where X can be C or N.

In some aspects, the compound can be according to Formula XVI

Formula XVI

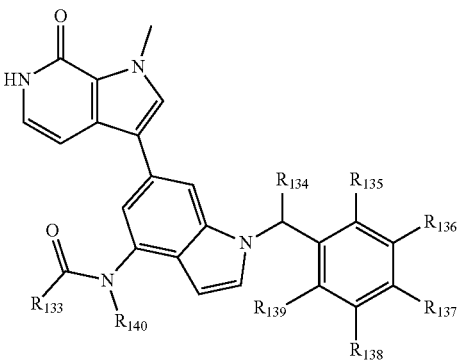

where $R_{133}$ can be selected from the group of: a $C_1$-$C_6$ alkenyl, a $C_1$-$C_6$ cycloalkyl, and a $C_1$-$C_6$ haloalkyl, where $R_{134}$ can be selected from the group of: a $C_1$-$C_6$ alkenyl, a $C_1$-$C_8$ cycloalkyl, —H, -D, a $C_1$-$C_8$ substituted cycloalkylenyl, a substituted aryl, and a substituted heteroaryl, which can include pure enantiomer if the molecule contains chiral center, where $R_{135}$, $R_{136}$, $R_{137}$, $R_{138}$, and $R_{139}$ are each independently selected from the group of: —H, a halogen, —CN, and a $C_1$-$C_3$ haloalkyl, and where $R_{140}$ can be selected from the group of: a $C_1$-$C_6$ alkenyl, a $C_1$-$C_8$ cycloalkyl, —H, -D, a $C_1$-$C_8$ substituted cycloalkylenyl, a substituted aryl, and a substituted heteroaryl.

In some aspects, the compound can be according to Formula XVII

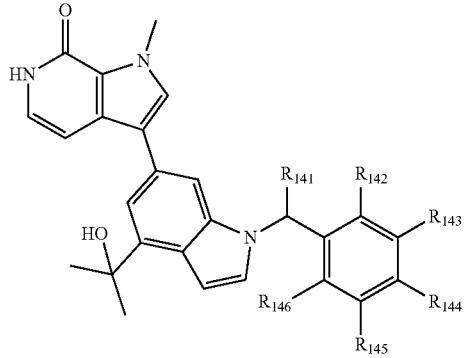

Formula XVII where $R_{141}$ can be selected from the group of: a $C_1$-$C_6$ alkenyl, $C_1$-$C_8$ cycloalkyl, —H, -D, a $C_1$-$C_8$ substituted cycloalkylenyl, a substituted aryl, and a substituted heteroaryl, which can include pure enantiomer if the molecule contains chiral center, and where $R_{142}$, $R_{143}$, $R_{144}$, $R_{145}$, and $R_{146}$ are each independently selected from the group of: —H, a halogen, —CN, and a $C_1$-$C_3$ haloalkyl.

In some aspects, the compound can be according to Formula XVIII

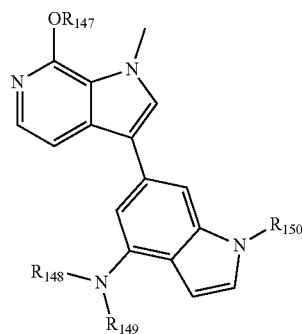

Formula XVIII where $R_{147}$ can be H or Me,
where $R_{148}$ can be

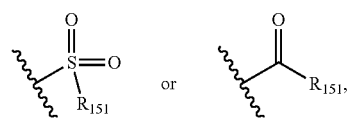

where $R_{149}$ can be H, $CH_2CH_3$, or

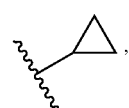

where $R_{150}$ can be

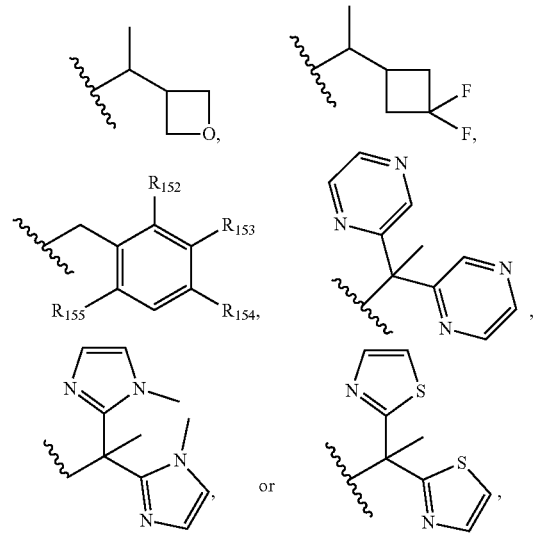

where $R_{151}$ can be Me, Et, or $CH(CH_2)_2$,
where $R_{152}$ can be H, Me, or Cl, where $R_{153}$ can be H or F,
where $R_{154}$ can be H or F,
and where $R_{155}$ can be H or Me.

In some aspects, the compound can be according to Formula XIX

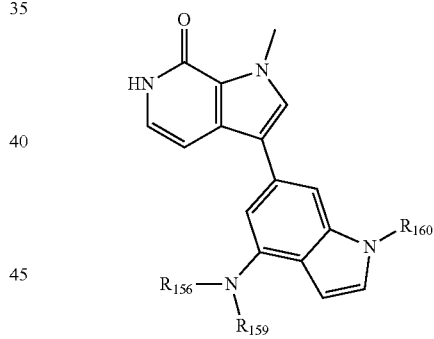

Formula XIX where $R_{156}$ can be

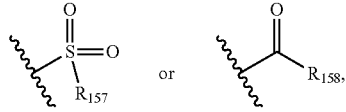

where $R_{157}$ can be Me or $CH_2CH_3$,
where $R_{158}$ can be Me, $CH_2CH_3$, or

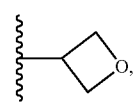

where R₁₅₉ can be H, CH₂CH₃, or

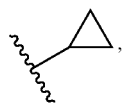 [SMILES: *C1CC1]

where R₁₆₀ can be

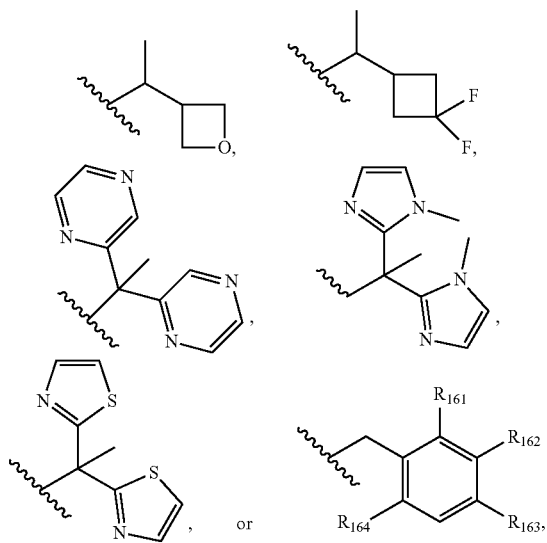

where R₁₆₁ can be H, Me, or Cl,
where R₁₆₂ can be H or F,
where R₁₆₃ can be H or F,
and where R₁₆₄ can be H or Me.

In some aspects, the compound can be according to Formula XX

Formula XX

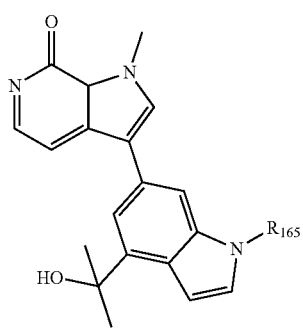

where R₁₆₅ can be

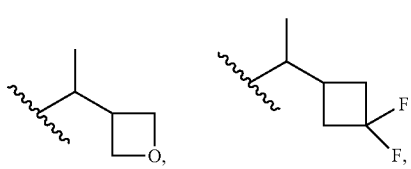

-continued

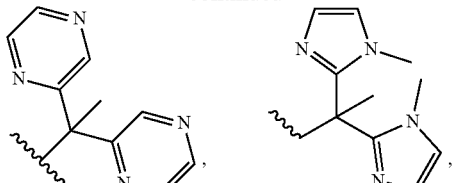

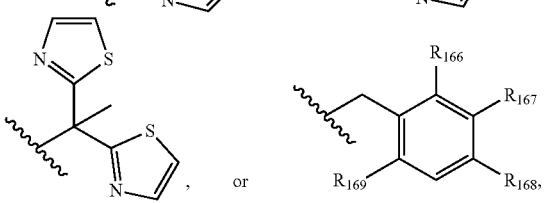

where R₁₆₆ can be H, Me, or Cl,
where R₁₆₇ can be H or F,
where R₁₆₈ can be H or F,
and where R₁₆₉ can be H or Me.

In some aspects, the compound can be according to Formula XXI

Formula XXI

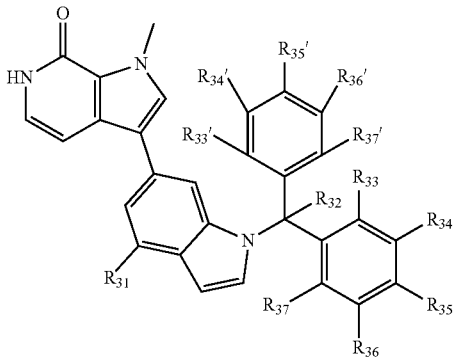

where R₃₁ can be

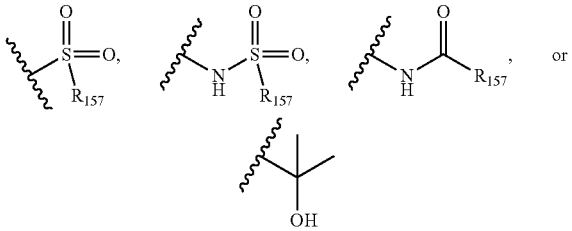

where R₁₅₇ can be Me or CH₂CH₃, CH(CH₃)₂ where R₁₅₈ can be Me, CH₂CH₃, CH(CH₃)₂

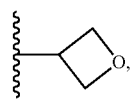 [SMILES: *C1COC1]

where R₃₁ can be selected from the group of: a $C_1$-$C_6$ alkyl, a $C_1$-$C_6$ alkenyl, a $C_1$-$C_6$ cycloalkyl, and a $C_1$-$C_6$ haloalkyl, where $R_{32}$ can be selected from the group of: a $C_1$-$C_6$ alkyl, a $C_1$-$C_6$ alkenyl, a $C_1$-$C_8$ cycloalkyl, —H, -D, a $C_1$-$C_8$ substituted cycloalkylenyl, a substituted aryl, and a substituted heteroaryl, which can include a pure enantiomer if the molecule contains chiral center, and where $R_{33}$, $R_{34}$, $R_{35}$, $R_{36}$, $R_{37}$, $R_{33}'$, $R_{34}'$, $R_{35}'$, $R_{36}'$, and $R_{37}'$ can each be independently selected from the group of: —H, a halogen, —CN, a $C_1$-$C_3$ haloalkyl, a $C_1$-$C_6$ cycloalkyl, a $C_1$-$C_6$ alkylamine, a $C_1$-$C_6$ cycloalkylamine, a $C_1$-$C_6$ alkylester and a $C_1$-$C_6$ alkylamide.

In some aspects, the compound can be according to Formula XXII,

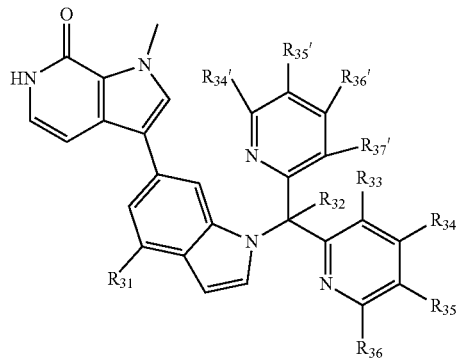

where $R_{31}$ can be

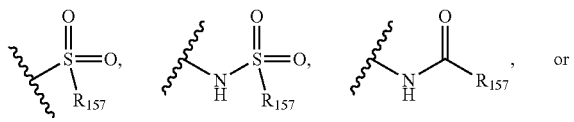

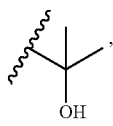

where $R_{157}$ can be Me or $CH_2CH_3$, $CH(CH_3)_2$ where $R_{32}$ can be selected from the group of: a $C_1$-$C_6$ alkyl, a $C_1$-$C_6$ alkenyl, a $C_1$-$C_8$ cycloalkyl, —H, -D, a $C_1$-$C_8$ substituted cycloalkylenyl, a substituted aryl, and a substituted heteroaryl, which can include a pure enantiomer if the molecule contains chiral center, and where $R_{33}$, $R_{34}$, $R_{35}$, $R_{36}$, $R_{37}$, R34', R35', R36' R37' can each be independently selected from the group of: —H, a halogen, —CN, $C_1$-$C_3$ haloalkyl, a $C_1$-$C_6$ cycloalkyl, a $C_1$-a $C_6$ alkylamine, a $C_1$-$C_6$ cycloalkylamine, a $C_1$-$C_6$ alkylester and a $C_1$-$C_6$ alkylamides.

In some aspects, the compound can be according to Formula XXIII,

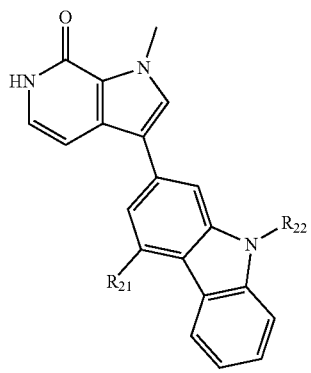

Formula XXIII where $R^{21}$ can be —$N(R^a)S(O)_2R^b$, —$S(O)_2NR^aR^b$, $S(O)_2$ $R^a$ —$C(O)NR^aR^b$ —$N(R^a)C(O)R^b$ —$NR^aR^b$, or a —$(C_1$-$C_6$ alkylenyl)$R^c$, where $R^a$ and $R^b$, at each occurrence, can each be independently selected from the group of: H, $C_1$-$C_6$ alkyl, $C_1$-$C_6$ alkenyl, $C_1$-$C_6$ alkynyl, $C_1$-$C_6$ haloalkyl, $R^c$, and $C_1$-$C_6$ alkyl where the $C_1$-$C_6$ alkyl can be substituted with one substituent selected from the group of: —$OR^{y1}$, —$NR^{y3}R^{y4}$, —$C(O)OR^{y2}$, —$C(O)NR^{y3}R^{y4}$, —$S(O)_2R^{y1}$, —$S(O)_2NR^{y3}R^{y4}$, and $R^c$, where $R^{y1}$, at each occurrence, can each be independently selected from the group of: H, Me or $CH_2CH_3$, $CH(CH_3)_2$ where $R^{y2}$, at each occurrence, can each be independently selected from the group of: H, Me or $CH_2CH_3$, $CH(CH_3)_2$ where $R^{y3}$, at each occurrence, can each be independently selected from the group of: H, Me or $CH_2CH_3$, $CH(CH_3)_2$ where $R^{y4}$, at each occurrence, can each be independently selected from the group of: H, Me or $CH_2CH_3$, $CH(CH_3)_2$ where $R^{22}$ can be selected from the group of: a —($C_1$-$C_6$ alkylenyl)$R^c$, a —($C_1$-$C_3$ cycloalkylenyl)$R^c$, and a —($C_1$-$C_6$ alkylenyl)$R^cR^{c'}$, where $R^c$ and $R^{c'}$, at each occurrence, can each be independently selected from the group of: an aryl, a heteroaryl, a heterocycle, a cycloalkyl, and a cycloalkenyl; and each $R^e$ group can be substituted with 1, 2, 3, 4, or 5 $R^d$ groups, where $R^d$, at each occurrence, can each be independently selected from the group of: a $C_1$-$C_6$ alkyl, a $C_2$-$C_6$ alkenyl, a $C_2$-$C_6$ alkynyl, a halogen, a $C_1$-$C_6$ haloalkyl, —CN, $NO_2$, —$OR^e$, —$S(O)_2NR^eR^f$, —$C(O)R^e$, —$C(O)NR^eR^f$, —$NR^eR^f$, —$N(R^e)C(O)R^f$, a —($C_1$-$C_6$ alkylenyl)-$OR^e$, a —($C_1$-$C_6$ alkylenyl)-$C(O)NR^eR^f$, a —($C_1$-$C_6$ alkylenyl)-$NR^eR^f$, and a —($C_1$-$C_6$ alkylenyl)-$N(R^e)C(O)R^f$, and where $R^e$ and $R^f$, at each occurrence, can each be independently selected from the group of: H, a $C_1$-$C_6$ alkyl, and a $C_1$-$C_6$ haloalkyl.

In some aspects, the compound can be according to Formula XXIV

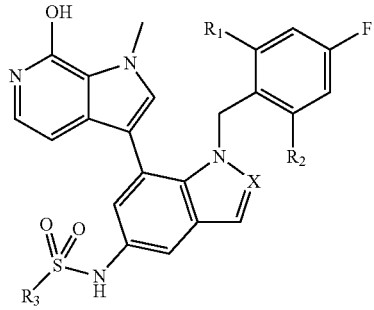

Formula XXIV wherein $R_1$ and $R_2$ can each be independently selected from $CH_3$ or H,
wherein $R_3$ can be $CH_3$ or $CH_2CH_3$, and
wherein X can be C or N.

In some aspects, the compound can be according to Formula XXV

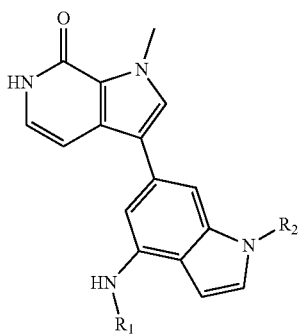

Formula XXV wherein $R_1$ can be

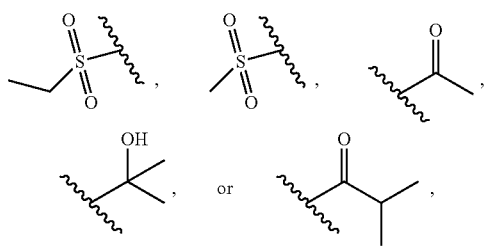

wherein $R_2$ can be

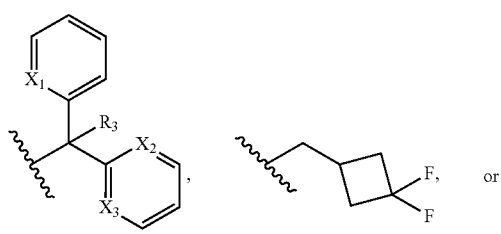

wherein $R_3$ can be H, $CH_3$, or $CH_2CH_3$,
and wherein $X_1$, $X_2$, and $X_3$, can each be independently selected from the group of: C or N.

In aspects, described herein are compounds according to Formula XXV

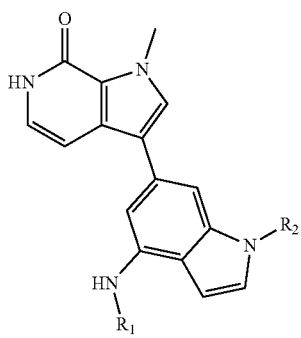

Formula XXV where $R_1$ can be

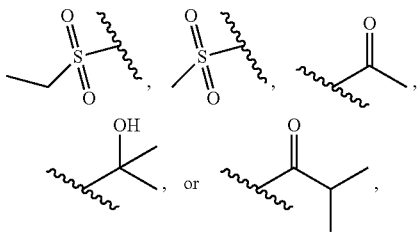

where $R_2$ can be

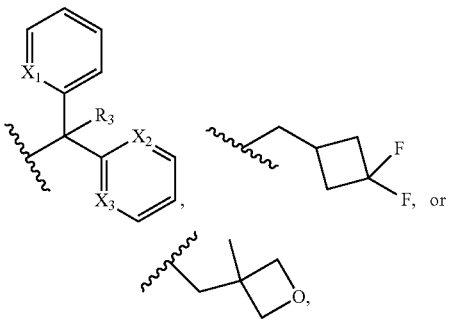

where $R_3$ can be H, $CH_3$, or $CH_2CH_3$, and
where $X_1$, $X_2$, and $X_3$, can each be independently selected from the group of: C or N.

In some aspects, the compound according to Formula XXV can be selected from the group of: (70), (71), (72), (73), (74), (126), (130), (131), and (132).

In some aspects, the compound can be according to Formula XXIV

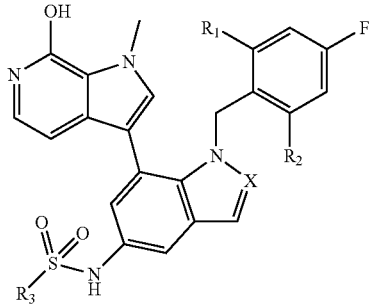

Formula XXIV where R₁ and R₂ can each be independently selected from CH₃ or H,
where R₃ can be CH₃ or CH₂CH₃, and
where X can be C or N.

In some aspects, the compound according to Formula XXV can be selected from the group of: (22), (23), (30), and (31).

In some aspects, the compound can be according to Formula XXVI

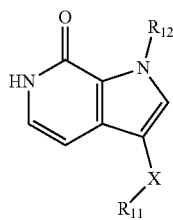

Formula XXVI where R₁₂ can be a C₁-C₃ alkyl, a C₁-C₃ haloalkyl, propylenyl, —CH₂(CO)CH═CH₂, oxiran-2-ylmethyl, or CH₂(CO)CH₂Cl, where R₁₁ is a nitrogen-containing bicyclic or tricyclic heteroaryl, an aryl, or a biaryl, each of which is optionally substituted with 1, 2, or 3 substituents can each be independently selected from the group of: —N(Rᵃ)S(O)₂Rᵇ, —S(O)₂ NRᵃRᵇ, —C(O)NRᵃRᵇ —N(Rᵃ)C(O)Rᵇ —NRᵃRᵇ, —(C₁-C₆ alkylenyl)Rᶜ, —(C₁-C₃ cycloalkylenyl)Rᶜ, an aryl, a heteroaryl, and —(C₁-C₆ alkylenyl)RᶜRᶜ′, —H, a halogen, —CN, a propylenyl, a C₁-C₃ alkyl, a C₁-C₃ haloalkyl, —OR₇₀, —NR₇₀R₇₀, —C(O)OR₇₀, —C(O)NR₇₀R₇₀, —S(O)₂R₇₀, —S(O)₂NR₇₀R₇₀, —CH₂(CO)CH═CH₂, oxiran-2-ylmethyl, and CH₂(CO)CH₂Cl, and R₇₀, where X can be optionally present, and when present, can be selected from —O—, —C(O)—, —N(R₇₇)—, and —CH (R₇₀)—, R₇₇ can be selected from the group of: —H, a halogen, —CN, a C₁-C₃ haloalkyl, —OR₇₀, —NR₇₀R₇₀, —C(O)OR₇₀, —C(O)NR₇₀R₇₀, —S(O)₂R₇₀, —S(O)₂NR₇₀R₇₀, and R₇₀, where R₇₀, at each occurrence, can be independently selected from the group of: a C₁-C₆ alkyl, a C₂-C₆ alkenyl, a C₂-C₆ alkynyl, a halogen, a C₁-C₆ haloalkyl, —CN, NO₂, —ORᵉ, —S(O)₂NRᵉRᶠ, —C(O)Rᵉ, —C(O)NRᵉRᶠ, —NRᵉRᶠ, —N(Rᵉ)C(O)Rᶠ, a —(C₁-C₆ alkylenyl)-ORᵉ, a —(C₁-C₆ alkylenyl)-C(O)NRᵉRᶠ, a —(C₁-C₆ alkylenyl)-NRᵉRᶠ, and a —(C₁-C₆ alkylenyl)-N(Rᵉ)C(O)Rᶠ, where Rᵃ and Rᵇ, at each occurrence, can each be independently selected from the group of: H, a C₁-C₆ alkenyl, a C₁-C₆ alkynyl, a C₁-C₆ haloalkyl, Rᶜ, and a C₁-C₆ alkyl, wherein the C₁-C₆ alkyl is optionally substituted with one substituent selected from the group of: —ORᵉ, —NRᵉRᶠ, —C(O)ORᵉ, —C(O)NRᵉRᶠ, —S(O)₂Rᵉ, —S(O)₂NRᵉRᶠ, and Rᶜ, where Rᶜ and Rᶜ′, at each occurrence, can each be independently selected from the group of: an aryl, a heteroaryl, a heterocycle, a cycloalkyl, and a cycloalkenyl, and wherein each Rᶜ group is optionally substituted with 1, 2, 3, 4, or 5 Rᵈ groups, where Rᵈ, at each occurrence, can each be independently selected from the group of: a C₁-C₆ alkyl, a C₂-C₆ alkenyl, a C₂-C₆ alkynyl, a halogen, a C₁-C₆ haloalkyl, —CN, NO₂, —ORᵉ, —S(O)₂NRᵉRᶠ, —C(O)Rᵉ, —C(O)NRᵉRᶠ, —NRᵉRᶠ, —N(Rᵉ)C(O)Rᶠ, a —(C₁-C₆ alkylenyl)-ORᵉ, a —(C₁-C₆ alkylenyl)-C(O)NRᵉRᶠ, a —(C₁-C₆ alkylenyl)-NRᵉRᶠ, and a —(C₁-C₆ alkylenyl)-N(Rᵉ)C(O)Rᶠ, and where Rᵉ and Rᶠ, at each occurrence, can each be independently selected from the group of: H, a C₁-C₆ alkyl, a C₁-C₆ cycloalkyl, a aryl, a heteroaryl and a C₁-C₆ haloalkyl.

In some aspects, the compound can be any one of compounds (1)-(132) as shown in Table 1. In some aspects, the compound can be any one of compounds (2), (10), (22), (23), (30), (31), (70), (71), (72), (73), (74), (126), (130), (131), or (132). In some aspects, the compound can be any one of compounds (2), (10), (22), (23), (30), or (31). In some aspects, the compound can be any one of compounds (3), (7), (12), (13), (14), (15), (16), (17), (18), (19), or (20). In some aspects, the compound can be any one of compounds 2 or 10. In some aspects, the compound can be any one of compounds (1), (4), (5), (6), (8), (9), or (11). In some aspects, the compound can be any one of compounds (70), (71), or (72). In some aspects, the compound can be any one of compounds (73) or (74). In some aspects, the compound can be any one of compounds (126), (130), (131), or (132). In some aspects, the compound can be (24), (25), (26), (32), (29), (34), or (35).

In some aspects, the free compound or pharmaceutical formulation thereof (discussed in greater detail elsewhere herein) can have an IC₅₀ that is less than 0.001, less than 0.01, less than 0.1, less than 1 μM, less than 3 μM, and/or less than 5 μM. In some aspects, the free compound or pharmaceutical formulation thereof (discussed in greater detail elsewhere herein) can have an IC₅₀ ranging from 0.0001 μM to 0.001 μM, from 0.001 to 0.01 μM, from 0.01 μM to 0.1 μM, 0.1 μM to 1 μM, 1 μM to 2 μM, 2 μM to 3 μM, 3 μM to 4 μM, or 4 μM to 5 μM. In some aspects, the free compound or pharmaceutical formulation thereof (discussed in greater detail elsewhere herein) can have an IC₅₀ against a cell, a cancer cell, and/or a resistant cancer cell that is less than 0.001, less than 0.01, less than 0.1, less than 1 μM, less than 3 μM, and/or less than 5 μM. In some aspects, the free compound or pharmaceutical formulation thereof (discussed in greater detail elsewhere herein) can have an IC₅₀ against a cell, a cancer cell, and/or a resistant cancer cell ranging from 0.0001 μM to 0.001 μM, from 0.001 to 0.01 μM, from 0.01 μM to 0.1 μM, 0.1 μM to 1 μM, 1 μM to 2 μM, 2 μM to 3 μM, 3 μM to 4 μM, or 4 μM to 5 μM.

The compounds described herein can be made by using techniques and methods generally known in the art.

TABLE 1

Structures and chemical characterization

| Compound | Structure | Chemical name | Chemical characterization |
|---|---|---|---|
| 1 | 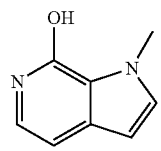 | 1-methyl-1H-pyrrolo[2,3-c]pyridin-7-ol | M + H⁺ = 149.1 |
| 2 | 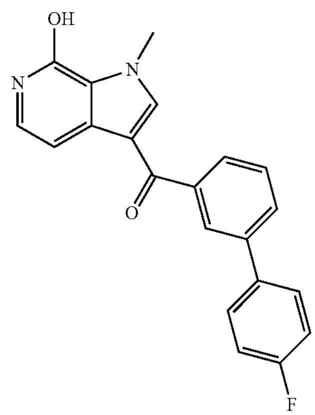 [SMILES: Cn1cc(C(=O)c2cccc(-c3ccc(F)cc3)c2)c2ccnc(O)c21] | (4'-fluoro-[1,1'-biphenyl]-3-yl)(7-hydroxy-1-methyl-1H-pyrrolo[2,3-c]pyridin-3-yl)methanone | M + H⁺ = 347.2 |
| 3 | 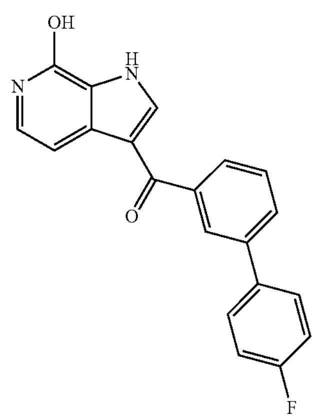 [SMILES: O=C(c1cccc(-c2ccc(F)cc2)c1)c1c[nH]c2c(O)nccc12] | (4'-fluoro-[1,1'-biphenyl]-3-yl)(7-hydroxy-1H-pyrrolo[2,3-c]pyridin-3-yl)methanone | M + H⁺ = 333.3 |
| 4 | 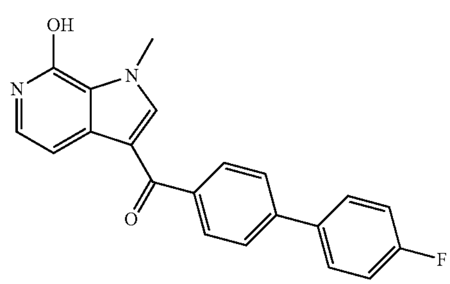 [SMILES: Cn1cc(C(=O)c2ccc(-c3ccc(F)cc3)cc2)c2ccnc(O)c21] | (4'-fluoro-[1,1'-biphenyl]-4-yl)(7-hydroxy-1-methyl-1H-pyrrolo[2,3-c]pyridin-3-yl)methanone | M + H⁺ = 347.4 |
| 5 | 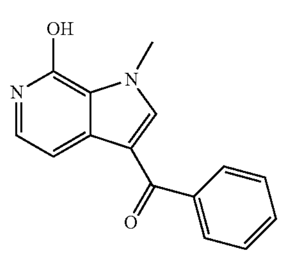 [SMILES: Cn1cc(C(=O)c2ccccc2)c2ccnc(O)c21] | (7-hydroxy-1-methyl-1H-pyrrolo[2,3-c]pyridin-3-yl)(phenyl)methanone | M + H⁺ = 253.1 |

TABLE 1-continued

Structures and chemical characterization

| Compound | Structure | Chemical name | Chemical characterization |
|---|---|---|---|
| 6 | 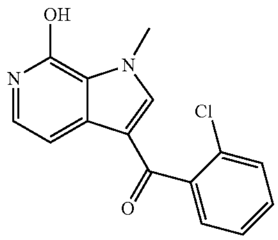 [SMILES: Cn1cc(C(=O)c2ccccc2Cl)c2ccnc(O)c21] | (2-chlorophenyl)(7-hydroxy-1-methyl-1H-pyrrolo[2,3-c]pyridin-3-yl)methanone | M + H$^+$ = 287.7 |
| 7 | 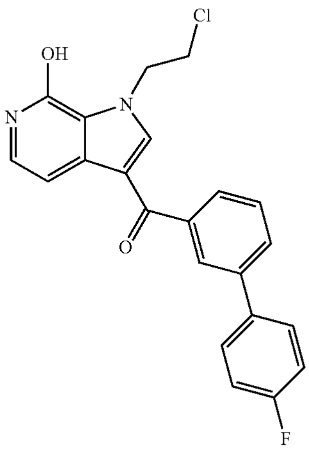 [SMILES: O=C(c1cccc(-c2ccc(F)cc2)c1)c1cn(CCCl)c2c(O)nccc12] | (1-(2-chloroethyl)-7-hydroxy-1H-pyrrolo[2,3-c]pyridin-3-yl)(4'-fluoro-[1,1'-biphenyl]-3-yl)methanone | M + H$^+$ = 395.7 |
| 8 | 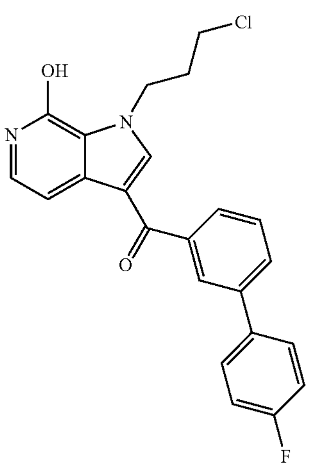 [SMILES: O=C(c1cccc(-c2ccc(F)cc2)c1)c1cn(CCCCl)c2c(O)nccc12] | (1-(3-chloropropyl)-7-hydroxy-1H-pyrrolo[2,3-c]pyridin-3-yl)(4'-fluoro-[1,1'-biphenyl]-3-yl)methanone | M + H$^+$ = 409.8 |

TABLE 1-continued

Structures and chemical characterization

| Compound | Structure | Chemical name | Chemical characterization |
|---|---|---|---|
| 9 | 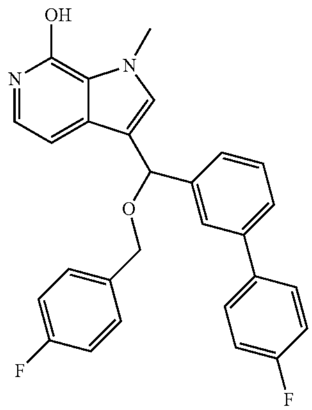 [SMILES: Cn1cc(C(OCc2ccc(F)cc2)c2cccc(-c3ccc(F)cc3)c2)c2ccnc(O)c21] | 3-((4'-fluoro-[1,1'-biphenyl]-3-yl)((4-fluorobenzyl)oxy)methyl)-1-methyl-1H-pyrrolo[2,3-c]pyridin-7-ol | M + H$^+$ = 457.5 |
| 10 | 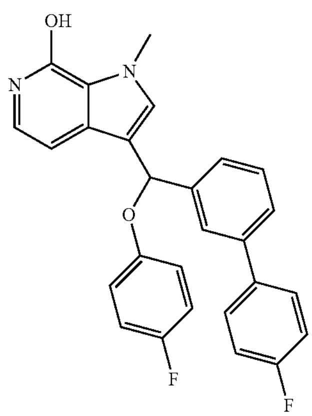 [SMILES: Cn1cc(C(Oc2ccc(F)cc2)c2cccc(-c3ccc(F)cc3)c2)c2ccnc(O)c21] | 3-((4'-fluoro-[1,1'-biphenyl]-3-yl)(4-fluorophenoxy)methyl)-1-methyl-1H-pyrrolo[2,3-c]pyridin-7-ol | M + H$^+$ = 443.5 |
| 11 | 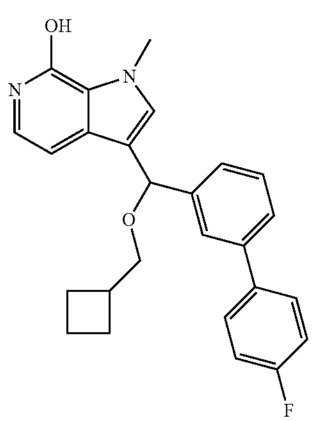 [SMILES: Cn1cc(C(OCC2CCC2)c2cccc(-c3ccc(F)cc3)c2)c2ccnc(O)c21] | 3-((cyclobutylmethoxy)(4'-fluoro-[1,1'-biphenyl]-3-yl)methyl)-1-methyl-1H-pyrrolo[2,3-c]pyridin-7-ol | M + H$^+$ = 417.5 |

TABLE 1-continued

Structures and chemical characterization

| Compound | Structure | Chemical name | Chemical characterization |
|---|---|---|---|
| 12 | 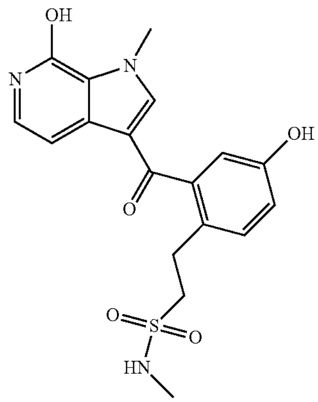 [SMILES: CNS(=O)(=O)CCc1ccc(O)cc1C(=O)c1cn(C)c2c(O)nccc12] | 2-(4-hydroxy-2-(7-hydroxy-1-methyl-1H-pyrrolo[2,3-c]pyridine-3-carbonyl)phenyl)-N-methylethane-1-sulfonamide | M + H$^+$ = 390.4 |
| 13 | 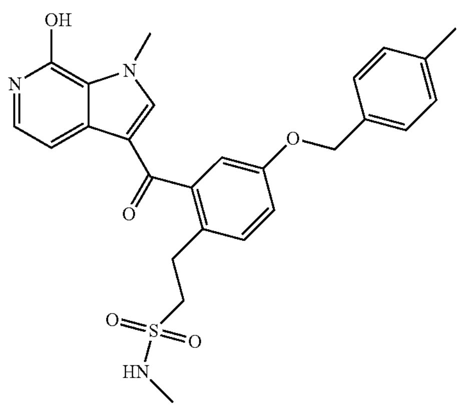 | 2-(4-((4-fluorobenzyl)oxy)-2-(7-hydroxy-1-methyl-1H-pyrrolo[2,3-c]pyridine-3-carbonyl)phenyl)-N-methylethane-1-sulfonamide | M + H$^+$ = 498.5 |
| 14 | 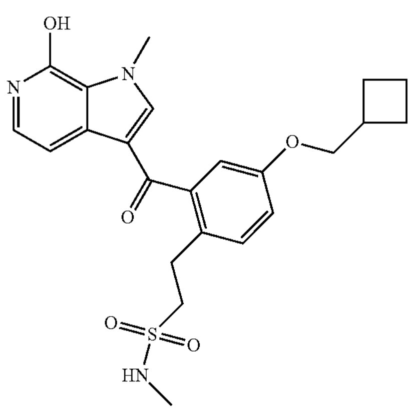 [SMILES: CNS(=O)(=O)CCc1ccc(OCC2CCC2)cc1C(=O)c1cn(C)c2c(O)nccc12] | 2-(4-(cyclobutylmethoxy)-2-(7-hydroxy-1-methyl-1H-pyrrolo[2,3-c]pyridine-3-carbonyl)phenyl)-N-methylethane-1-sulfonamide | M + H$^+$ = 458.5 |

TABLE 1-continued

Structures and chemical characterization

| Compound | Structure | Chemical name | Chemical characterization |
|---|---|---|---|
| 15 | 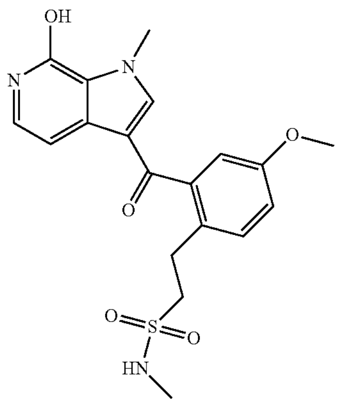 [SMILES: CNS(=O)(=O)CCc1ccc(OC)cc1C(=O)c1cn(C)c2c(O)nccc12] | 2-(2-(7-hydroxy-1-methyl-1H-pyrrolo[2,3-c]pyridine-3-carbonyl)-4-methoxyphenyl)-N-methylethane-1-sulfonamide | M + H$^+$ = 404.5 |
| 16 | 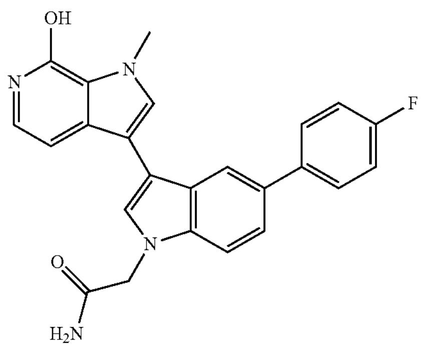 [SMILES: Cn1cc(-c2cn(CC(N)=O)c3ccc(-c4ccc(F)cc4)cc23)c2ccnc(O)c21] | 2-(5-(4-fluorophenyl)-3-(7-hydroxy-1-methyl-1H-pyrrolo[2,3-c]pyridin-3-yl)-1H-indol-1-yl)acetamide | M + H$^+$ = 415.4 |
| 17 | 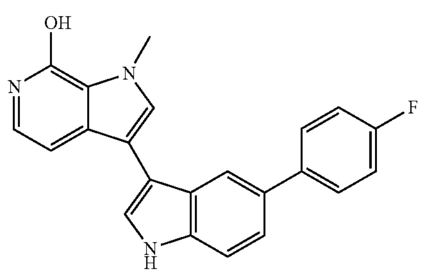 [SMILES: Cn1cc(-c2c[nH]c3ccc(-c4ccc(F)cc4)cc23)c2ccnc(O)c21] | 3-(5-(4-fluorophenyl)-1H-indol-3-yl)-1-methyl-1H-pyrrolo[2,3-c]pyridin-7-ol | M + H$^+$ = 358.4 |
| 18 | 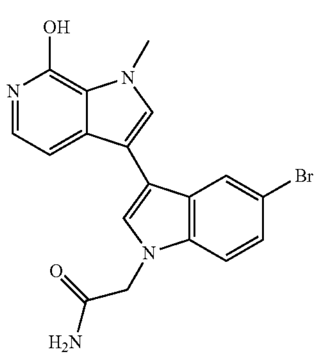 [SMILES: Cn1cc(-c2cn(CC(N)=O)c3ccc(Br)cc23)c2ccnc(O)c21] | 2-(5-bromo-3-(7-hydroxy-1-methyl-1H-pyrrolo[2,3-c]pyridin-3-yl)-1H-indol-1-yl)acetamide | M + H$^+$ = 400.2 |

TABLE 1-continued

Structures and chemical characterization

| Compound | Structure | Chemical name | Chemical characterization |
|---|---|---|---|
| 19 | 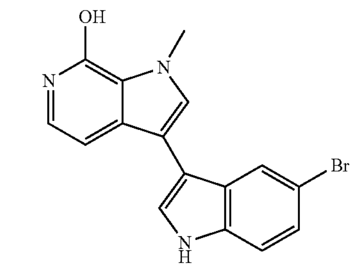 [SMILES: Cn1cc(-c2c[nH]c3ccc(Br)cc23)c2ccnc(O)c21] | 3-(5-bromo-1H-indol-3-yl)-1-methyl-1H-pyrrolo[2,3-c]pyridin-7-ol | M + H⁺ = 343.2 |
| 20 | 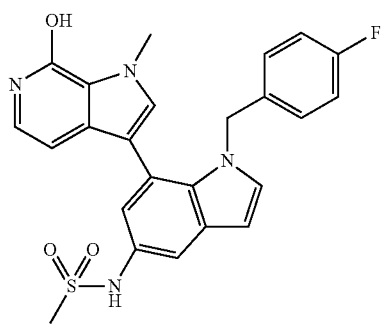 [SMILES: Cn1cc(-c2cc(NS(C)(=O)=O)cc3ccn(Cc4ccc(F)cc4)c23)c2ccnc(O)c21] | N-(1-(4-fluorobenzyl)-7-(7-hydroxy-1-methyl-1H-pyrrolo[2,3-c]pyridin-3-yl)-1H-indol-5-yl)methanesulfonamide | M + H⁺ = 465.5 |
| 21 | 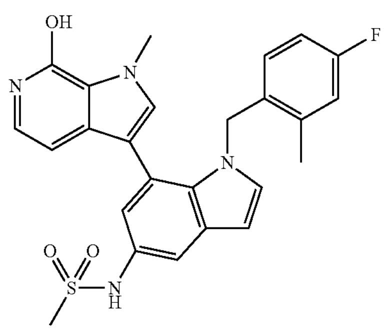 [SMILES: Cc1cc(F)ccc1Cn1ccc2cc(NS(C)(=O)=O)cc(-c3cn(C)c4c(O)nccc34)c21] | N-(1-(4-fluoro-2-methylbenzyl)-7-(7-hydroxy-1-methyl-1H-pyrrolo[2,3-c]pyridin-3-yl)-1H-indol-5-yl)methanesulfonamide | M + H⁺ = 479.5. $^1$H NMR (400 MHz, DMSO) δ 10.84 (d, J = 5.4 Hz, 1H), 9.38 (s, 1H), 7.49 (d, J = 2.0 Hz, 1H), 7.38 (d, J = 3.1 Hz, 1H), 6.85 (dd, J = 9.9, 2.3 Hz, 1H), 6.76-6.65 (m, 4H), 6.61 (d, J = 3.1 Hz, 1H), 5.84-5.79 (m, 2H), 4.90 (s, 2H), 3.90 (s, 3H), 2.92 (s, 3H), 1.70 (s, 3H). $^{13}$C NMR (100 MHz, DMSO) δ 160.71 (d, J = 241.6 Hz), 155.59, 136.07 (d, J = 7.8 Hz), 133.36, 132.33, 131.70, 131.17, 130.38, 130.09, 130.02, 125.76 (d, J = 8.5 Hz), 125.29, 121.82, 120.57, 118.46, 115.85 (d, J = 21.2 Hz), 113.00, 112.81, 112.20 (d, J = 21.0 Hz), 101.54, 98.99, 48.39, 38.60, 34.95, 17.45. |

TABLE 1-continued

Structures and chemical characterization

| Compound | Structure | Chemical name | Chemical characterization |
|---|---|---|---|
| 22 | 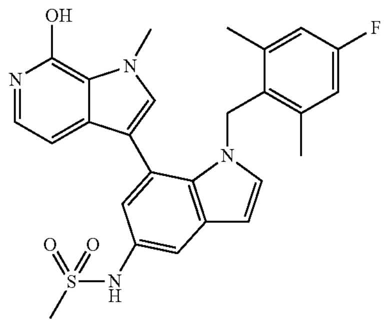 [SMILES: Cc1cc(F)cc(C)c1Cn1ccc2cc(NS(C)(=O)=O)cc(-c3cn(C)c4c(O)nccc34)c21] | N-(1-(4-fluoro-2,6-dimethylbenzyl)-7-(7-hydroxy-1-methyl-1H-pyrrolo[2,3-c]pyridin-3-yl)-1H-indol-5-yl)methanesulfonamide | M + H$^+$ = 493.5 $^1$H NMR (400 MHz, Acetone) δ 10.03 (s, 1H), 8.30 (s, 1H), 7.60 (s, 1H), 7.46 (s, 1H), 7.10 (d, J = 2.1 Hz, 1H), 7.04-6.96 (m, 1H), 6.82 (d, J = 9.6 Hz, 2H), 6.52 (d, J = 3.3 Hz, 1H), 6.44 (d, J = 3.3 Hz, 1H), 6.25 (d, J = 7.0 Hz, 1H), 4.88 (s, 2H), 4.23 (s, 3H), 2.95 (s, 3H), 2.06 (s, 6H). $^{13}$C NMR (100 MHz, Acetone) δ 162.88 (d, J = 244.2 Hz), 157.04, 141.62 (d, J = 8.4 Hz), 134.41, 132.75, 131.49, 131.27, 130.98, 130.10, 128.39, 126.27, 123.91, 122.27, 119.72, 115.79, 115.49 (d, J = 21.0 Hz), 114.76, 102.41, 100.55, 46.30, 38.79, 35.87, 19.73. |
| 23 | 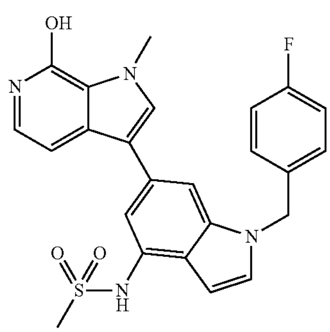 [SMILES: Cn1cc(-c2cc(NS(C)(=O)=O)c3ccn(Cc4ccc(F)cc4)c3c2)c2ccnc(O)c21] | N-(1-(4-fluorobenzyl)-6-(7-hydroxy-1-methyl-1H-pyrrolo[2,3-c]pyridin-3-yl)-1H-indol-4-yl)methanesulfonamide | M + H$^+$ = 465.5 $^1$H NMR (400 MHz, Acetone-d6) δ 8.51 (s, 1H), 7.46-7.39 (m, 4H), 7.33 (dd, J = 8.5, 5.5 Hz, 2H), 7.11 (t, J = 8.8 Hz, 2H), 6.98 (d, J = 7.0 Hz, 1H), 6.90 (d, J = 3.2 Hz, 1H), 6.64 (d, J = 7.1 Hz, 1H), 5.51 (s, 2H), 4.19 (s. 3H), 3.01 (s, 3H). $^{13}$C NMR (100 MHz, Acetone-d6) δ 163.04 (d, J = 243.8 Hz), 157.09, 138.71, 135.22, 131.27, 130.10, 130.03 (d, J = 8.3 Hz), 129.80, 129.48, 125.84, 124.85, 122.28, 119.25, 116.22 (d, J = 21.7 Hz), 113.41, 106.49, 100.81, 99.92, 50.00, 39.74, 35.83. |

TABLE 1-continued

Structures and chemical characterization

| Compound | Structure | Chemical name | Chemical characterization |
|---|---|---|---|
| 24 | 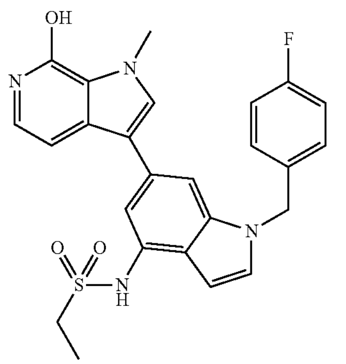 [SMILES: CCS(=O)(=O)Nc1cc(-c2cn(C)c3c(O)nccc23)cc2c1ccn2Cc1ccc(F)cc1] | N-(1-(4-fluorobenzyl)-6-(7-hydroxy-1-methyl-1H-pyrrolo[2,3-c]pyridin-3-yl)-1H-indol-4-yl)ethanesulfonamide | M + H$^+$ = 479.5 |
| 25 | 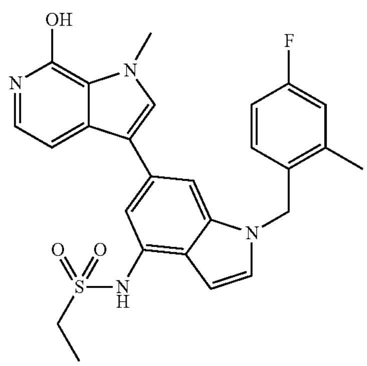 [SMILES: CCS(=O)(=O)Nc1cc(-c2cn(C)c3c(O)nccc23)cc2c1ccn2Cc1ccc(F)cc1C] | N-(1-(4-fluoro-2-methylbenzyl)-6-(7-hydroxy-1-methyl-1H-pyrrolo[2,3-c]pyridin-3-yl)-1H-indol-4-yl)ethanesulfonamide | M + H$^+$ = 493.5 |
| 26 | 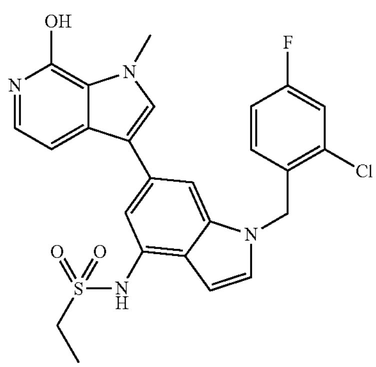 [SMILES: CCS(=O)(=O)Nc1cc(-c2cn(C)c3c(O)nccc23)cc2c1ccn2Cc1ccc(F)cc1Cl] | N-(1-(2-chloro-4-fluorobenzyl)-6-(7-hydroxy-1-methyl-1H-pyrrolo[2,3-c]pyridin-3-yl)-1H-indol-4-yl)ethanesulfonamide | M + H$^+$ = 513.9 |
| 27 | 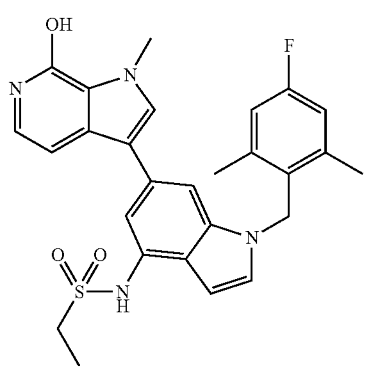 [SMILES: CCS(=O)(=O)Nc1cc(-c2cn(C)c3c(O)nccc23)cc2c1ccn2Cc1c(C)cc(F)cc1C] | N-(1-(4-fluoro-2,6-dimethylbenzyl)-6-(7-hydroxy-1-methyl-1H-pyrrolo[2,3-c]pyridin-3-yl)-1H-indol-4-yl)ethanesulfonamide | M + H$^+$ = 507.6 |

TABLE 1-continued

Structures and chemical characterization

| Compound | Structure | Chemical name | Chemical characterization |
|---|---|---|---|
| 28 | 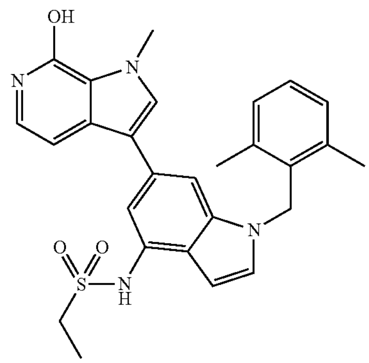 [SMILES: CCS(=O)(=O)Nc1cc(-c2cn(C)c3c(O)nccc23)cc2c1ccn2Cc1c(C)cccc1C] | N-(1-(2,6-dimethylbenzyl)-6-(7-hydroxy-1-methyl-1H-pyrrolo[2,3-c]pyridin-3-yl)-1H-indol-4-yl)ethanesulfonamide | M + H$^+$ = 489.6 |
| 29 | 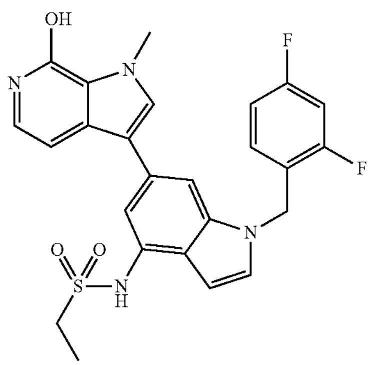 [SMILES: CCS(=O)(=O)Nc1cc(-c2cn(C)c3c(O)nccc23)cc2c1ccn2Cc1ccc(F)cc1F] | N-(1-(2,4-difluorobenzyl)-6-(7-hydroxy-1-methyl-1H-pyrrolo[2,3-c]pyridin-3-yl)-1H-indol-4-yl)ethanesulfonamide | M + H$^+$ = 497.5 |
| 30 | 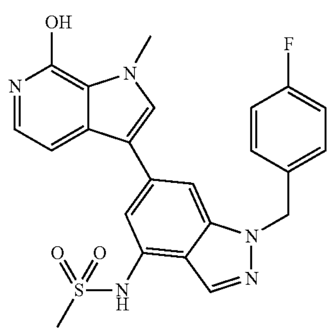 [SMILES: Cn1cc(-c2cc(NS(C)(=O)=O)c3cnn(Cc4ccc(F)cc4)c3c2)c2ccnc(O)c21] | N-(1-(4-fluorobenzyl)-6-(7-hydroxy-1-methyl-1H-pyrrolo[2,3-c]pyridin-3-yl)-1H-indazol-4-yl)methanesulfonamide | M + H$^+$ = 466.5<br>$^1$H NMR (400 MHz, Acetone-d$_6$) δ 10.05 (s, 1H), 8.94 (s, 1H), 8.34 (d, J = 0.9 Hz, 1H), 7.54 (s, 1H), 7.53 (s, 1H), 7.49 (d, J = 1.1 Hz, 1H), 7.45-7.36 (m, 2H), 7.13-7.07 (m, 2H), 7.02 (d, J = 7.1 Hz, 1H), 6.70 (d, J = 7.1 Hz, 1H), 5.71 (s, 2H), 4.20 (s, 3H), 3.11 (s, 3H). |
| 31 | 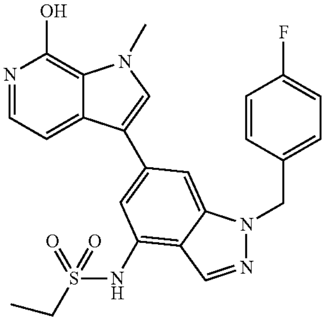 [SMILES: CCS(=O)(=O)Nc1cc(-c2cn(C)c3c(O)nccc23)cc2c1cnn2Cc1ccc(F)cc1] | N-(1-(4-fluorobenzyl)-6-(7-hydroxy-1-methyl-1H-pyrrolo[2,3-c]pyridin-3-yl)-1H-indazol-4-yl)ethanesulfonamide | M + H$^+$ = 480.5<br>$^1$H NMR (400 MHz, Acetone-d$_6$) δ 10.21 (s, 1H), 9.00 (s, 1H), 8.38 (s, 1H), 7.60-7.48 (m, 3H), 7.44-7.35 (m, 2H), 7.10 (t, J = 8.8 Hz, 2H), 7.05 (d, J = 7.1 Hz, 1H), 6.73 (d, J = 7.0 Hz, 1H), 5.70 (s, 2H), 4.20 (s, 3H), 3.23 (q, J = 7.4 Hz, 2H), 1.32 (t, J = 7.4 Hz, 3H). |

TABLE 1-continued

Structures and chemical characterization

| Compound | Structure | Chemical name | Chemical characterization |
|---|---|---|---|
| 32 | 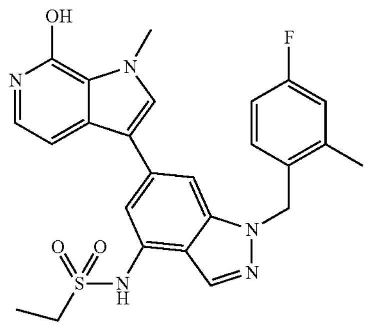 [SMILES: CCS(=O)(=O)Nc1cc(-c2cn(C)c3c(O)nccc23)cc2c1cnn2Cc1ccc(F)cc1C] | N-(1-(4-fluoro-2-methylbenzyl)-6-(7-hydroxy-1-methyl-1H-pyrrolo[2,3-c]pyridin-3-yl)-1H-indazol-4-yl)ethanesulfonamide | M + H$^+$ = 494.2 |
| 33 | 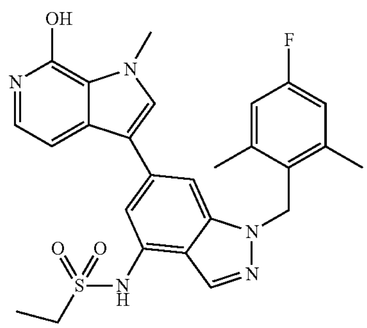 [SMILES: CCS(=O)(=O)Nc1cc(-c2cn(C)c3c(O)nccc23)cc2c1cnn2Cc1c(C)cc(F)cc1C] | N-(1-(4-fluoro-2,6-dimethylbenzyl)-6-(7-hydroxy-1-methyl-1H-pyrrolo[2,3-c]pyridin-3-yl)-1H-indazol-4-yl)ethanesulfonamide | M + H$^+$ = 508.2 |
| 34 | 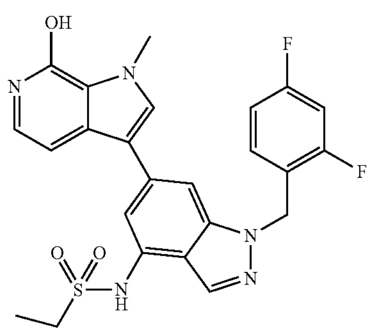 [SMILES: CCS(=O)(=O)Nc1cc(-c2cn(C)c3c(O)nccc23)cc2c1cnn2Cc1ccc(F)cc1F] | N-(1-(2,4-difluorobenzyl)-6-(7-hydroxy-1-methyl-1H-pyrrolo[2,3-c]pyridin-3-yl)-1H-indazol-4-yl)ethanesulfonamide | M + H$^+$ = 498.5 |
| 35 | 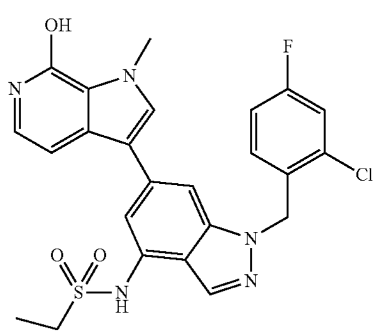 [SMILES: CCS(=O)(=O)Nc1cc(-c2cn(C)c3c(O)nccc23)cc2c1cnn2Cc1ccc(F)cc1Cl] | N-(1-(2-chloro-4-fluorobenzyl)-6-(7-hydroxy-1-methyl-1H-pyrrolo[2,3-c]pyridin-3-yl)-1H-indazol-4-yl)ethanesulfonamide | M + H$^+$ = 515.0 |

TABLE 1-continued

Structures and chemical characterization

| Compound | Structure | Chemical name | Chemical characterization |
|---|---|---|---|
| 36 | 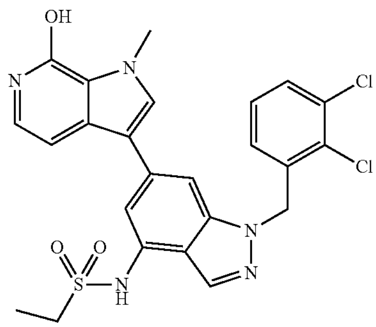 [SMILES: CCS(=O)(=O)Nc1cc(-c2cn(C)c3c(O)nccc23)cc2c1cnn2Cc1cccc(Cl)c1Cl] | N-(1-(2,3-dichlorobenzyl)-6-(7-hydroxy-1-methyl-1H-pyrrolo[2,3-c]pyridin-3-yl)-1H-indazol-4-yl)ethanesulfonamide | M + H$^+$ = 531.4 |
| 37 | 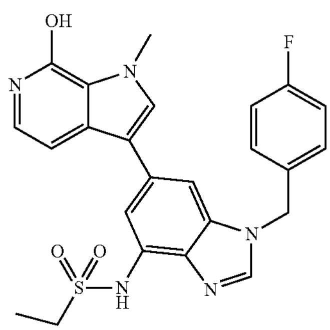 [SMILES: CCS(=O)(=O)Nc1cc(-c2cn(C)c3c(O)nccc23)cc2c1ncn2Cc1ccc(F)cc1] | N-(1-(4-fluorobenzyl)-6-(7-hydroxy-1-methyl-1H-pyrrolo[2,3-c]pyridin-3-yl)-1H-benzo[d]imidazol-4-yl)ethanesulfonamide | M + H$^+$ = 480.5 |
| 38 | 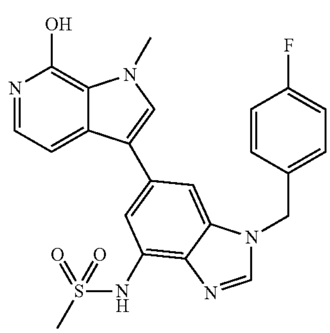 [SMILES: Cn1cc(-c2cc(NS(C)(=O)=O)c3ncn(Cc4ccc(F)cc4)c3c2)c2ccnc(O)c21] | N-(1-(4-fluorobenzyl)-6-(7-hydroxy-1-methyl-1H-pyrrolo[2,3-c]pyridin-3-yl)-1H-benzo[d]imidazol-4-yl)methanesulfonamide | M + H$^+$ = 466.5 |
| 39 | 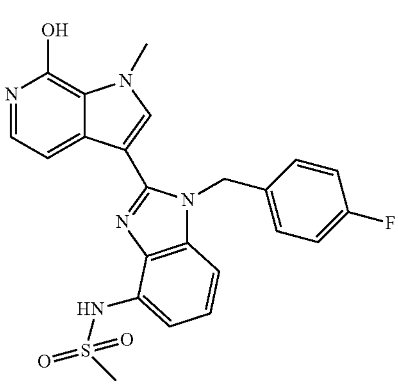 [SMILES: Cn1cc(-c2nc3c(NS(C)(=O)=O)cccc3n2Cc2ccc(F)cc2)c2ccnc(O)c21] | N-(1-(4-fluorobenzyl)-2-(7-hydroxy-1-methyl-1H-pyrrolo[2,3-c]pyridin-3-yl)-1H-benzo[d]imidazol-4-yl)methanesulfonamide | M + H$^+$ = 466.5 |

TABLE 1-continued

Structures and chemical characterization

| Compound | Structure | Chemical name | Chemical characterization |
|---|---|---|---|
| 40 | 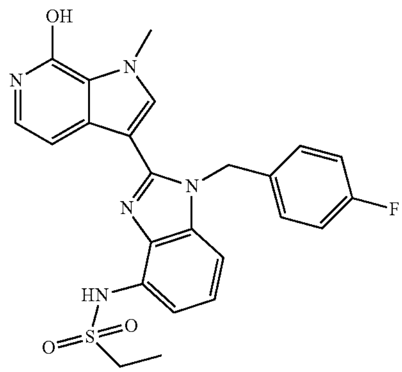 [SMILES: CCS(=O)(=O)Nc1cccc2c1nc(-c1cn(C)c3c(O)nccc13)n2Cc1ccc(F)cc1] | N-(1-(4-fluorobenzyl)-2-(7-hydroxy-1-methyl-1H-pyrrolo[2,3-c]pyridin-3-yl)-1H-benzo[d]imidazol-4-yl)ethanesulfonamide | M + H$^+$ = 480.5 |
| 41 | 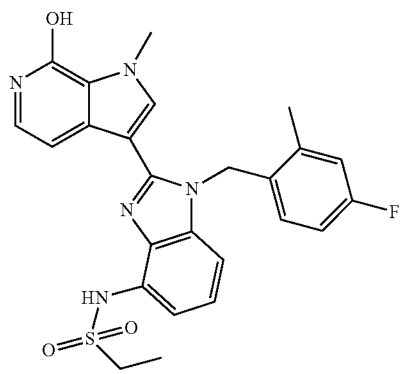 [SMILES: CCS(=O)(=O)Nc1cccc2c1nc(-c1cn(C)c3c(O)nccc13)n2Cc1ccc(F)cc1C] | N-(1-(4-fluoro-2-methylbenzyl)-2-(7-hydroxy-1-methyl-1H-pyrrolo[2,3-c]pyridin-3-yl)-1H-benzo[d]imidazol-4-yl)ethanesulfonamide | M + H$^+$ = 494.5 |
| 42 | 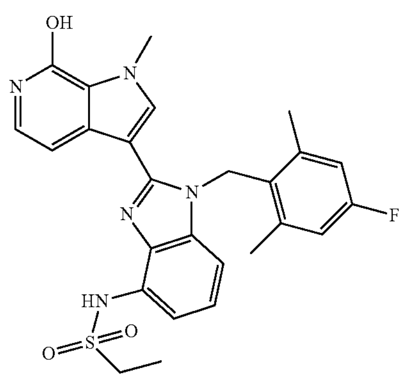 [SMILES: CCS(=O)(=O)Nc1cccc2c1nc(-c1cn(C)c3c(O)nccc13)n2Cc1c(C)cc(F)cc1C] | N-(1-(4-fluoro-2,6-dimethylbenzyl)-2-(7-hydroxy-1-methyl-1H-pyrrolo[2,3-c]pyridin-3-yl)-1H-benzo[d]imidazol-4-yl)ethanesulfonamide | M + H$^+$ = 508.6 |
| 43 | 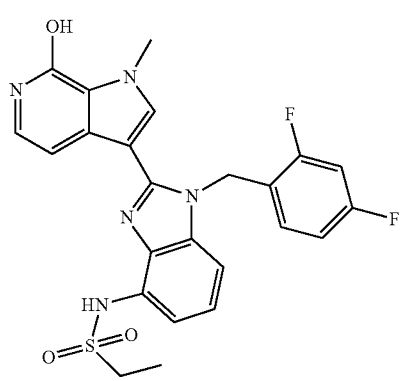 [SMILES: CCS(=O)(=O)Nc1cccc2c1nc(-c1cn(C)c3c(O)nccc13)n2Cc1ccc(F)cc1F] | N-(1-(2,4-difluorobenzyl)-2-(7-hydroxy-1-methyl-1H-pyrrolo[2,3-c]pyridin-3-yl)-1H-benzo[d]imidazol-4-yl)ethanesulfonamide | M + H$^+$ = 498.5 |

TABLE 1-continued

Structures and chemical characterization

| Compound | Structure | Chemical name | Chemical characterization |
|---|---|---|---|
| 44 | 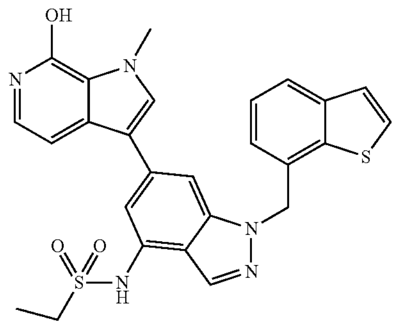 [SMILES: CCS(=O)(=O)Nc1cc(-c2cn(C)c3c(O)nccc23)cc2c1cnn2Cc1cccc2ccsc12] | N-(1-(benzo[b]thiophen-7-ylmethyl)-6-(7-hydroxy-1-methyl-1H-pyrrolo[2,3-c]pyridin-3-yl)-1H-indazol-4-yl)ethanesulfonamide | M + H⁺ = 518.6 |
| 45 | 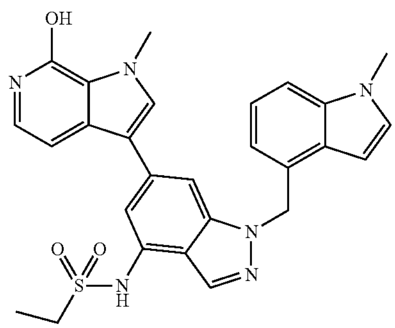 [SMILES: CCS(=O)(=O)Nc1cc(-c2cn(C)c3c(O)nccc23)cc2c1cnn2Cc1cccc2c1ccn2C] | N-(6-(7-hydroxy-1-methyl-1H-pyrrolo[2,3-c]pyridin-3-yl)-1-((1-methyl-1H-indol-4-yl)methyl)-1H-indazol-4-yl)ethanesulfonamide | M + H⁺ = 515.6 |
| 46 | 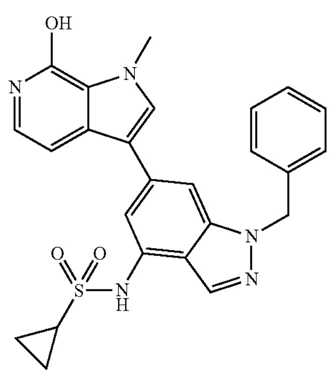 [SMILES: Cn1cc(-c2cc(NS(=O)(=O)C3CC3)c3cnn(Cc4ccccc4)c3c2)c2ccnc(O)c21] | N-(1-benzyl-6-(7-hydroxy-1-methyl-1H-pyrrolo[2,3-c]pyridin-3-yl)-1H-indazol-4-yl)cyclopropanesulfonamide | M + H⁺ = 474.5 |
| 47 | 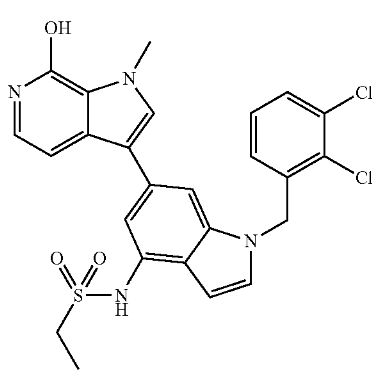 [SMILES: CCS(=O)(=O)Nc1cc(-c2cn(C)c3c(O)nccc23)cc2c1ccn2Cc1cccc(Cl)c1Cl] | N-(1-(2,3-dichlorobenzyl)-6-(7-hydroxy-1-methyl-1H-pyrrolo[2,3-c]pyridin-3-yl)-1H-indol-4-yl)ethanesulfonamide | M + H⁺ = 530.4 |

TABLE 1-continued

Structures and chemical characterization

| Compound | Structure | Chemical name | Chemical characterization |
|---|---|---|---|
| 48 | 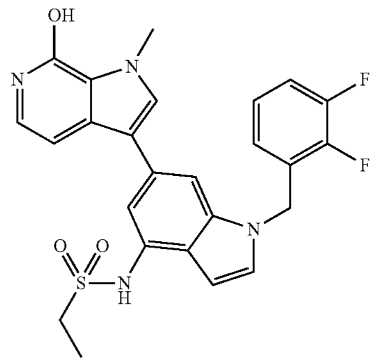 [SMILES: CCS(=O)(=O)Nc1cc(-c2cn(C)c3c(O)nccc23)cc2c1ccn2Cc1cccc(F)c1F] | N-(1-(2,3-difluorobenzyl)-6-(7-hydroxy-1-methyl-1H-pyrrolo[2,3-c]pyridin-3-yl)-1H-indol-4-yl)ethanesulfonamide | M + H$^+$ = 497.5 |
| 49 | 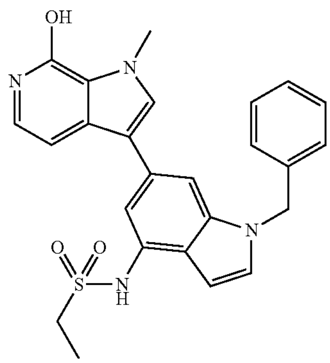 [SMILES: CCS(=O)(=O)Nc1cc(-c2cn(C)c3c(O)nccc23)cc2c1ccn2Cc1ccccc1] | N-(1-benzyl-6-(7-hydroxy-1-methyl-1H-pyrrolo[2,3-c]pyridin-3-yl)-1H-indol-4-yl)ethanesulfonamide | M + H$^+$ = 461.5 |
| 50 | 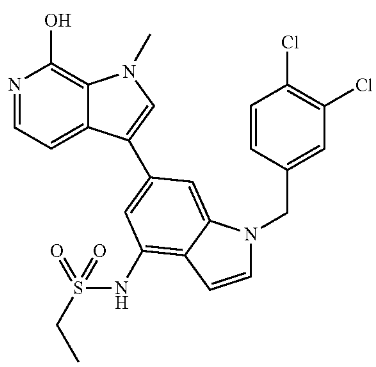 [SMILES: CCS(=O)(=O)Nc1cc(-c2cn(C)c3c(O)nccc23)cc2c1ccn2Cc1ccc(Cl)c(Cl)c1] | N-(1-(3,4-dichlorobenzyl)-6-(7-hydroxy-1-methyl-1H-pyrrolo[2,3-c]pyridin-3-yl)-1H-indol-4-yl)ethanesulfonamide | M + H$^+$ = 530.4 |
| 51 | 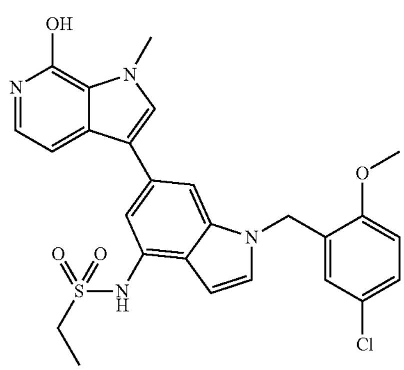 [SMILES: CCS(=O)(=O)Nc1cc(-c2cn(C)c3c(O)nccc23)cc2c1ccn2Cc1cc(Cl)ccc1OC] | N-(1-(5-chloro-2-methoxybenzyl)-6-(7-hydroxy-1-methyl-1H-pyrrolo[2,3-c]pyridin-3-yl)-1H-indol-4-yl)ethanesulfonamide | M + H$^+$ = 526.1 |

TABLE 1-continued

Structures and chemical characterization

| Compound | Structure | Chemical name | Chemical characterization |
|---|---|---|---|
| 52 | 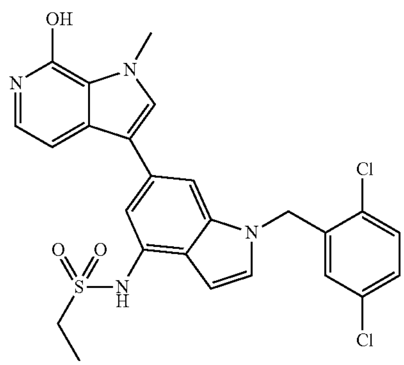 [SMILES: CCS(=O)(=O)Nc1cc(-c2cn(C)c3c(O)nccc23)cc2c1ccn2Cc1cc(Cl)ccc1Cl] | N-(1-(2,5-dichlorobenzyl)-6-(7-hydroxy-1-methyl-1H-pyrrolo[2,3-c]pyridin-3-yl)-1H-indol-4-yl)ethanesulfonamide | M + H⁺ = 530.4 |
| 53 | 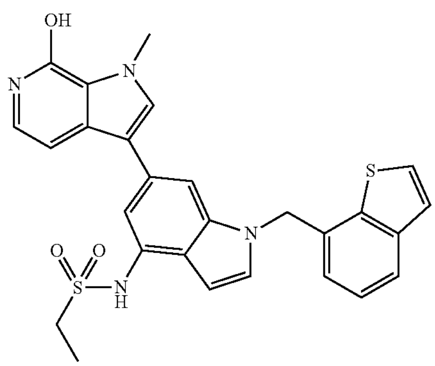 [SMILES: CCS(=O)(=O)Nc1cc(-c2cn(C)c3c(O)nccc23)cc2c1ccn2Cc1cccc2ccsc12] | N-(1-(benzo[b]thiophen-7-ylmethyl)-6-(7-hydroxy-1-methyl-1H-pyrrolo[2,3-c]pyridin-3-yl)-1H-indol-4-yl)ethanesulfonamide | M + H⁺ = 517.6 |
| 54 | 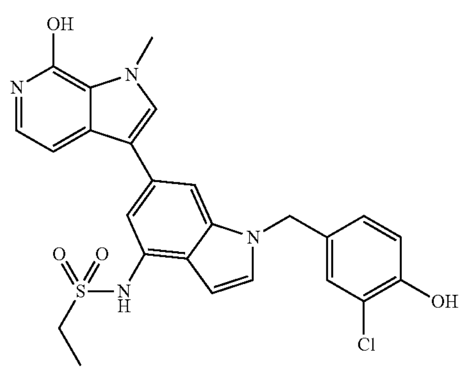 [SMILES: CCS(=O)(=O)Nc1cc(-c2cn(C)c3c(O)nccc23)cc2c1ccn2Cc1ccc(O)c(Cl)c1] | N-(1-(3-chloro-4-hydroxybenzyl)-6-(7-hydroxy-1-methyl-1H-pyrrolo[2,3-c]pyridin-3-yl)-1H-indol-4-yl)ethanesulfonamide | M + H⁺ = 511.9 |
| 55 | 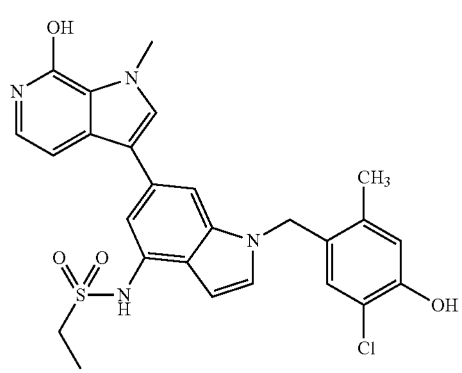 [SMILES: CCS(=O)(=O)Nc1cc(-c2cn(C)c3c(O)nccc23)cc2c1ccn2Cc1cc(Cl)c(O)cc1C] | N-(1-(5-chloro-4-hydroxy-2-methylbenzyl)-6-(7-hydroxy-1-methyl-1H-pyrrolo[2,3-c]pyridin-3-yl)-1H-indol-4-yl)ethanesulfonamide | M + H⁺ = 526.1 |

TABLE 1-continued

Structures and chemical characterization

| Compound | Structure | Chemical name | Chemical characterization |
|---|---|---|---|
| 56 | 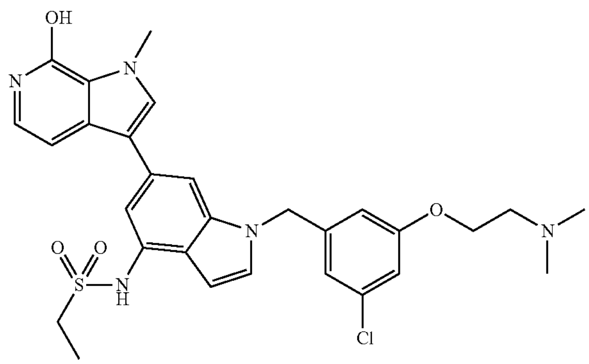 [SMILES: CCS(=O)(=O)Nc1cc(-c2cn(C)c3c(O)nccc23)cc2c1ccn2Cc1cc(Cl)cc(OCCN(C)C)c1] | N-(1-(3-chloro-5-(2-(dimethylamino)ethoxy)benzyl)-6-(7-hydroxy-1-methyl-1H-pyrrolo[2,3-c]pyridin-3-yl)-1H-indol-4-yl)ethanesulfonamide | M + H$^+$ = 583.1 |
| 57 | 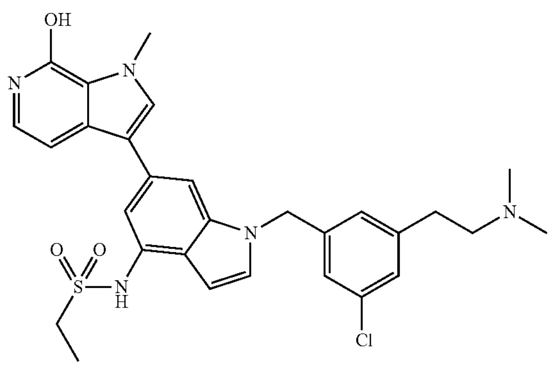 [SMILES: CCS(=O)(=O)Nc1cc(-c2cn(C)c3c(O)nccc23)cc2c1ccn2Cc1cc(Cl)cc(CCN(C)C)c1] | N-(1-(3-chloro-5-(2-(dimethylamino)ethyl)benzyl)-6-(7-hydroxy-1-methyl-1H-pyrrolo[2,3-c]pyridin-3-yl)-1H-indol-4-yl)ethanesulfonamide | M + H$^+$ = 567.1 |
| 58 | 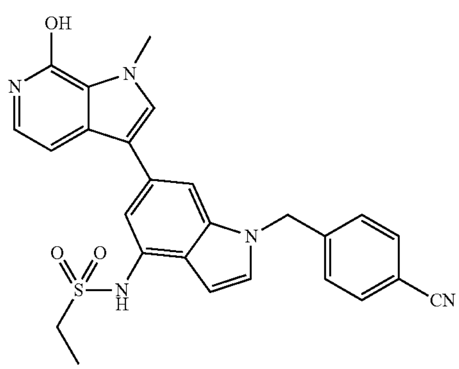 [SMILES: CCS(=O)(=O)Nc1cc(-c2cn(C)c3c(O)nccc23)cc2c1ccn2Cc1ccc(C#N)cc1] | N-(1-(4-cyanobenzyl)-6-(7-hydroxy-1-methyl-1H-pyrrolo[2,3-c]pyridin-3-yl)-1H-indol-4-yl)ethanesulfonamide | M + H$^+$ = 486.6 |
| 59 | 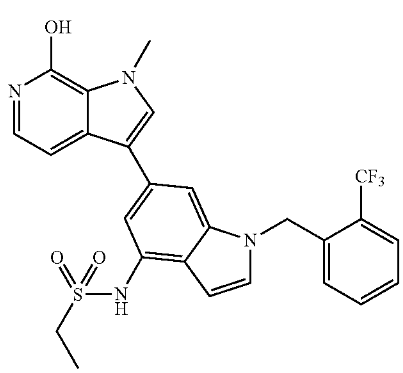 [SMILES: CCS(=O)(=O)Nc1cc(-c2cn(C)c3c(O)nccc23)cc2c1ccn2Cc1ccccc1C(F)(F)F] | N-(6-(7-hydroxy-1-methyl-1H-pyrrolo[2,3-c]pyridin-3-yl)-1-(2-(trifluoromethyl)benzyl)-1H-indol-4-yl)ethanesulfonamide | M + H$^+$ = 529.6 |

TABLE 1-continued

Structures and chemical characterization

| Compound | Structure | Chemical name | Chemical characterization |
|---|---|---|---|
| 60 | 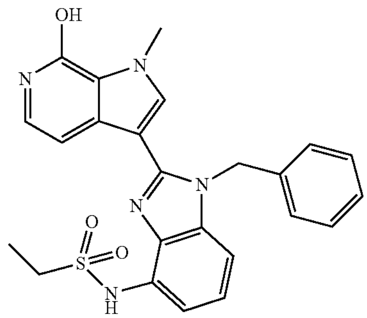 [SMILES: CCS(=O)(=O)Nc1cccc2c1nc(-c1cn(C)c3c(O)nccc13)n2Cc1ccccc1] | N-(1-benzyl-2-(7-hydroxy-1-methyl-1H-pyrrolo[2,3-c]pyridin-3-yl)-1H-benzo[d]imidazol-4-yl)ethanesulfonamide | M + H$^+$ = 462.5 |
| 61 | 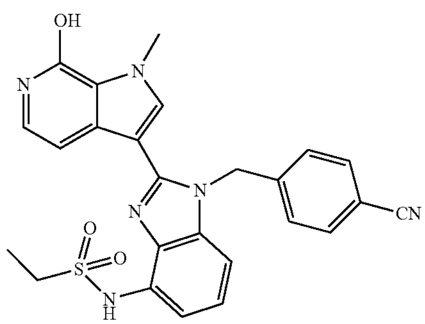 [SMILES: CCS(=O)(=O)Nc1cccc2c1nc(-c1cn(C)c3c(O)nccc13)n2Cc1ccc(C#N)cc1] | N-(1-benzyl-2-(7-hydroxy-1-methyl-1H-pyrrolo[2,3-c]pyridin-3-yl)-1H-benzo[d]imidazol-4-yl)ethanesulfonamide | M + H$^+$ = 487.6 |
| 62 | 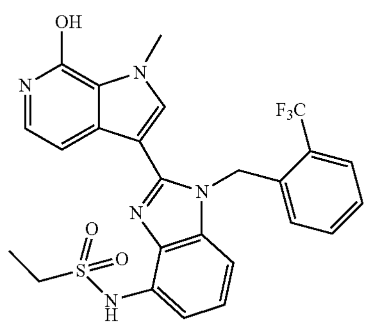 [SMILES: CCS(=O)(=O)Nc1cccc2c1nc(-c1cn(C)c3c(O)nccc13)n2Cc1ccccc1C(F)(F)F] | N-(2-(7-hydroxy-1-methyl-1H-pyrrolo[2,3-c]pyridin-3-yl)-1-(2-(trifluoromethyl)benzyl)-1H-benzo[d]imidazol-4-yl)ethanesulfonamide | M + H$^+$ = 530.5 |
| 63 | 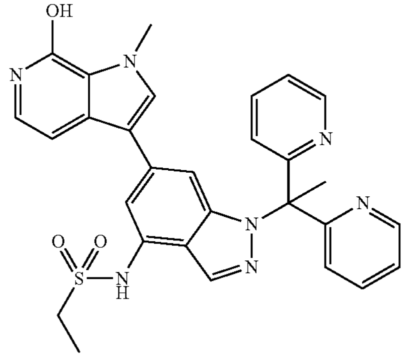 [SMILES: CCS(=O)(=O)Nc1cc(-c2cn(C)c3c(O)nccc23)cc2c1cnn2C(C)(c1ccccn1)c1ccccn1] | N-(1-(1,1-di(pyridin-2-yl)ethyl)-6-(7-hydroxy-1-methyl-1H-pyrrolo[2,3-c]pyridin-3-yl)-1H-indazol-4-yl)ethanesulfonamide | M + H$^+$ = 554.6 |

TABLE 1-continued

Structures and chemical characterization

| Compound | Structure | Chemical name | Chemical characterization |
|---|---|---|---|
| 64 | 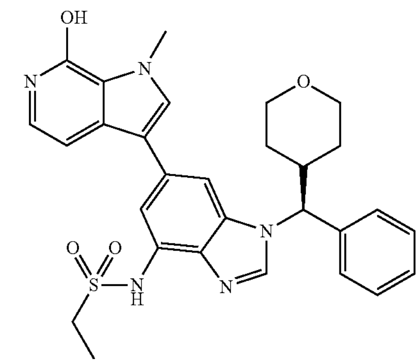 [SMILES: CCS(=O)(=O)Nc1cc(-c2cn(C)c3c(O)nccc23)cc2c1ncn2[C@H](c1ccccc1)C1CCOCC1] | (S)-N-(6-(7-hydroxy-1-methyl-1H-pyrrolo[2,3-c]pyridin-3-yl)-1-(phenyl(tetrahydro-2H-pyran-4-yl)methyl)-1H-benzo[d]imidazol-4-yl)ethanesulfonamide | M + H⁺ = 546.6 |
| 65 | 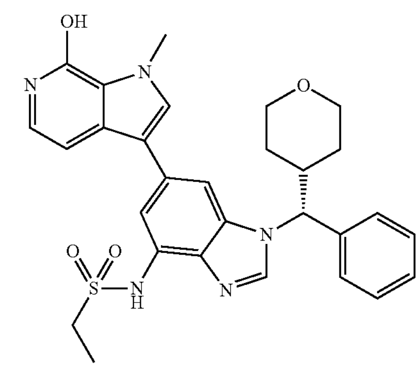 [SMILES: CCS(=O)(=O)Nc1cc(-c2cn(C)c3c(O)nccc23)cc2c1ncn2[C@@H](c1ccccc1)C1CCOCC1] | (S)-N-(6-(7-hydroxy-1-methyl-1H-pyrrolo[2,3-c]pyridin-3-yl)-1-(phenyl(tetrahydro-2H-pyran-4-yl)methyl)-1H-indol-4-yl)ethanesulfonamide | M + H⁺ = 546.6 |
| 66 | 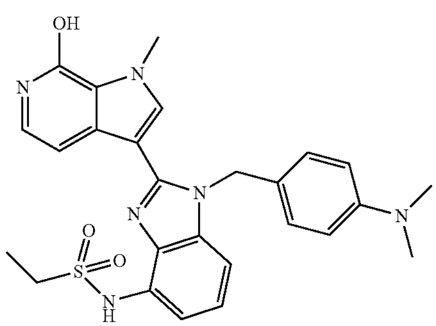 [SMILES: CCS(=O)(=O)Nc1cccc2c1nc(-c1cn(C)c3c(O)nccc13)n2Cc1ccc(N(C)C)cc1] | N-(1-(4-(dimethylamino)benzyl)-2-(7-hydroxy-1-methyl-1H-pyrrolo[2,3-c]pyridin-3-yl)-1H-benzo[d]imidazol-4-yl)ethanesulfonamide | M + H⁺ = 505.6 |
| 67 | 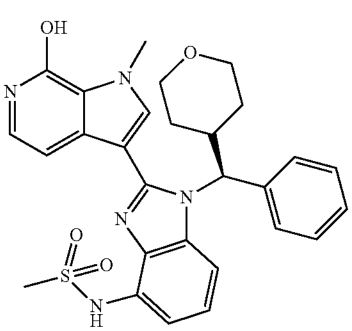 | (S)-N-(2-(7-hydroxy-1-methyl-1H-pyrrolo[2,3-c]pyridin-3-yl)-1-(phenyl(tetrahydro-2H-pyran-4-yl)methyl)-1H-benzo[d]imidazol-4-yl)methanesulfonamide | M + H⁺ = 532.6 |

TABLE 1-continued

Structures and chemical characterization

| Compound | Structure | Chemical name | Chemical characterization |
|---|---|---|---|
| 68 | 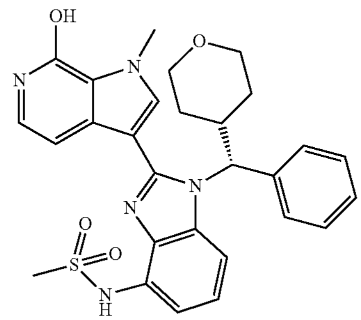 | (R)-N-(2-(7-hydroxy-1-methyl-1H-pyrrolo[2,3-c]pyridin-3-yl)-1-(phenyl(tetrahydro-2H-pyran-4-yl)methyl)-1H-benzo[d]imidazol-4-yl)methanesulfonamide | M + H$^+$ = 532.6 |
| 69 | 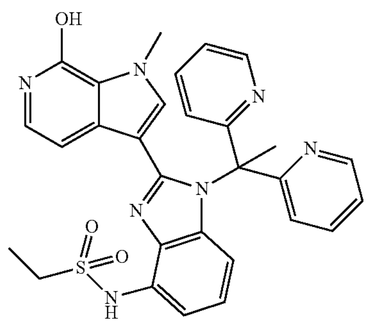 [SMILES: CCS(=O)(=O)Nc1cccc2c1nc(-c1cn(C)c3c(O)nccc13)n2C(C)(c1ccccn1)c1ccccn1] | N-(1-(1,1-di(pyridin-2-yl)ethyl)-2-(7-hydroxy-1-methyl-1H-pyrrolo[2,3-c]pyridin-3-yl)-1H-benzo[d]imidazol-4-yl)ethanesulfonamide | M + H$^+$ = 554.6 |
| 70 | 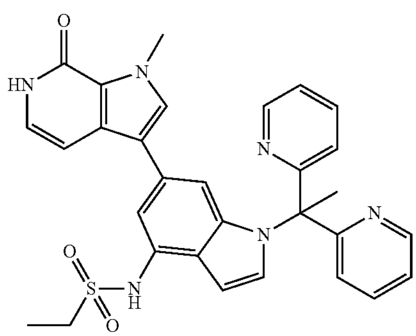 [SMILES: CCS(=O)(=O)Nc1cc(-c2cn(C)c3c(=O)[nH]ccc23)cc2c1ccn2C(C)(c1ccccn1)c1ccccn1] | N-(1-(1,1-di(pyridin-2-yl)ethyl)-2-(7-hydroxy-1-methyl-1H-pyrrolo[2,3-c]pyridin-3-yl)-1H-benzo[d]imidazol-4-yl)ethanesulfonamide | M + H$^+$ = 553.6 $^1$H NMR (400 MHz, DMSO-d$_6$) δ 10.92 (d, J = 5.4 Hz, 1H), 9.66 (s, 1H), 8.63 (d, J = 3.9 Hz, 2H), 7.79 (td, J = 7.8, 1.9 Hz, 2H), 7.38 (dd, J = 7.5, 4.8 Hz, 2H), 7.22 (s, 1H), 7.16 (d, J = 8.0 Hz, 2H), 7.12 (s, 1H), 7.10 (d, J = 3.4 Hz, 1H), 6.87 (d, J = 3.4 Hz, 1H), 6.77 (t, J = 6.3 Hz, 1H), 6.32 (s, 1H), 5.78 (d, J = 7.0 Hz, 1H), 4.03 (s, 3H), 3.12 (q, J = 7.3 Hz, 2H), 2.43 (s, 3H), 1.25 (t, J = 7.3 Hz, 3H). $^{13}$C NMR (101 MHz, , DMSO-d$_6$) δ 161.09, 155.77, 148.91, 137.05, 137.00, 130.28, 128.87, 127.87, 127.49, 127.40, 125.09, 123.17, 122.81, 122.54, 121.82, 117.19, 111.42, 108.15, 99.37, 99.12, 69.90, 45.64, 35.27, 27.92, 8.24. |

TABLE 1-continued

Structures and chemical characterization

| Compound | Structure | Chemical name | Chemical characterization |
|---|---|---|---|
| 71 | 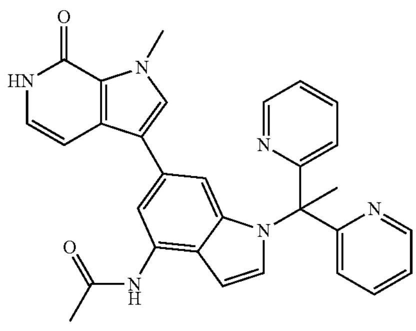 [SMILES: CC(=O)Nc1cc(-c2cn(C)c3c(=O)[nH]ccc23)cc2c1ccn2C(C)(c1ccccn1)c1ccccn1] | N-(1-(1,1-di(pyridin-2-yl)ethyl)-6-(1-methyl-7-oxo-6,7-dihydro-1H-pyrrolo[2,3-c]pyridin-3-yl)-1H-indol-4-yl)acetamide | M + H$^+$ = 503.5 $^1$H NMR (400 MHz, DMSO-d$_6$) δ 10.89 (d, J = 5.3 Hz, 1H), 9.67 (s, 1H), 8.63 (ddd, J = 4.8, 1.9, 0.9 Hz, 2H), 7.82-7.74 (m, 3H), 7.37 (ddd, J = 7.5, 4.8, 1.0 Hz, 2H), 7.18-7.13 (m, 3H), 7.08 (d, J = 3.5 Hz, 1H), 6.82 (d, J = 3.4 Hz, 1H), 6.76 (dd, J = 7.0, 5.7 Hz, 1H), 6.26 (s, 1H), 5.83 (d, J = 7.0 Hz, 1H), 4.03 (s, 3H), 2.44 (s, 3H), 2.16 (s, 3H). $^{13}$C NMR (101 MHz, DMSO-d$_6$) δ 168.55, 161.22, 155.78, 148.91, 136.92, 136.81, 131.31, 128.68, 127.94, 127.18, 126.73, 124.95, 123.13, 122.76, 122.54, 120.30, 117.66, 110.77, 107.29, 99.27, 99.06, 69.82, 35.23, 27.90, 23.92. |
| 72 | 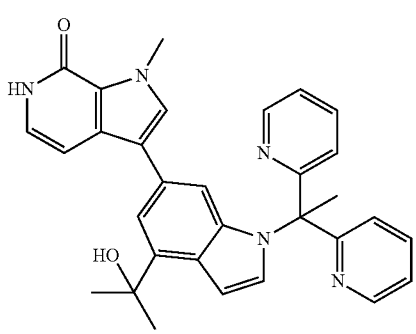 [SMILES: Cn1cc(-c2cc(C(C)(C)O)c3ccn(C(C)(c4ccccn4)c4ccccn4)c3c2)c2cc[nH]c(=O)c21] | 3-(1-(1,1-di(pyridin-2-yl)ethyl)-4-(2-hydroxypropan-2-yl)-1H-indol-6-yl)-1-methyl-1H-pyrrolo[2,3-c]pyridin-7(6H)-one | M + H$^+$ = 504.6 $^1$H NMR (400 MHz, Acetone-d$_6$) δ 10.06 (s, 1H), 8.65 (ddd, J = 4.8, 1.9, 0.9 Hz, 2H), 7.77 (td, J = 7.8, 1.9 Hz, 2H), 7.37-7.35 (m, 2H), 7.34 (dd, J = 4.8, 1.1 Hz, 1H), 7.28 (dt, J = 8.0, 1.0 Hz, 2H), 7.16 (s, 1H), 6.98 (d, J = 3.5 Hz, 1H), 6.85 (d, J = 7.3 Hz, 2H), 6.83 (dd, J = 3.5, 0.9 Hz, 1H), 6.65 (t, J = 1.2 Hz, 1H), 5.96 (d, J = 7.0 Hz, 1H), 4.11 (s, 3H), 2.53 (s, 3H), 1.73 (s, 6H). |

TABLE 1-continued

Structures and chemical characterization

| Compound | Structure | Chemical name | Chemical characterization |
|---|---|---|---|
| 73 | 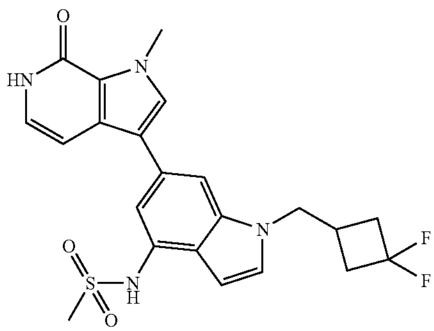 [SMILES: Cn1cc(-c2cc(NS(C)(=O)=O)c3ccn(CC4CC(F)(F)C4)c3c2)c2cc[nH]c(=O)c21] | N-(1-((3,3-difluorocyclobutyl)methyl)-6-(1-methyl-7-oxo-6,7-dihydro-1H-pyrrolo[2,3-c]pyridin-3-yl)-1H-indol-4-yl)methanesulfonamide | M + H$^+$ = 461.5 $^1$H NMR (400 MHz, Acetone-d$_6$) δ 10.63 (s, 1H), 8.54 (s, 1H), 7.54 (s, 1H), 7.52 (s, 1H), 7.48 (d, J = 1.3 Hz, 1H), 7.39 (d, J = 3.2 Hz, 1H), 7.07 (d, J = 7.0 Hz, 1H), 6.93-6.85 (m, 2H), 4.45 (d, J = 7.4 Hz, 2H), 4.22 (s, 3H), 3.02 (s, 3H), 2.83 (m, 1H), 2.75-2.59 (m, 2H), 2.49 (m, 2H). |
| 74 | 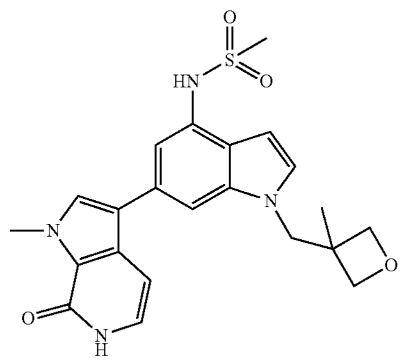 [SMILES: Cn1cc(-c2cc(NS(C)(=O)=O)c3ccn(CC4(C)COC4)c3c2)c2cc[nH]c(=O)c21] | N-(6-(1-methyl-7-oxo-6,7-dihydro-1H-pyrrolo[2,3-c]pyridin-3-yl)-1-((3-methyloxetan-3-yl)methyl)-1H-indol-4-yl)methanesulfonamide | M + H$^+$ = 441.5 $^1$H NMR (400 MHz, Acetone-d$_6$) δ 10.85 (s, 1H), 8.54 (s, 1H), 7.68 (s, 1H), 7.54 (s, 1H), 7.46 (d, J = 1.1 Hz, 1H), 7.37 (d, J = 3.1 Hz, 1H), 7.05 (dd, J = 40.5, 6.9 Hz, 2H), 6.90 (d, J = 3.2 Hz, 1H), 4.38-4.27 (m, 2H), 4.21 (s, 3H), 3.50-3.45 (m, 3H), 3.39 (d, J = 9.9 Hz, 1H), 3.02 (s, 3H), 1.02 (s, 3H). |
| 75 | 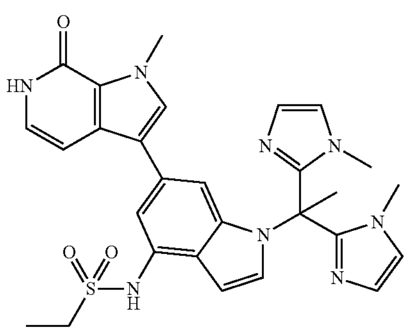 [SMILES: CCS(=O)(=O)Nc1cc(-c2cn(C)c3c(=O)[nH]ccc23)cc2c1ccn2C(C)(c1nccn1C)c1nccn1C] | N-(1-(1,1-bis(1-methyl-1H-imidazol-2-yl)ethyl)-6-(7-hydroxy-1-methyl-1H-pyrrolo[2,3-c]pyridin-3-yl)-1H-indol-4-yl)ethanesulfonamide | M + H$^+$ = 559.6 |
| 76 | 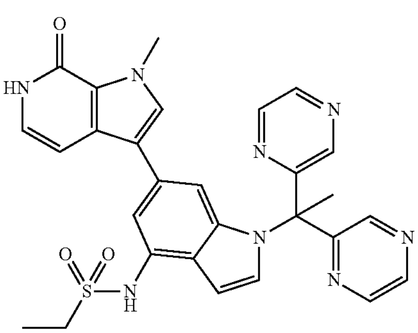 [SMILES: CCS(=O)(=O)Nc1cc(-c2cn(C)c3c(=O)[nH]ccc23)cc2c1ccn2C(C)(c1cnccn1)c1cnccn1] | N-(1-(1,1-di(pyrazin-2-yl)ethyl)-6-(7-hydroxy-1-methyl-1H-pyrrolo[2,3-c]pyridin-3-yl)-1H-indol-4-yl)ethanesulfonamide | M + H$^+$ = 555.6 |

TABLE 1-continued

Structures and chemical characterization

| Compound | Structure | Chemical name | Chemical characterization |
|---|---|---|---|
| 77 | 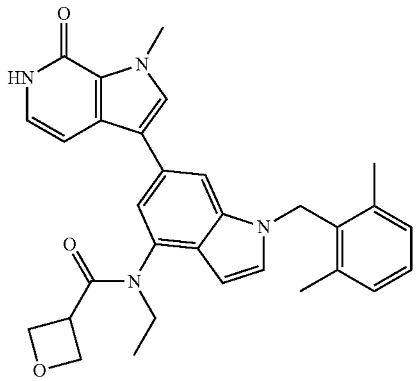 [SMILES: CCN(C(=O)C1COC1)c1cc(-c2cn(C)c3c(=O)[nH]ccc23)cc2c1ccn2Cc1c(C)cccc1C] | N-(1-(2,6-dimethylbenzyl)-6-(7-hydroxy-1-methyl-1H-pyrrolo[2,3-c]pyridin-3-yl)-1H-indol-4-yl)-N-ethyloxetane-3-carboxamide | M + H⁺ = 509.6 |
| 78 | 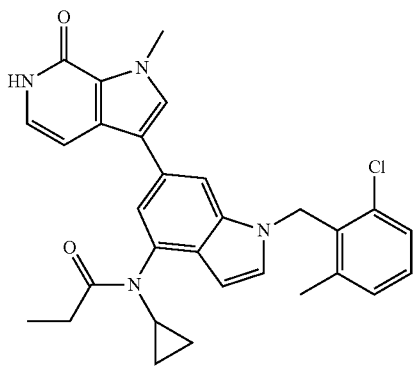 [SMILES: CCC(=O)N(c1cc(-c2cn(C)c3c(=O)[nH]ccc23)cc2c1ccn2Cc1c(C)cccc1Cl)C1CC1] | N-(1-(2-chloro-6-methylbenzyl)-6-(7-hydroxy-1-methyl-1H-pyrrolo[2,3-c]pyridin-3-yl)-1H-indol-4-yl)-N-cyclopropylpropionamide | M + H⁺ = 514.1 |
| 79 | 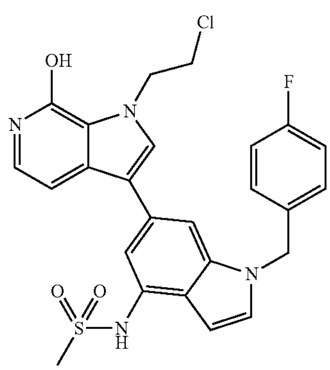 [SMILES: CS(=O)(=O)Nc1cc(-c2cn(CCCl)c3c(O)nccc23)cc2c1ccn2Cc1ccc(F)cc1] | N-(6-(1-(2-chloroethyl)-7-hydroxy-1H-pyrrolo[2,3-c]pyridin-3-yl)-1-(4-fluorobenzyl)-1H-indol-4-yl)methanesulfonamide | M + H⁺ = 513.9 |
| 80 | 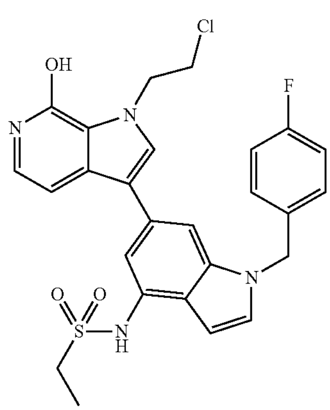 [SMILES: CCS(=O)(=O)Nc1cc(-c2cn(CCCl)c3c(O)nccc23)cc2c1ccn2Cc1ccc(F)cc1] | N-(6-(1-(2-chloroethyl)-7-hydroxy-1H-pyrrolo[2,3-c]pyridin-3-yl)-1-(4-fluorobenzyl)-1H-indol-4-yl)ethanesulfonamide | M + H⁺ = 528.0 |

TABLE 1-continued

Structures and chemical characterization

| Compound | Structure | Chemical name | Chemical characterization |
|---|---|---|---|
| 81 | 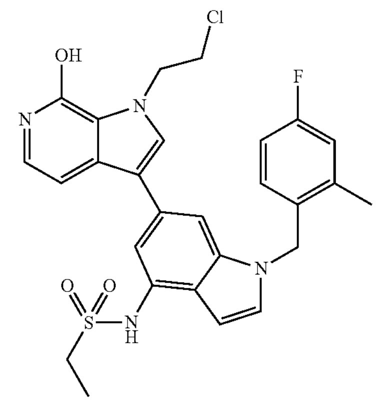 [SMILES: CCS(=O)(=O)Nc1cc(-c2cn(CCCl)c3c(O)nccc23)cc2c1ccn2Cc1ccc(F)cc1C] | N-(6-(1-(2-chloroethyl)-7-hydroxy-1H-pyrrolo[2,3-c]pyridin-3-yl)-1-(4-fluoro-2-methylbenzyl)-1H-indol-4-yl)ethanesulfonamide | M + H$^+$ = 542.1 |
| 82 | 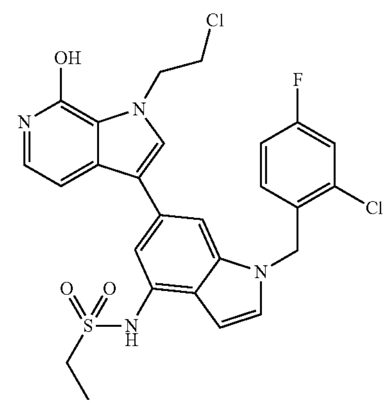 [SMILES: CCS(=O)(=O)Nc1cc(-c2cn(CCCl)c3c(O)nccc23)cc2c1ccn2Cc1ccc(F)cc1Cl] | N-(1-(2-chloro-4-fluorobenzyl)-6-(1-(2-chloroethyl)-7-hydroxy-1H-pyrrolo[2,3-c]pyridin-3-yl)-1H-indol-4-yl)ethanesulfonamide | M + H$^+$ = 562.4 |
| 83 | 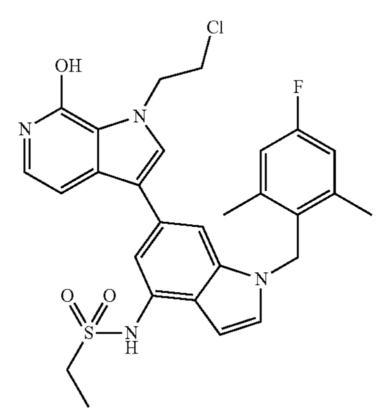 [SMILES: CCS(=O)(=O)Nc1cc(-c2cn(CCCl)c3c(O)nccc23)cc2c1ccn2Cc1c(C)cc(F)cc1C] | N-(6-(1-(2-chloroethyl)-7-hydroxy-1H-pyrrolo[2,3-c]pyridin-3-yl)-1-(4-fluoro-2,6-dimethylbenzyl)-1H-indol-4-yl)ethanesulfonamide | M + H$^+$ = 556.1 |

TABLE 1-continued

Structures and chemical characterization

| Compound | Structure | Chemical name | Chemical characterization |
|---|---|---|---|
| 84 | 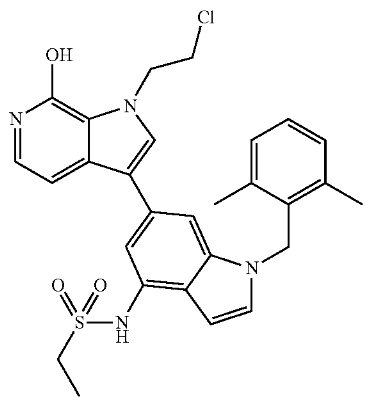 [SMILES: CCS(=O)(=O)Nc1cc(-c2cn(CCCl)c3c(O)nccc23)cc2c1ccn2Cc1c(C)cccc1C] | N-(6-(1-(2-chloroethyl)-7-hydroxy-1H-pyrrolo[2,3-c]pyridin-3-yl)-1-(2,6-dimethylbenzyl)-1H-indol-4-yl)ethanesulfonamide | M + H⁺ = 538.1 |
| 85 | 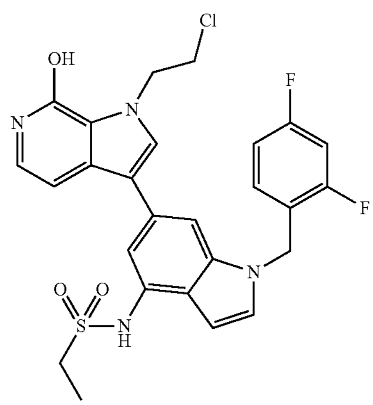 [SMILES: CCS(=O)(=O)Nc1cc(-c2cn(CCCl)c3c(O)nccc23)cc2c1ccn2Cc1ccc(F)cc1F] | N-(6-(1-(2-chloroethyl)-7-hydroxy-1H-pyrrolo[2,3-c]pyridin-3-yl)-1-(2,4-difluorobenzyl)-1H-indol-4-yl)ethanesulfonamide | M + H⁺ = 546.0 |
| 86 | 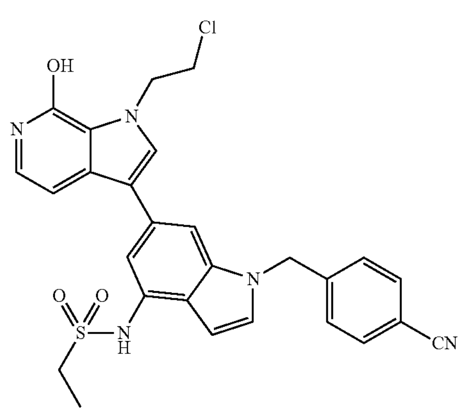 [SMILES: CCS(=O)(=O)Nc1cc(-c2cn(CCCl)c3c(O)nccc23)cc2c1ccn2Cc1ccc(C#N)cc1] | N-(6-(1-(2-chloroethyl)-7-hydroxy-1H-pyrrolo[2,3-c]pyridin-3-yl)-1-(4-cyanobenzyl)-1H-indol-4-yl)ethanesulfonamide | M + H⁺ = 535.1 |

TABLE 1-continued

Structures and chemical characterization

| Compound | Structure | Chemical name | Chemical characterization |
|---|---|---|---|
| 87 | 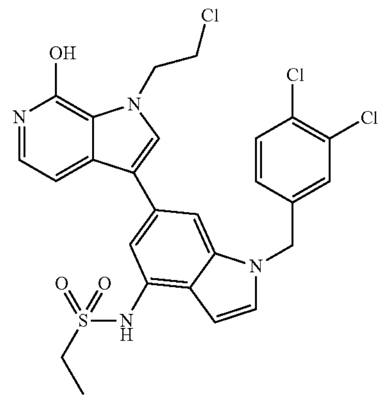 [SMILES: CCS(=O)(=O)Nc1cc(-c2cn(CCCl)c3c(O)nccc23)cc2c1ccn2Cc1ccc(Cl)c(Cl)c1] | N-(6-(1-(2-chloroethyl)-7-hydroxy-1H-pyrrolo[2,3-c]pyridin-3-yl)-1-(3,4-dichlorobenzyl)-1H-indol-4-yl)ethanesulfonamide | M + H⁺ = 578.9 |
| 88 | 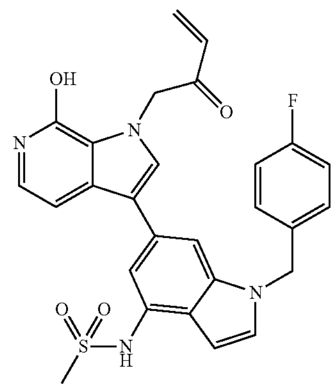 [SMILES: C=CC(=O)Cn1cc(-c2cc(NS(C)(=O)=O)c3ccn(Cc4ccc(F)cc4)c3c2)c2ccnc(O)c21] | N-(1-(4-fluorobenzyl)-6-(7-hydroxy-1-(2-oxobut-3-en-1-yl)-1H-pyrrolo[2,3-c]pyridin-3-yl)-1H-indol-4-yl)methanesulfonamide | M + H⁺ = 519.6 |
| 89 | 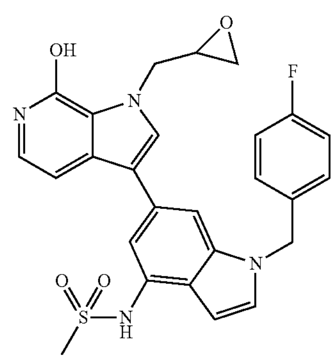 [SMILES: CS(=O)(=O)Nc1cc(-c2cn(CC3CO3)c3c(O)nccc23)cc2c1ccn2Cc1ccc(F)cc1] | N-(1-(4-fluorobenzyl)-6-(7-hydroxy-1-(oxiran-2-ylmethyl)-1H-pyrrolo[2,3-c]pyridin-3-yl)-1H-indol-4-yl)methanesulfonamide | M + H⁺ = 507.5 |
| 90 | 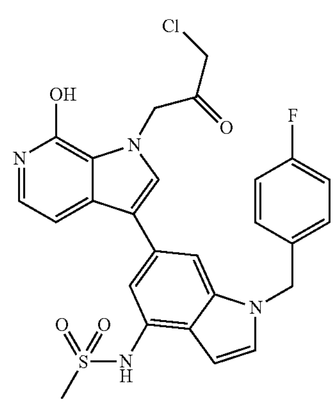 [SMILES: CS(=O)(=O)Nc1cc(-c2cn(CC(=O)CCl)c3c(O)nccc23)cc2c1ccn2Cc1ccc(F)cc1] | N-(6-(1-(3-chloro-2-oxopropyl)-7-hydroxy-1H-pyrrolo[2,3-c]pyridin-3-yl)-1-(4-fluorobenzyl)-1H-indol-4-yl)methanesulfonamide | M + H⁺ = 542.0 |

TABLE 1-continued

Structures and chemical characterization

| Compound | Structure | Chemical name | Chemical characterization |
|---|---|---|---|
| 91 | 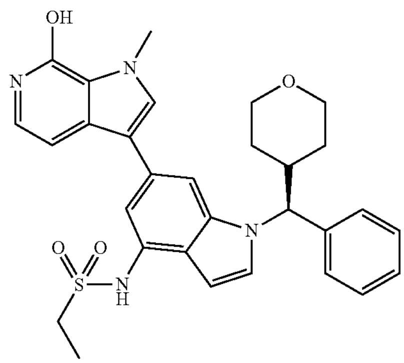 [SMILES: CCS(=O)(=O)Nc1cc(-c2cn(C)c3c(O)nccc23)cc2c1ccn2[C@H](c1ccccc1)C1CCOCC1] | (S)-N-(6-(7-hydroxy-1-methyl-1H-pyrrolo[2,3-c]pyridin-3-yl)-1-(phenyl(tetrahydro-2H-pyran-4-yl)methyl)-1H-indol-4-yl)ethanesulfonamide | M + H$^+$ = 545.6 |
| 92 | 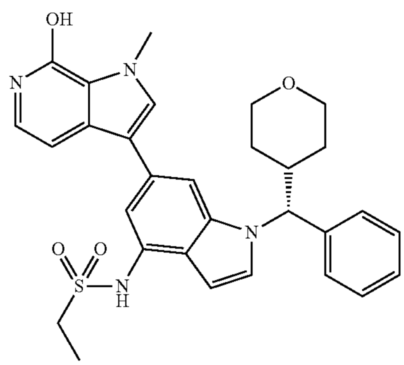 [SMILES: CCS(=O)(=O)Nc1cc(-c2cn(C)c3c(O)nccc23)cc2c1ccn2[C@@H](c1ccccc1)C1CCOCC1] | (R)-N-(6-(7-hydroxy-1-methyl-1H-pyrrolo[2,3-c]pyridin-3-yl)-1-(phenyl(tetrahydro-2H-pyran-4-yl)methyl)-1H-indol-4-yl)ethanesulfonamide | M + H$^+$ = 545.6 |
| 93 | 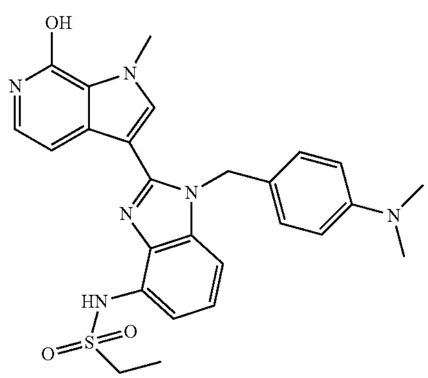 [SMILES: CCS(=O)(=O)Nc1cccc2c1nc(-c1cn(C)c3c(O)nccc13)n2Cc1ccc(N(C)C)cc1] | N-(1-(4-(dimethylamino)benzyl)-2-(7-hydroxy-1-methyl-1H-pyrrolo[2,3-c]pyridin-3-yl)-1H-benzo[d]imidazol-4-yl)ethanesulfonamide | M + H$^+$ = 504.6 |
| 94 | 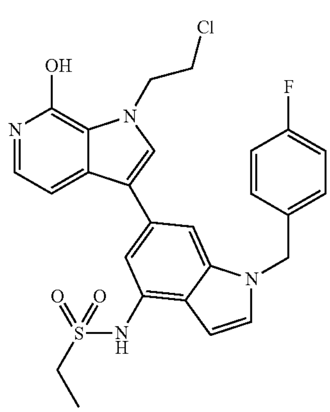 [SMILES: CCS(=O)(=O)Nc1cc(-c2cn(CCCl)c3c(O)nccc23)cc2c1ccn2Cc1ccc(F)cc1] | N-(6-(1-(2-chloroethyl)-7-hydroxy-1H-pyrrolo[2,3-c]pyridin-3-yl)-1-(4-fluorobenzyl)-1H-indol-4-yl)ethanesulfonamide | M + H$^+$ = 528.0 |

TABLE 1-continued

Structures and chemical characterization

| Compound | Structure | Chemical name | Chemical characterization |
|---|---|---|---|
| 95 | 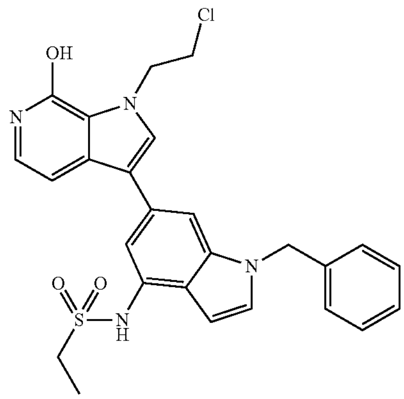 [SMILES: CCS(=O)(=O)Nc1cc(-c2cn(CCCl)c3c(O)nccc23)cc2c1ccn2Cc1ccccc1] | N-(1-benzyl-6-(1-(2-chloroethyl)-7-hydroxy-1H-pyrrolo[2,3-c]pyridin-3-yl)-1H-indol-4-yl)ethanesulfonamide | M + H⁺ = 510.0 |
| 96 | 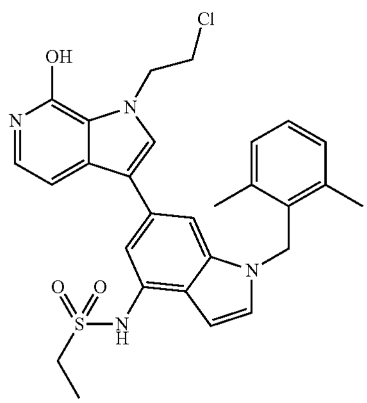 [SMILES: CCS(=O)(=O)Nc1cc(-c2cn(CCCl)c3c(O)nccc23)cc2c1ccn2Cc1c(C)cccc1C] | N-(6-(1-(2-chloroethyl)-7-hydroxy-1H-pyrrolo[2,3-c]pyridin-3-yl)-1-(2,6-dimethylbenzyl)-1H-indol-4-yl)ethanesulfonamide | M + H⁺ = 538.1 |
| 97 | 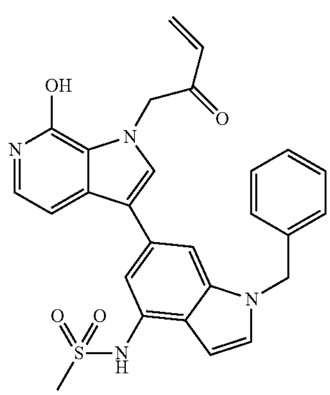 [SMILES: C=CC(=O)Cn1cc(-c2cc(NS(C)(=O)=O)c3ccn(Cc4ccccc4)c3c2)c2ccnc(O)c21] | N-(1-benzyl-6-(7-hydroxy-1-(2-oxobut-3-en-1-yl)-1H-pyrrolo[2,3-c]pyridin-3-yl)-1H-indol-4-yl)methanesulfonamide | M + H⁺ = 501.5 |
| 98 | 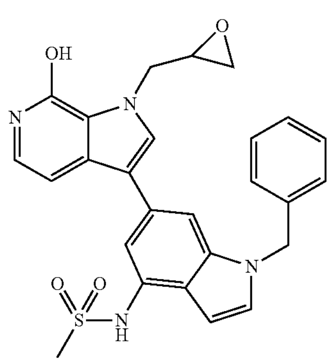 [SMILES: CS(=O)(=O)Nc1cc(-c2cn(CC3CO3)c3c(O)nccc23)cc2c1ccn2Cc1ccccc1] | N-(1-benzyl-6-(7-hydroxy-1-(oxiran-2-ylmethyl)-1H-pyrrolo[2,3-c]pyridin-3-yl)-1H-indol-4-yl)methanesulfonamide | M + H⁺ = 489.5 |

TABLE 1-continued

Structures and chemical characterization

| Compound | Structure | Chemical name | Chemical characterization |
|---|---|---|---|
| 99 | 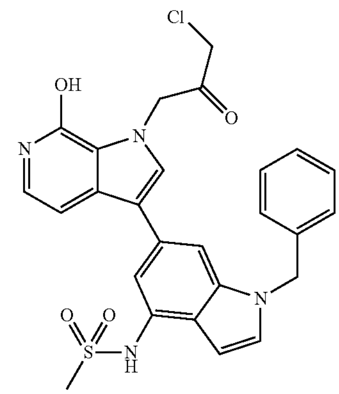 [SMILES: CS(=O)(=O)Nc1cc(-c2cn(CC(=O)CCl)c3c(O)nccc23)cc2c1ccn2Cc1ccccc1] | N-(1-benzyl-6-(1-(3-chloro-2-oxopropyl)-7-hydroxy-1H-pyrrolo[2,3-c]pyridin-3-yl)-1H-indol-4-yl)methanesulfonamide | M + H⁺ = 524.1 |
| 100 | 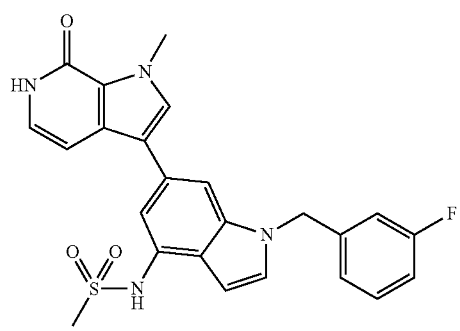 [SMILES: Cn1cc(-c2cc(NS(C)(=O)=O)c3ccn(Cc4cccc(F)c4)c3c2)c2cc[nH]c(=O)c21] | N-(1-(3-fluorobenzyl)-6-(1-methyl-7-oxo-6,7-dihydro-1H-pyrrolo[2,3-c]pyridin-3-yl)-1H-indol-4-yl)methanesulfonamide | M + H⁺ = 465.5 |
| 101 | 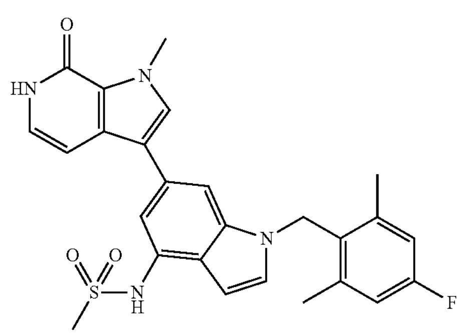 [SMILES: Cc1cc(F)cc(C)c1Cn1ccc2c(NS(C)(=O)=O)cc(-c3cn(C)c4c(=O)[nH]ccc34)cc21] | N-(1-(4-fluoro-2,6-dimethylbenzyl)-6-(1-methyl-7-oxo-6,7-dihydro-1H-pyrrolo[2,3-c]pyridin-3-yl)-1H-indol-4-yl)methanesulfonamide | M + H⁺ = 493.6 |
| 102 | 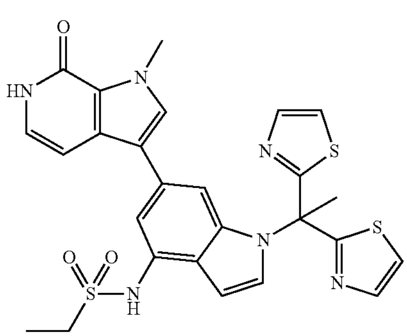 [SMILES: CCS(=O)(=O)Nc1cc(-c2cn(C)c3c(=O)[nH]ccc23)cc2c1ccn2C(C)(c1nccs1)c1nccs1] | N-(1-(1,1-di(thiazol-2-yl)ethyl)-6-(1-methyl-7-oxo-6,7-dihydro-1H-pyrrolo[2,3-c]pyridin-3-yl)-1H-indol-4-yl)ethanesulfonamide | M + H⁺ = 565.7 |

TABLE 1-continued

Structures and chemical characterization

| Compound | Structure | Chemical name | Chemical characterization |
|---|---|---|---|
| 103 | 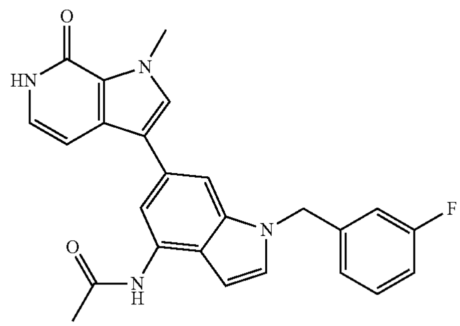 [SMILES: CC(=O)Nc1cc(-c2cn(C)c3c(=O)[nH]ccc23)cc2c1ccn2Cc1cccc(F)c1] | N-(1-(3-fluorobenzyl)-6-(1-methyl-7-oxo-6,7-dihydro-1H-pyrrolo[2,3-c]pyridin-3-yl)-1H-indol-4-yl)acetamide | M + H⁺ = 429.5 |
| 104 | 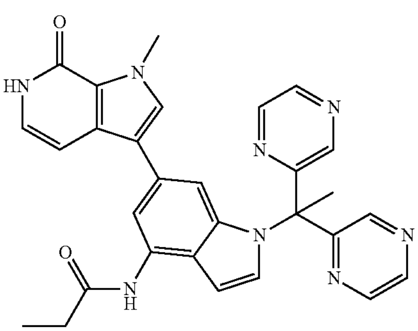 [SMILES: CCC(=O)Nc1cc(-c2cn(C)c3c(=O)[nH]ccc23)cc2c1ccn2C(C)(c1cnccn1)c1cnccn1] | N-(1-(1,1-di(pyrazin-2-yl)ethyl)-6-(1-methyl-7-oxo-6,7-dihydro-1H-pyrrolo[2,3-c]pyridin-3-yl)-1H-indol-4-yl)propionamide | M + H⁺ = 519.6 |
| 105 | 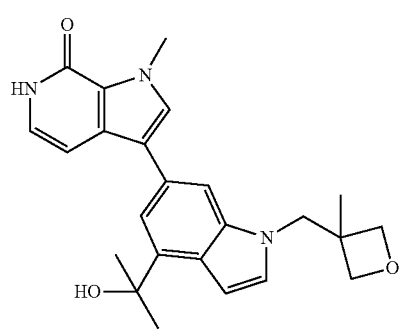 [SMILES: Cn1cc(-c2cc(C(C)(C)O)c3ccn(CC4(C)COC4)c3c2)c2cc[nH]c(=O)c21] | 3-(4-(2-hydroxypropan-2-yl)-1-((3-methyloxetan-3-yl)methyl)-1H-indol-6-yl)-1-methyl-1,6-dihydro-7H-pyrrolo[2,3-c]pyridin-7-one | M + H⁺ = 406.5 |
| 106 | 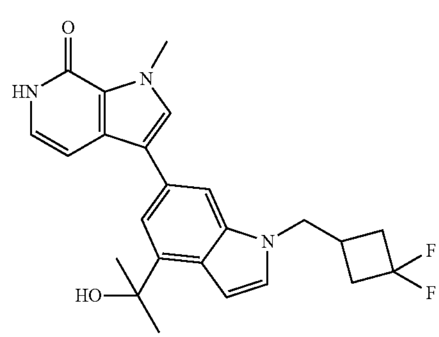 [SMILES: Cn1cc(-c2cc(C(C)(C)O)c3ccn(CC4CC(F)(F)C4)c3c2)c2cc[nH]c(=O)c21] | 3-(1-((3,3-difluorocyclobutyl)methyl)-4-(2-hydroxypropan-2-yl)-1H-indol-6-yl)-1-methyl-1,6-dihydro-7H-pyrrolo[2,3-c]pyridin-7-one | M + H⁺ = 426.4 |

TABLE 1-continued

Structures and chemical characterization

| Compound | Structure | Chemical name | Chemical characterization |
|---|---|---|---|
| 107 | 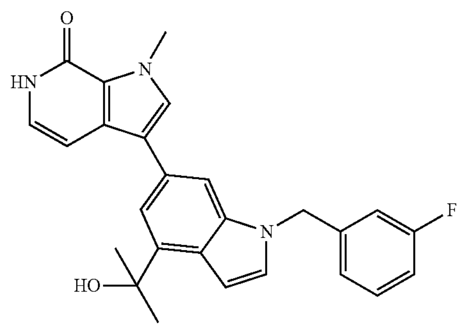 [SMILES: Cn1cc(-c2cc(C(C)(C)O)c3ccn(Cc4cccc(F)c4)c3c2)c2cc[nH]c(=O)c21] | 3-(1-(3-fluorobenzyl)-4-(2-hydroxypropan-2-yl)-1H-indol-6-yl)-1-methyl-1,6-dihydro-7H-pyrrolo[2,3-c]pyridin-7-one | M + H$^+$ = 430.5 |
| 108 | 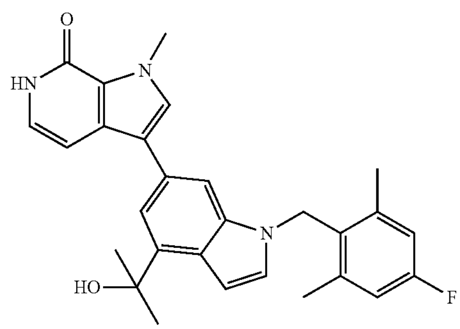 [SMILES: Cc1cc(F)cc(C)c1Cn1ccc2c(C(C)(C)O)cc(-c3cn(C)c4c(=O)[nH]ccc34)cc21] | 3-(1-(4-fluoro-2,6-dimethylbenzyl)-4-(2-hydroxypropan-2-yl)-1H-indol-6-yl)-1-methyl-1,6-dihydro-7H-pyrrolo[2,3-c]pyridin-7-one | M + H$^+$ = 458.5 |
| 109 | 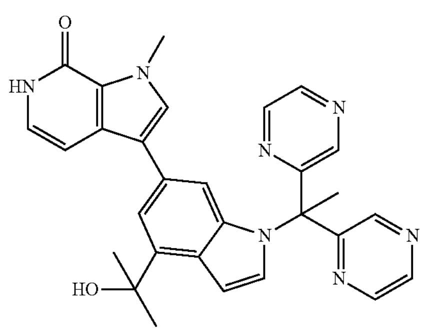 [SMILES: Cn1cc(-c2cc(C(C)(C)O)c3ccn(C(C)(c4cnccn4)c4cnccn4)c3c2)c2cc[nH]c(=O)c21] | 3-(1-(1,1-di(pyrazin-2-yl)ethyl)-4-(2-hydroxypropan-2-yl)-1H-indol-6-yl)-1-methyl-1,6-dihydro-7H-pyrrolo[2,3-c]pyridin-7-one | M + H$^+$ = 506.6 |
| 110 | 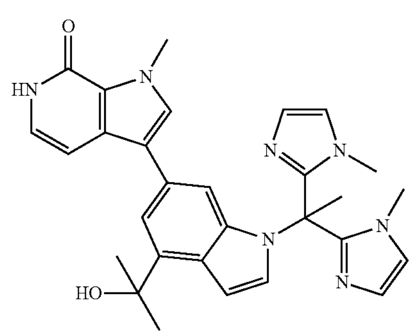 [SMILES: Cn1ccnc1C(C)(c1nccn1C)n1ccc2c(C(C)(C)O)cc(-c3cn(C)c4c(=O)[nH]ccc34)cc21] | 3-(1-(1,1-bis(1-methyl-1H-imidazol-2-yl)ethyl)-4-(2-hydroxypropan-2-yl)-1H-indol-6-yl)-1-methyl-1,6-dihydro-7H-pyrrolo[2,3-c]pyridin-7-one | M + H$^+$ = 510.6 |

TABLE 1-continued

Structures and chemical characterization

| Compound | Structure | Chemical name | Chemical characterization |
|---|---|---|---|
| 111 | 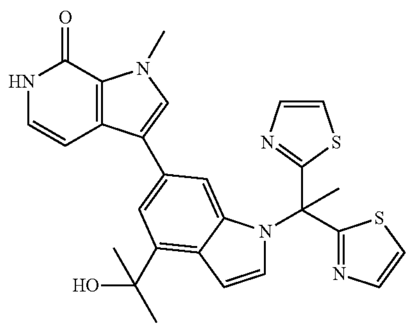 [SMILES: Cn1cc(-c2cc(C(C)(C)O)c3ccn(C(C)(c4nccs4)c4nccs4)c3c2)c2cc[nH]c(=O)c21] | 3-(1-(1,1-di(thiazol-2-yl)ethyl)-4-(2-hydroxypropan-2-yl)-1H-indol-6-yl)-1-methyl-1,6-dihydro-7H-pyrrolo[2,3-c]pyridin-7-one | M + H$^+$ = 516.6 |
| 112 | 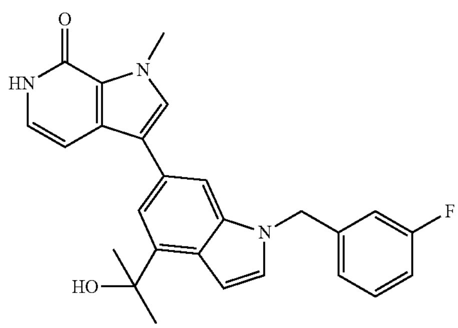 [SMILES: Cn1cc(-c2cc(C(C)(C)O)c3ccn(Cc4cccc(F)c4)c3c2)c2cc[nH]c(=O)c21] | 3-(1-(3-fluorobenzyl)-4-(2-hydroxypropan-2-yl)-1H-indol-6-yl)-1-methyl-1,6-dihydro-7H-pyrrolo[2,3-c]pyridin-7-one | M + H$^+$ = 430.5 |
| 113 | 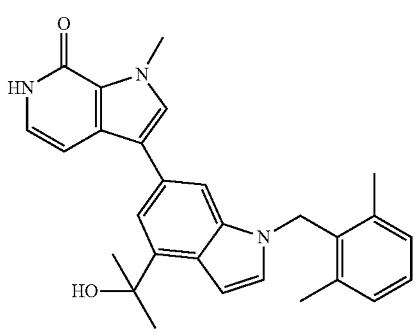 [SMILES: Cc1cccc(C)c1Cn1ccc2c(C(C)(C)O)cc(-c3cn(C)c4c(=O)[nH]ccc34)cc21] | 3-(1-(2,6-dimethylbenzyl)-4-(2-hydroxypropan-2-yl)-1H-indol-6-yl)-1-methyl-1,6-dihydro-7H-pyrrolo[2,3-c]pyridin-7-one | M + H$^+$ = 440.5 |
| 114 | 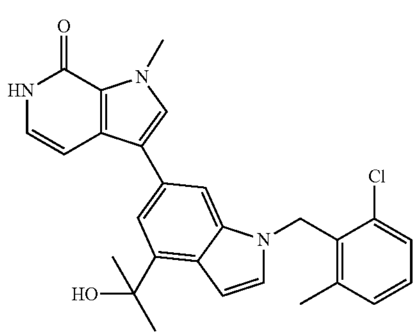 [SMILES: Cc1cccc(Cl)c1Cn1ccc2c(C(C)(C)O)cc(-c3cn(C)c4c(=O)[nH]ccc34)cc21] | 3-(1-(2-chloro-6-methylbenzyl)-4-(2-hydroxypropan-2-yl)-1H-indol-6-yl)-1-methyl-1,6-dihydro-7H-pyrrolo[2,3-c]pyridin-7-one | M + H$^+$ = 461.1 |

TABLE 1-continued

Structures and chemical characterization

| Compound | Structure | Chemical name | Chemical characterization |
|---|---|---|---|
| 115 | 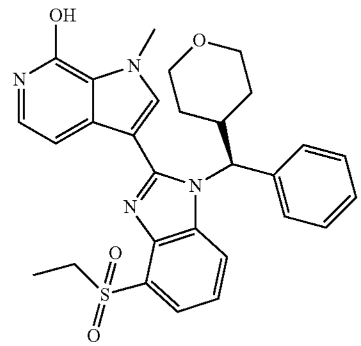 [SMILES: CCS(=O)(=O)c1cccc2c1nc(-c1cn(C)c3c(O)nccc13)n2[C@H](c1ccccc1)C1CCOCC1] | (S)-3-(4-(ethylsulfonyl)-1-(phenyl(tetrahydro-2H-pyran-4-yl)methyl)-1H-benzo[d]imidazol-2-yl)-1-methyl-1H-pyrrolo[2,3-c]pyridin-7-ol | M + H$^+$ = 531.6 |
| 116 | 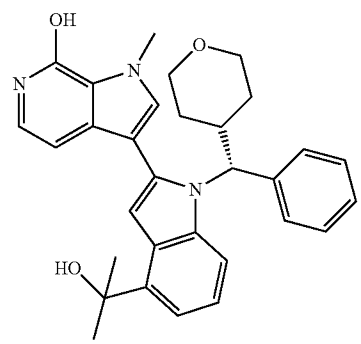 [SMILES: Cn1cc(-c2cc3c(C(C)(C)O)cccc3n2[C@@H](c2ccccc2)C2CCOCC2)c2ccnc(O)c21] | (R)-3-(4-(2-hydroxypropan-2-yl)-1-(phenyl(tetrahydro-2H-pyran-4-yl)methyl)-1H-indol-2-yl)-1-methyl-1H-pyrrolo[2,3-c]pyridin-7-ol | M + H$^+$ = 496.6 |
| 117 | 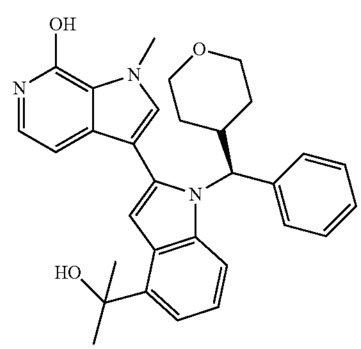 [SMILES: Cn1cc(-c2cc3c(C(C)(C)O)cccc3n2[C@H](c2ccccc2)C2CCOCC2)c2ccnc(O)c21] | (S)-3-(4-(2-hydroxypropan-2-yl)-1-(phenyl(tetrahydro-2H-pyran-4-yl)methyl)-1H-indol-2-yl)-1-methyl-1H-pyrrolo[2,3-c]pyridin-7-ol | M + H$^+$ = 496.6 |
| 118 | 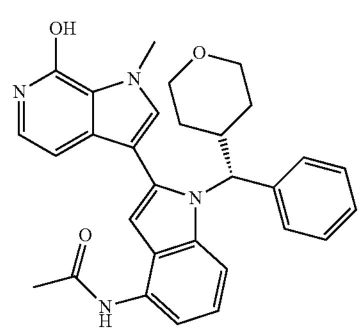 [SMILES: CC(=O)Nc1cccc2c1cc(-c1cn(C)c3c(O)nccc13)n2[C@@H](c1ccccc1)C1CCOCC1] | (R)-N-(2-(7-hydroxy-1-methyl-1H-pyrrolo[2,3-c]pyridin-3-yl)-1-(phenyl(tetrahydro-2H-pyran-4-yl)methyl)-1H-indol-4-yl)acetamide | M + H$^+$ = 495.6 |

TABLE 1-continued

Structures and chemical characterization

| Compound | Structure | Chemical name | Chemical characterization |
|---|---|---|---|
| 119 | 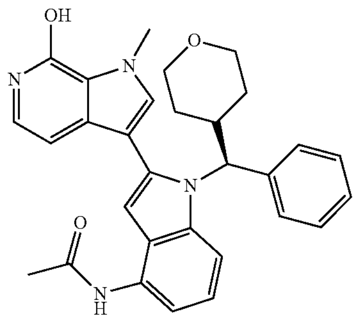 [SMILES: CC(=O)Nc1cccc2c1cc(-c1cn(C)c3c(O)nccc13)n2[C@H](c1ccccc1)C1CCOCC1] | (S)-N-(2-(7-hydroxy-1-methyl-1H-pyrrolo[2,3-c]pyridin-3-yl)-1-(phenyl(tetrahydro-2H-pyran-4-yl)methyl)-1H-indol-4-yl)acetamide | M + H⁺ = 495.6 |
| 120 | 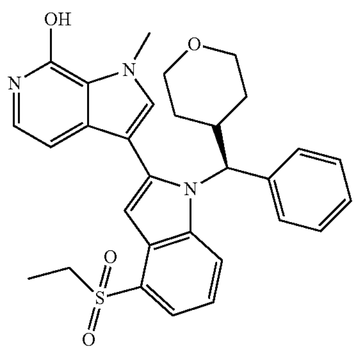 [SMILES: CCS(=O)(=O)c1cccc2c1cc(-c1cn(C)c3c(O)nccc13)n2[C@H](c1ccccc1)C1CCOCC1] | (S)-3-(4-(ethylsulfonyl)-1-(phenyl(tetrahydro-2H-pyran-4-yl)methyl)-1H-indol-2-yl)-1-methyl-1H-pyrrolo[2,3-c]pyridin-7-ol | M + H⁺ = 530.6 |
| 121 | 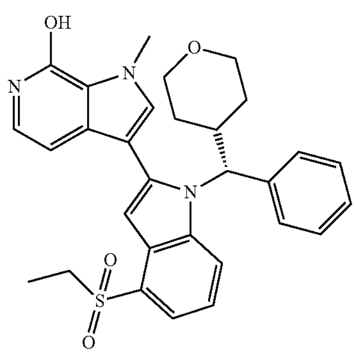 [SMILES: CCS(=O)(=O)c1cccc2c1cc(-c1cn(C)c3c(O)nccc13)n2[C@@H](c1ccccc1)C1CCOCC1] | (R)-3-(4-(ethylsulfonyl)-1-(phenyl(tetrahydro-2H-pyran-4-yl)methyl)-1H-indol-2-yl)-1-methyl-1H-pyrrolo[2,3-c]pyridin-7-ol | M + H⁺ = 530.6 |
| 122 | 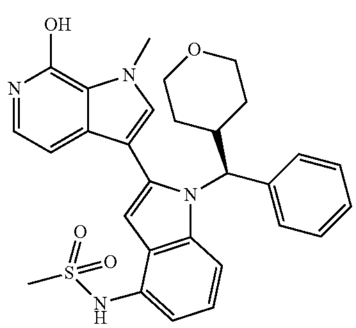 [SMILES: Cn1cc(-c2cc3c(NS(C)(=O)=O)cccc3n2[C@H](c2ccccc2)C2CCOCC2)c2ccnc(O)c21] | (S)-N-(2-(7-hydroxy-1-methyl-1H-pyrrolo[2,3-c]pyridin-3-yl)-1-(phenyl(tetrahydro-2H-pyran-4-yl)methyl)-1H-indol-4-yl)methanesulfonamide | M + H⁺ = 531.6 |

TABLE 1-continued

Structures and chemical characterization

| Compound | Structure | Chemical name | Chemical characterization |
|---|---|---|---|
| 123 | 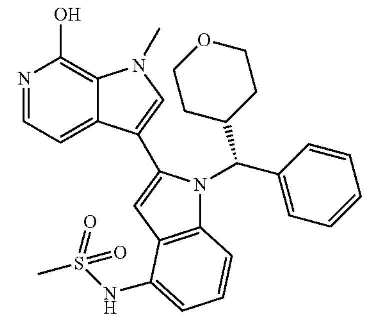 [SMILES: Cn1cc(-c2cc3c(NS(C)(=O)=O)cccc3n2[C@@H](c2ccccc2)C2CCOCC2)c2ccnc(O)c21] | (R)-N-(2-(7-hydroxy-1-methyl-1H-pyrrolo[2,3-c]pyridin-3-yl)-1-(phenyl(tetrahydro-2H-pyran-4-yl)methyl)-1H-indol-4-yl)methanesulfonamide | M + H$^+$ = 531.6 |
| 124 | 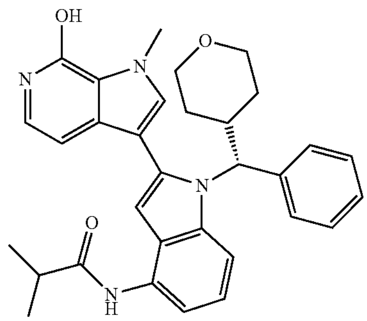 [SMILES: CC(C)C(=O)Nc1cccc2c1cc(-c1cn(C)c3c(O)nccc13)n2[C@@H](c1ccccc1)C1CCOCC1] | (R)-N-(2-(7-hydroxy-1-methyl-1H-pyrrolo[2,3-c]pyridin-3-yl)-1-(phenyl(tetrahydro-2H-pyran-4-yl)methyl)-1H-indol-4-yl)isobutyramide | M + H$^+$ = 523.6 |
| 125 | 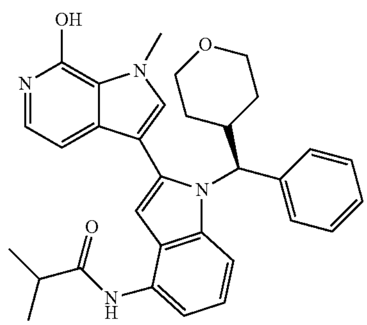 [SMILES: CC(C)C(=O)Nc1cccc2c1cc(-c1cn(C)c3c(O)nccc13)n2[C@H](c1ccccc1)C1CCOCC1] | (S)-N-(2-(7-hydroxy-1-methyl-1H-pyrrolo[2,3-c]pyridin-3-yl)-1-(phenyl(tetrahydro-2H-pyran-4-yl)methyl)-1H-indol-4-yl)isobutyramide | M + H$^+$ = 523.6 |
| 126 | 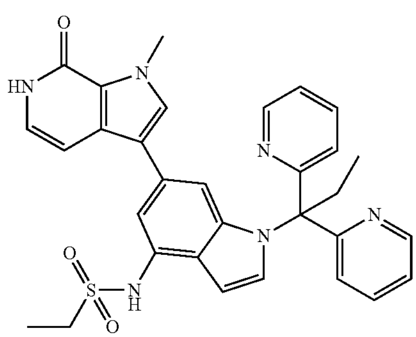 [SMILES: CCC(c1ccccn1)(c1ccccn1)n1ccc2c(NS(=O)(=O)CC)cc(-c3cn(C)c4c(=O)[nH]ccc34)cc21] | N-(1-(1,1-di(pyridin-2-yl)propyl)-6-(1-methyl-7-oxo-6,7-dihydro-1H-pyrrolo[2,3-c]pyridin-3-yl)-1H-indol-4-yl)ethanesulfonamide | M + H$^+$ = 567.7<br>$^1$H NMR (400 MHz, Methanol-d$_4$) δ 8.93 (dd, J = 5.4, 1.7 Hz, 2H), 8.13 (td, J = 8.0, 1.7 Hz, 2H), 8.07 (s, 0H), 7.95 (d, J = 3.6 Hz, 1H), 7.75 (dd, J = 7.6, 5.3 Hz, 2H), 7.25 (d, J = 1.2 Hz, 1H), 7.21 (d, J = 8.2 Hz, 2H), 7.09 (d, J = 3.5 Hz, 1H), 7.05 (s, 1H), 6.80 (d, J = 7.0 Hz, 1H), 6.05 (s, 1H), 5.76 (d, J = 7.0 Hz, 1H), 4.03 (s, 3H), 3.17 (q, J = 7.4 Hz, 2H), 2.96 (q, J = 7.3 Hz, 2H), 1.37 (t, J = 7.4 Hz, 3H), 0.84 (t, J = 7.2 Hz, 3H). |

TABLE 1-continued

Structures and chemical characterization

| Compound | Structure | Chemical name | Chemical characterization |
|---|---|---|---|
| | | | $^{13}$C NMR (101 MHz, MeOD) δ 164.43, 160.54, 157.97, 146.03, 144.01, 138.05, 132.24, 131.24, 131.17, 130.66, 128.01, 126.27, 125.76, 125.70, 124.61, 124.02, 118.85, 114.61, 108.95, 102.23, 101.95, 68.48, 47.17, 38.39, 36.07, 8.98, 8.63. |
| 127 | 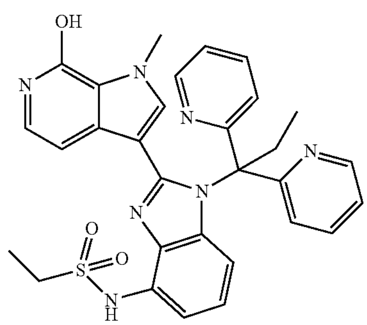 [SMILES: CCC(c1ccccn1)(c1ccccn1)n1c(-c2cn(C)c3c(O)nccc23)nc2c(NS(=O)(=O)CC)cccc21] | N-(1-(1,1-di(pyridin-2-yl)propyl)-2-(7-hydroxy-1-methyl-1H-pyrrolo[2,3-c]pyridin-3-yl)-1H-benzo[d]imidazol-4-yl)ethanesulfonamide | M + H$^+$ = 568.7 |
| 128 | 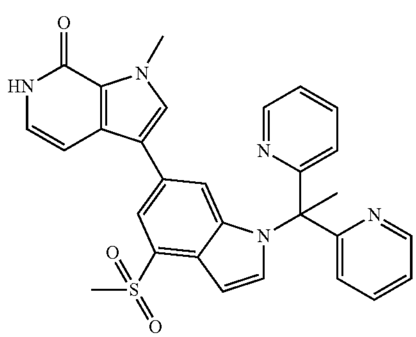 [SMILES: Cn1cc(-c2cc(S(C)(=O)=O)c3ccn(C(C)(c4ccccn4)c4ccccn4)c3c2)c2cc[nH]c(=O)c21] | 3-(1-(1,1-di(pyridin-2-yl)ethyl)-4-(methylsulfonyl)-1H-indol-6-yl)-1-methyl-1,6-dihydro-7H-pyrrolo[2,3-c]pyridin-7-one | M + H$^+$ = 524.6 |
| 129 | 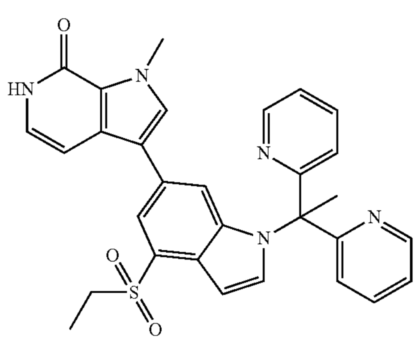 [SMILES: CCS(=O)(=O)c1cc(-c2cn(C)c3c(=O)[nH]ccc23)cc2c1ccn2C(C)(c1ccccn1)c1ccccn1] | 3-(1-(1,1-di(pyridin-2-yl)ethyl)-4-(ethylsulfonyl)-1H-indol-6-yl)-1-methyl-1,6-dihydro-7H-pyrrolo[2,3-c]pyridin-7-one | M + H$^+$ = 538.6 |

TABLE 1-continued

Structures and chemical characterization

| Compound | Structure | Chemical name | Chemical characterization |
|---|---|---|---|
| 130 | 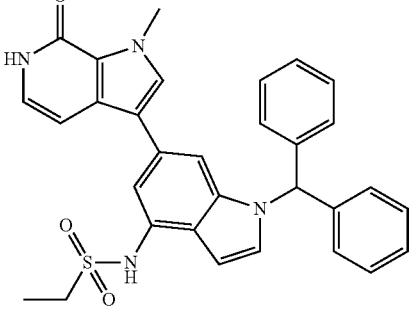 | N-(1-benzhydryl-6-(1-methyl-7-oxo-6,7-dihydro-1H-pyrrolo[2,3-c]pyridin-3-yl)-1H-indol-4-yl)ethanesulfonamide | M + H⁺ = 537.6<br>¹H NMR (400 MHz, DMSO-d₆) δ 10.93 (d, J = 5.6 Hz, 1H), 9.68 (s, 1H), 7.47 (s, 1H), 7.43-7.30 (m, 7H), 7.24 (d, J = 1.2 Hz, 1H), 7.22-7.15 (m, 5H), 6.97 (d, J = 3.3 Hz, 1H), 6.87-6.80 (m, 2H), 6.36 (dd, J = 7.0, 1.1 Hz, 1H), 4.09 (s, 3H), 3.09 (q, J = 7.3 Hz, 2H), 1.22 (t, J = 7.3 Hz, 3H).<br>¹³C NMR (101 MHz, DMSO) δ 155.86, 139.87, 137.65, 130.23, 129.14, 128.76, 128.29, 128.18, 127.87, 126.60, 125.21, 123.35, 120.67, 117.32, 111.56, 105.63, 99.63, 99.44, 62.64, 45.48, 35.35, 8.23. |
| 131 | 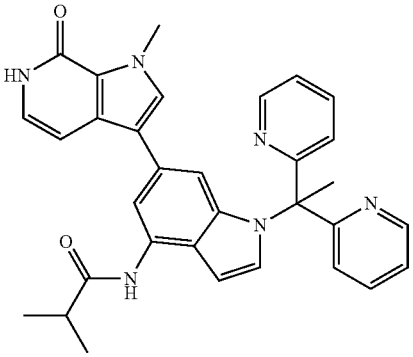 [SMILES: CC(C)C(=O)Nc1cc(-c2cn(C)c3c(=O)[nH]ccc23)cc2c1ccn2C(C)(c1ccccn1)c1ccccn1] | N-(1-(1,1-di(pyridin-2-yl)ethyl)-6-(1-methyl-7-oxo-6,7-dihydro-1H-pyrrolo[2,3-c]pyridin-3-yl)-1H-indol-4-yl)isobutyramide | M + H⁺ = 531.6<br>¹H NMR (400 MHz, Acetone-d₆) δ 10.11 (s, 1H), 8.89 (s, 1H), 8.64 (ddd, J = 4.7, 1.9, 0.9 Hz, 2H), 8.10 (s, 1H), 7.76 (td, J = 7.8, 1.9 Hz, 2H), 7.35 (ddd, J = 7.6, 4.7, 1.1 Hz, 2H), 7.23 (dt, J = 8.1, 1.1 Hz, 2H), 7.12 (s, 1H), 7.00 (d, J = 3.5 Hz, 1H), 6.87 (d, J = 7.1 Hz, 1H), 6.76 (dd, J = 3.5, 0.9 Hz, 1H), 6.47 (t, J = 1.1 Hz, 1H), 6.08 (d, J = 7.1 Hz, 1H), 4.13 (s, 3H), 2.82 (m, 1H), 2.53 (s, 3H), 1.22 (d, J = 6.8 Hz, 6H).<br>¹³C NMR (101 MHz, Acetone) δ 176.20, 162.72, 157.10, 149.88, 138.09, 137.46, 132.62, 132.04, 129.53, 128.86, 127.58, 125.47, 124.62, 123.84, 123.47, 121.35, 119.77, 111.77, 108.75, 100.94, 98.92, 71.15, 36.36, 35.72, 27.93, 20.18. |

TABLE 1-continued

Structures and chemical characterization

| Compound | Structure | Chemical name | Chemical characterization |
|---|---|---|---|
| 132 | 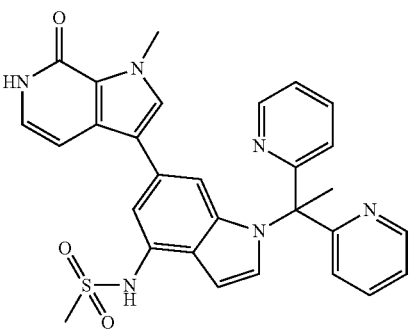 [SMILES: Cn1cc(-c2cc(NS(C)(=O)=O)c3ccn(C(C)(c4ccccn4)c4ccccn4)c3c2)c2cc[nH]c(=O)c21] | N-(1-(1,1-di(pyridin-2-yl)ethyl)-6-(1-methyl-7-oxo-6,7-dihydro-1H-pyrrolo[2,3-c]pyridin-3-yl)-1H-indol-4-yl)methanesulfonamide | M + H$^+$ = 539.6 $^1$H NMR (400 MHz, DMSO-d$_6$) δ 10.91 (d, J = 5.6 Hz, 1H), 9.62 (s, 1H), 8.63 (ddd, J = 4.8, 1.9, 0.9 Hz, 2H), 7.79 (td, J = 7.8, 1.9 Hz, 2H), 7.38 (ddd, J = 7.6, 4.8, 1.1 Hz, 2H), 7.24 (s, 1H), 7.17 (dd, J = 8.1, 1.0 Hz, 2H), 7.11 (d, J = 3.5 Hz, 1H), 7.09 (d, J = 1.2 Hz, 1H), 6.83 (d, J = 3.4 Hz, 1H), 6.79-6.75 (m, 1H), 6.33 (s, 1H), 5.80-5.74 (m, 1H), 4.04 (s, 3H), 3.03 (s, 3H), 2.43 (s, 3H). $^{13}$C NMR (101 MHz, DMSO) δ 161.12, 155.77, 148.92, 137.05, 136.96, 130.45, 128.90, 127.87, 127.50, 127.41, 125.06, 123.16, 122.79, 122.53, 122.17, 117.20, 111.94, 108.24, 99.45, 99.12, 69.89, 35.25, 30.69, 27.93. |

In some aspects, the pyridinone-based compound(s) and/or derivative(s) thereof can specifically bind a bromodomain. In some aspects, the pyridinone-based compound(s) and/or derivative(s) thereof can specifically bind a BRD or BET protein. In some aspects, the pyridinone-based compound(s) and/or derivative(s) thereof can specifically bind a bromodomain of a BRD or BET protein. In some aspects, the pyridinone-based compound(s) and/or derivative(s) thereof can modulate the activity of a BRD and/or BET protein. In some aspects, the pyridinone-based compound(s) and/or derivative(s) thereof can decrease, inhibit, and/or eliminate the activity of a BRD or BET protein. In some aspects, the pyridinone-based compound(s) and/or derivative(s) thereof can specifically bind a BRD and/or BET protein and can modulate the activity of the BRD and/or BET protein. In some aspects, the pyridinone-based compound(s) and/or derivative(s) thereof can specifically bind a BRD and/or BET protein can decrease, inhibit, and/or eliminate the activity of the BRD and/or BET protein. In some aspects, these functionalities of the pyridinone-based compound(s) and/or derivative(s) thereof can be maintained when included in a pharmaceutical formulation as described elsewhere herein.

Pharmaceutical Formulations

The pyridinone-based compounds (e.g. any compound having a structure according to anyone of Formulas I-XX or any other compound or formula described herein) described herein can be included as an ingredient, such as an active ingredient, in a pharmaceutical formulation, which can include but is not limited to any pharmaceutical formulation and/or derivative thereof (e.g. such as pharmaceutically acceptable salts thereof and prodrugs thereof). As such, also described are pharmaceutical formulations containing one or more of the compounds, and/or pharmaceutically acceptable salts, and/or prodrugs thereof described herein. Suitable salts include, but are not limited to, sulfate, citrate, acetate, oxalate, chloride, hydrochloride, bromide, hydrobromide, iodide, nitrate, bisulfate, phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, napthalenesulfonate, propionate, malonate, mandelate, malate, phthalate, and pamoate. The pharmaceutical formulation can contain a racemic mixture of one or more pyridinone-based compounds. The pharmaceutical formulations can contain enatiomerically pure amount of a pyridinone-based compound. The pharmaceutical formulations described herein can include an effective amount of any one or more of the pyridinone-based compounds described herein.

The pharmaceutical formulations described herein can be administered to a subject in need thereof. In some aspects, the subject can have or be suspected of having a cancer or other disease that histone modifications can be modulated to treat and/or prevent a disease and/or a symptom thereof, which can include, but is not limited to, arthritis, lupus, pulmonary arterial hypertension, heart remodeling, and/or a neurodegenerative disease.

Pharmaceutically Acceptable Carriers and Auxiliary Ingredients and Agents

The pharmaceutical formulations containing an amount of a pyridinone-based compound described herein (e.g. compounds having a structure according to any one of Formulas 1-XX or any other formula described herein) and/or a derivative thereof can further include a pharmaceutically acceptable carrier. Suitable pharmaceutically acceptable carriers include, but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations and derivatives thereof described herein can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active corn pound.

In addition to an amount, such as an effective amount, of a pyridinone-based compound and/or derivative thereof described herein, the pharmaceutical formulations can also include an effective amount of one or more auxiliary active agents, including but not limited to, antisense or RNA interference molecules, chemotherapeutics, or antineoplastic agents, hormones, antibiotics, antivirals, immunomodulating agents, antinausea, pain modifying compounds (such as opiates), anti-inflammatory agents, antipyretics, antibiotics, and/or antibodies or fragments thereof.

In some aspects the auxiliary active agent is a conventional chemotherapeutic agent or pharmaceutical formulation thereof. Chemotherapeutic agents can include busulfan, improsulfan, piposulfan, benzodepa, carboquone, meturedepa, uredepa, altretamine, triethylenemelamine, trietylenephosphoramide, triethiylenethiophosphoramide, trimethylolomelamine, chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, dacarbazine, mannomustine, mitobronitol, mitolactol, pipobroman, aclacinomycins, actinomycin F(1), anthramycin, azaserine, bleomycin, cactinomycin, carubicin, carzinophilin, chromomycin, dactinomycin, daunorubicin, daunomycin, 6-diazo-5-oxo-1-norleucine, doxorubicin, epirubicin, mitomycin C, mycophenolic acid, nogalamycin, olivomycin, peplomycin, plicamycin, porfiromycin, puromycin, streptonigrin, streptozocin, tubercidin, ubenimex, zinostatin, zorubicin, denopterin, methotrexate, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, fluoruracil, tegafur, L-asparaginase, pulmozyme, aceglatone, aldophosphamide glycoside, aminolevulinic acid, amsacrine, bestrabucil, bisantrene, carboplatin, cisplatin, defofamide, demecolcine, diaziquone, eflornithine, elliptinium acetate, etoglucid, etoposide, flutamide, gallium nitrate, hydroxyurea, interferon-alpha, interferon-beta, interferon-gamma, interleukin-2, lentinan, lonidamine, mitoguazone, mitoxantrone, mopidamol, nitracrine, pentostatin, phenamet, pirarubicin, podophyllinic acid, 2-ethylhydrazide, procarbazine, razoxane, sizofiran, spirogermanium, paclitaxel, tamoxifen, teniposide, tenuazonic acid, triaziquone, 2,2',2"-trichlorotriethylamine, urethan, vinblastine, vincristine, vindesine, and combinations thereof.

Effective Amounts of the Pyridinone-Based Compounds, Derivatives Thereof, and/or Auxiliary Active Agents The amount of the pyridinone-based compounds included in the pharmaceutical formulation or derivative thereof can be an effective amount. Where an auxiliary active agent is included, the amount included in the pharmaceutical formulation or derivative thereof can be an effective amount of the auxiliary active agent. The effective amount of the pyridinone-based compound (e.g. compounds having a structure according to any one of Formulas I-XX or any other formula or described herein) or a derivative thereof contained in the pharmaceutical formulation can range from about 0.001 micrograms to about 1000 grams. In some aspects, the effective amount of the compound and/or derivative thereof can range from about 0.001 micrograms to about 0.01 micrograms. In other aspects, the effective amount of compound and/or derivative thereof can range from about 0.01 micrograms to about 0.1 micrograms. In further aspects, the effective amount of the compound and/or derivative thereof can range from about 0.1 micrograms to about 1.0 grams. In yet further aspects, the effective amount of the compound and/or derivative thereof can range from about 1.0 grams to about 10 grams. In other aspects, the effective amount of the compound and/or derivative thereof can range from about 10 grams to about 100 grams. In still other aspects, the effective amount of the compound and/or derivative thereof can range from about 100 grams to about 1000 grams. The amount(s) administered can be calculated based on the free or salt form of the pyridinone-based compound or derivative thereof.

In aspects where an auxiliary active agent is included with the pyridinone-based compound or derivative thereof in the pharmaceutical formulation, the effective amount of the auxiliary active agent will vary depending on, for example, the auxiliary active agent and/or the amount of the pyridinone-based compound. In some aspects, the effective amount of the auxiliary active agent can range from 0.001 micrograms to about 1000 grams. In other aspects, the effective amount of the auxiliary active agent can range from about 0.01 IU to about 1000 IU. In further aspects, the effective amount of the auxiliary active agent can range from 0.001 mL to about 1000 mL. In yet other aspects, the effective amount of the auxiliary active agent can range from about 0% w/w to about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88% to about 90% or more w/w, v/v, or w/v of the total pharmaceutical formulation.

The auxiliary active agent can be included in the same pharmaceutical formulation as the pyridinone-based compound or can exist as a stand-alone compound or pharmaceutical formulation that can be administered to a subject simultaneously, contemporaneously, or sequentially with a pyridinone-based compound, derivative thereof, or pharmaceutical formulation thereof. In aspects where the auxiliary active agent is a stand-alone compound or pharmaceutical formulation separate from the pyridinone-based compound, the effective amount of the auxiliary active agent can vary depending on the auxiliary active agent used. In some of these aspects, the effective amount of the auxiliary active agent can range from 0.001 micrograms to about 1000 grams. In other aspects, the effective amount of the auxiliary active agent can range from about 0.01 IU to about 1000 IU. In further aspects, the effective amount of the auxiliary active agent can range from 0.001 mL to about 1000 mL. The amount(s) administered can be calculated based on the free or salt form of the auxiliary active agent.

Dosage Forms

In some aspects, the pharmaceutical formulation or derivative thereof described herein can be in a dosage form. The dosage form can be administered to a subject in need thereof. In some aspects, the subject in need thereof has or is suspected of having a cancer or other disease that histone modifications can be modulated to treat and/or prevent a disease and/or a symptom thereof, which can include, but is not limited to, arthritis, lupus, pulmonary arterial hypertension, heart remodeling, and/or a neurodegenerative disease.

The dosage forms can be adapted for administration by any appropriate route. Appropriate routes include, but are not limited to, oral (including buccal or sublingual), rectal, intraocular, inhaled, intranasal, topical (including buccal, sublingual, or transdermal), vaginal, parenteral, subcutaneous, intramuscular, intravenous, internasal, and intradermal. Such formulations can be prepared by any method known in the art.

Dosage forms adapted for oral administration can discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some aspects, the pharmaceutical formulations adapted for oral administration also include one or more agents which flavor, preserve, color, or help disperse the pharmaceutical formulation. Dosage forms prepared for oral administration can also be in the form of a liquid solution that can be delivered as a foam, spray, or liquid solution. The oral dosage form can be administered to a subject in need thereof. In some aspects, the subject in need thereof can have or be suspected of having a cancer or other disease that histone modifications can be modulated to treat and/or prevent a disease and/or a symptom thereof, which can include, but is not limited to, arthritis, lupus, pulmonary arterial hypertension, heart remodeling, and/or a neurodegenerative disease.

Where appropriate, the dosage forms described herein can be microencapsulated. The dosage form can also be prepared to prolong or sustain the release of any ingredient. In some aspects, the compound or derivative thereof is the ingredient whose release is delayed. In other aspects, the release of an auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Where appropriate, the dosage forms described herein can be a liposome. In these aspects, compound, derivative thereof, auxiliary active ingredient, and/or pharmaceutically acceptable salt thereof are incorporated into a liposome. In some aspects, a compound, derivative thereof, auxiliary active ingredient, and/or pharmaceutically acceptable salts thereof is integrated into the lipid membrane of the liposome. In other aspects, a compound, derivative thereof, auxiliary active ingredient, and/or pharmaceutically acceptable salt thereof are contained in the aqueous phase of the liposome. In aspects where the dosage form is a liposome, the pharmaceutical formulation is thus a liposomal formulation. The liposomal formulation can be administered to a subject in need thereof. In some aspects, the subject in need thereof can have or be suspected of having a cancer or other disease that histone modifications can be modulated to treat and/or prevent a disease and/or a symptom thereof, which can include, but is not limited to, arthritis, lupus, pulmonary arterial hypertension, heart remodeling, and/or a neurodegenerative disease.

Dosage forms adapted for topical administration can be formulated as ointments, creams, suspensions, lotions, powders, solutions, pastes, gels, sprays, aerosols, or oils. In some aspects for treatments of the eye or other external tissues, for example the mouth or the skin, the pharmaceutical formulations are applied as a topical ointment or cream. When formulated in an ointment, the compound, derivative thereof, auxiliary active ingredient, and/or pharmaceutically acceptable salt thereof can be formulated with a paraffinic or water-miscible ointment base. In other aspects, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some aspects, the compound, derivative thereof, auxiliary active ingredient, and/or pharmaceutically acceptable salt thereof in a dosage form adapted for inhalation is in a particle-size-reduced form that is obtained or obtainable by micronization. In some aspects, the particle size of the size reduced (e.g. micronized) compound or salt or solvate thereof, is defined by a $D_{50}$ value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient, which may be generated by various types of metered dose pressurized aerosols, nebulizers, or insufflators. The nasal/inhalation formulations can be administered to a subject in need thereof. In some aspects, the subject in need thereof can have or be suspected of having a cancer or other disease that histone modifications can be modulated to treat and/or prevent a disease and/or a symptom thereof, which can include, but is not limited to, arthritis, lupus, pulmonary arterial hypertension, heart remodeling, and/or a neurodegenerative disease.

In some aspects, the dosage forms are aerosol formulations suitable for administration by inhalation. In some of these aspects, the aerosol formulation contains a solution or fine suspension of a compound, derivative thereof, auxiliary active ingredient, and/or pharmaceutically acceptable salt thereof a pharmaceutically acceptable aqueous or non-aqueous solvent. Aerosol formulations can be presented in single or multi-dose quantities in sterile form in a sealed container. For some of these aspects, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other aspects are contained in a pump-atomizer. The pressurized aerosol formulation can also contain a solution or a suspension of a compound, derivative thereof, auxiliary active ingredient, and/or pharmaceutically acceptable salt thereof. In further aspects, the aerosol formulation also contains co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses are delivered each time. The aerosol formulations can be administered to a subject in need thereof. In some aspects, the subject in need thereof can have or be suspected of having a cancer or other disease that histone modifications can be modulated to treat and/or prevent a disease and/or a symptom thereof, which can include, but is not limited to, arthritis, lupus, pulmonary arterial hypertension, heart remodeling, and/or a neurodegenerative disease.

For some dosage forms suitable and/or adapted for inhaled administration, the pharmaceutical formulation is a dry powder inhalable formulations. In addition to the compound, derivative thereof, auxiliary active ingredient, and/or pharmaceutically acceptable salt thereof, such a dosage form can contain a powder base such as lactose, glucose, trehalose, manitol, and/or starch. In some of these aspects, the compound, derivative thereof, auxiliary active ingredient, and/or pharmaceutically acceptable salt thereof is in a particle-size reduced form. In further aspects, a performance modifier, such as L-leucine or another amino acid, cellobiose octaacetate, and/or metals salts of stearic acid, such as magnesium or calcium stearate.

In some aspects, the aerosol formulations are arranged so that each metered dose of aerosol contains a predetermined amount of an active ingredient, such as the one or more of the pyridinone-based compounds described herein.

Dosage forms adapted for vaginal administration can be presented as pessaries, tampons, creams, gels, pastes, foams, or spray formulations. Dosage forms adapted for rectal administration include suppositories or enemas. The vaginal formulations can be administered to a subject in need thereof. In some aspects, the subject in need thereof can have or be suspected of having a cancer or other disease that histone modifications can be modulated to treat and/or prevent a disease and/or a symptom thereof, which can include, but is not limited to, arthritis, lupus, pulmonary arterial hypertension, heart remodeling, and/or a neurodegenerative disease.

Dosage forms adapted for parenteral administration and/or adapted for injection can include aqueous and/or non-aqueous sterile injection solutions, which can contain antioxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and re-suspended in a sterile carrier to reconstitute the dose prior to administration. Extemporaneous injection solutions and suspensions can be prepared in some aspects, from sterile powders, granules, and tablets. The parenteral formulations can be administered to a subject in need thereof. In some aspects, the subject in need thereof can have or be suspected of having a cancer or other disease that histone modifications can be modulated to treat and/or prevent a disease and/or a symptom thereof, which can include, but is not limited to, arthritis, lupus, pulmonary arterial hypertension, heart remodeling, and/or a neurodegenerative disease.

For some aspects, the dosage form contains a predetermined amount of a compound and/or derivative thereof per unit dose. In an aspect, the predetermined amount of the compound or derivative thereof is an effective amount of the compound and/or derivative thereof to treat, prevent, or mitigate one or more symptoms of a cancer or other disease that histone modifications can be modulated to treat and/or prevent a disease and/or a symptom thereof, which can include, but is not limited to, arthritis, lupus, pulmonary arterial hypertension, heart remodeling, and/or a neurodegenerative disease. In other aspects, the predetermined amount of the compound and/or derivative thereof can be an appropriate fraction of the effective amount of the active ingredient. Such unit doses may therefore be administered once or more than once a day (e.g. 1, 2, 3, 4, 5, 6, or more times per day). Such pharmaceutical formulations can be prepared by any of the methods well known in the art.

Methods of Making the Compounds and Derivatives Thereof

The compounds (e.g. compounds having a structure according to any one of Formulas I-XX or any other formula or compound provided herein) and derivatives, such as salts, thereof can be synthesized via many methods generally known to those of ordinary skill in the art and others as provided elsewhere herein. The present disclosure is not intended to be limited by the particular methods of synthesizing the compounds described herein. The skilled artisan will recognize additional methods of synthesizing the compounds described herein.

The compounds described herein, including compounds of Formula (I) and specific examples, can be prepared by methodologies in the reaction schemes depicted in schemes 1-7.
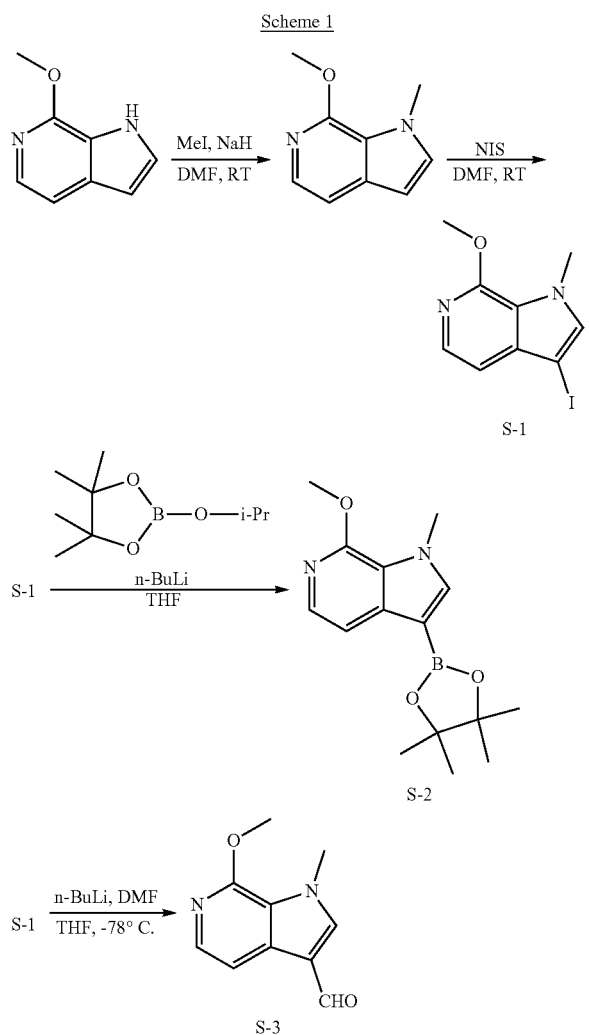
Scheme 1
Scheme 2
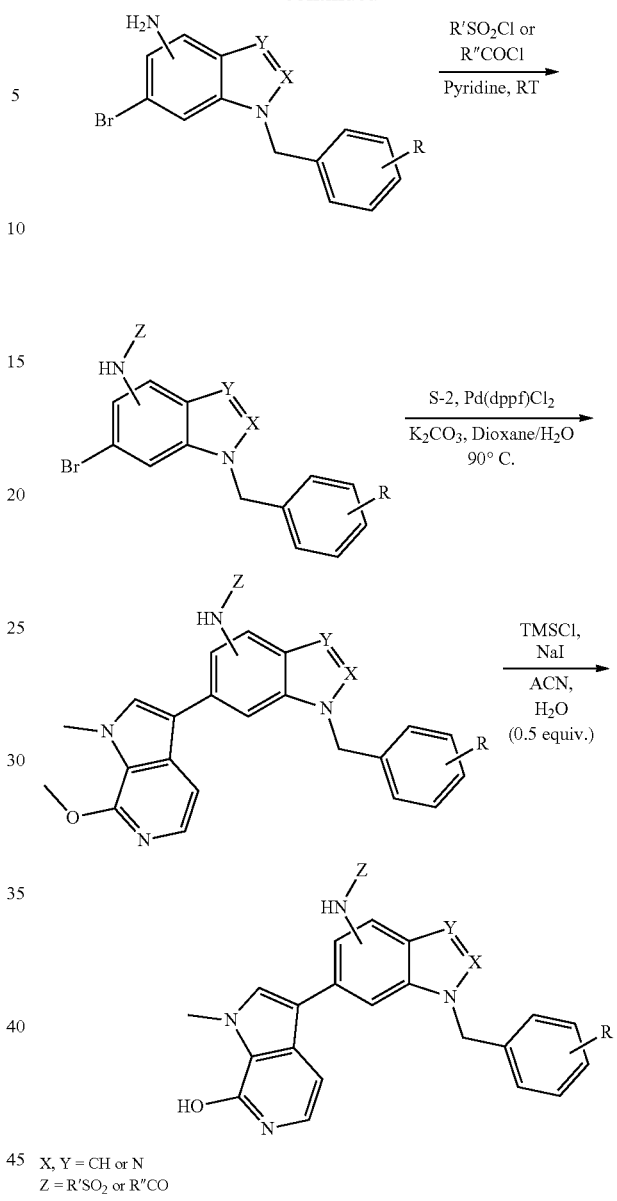
X, Y = CH or N
Z = R'SO₂ or R"CO
Scheme 3

141
-continued
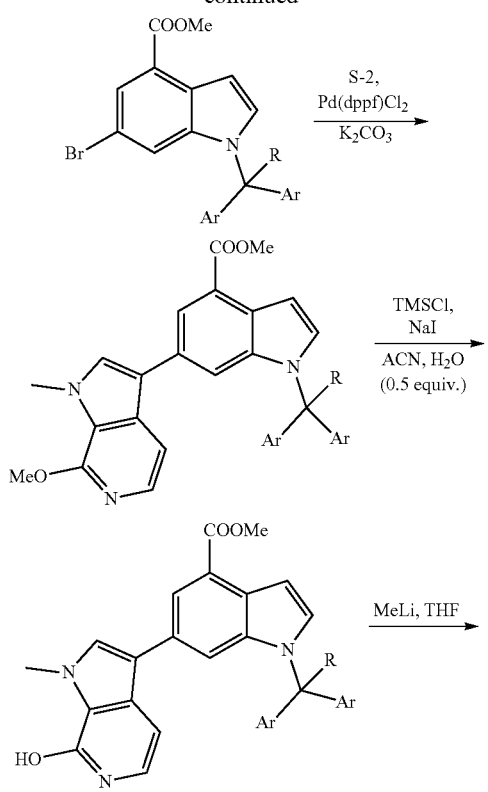
142
-continued
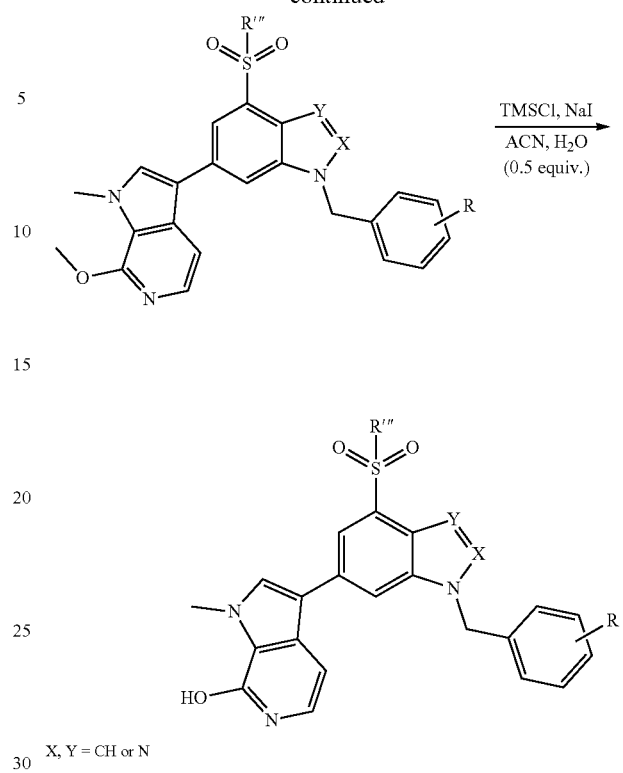
X, Y = CH or N
Scheme 5
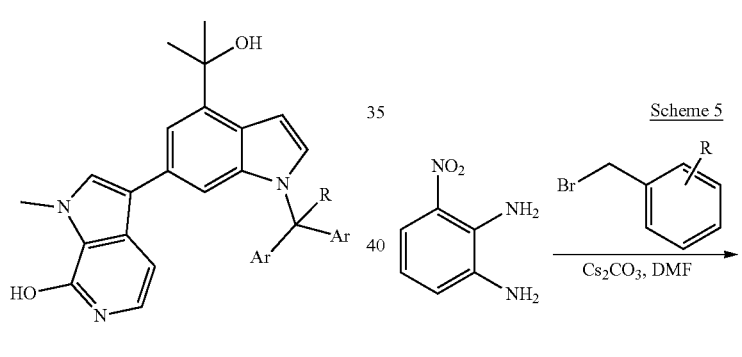
Scheme 4
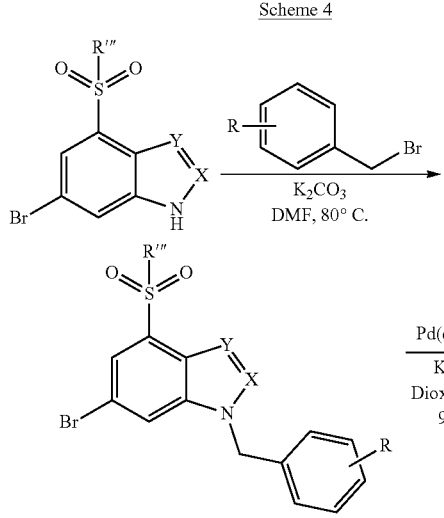
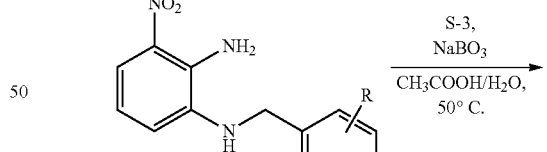
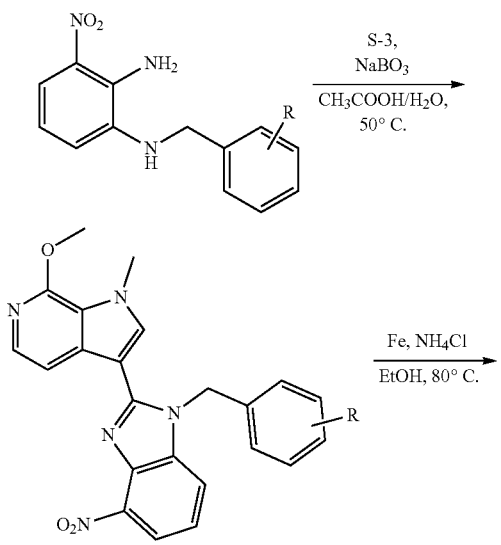

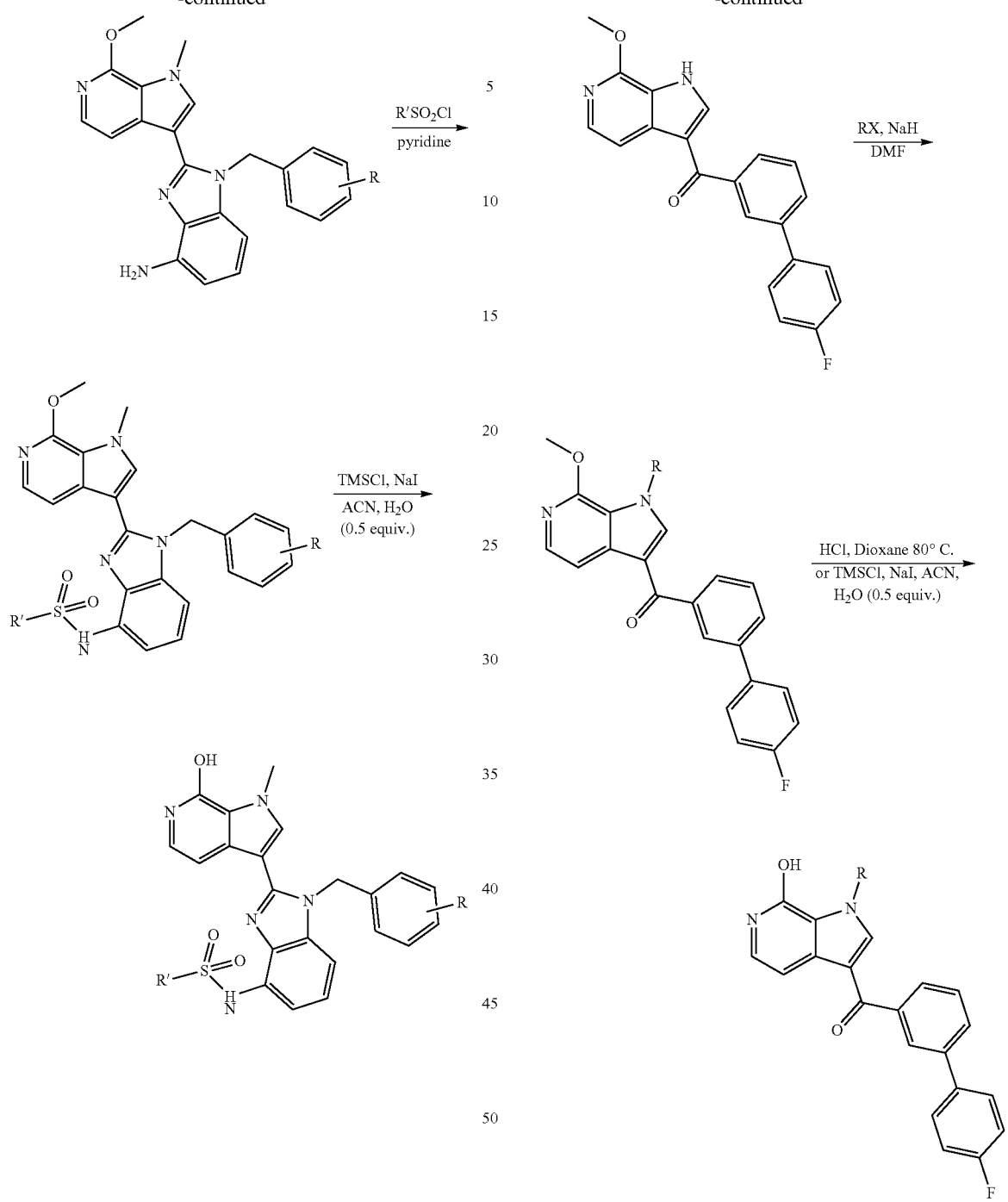
Scheme 6
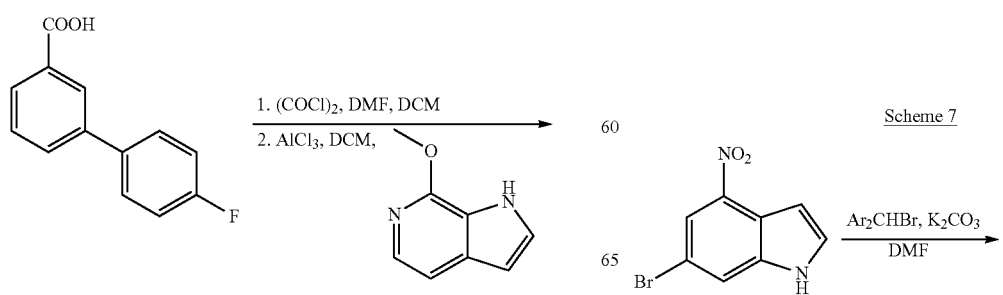
Scheme 7
X = Cl, Br, I

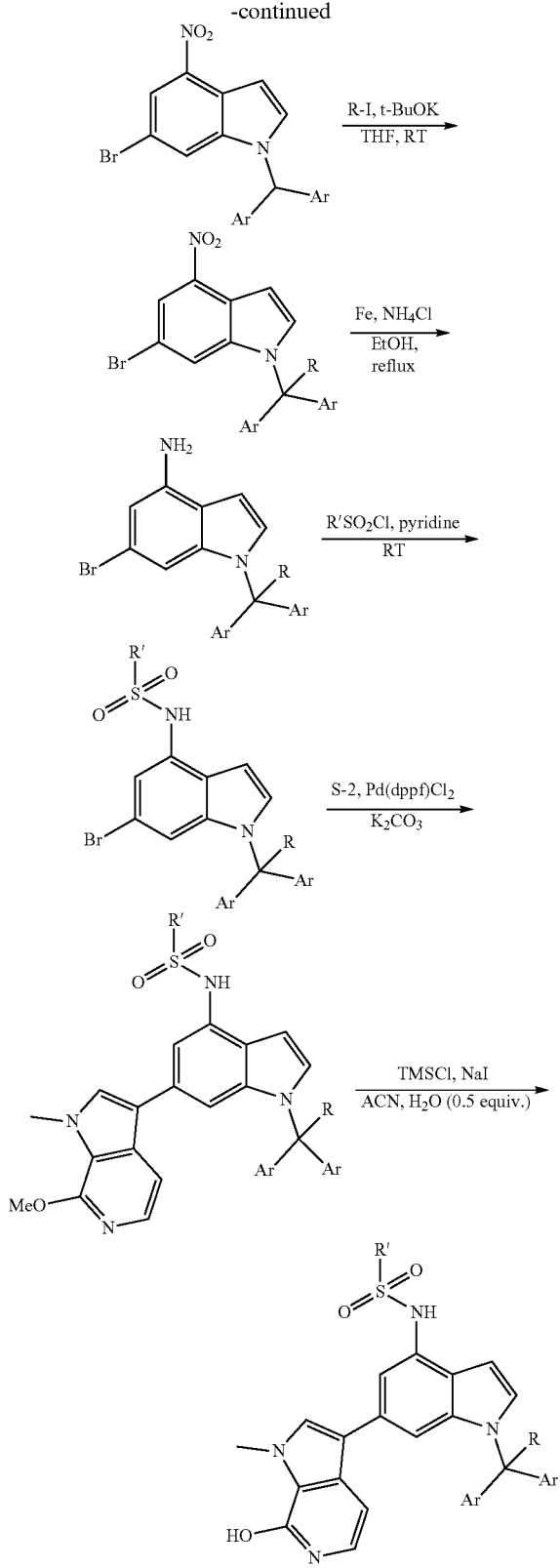

Methods of Using the Pyridinone-Based Compounds and Formulations Thereof

Any amount of the pyridinone-based compounds (e.g. compounds having a structure according to any one of Formulas I-XX or any other formula or compound provided herein) and derivatives thereof, and pharmaceutical formulations thereof described herein can be administered to a subject in need thereof one or more times per day, week, month, or year. In some aspects, the amount administered is the effective amount of the pyridinone-based compound(s), derivatives thereof, and/or pharmaceutical formulations thereof. For example, the pyridinone-based compound(s), derivative(s) thereof, and/or pharmaceutical formulation(s) thereof can be administered in a total daily dose. The total daily dose can be given in a single dose per day. In other aspects, the total daily dose can be administered over multiple doses per day, in which each dose can contain a fraction of the total daily dose to be administered (sub-doses). In some aspects, the amount of doses delivered per day can be 2, 3, 4, 5, 6 or more. In further aspects, the pyridinone-based compounds, derivatives thereof, and/or pharmaceutical formulations thereof can be administered to a subject one or more times per week, such as 1, 2, 3, 4, 5, or 6 times per week. In other aspects, the pyridinone-based compounds, derivatives thereof, and/or pharmaceutical formulations thereof are administered to a subject one or more times per month, such as 1, 2, 3, 4 to 5 or more times per month. In still further aspects, the pyridinone-based compounds, derivatives thereof, pharmaceutical formulations thereof can be administered to a subject one or more times per year, such as 1, 2, 3, 4, 5, 6, 7, 8, 9, 10 to 11 or more times per year.

In some aspects, the subject in need thereof to which the pyridinone-based compounds, derivatives thereof, and/or pharmaceutical formulations thereof can be administered can have or be suspected of having a cancer or other disease that histone modifications can be modulated to treat and/or prevent a disease and/or a symptom thereof, which can include, but is not limited to, arthritis, lupus, pulmonary arterial hypertension, heart remodeling, and/or a neurodegenerative disease.

In some aspects, the pyridinone-based compounds, derivatives thereof, and/or pharmaceutical formulations thereof can be used as a co-therapy or combination therapy with one or more other auxiliary active agents or treatment modalities. In some aspects, the pyridinone-based compounds, derivatives thereof, and/or pharmaceutical formulations thereof can be administered in simultaneously with, contemporaneously with, and/or sequentially with a conventional chemotherapeutic agent or pharmaceutical formulation thereof, radiation, and/or other cancer treatment modality.

In aspects where more than one of pyridinone-based compounds, derivatives thereof, pharmaceutical formulations thereof, additional therapeutic and/or auxiliary active agents or pharmaceutical formulations thereof, and/or other treatment modality are administered to a subject sequentially; the sequential administration may be close in time or remote in time. For example, administration of the second compound, formulation, or other therapeutic agent or treatment modality can occur within seconds or minutes (up to about 1 hour) after administration of the first agent (close in time). In other aspects, administration of the second compound, formulation, other therapeutic agent, and/or other treatment modality occurs at some other time that is more than an hour after administration of the first agent administered. In some aspects, the pyridinone-based compound(s), derivative(s) thereof, and/or pharmaceutical formulations thereof, and/or other treatment modality can be administered first before administration of an auxiliary active agent or therapeutic agent. In some aspects, the pyridinone-based compound(s), derivative(s) thereof, and/or pharmaceutical formulations thereof, and/or other treatment modality can be administered after administration of an auxiliary active agent.

The amount of pyridinone-based compound(s), derivative(s) thereof, and/or pharmaceutical formulation(s) thereof described herein can be administered in an amount ranging from about 0.001 mg to about 1000 mg per day, as calculated as the free or unsalted compound. In some aspects, the amount of pyridinone-based compound(s), derivative(s) thereof, and/or pharmaceutical formulation(s) thereof described herein can range from 0.001 mg/kg bodyweight to 1000 mg/kg bodyweight. In some aspects, the amount of pyridinone-based compound(s), derivative(s) thereof, and/or pharmaceutical formulation(s) thereof described herein can be about 0.1, 0.5, 1, 2, 3, 4, 5, 6, 7, 8, 9, 10, 11, 12, 13, 14, 15, 16, 17, 18, 19, 20, 25, 50, to about 100 mg/kg bodyweight. In some aspects, the amount administered is an effective amount when considered as a single dose or as a totality of sub-doses.

The pyridinone-based compounds, derivatives thereof, and/or pharmaceutical formulations thereof described herein can be administered in combinations with or include one or more other auxiliary agents or therapeutic compounds as discussed elsewhere herein. Suitable auxiliary agents include, but are not limited to antisense or RNA interference molecules, chemotherapeutics, anti-neoplasic agents, hormones, antibiotics, antivirals, immunomodulating agents, anti-nausea, pain modifying compounds (such as opiates), anti-inflammatory agents, antipyretics, antibiotics, and/or antibodies or fragments thereof. The compound(s), and/or formulation(s), and/or additional therapeutic agent(s) can be administered simultaneously or sequentially by any convenient route in separate or combined pharmaceutical formulations. The additional therapeutic agents can be provided in their optically pure form or a pharmaceutically acceptable salt thereof.

The pyridinone-based compound(s) and/or derivative(s) thereof described herein can be used in the manufacture of a medicament for treatment and/or prevention of a cancer or other disease that histone modifications can be modulated to treat and/or prevent a disease and/or a symptom thereof, which can include, but is not limited to, arthritis, lupus, pulmonary arterial hypertension, heart remodeling, and/or a neurodegenerative disease. The pyridinone-based compound(s) and/or derivative(s) thereof described herein can be for use in the treatment and/or prevention of a cancer or other disease that histone modifications can be modulated to treat and/or prevent a disease and/or a symptom thereof, which can include, but is not limited to, arthritis, lupus, pulmonary arterial hypertension, heart remodeling, and/or a neurodegenerative disease.

Kits

The pyridinone-based compounds (e.g. compounds having a structure according to any one of Formulas I-XX or any other compounds or formulas described herein), derivatives thereof, pharmaceutical formulations thereof described herein can be presented as a combination kit. As used herein, the terms "combination kit" or "kit of parts" refers to the any of the compounds, derivatives thereof, or pharmaceutical formulations described herein, and any additional components that are used to package, sell, market, deliver, and/or administer the combination of elements or a single element, such as the primary active ingredient, contained therein. Such additional components include but are not limited to, packaging, syringes, blister packages, bottles, and the like. When one or more of the components (e.g. active agents) contained in the kit are administered simultaneously, the combination kit can contain the active agents in a single pharmaceutical formulation (e.g. a tablet) or in separate pharmaceutical formulations.

When the agents are not administered simultaneously, the combination kit can contain each agent in separate pharmaceutical formulations. The separate pharmaceutical formulations can be contained in a single package or in separate packages within the kit.

In some aspects, the combination kit also includes instructions printed on or otherwise contained in a tangible medium of expression. The instructions can provide information regarding the content of the compound or pharmaceutical formulations contained therein, safety information regarding the content of the compound(s) or pharmaceutical formulation(s) contained therein, information regarding the dosages, indications for use, and/or recommended treatment regimen(s) for the compound(s) and/or pharmaceutical formulations contained therein. In some aspects, the instructions provide directions for administering the compounds, pharmaceutical formulations, or salts thereof to a subject in need thereof. The subject in need thereof can have or be suspected of having a cancer or other disease that histone modifications can be modulated to treat and/or prevent a disease and/or a symptom thereof, which can include, but is not limited to, arthritis, lupus, pulmonary arterial hypertension, heart remodeling, and/or a neurodegenerative disease.

In some aspects, the kit can include one or more auxiliary active agents in addition to a pyridinone-based compound, derivative thereof, or a pharmaceutical formulation thereof. In some aspects the auxiliary active agent is a conventional chemotherapeutic agent or pharmaceutical formulation thereof. Chemotherapeutic agents can include busulfan, improsulfan, piposulfan, benzodepa, carboquone, meturedepa, uredepa, altretamine, triethylenemelamine, trietylenephosphoramide, triethiylenethiophosphoramide, trimethylolomelamine, chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, dacarbazine, mannomustine, mitobronitol, mitolactol, pipobroman, aclacinomycins, actinomycin F(1), anthramycin, azaserine, bleomycin, cactinomycin, carubicin, carzinophilin, chromomycin, dactinomycin, daunorubicin, daunomycin, 6-diazo-5-oxo-1-norleucine, doxorubicin, epirubicin, mitomycin C, mycophenolic acid, nogalamycin, olivomycin, peplomycin, plicamycin, porfiromycin, puromycin, streptonigrin, streptozocin, tubercidin, ubenimex, zinostatin, zorubicin, denopterin, methotrexate, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, fluororacil, tegafur, L-asparaginase, pulmozyme, aceglatone, aldophosphamide glycoside, aminolevulinic acid, amsacrine, bestrabucil, bisantrene, carboplatin, cisplatin, defofamide, demecolcine, diaziquone, eflornithine, elliptinium acetate, etoglucid, etoposide, flutamide, gallium nitrate, hydroxyurea, interferon-alpha, interferon-beta, interferon-gamma, interleukin-2, lentinan, lonidamine, mitoguazone, mitoxantrone, mopidamol, nitracrine, pentostatin, phenamet, pirarubicin, podophyllinic acid, 2-ethylhydrazide, procarbazine, razoxane, sizofiran, spirogermanium, paclitaxel, tamoxifen, teniposide, tenuazonic acid, triaziquone, 2,2',2"-trichlorotriethylamine, urethan, vinblastine, vincristine, vindesine, and combinations thereof.

EXAMPLES

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of aspects of the present disclosure. The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Example 1

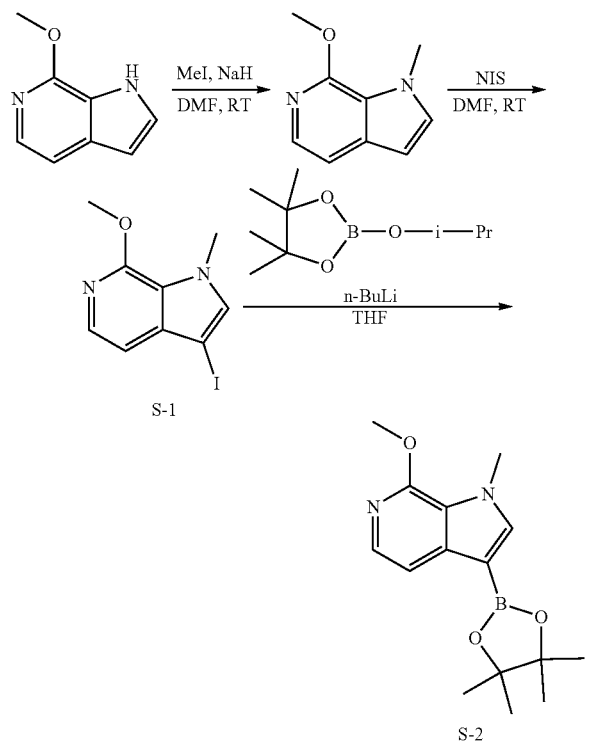

Scheme 8

7-methoxy-1-methyl-1H-pyrrolo[2,3-c]pyridine: To a solution of 7-methoxy-1H-pyrrolo[2,3-c]pyridine (5.00 g, 33.8 mmol) in 50 mL of DMF was added NaH (2.0 g, 50 mmol) at 0° C. The resulting solution was stirred for 30 min and then MeI (9.6 g, 67.6 mmol) was added. The reaction was stirred at room temperature for 24 hours. TLC (EtOAc/petroleum ether=1/5) showed the reaction was complete. The reaction was poured into 200 g of ice-water, extracted with EtOAc twice. The extracts were dried and concentrated to give 5.5 g of 7-methoxy-1-methyl-1H-pyrrolo[2,3-c]pyridine, which was used for the next step without further purification.

3-iodo-7-methoxy-1-methyl-1H-pyrrolo[2,3-c]pyridine: A solution of 7-methoxy-1-methyl-1H-pyrrolo[2,3-c]pyridine (5.5 g) and NIS (7.0 g, 40.6 mmol) in 100 mL of DMF was stirred at room temperature for 24 hours. TLC (EtOAc/petroleum ether=1/3) showed the reaction was complete. The reaction was poured into 200 mL water, extracted with EtOAc twice. The extracts were dried, concentrated and purified by column (EtOAc/petroleum ether=1/5) to give (S-1) (4.5 g, 46.4% yield) as a white solid.

7-methoxy-1-methyl-3-(4,4,5,5-tetramethyl-1,3,2-dioxaborolan-2-yl)-1H-pyrrolo[2,3-c]pyridine: To a solution of (S-1) (4.3 g, 14.9 mmol) in 70 mL of anhydrous THF was added n-BuLi (11.25 mL, 18 mmol) dropwise at −78 deg. After that, 2-Isopropoxy-4,4,5,5-tetramethyl-[1,3,2]dioxaborolane (4.2 g, 22.5 mmol) was added at the same temperature. The resulting solution was stirred at room temperature for 24 hours. The reaction was quenched by 30 mL of NH$_4$Cl (aq.), extracted with EtOAc twice. The extracts were dried, concentrated and purified by column (EtOAc/petroleum ether=1/5) to give (S-2) (2.2 g, 51.1% yield) as a white solid. $^1$H NMR (400 MHz, CDCl$_3$) δ 7.75 (d, J=5.6 Hz, 1H), 7.48 (d, J=5.6 Hz, 1H), 7.44 (s, 1H), 4.06 (s, 3H), 4.04 (s, 3H), 1.34 (s, 12H).

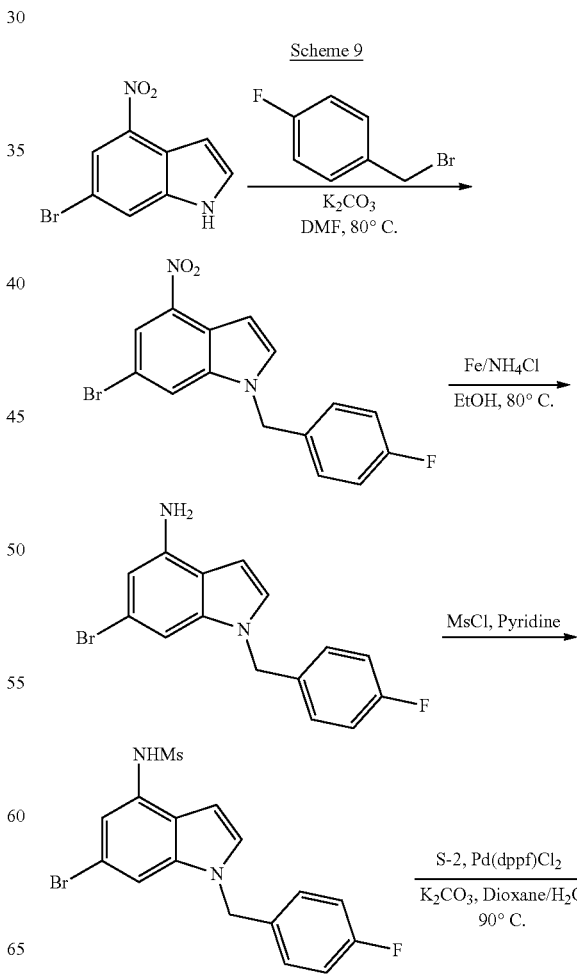

Scheme 9

-continued

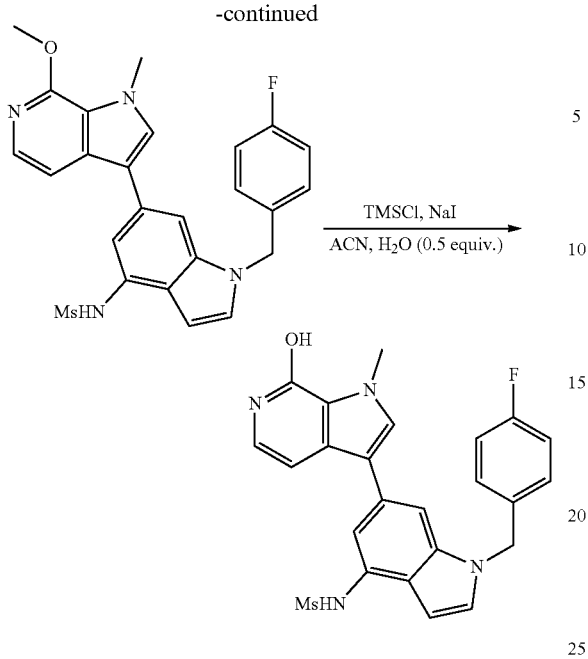

6-bromo-1-(4-fluorobenzyl)-4-nitro-1H-indole: A mixture of 6-bromo-4-nitro-1H-indole (400 mg, 1 eq.) and 1-(bromomethyl)-4-fluorobenzene (1.5 eq), K$_2$CO$_3$ (1.5 eq) in DMF (3 mL) was heated at 80° C. for 2 h. TLC showed the reaction was complete and the mixture was cooled to RT, then quenched with H$_2$O (6 mL). The solid was collected by filtration and dried to yield 6-bromo-1-(4-fluorobenzyl)-4-nitro-1H-indole (550 mg) as a pale yellow solid.

6-bromo-1-(4-fluorobenzyl)-1H-indol-4-amine: A mixture of 6-bromo-1-(4-fluorobenzyl)-4-nitro-1H-indole (550 mg, 1 eq) and Fe (10 eq) in NH$_4$Cl/EtOH (20 mL, 1:5 V/V) was heated at 80° C. for 1 h. TLC showed the reaction was complete. The mixture was filtered and the filtrate was concentrated. The residue was dissolved in H$_2$O (10 mL) and extracted with EtOAc (50 mL×2). The combined organic layers were dried over anhydrous Na$_2$SO$_4$ and concentrated to give 6-bromo-1-(4-fluorobenzyl)-1H-indol-4-amine (350 mg) as pale yellow solid.

N-(6-bromo-1-(4-fluorobenzyl)-1H-indol-4-yl)methanesulfonamide: To a solution of 6-bromo-1-(4-fluorobenzyl)-1H-indol-4-amine (180 mg, 1 eq) and pyridine (3 mL) was added MsCl (2 eq) at 0° C. and stirred at RT for 2 h. TLC showed the reaction was complete. The mixture was concentrated and the residue was purified with silica gel column (EtOAc/petroleum ether=1/1) to give the target (N-(6-bromo-1-(4-fluorobenzyl)-1H-indol-4-yl)methanesulfonamide, 200 mg) as a pale yellow solid.

N-(1-(4-fluorobenzyl)-6-(7-methoxy-1-methyl-1H-pyrrolo[2,3-c]pyridin-3-yl)-H-indol-4-yl)methanesulfonamide: A mixture of N-(6-bromo-1-(4-fluorobenzyl)-H-indol-4-yl)methanesulfonamide (200 mg, 1 eq), (S-2) (1.1 eq), K$_2$CO$_3$ (2 eq) and Pd(dppf)Cl$_2$ (0.1 eq) in dioxane/H$_2$O (50 mL, 5:1, V/V) was heated at 90° C. for 3 h. TLC showed the reaction was complete. The mixture was concentrated and the residue was purified with silica gel column (EtOAc/petroleum ether=1/1) to give the target (170 mg) as a pale yellow solid.

N-(1-(4-fluorobenzyl)-6-(7-hydroxy-1-methyl-1H-pyrrolo[2,3-c]pyridin-3-yl)-H-indol-4-yl)methanesulfonamide: Compound N-(1-(4-fluorobenzyl)-6-(7-methoxy-1-methyl-1H-pyrrolo[2,3-c]pyridin-3-yl)-1H-indol-4-yl)methanesulfonamide was dissolved in acetonitrile (1.0 M), Sodium iodide (1.6 eq) was then added to the solution followed by slow addition of trimethylsilyl chloride (1.6 eq) and dropwise addition of water (0.5 eq). The thick slurry was heated to 50° C. for 3 h. The reaction mixture was cooled to room temperature and water was added dropwise. The solution was held for 1 h followed by vacuum filtration. The solids were washed with cold ethyl acetate and dried under vacuum to yield 70% desired product.

Example NMR Spectra

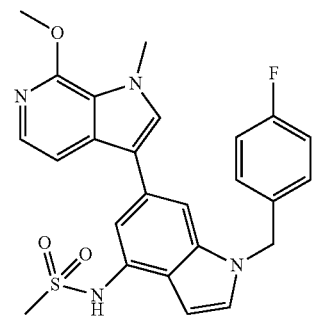 [SMILES: COc1nccc2c(-c3cc(NS(C)(=O)=O)c4ccn(Cc5ccc(F)cc5)c4c3)cn(C)c12]

N-(1-(4-fluorobenzyl)-6-(7-methoxy-1-methyl-1H-pyrrolo[2,3-c]pyridin-3-yl)-1H-indol-4-yl)methanesulfonamide $^1$H NMR (400 MHz, Acetone) δ 8.47 (s, 1H), 7.67 (d, J=5.7 Hz, 1H), 7.54-7.48 (m, 3H), 7.42 (d, J=3.2 Hz, 1H), 7.36-7.30 (m, 3H), 7.11 (t, J=8.8 Hz, 2H), 6.91 (d, J=2.9 Hz, 1H), 5.51 (s, 2H), 4.11 (s, 3H), 4.05 (s, 3H), 3.02 (s, 3H).

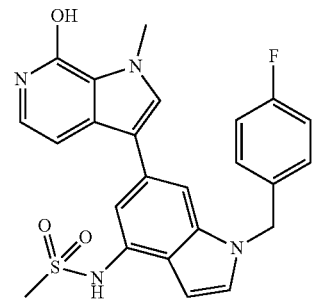 [SMILES: Cn1cc(-c2cc(NS(C)(=O)=O)c3ccn(Cc4ccc(F)cc4)c3c2)c2ccnc(O)c21]

N-(1-(4-fluorobenzyl)-6-(7-hydroxy-1-methyl-1H-pyrrolo[2,3-c]pyridin-3-yl)-H-indol-4-yl)methanesulfonamide $^1$H NMR (400 MHz, Acetone-d6) δ 8.51 (s, 1H), 7.46-7.39 (m, 4H), 7.33 (dd, J=8.5, 5.5 Hz, 2H), 7.11 (t, J=8.8 Hz, 2H), 6.98 (d, J=7.0 Hz, 1H), 6.90 (d, J=3.2 Hz, 1H), 6.64 (d, J=7.1 Hz, 1H), 5.51 (s, 2H), 4.19 (s, 3H), 3.01 (s, 3H). $^{13}$C NMR (100 MHz, Acetone-d6) δ 163.04 (d, J=243.8 Hz), 157.09, 138.71, 135.22, 131.27, 130.10, 130.03 (d, J=8.3 Hz), 129.80, 129.48, 125.84, 124.85, 122.28, 119.25, 116.22 (d, J=21.7 Hz), 113.41, 106.49, 100.81, 99.92, 50.00, 39.74, 35.83.

Scheme 10

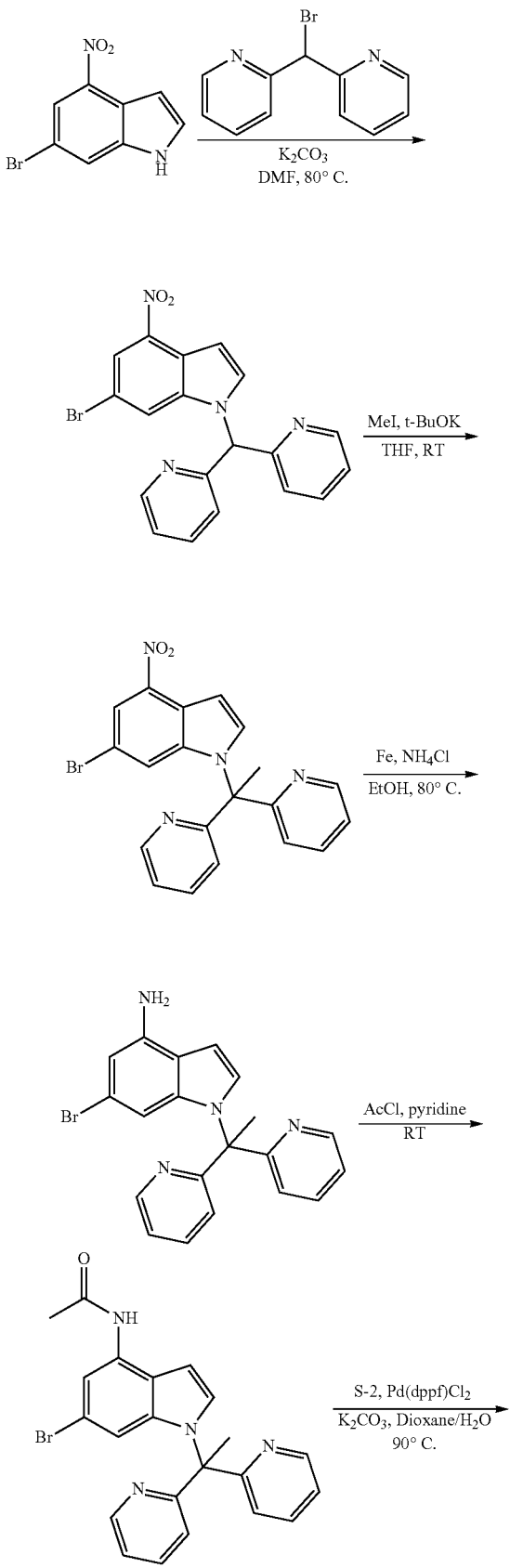

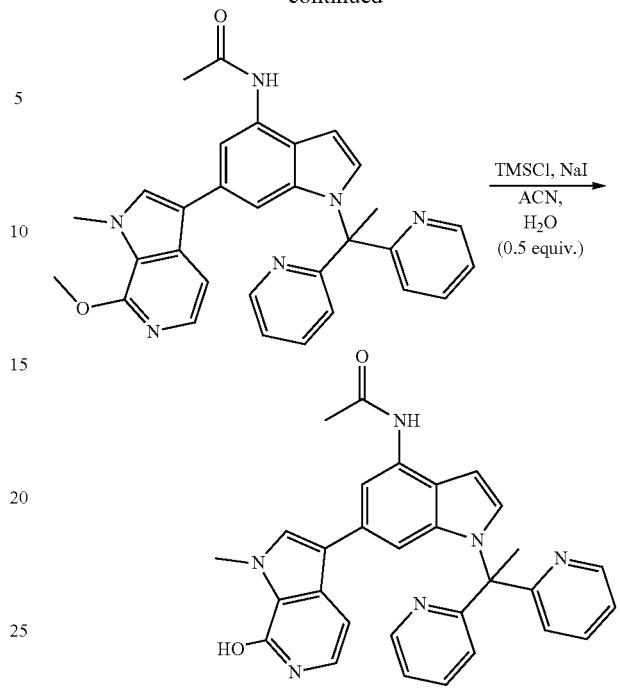

6-bromo-1-(di(pyridin-2-yl)methyl)-4-nitro-1H-indole: A mixture of 6-bromo-4-nitro-1H-indole (400 mg, 1 eq.) and 2,2'-(bromomethylene)dipyridine (1.5 eq), $K_2CO_3$ (1.5 eq) in DMF (3 mL) was heated at 80° C. for 2 h. TLC showed the reaction was complete and the mixture was cooled to RT, then quenched with $H_2O$ (6 mL). The solid was collected by filtration and dried to 6-bromo-1-(di(pyridin-2-yl)methyl)-4-nitro-1H-indole (580 mg) as a pale yellow solid.

6-bromo-1-(1,1-di(pyridin-2-yl)ethyl)-4-nitro-1H-indole: To a solution of 6-bromo-1-(di(pyridin-2-yl)methyl)-4-nitro-1H-indole (500 mg) in THF at 0° C. was added t-BuOK (2.2 eq) and MeI (3 eq) successively. Ice bath was removed after adding. The solution was stirred at RT for 2 hrs. water was added to quench the reaction. The mixture was extracted with ethyl acetate and dried over anhydrous $Na_2SO_4$. And then filtration and concentration in vacuo gave a residue, which was purified by flash column chromatography on silica gel (EtOAc/petroleum ether=1/3) to yield 6-bromo-1-(1,1-di(pyridin-2-yl)ethyl)-4-nitro-1H-indole (510 mg) as a yellow solid.

6-bromo-1-(1,1-di(pyridin-2-yl)ethyl)-1H-indol-4-amine: To a solution of 6-bromo-1-(1,1-di(pyridin-2-yl)ethyl)-4-nitro-1H-indole (450 mg) in EtOH at RT was added iron powder (5 eq) and sat. ammonia chloride. The reaction was refluxed for 2 hours, and then cooled to room temperature. The mixture was filtered to obtain a clear solution, followed by extraction with ethyl acetate. Organic layers were combined and dried over anhydrous $Na_2SO_4$. Then filtration and concentration in vacuo gave 6-bromo-1-(1,1-di(pyridin-2-yl)ethyl)-1H-indol-4-amine as a brown sold without further purification.

N-(6-bromo-1-(1,1-di(pyridin-2-yl)ethyl)-1H-indol-4-yl) acetamide: To a solution of 6-bromo-1-(1,1-di(pyridin-2-yl)ethyl)-1H-indol-4-amine (350 mg) in pyridine at 0° C. was added AcCl. Ice bath was removed after adding. The solution was stirred at RT for 3 hours. water was added to quench the reaction. The mixture was extracted with ethyl acetate and dried over anhydrous $Na_2SO_4$. And then filtration and concentration in vacuo gave a residue, which was purified by flash column chromatography on silica gel (EtOAc/petroleum ether=1/1) to yield N-(6-bromo-1-(1,1-di(pyridin-2-yl)ethyl)-1H-indol-4-yl)acetamide (340 mg) as a dark yellow solid.

N-(1-(1,1-di(pyridin-2-yl)ethyl)-6-(7-methoxy-1-methyl-1H-pyrrolo[2,3-c]pyridin-3-yl)-H-indol-4-yl)acetamide: A mixture of N-(6-bromo-1-(1,1-di(pyridin-2-yl)ethyl)-1H-indol-4-yl)acetamide (300 mg, 1 eq), Pd(dppf)$_2$Cl$_2$ (0.1 eq), S-2 (1.3 eq), and K$_2$CO$_3$ (3 eq) in dioxane-water (4:1, V/V) was heated at 90° C. in a sealed-tube for 24 hours. The mixture was then diluted with ethyl acetate and filtered to obtain a clear solution, which was washed three times with brine. The organic layer was dried over anhydrous Na$_2$SO$_4$, filtered and concentrated. The crude product was purified by flash column chromatography on silica gel (EtOAc/petroleum ether=1/1) to yield N-(1-(1,1-di(pyridin-2-yl)ethyl)-6-(7-methoxy-1-methyl-1H-pyrrolo[2,3-c]pyridin-3-yl)-1H-indol-4-yl)acetamide (340 mg) as a gray solid.

N-(1-(1,1-di(pyridin-2-yl)ethyl)-6-(7-hydroxy-1-methyl-1H-pyrrolo[2,3-c]pyridin-3-yl)-1H-indol-4-yl)acetamide: A mixture of N-(1-(1,1-di(pyridin-2-yl)ethyl)-6-(7-methoxy-1-methyl-1H-pyrrolo[2,3-c]pyridin-3-yl)-1H-indol-4-yl)acetamide (250 mg, 1 eq), TMSCl (1.6 eq), NaI (1.6 eq), and H$_2$O (0.5 eq) in acetonitrile was heated at 50° C. for 3 hours, and then cooled to room temperature. The mixture was then diluted with ethyl acetate and washed three times with aqueous NaHCO$_3$. The organic layer was dried over anhydrous Na$_2$SO$_4$, filtered and concentrated. The crude product was purified by preparative-LC system to get the final product N-(1-(1,1-di(pyridin-2-yl)ethyl)-6-(7-hydroxy-1-methyl-1H-pyrrolo[2,3-c]pyridin-3-yl)-1H-indol-4-yl)acetamide.

Example NMR Spectra

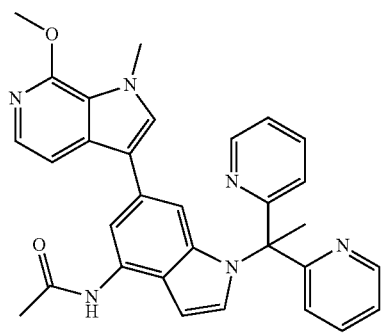 [SMILES: COc1nccc2c(-c3cc(NC(C)=O)c4ccn(C(C)(c5ccccn5)c5ccccn5)c4c3)cn(C)c12]

N-(1-(1,1-di(pyridin-2-yl)ethyl)-6-(7-methoxy-1-methyl-1H-pyrrolo[2,3-c]pyridin-3-yl)-H-indol-4-yl)acetamide $^1$H NMR (400 MHz, Chloroform-d) δ 8.69 (d, J=3.6 Hz, 2H), 7.96 (s, 1H), 7.62 (td, J=7.8, 1.9 Hz, 2H), 7.56 (d, J=5.8 Hz, 1H), 7.44 (s, 1H), 7.28-7.20 (m, 2H), 7.16 (d, J=8.0 Hz, 2H), 7.03 (d, J=3.4 Hz, 2H), 6.64 (d, J=5.8 Hz, 1H), 6.58 (s, 1H), 6.48 (d, J=3.4 Hz, 1H), 4.04 (s, 3H), 4.00 (s, 3H), 2.55 (s, 3H), 2.28 (s, 3H).

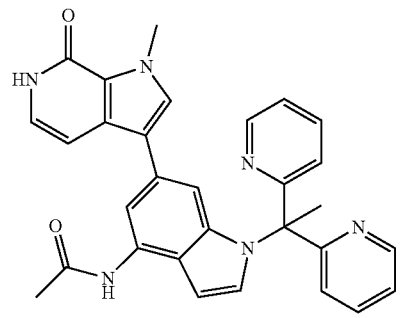 [SMILES: CC(=O)Nc1cc(-c2cn(C)c3c(=O)[nH]ccc23)cc2c1ccn2C(C)(c1ccccn1)c1ccccn1]

N-(1-(1,1-di(pyridin-2-yl)ethyl)-6-(1-methyl-7-oxo-6,7-dihydro-1H-pyrrolo[2,3-c]pyridin-3-yl)-1H-indol-4-yl)acetamide $^1$H NMR (400 MHz, DMSO-d$_6$) δ 10.89 (d, J=5.3 Hz, 1H), 9.67 (s, 1H), 8.63 (ddd, J=4.8, 1.9, 0.9 Hz, 2H), 7.82-7.74 (m, 3H), 7.37 (ddd, J=7.5, 4.8, 1.0 Hz, 2H), 7.18-7.13 (m, 3H), 7.08 (d, J=3.5 Hz, 1H), 6.82 (d, J=3.4 Hz, 1H), 6.76 (dd, J=7.0, 5.7 Hz, 1H), 6.26 (s, 1H), 5.83 (d, J=7.0 Hz, 1H), 4.03 (s, 3H), 2.44 (s, 3H), 2.16 (s, 3H).

Scheme 11

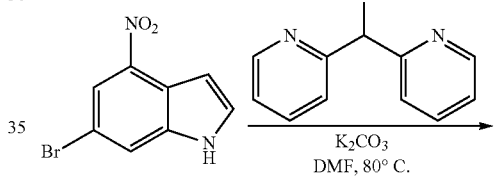

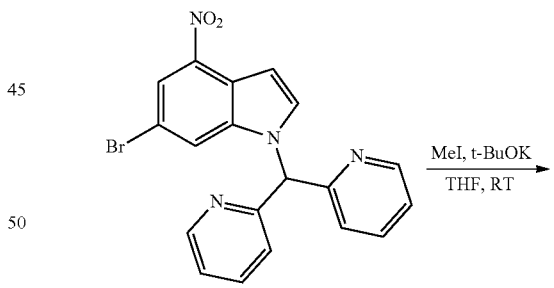

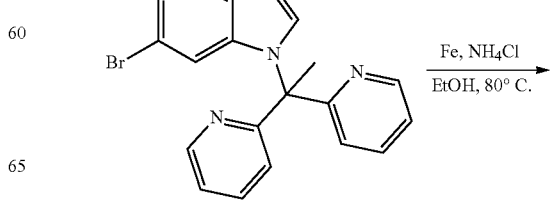

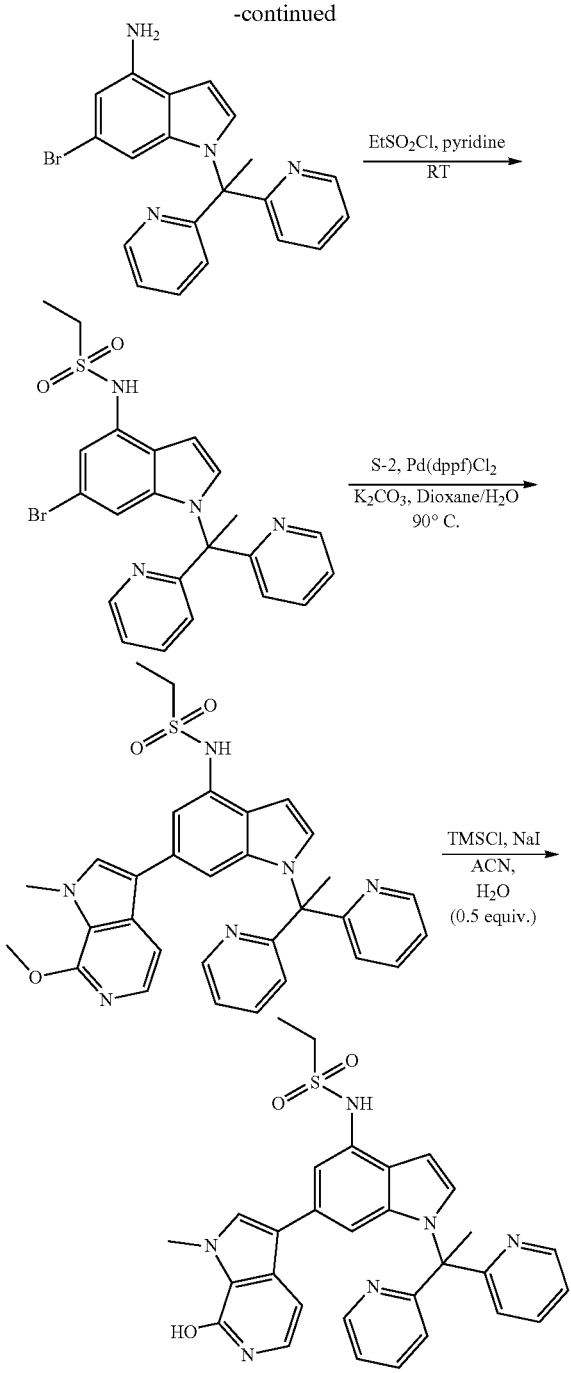

N-(6-bromo-1-(1,1-di(pyridin-2-yl)ethyl)-1H-indol-4-yl)ethanesulfonamide: To a solution of 6-bromo-1-(1,1-di(pyridin-2-yl)ethyl)-1H-indol-4-amine (400 mg) in pyridine at 0° C. was added EtSO$_2$Cl (5 eq). Ice bath was removed after adding. The solution was stirred at RT for 3 hours. Water was added to quench the reaction. The mixture was extracted with ethyl acetate and dried over anhydrous Na$_2$SO$_4$. And then filtration and concentration in vacuo gave a residue, which was purified by flash column chromatography on silica gel (EtOAc/petroleum ether=1/1) to yield N-(6-bromo-1-(1,1-di(pyridin-2-yl)ethyl)-1H-indol-4-yl)ethanesulfonamide (470 mg) as a dark yellow solid.

N-(1-(1,1-di(pyridin-2-yl)ethyl)-6-(7-methoxy-1-methyl-1H-pyrrolo[2,3-c]pyridin-3-yl)-H-indol-4-yl)ethanesulfonamide: A mixture of N-(6-bromo-1-(1,1-di(pyridin-2-yl)ethyl)-1H-indol-4-yl)ethanesulfonamide (250 mg, 1 eq), Pd(dppf)$_2$Cl$_2$ (0.1 eq), S-2 (1.3 eq), and K$_2$CO$_3$ (5 eq) in dioxane-water (4:1, V/V) was heated at 90° C. in a sealed-tube for 24 hours. The mixture was then diluted with ethyl acetate and filtered to obtain a clear solution, which was washed three times with brine. The organic layer was dried over anhydrous Na$_2$SO$_4$, filtered and concentrated. The crude product was purified by flash column chromatography on silica gel (EtOAc/petroleum ether=1/1) to yield N-(1-(1,1-di(pyridin-2-yl)ethyl)-6-(7-methoxy-1-methyl-1H-pyrrolo[2,3-c]pyridin-3-yl)-1H-indol-4-yl)ethanesulfonamide (330 mg) as a gray solid.

N-(1-(1,1-di(pyridin-2-yl)ethyl)-6-(7-hydroxy-1-methyl-1H-pyrrolo[2,3-c]pyridin-3-yl)-H-indol-4-yl)ethanesulfonamide: A mixture of N-(1-(1,1-di(pyridin-2-yl)ethyl)-6-(7-methoxy-1-methyl-1H-pyrrolo[2,3-c]pyridin-3-yl)-1H-indol-4-yl)ethanesulfonamide (200 mg, 1 eq), TMSCl (1.6 eq), NaI (1.6 eq), and H$_2$O (0.5 eq) in acetonitrile was heated at 50° C. for 3 hours, and then cooled to room temperature. The mixture was then diluted with ethyl acetate and washed three times with aqueous NaHCO$_3$. The organic layer was dried over anhydrous Na$_2$SO$_4$, filtered and concentrated. The crude product was purified by preparative-LC system to get the final product N-(1-(1,1-di(pyridin-2-yl)ethyl)-6-(7-hydroxy-1-methyl-1H-pyrrolo[2,3-c]pyridin-3-yl)-1H-indol-4-yl)ethanesulfonamide.

Example NMR Spectra

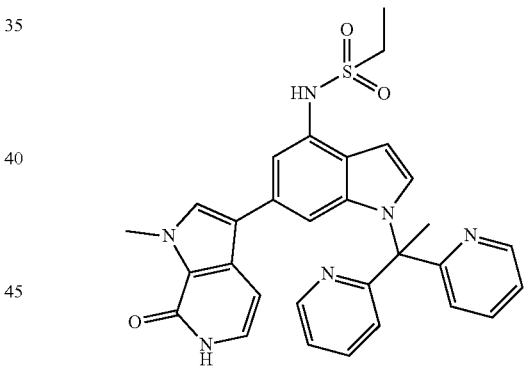

N-(1-(1,1-di(pyridin-2-yl)ethyl)-6-(1-methyl-7-oxo-6,7-dihydro-1H-pyrrolo[2,3-c]pyridin-3-yl)-1H-indol-4-yl)ethanesulfonamide $^1$H NMR (400 MHz, DMSO-d$_6$) δ 10.92 (d, J=5.4 Hz, 1H), 9.66 (s, 1H), 8.63 (d, J=3.9 Hz, 2H), 7.79 (td, J=7.8, 1.9 Hz, 2H), 7.38 (dd, J=7.5, 4.8 Hz, 2H), 7.22 (s, 1H), 7.16 (d, J=8.0 Hz, 2H), 7.12 (s, 1H), 7.10 (d, J=3.4 Hz, 1H), 6.87 (d, J=3.4 Hz, 1H), 6.77 (t, J=6.3 Hz, 1H), 6.32 (s, 1H), 5.78 (d, J=7.0 Hz, 1H), 4.03 (s, 3H), 3.12 (q, J=7.3 Hz, 2H), 2.43 (s, 3H), 1.25 (t, J=7.3 Hz, 3H).

$^{13}$C NMR (101 MHz, DMSO-d$_6$) δ 161.09, 155.77, 148.91, 137.05, 137.00, 130.28, 128.87, 127.87, 127.49, 127.40, 125.09, 123.17, 122.81, 122.54, 121.82, 117.19, 111.42, 108.15, 99.37, 99.12, 69.90, 45.64, 35.27, 27.92, 8.24.

Scheme 12

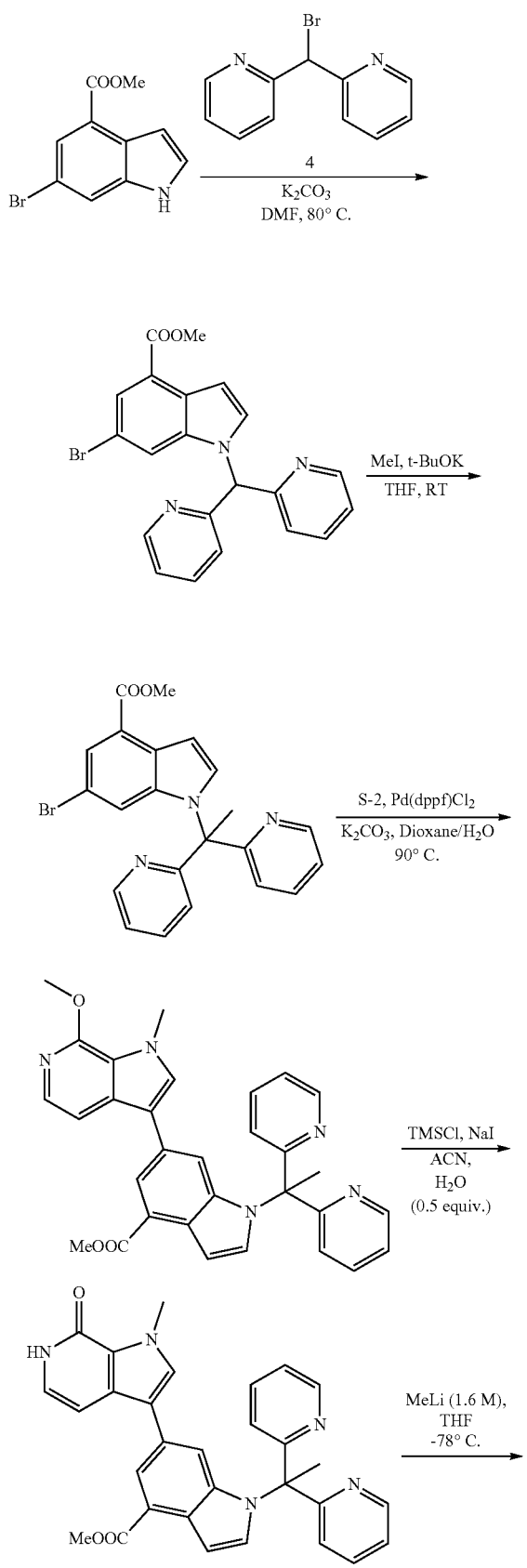

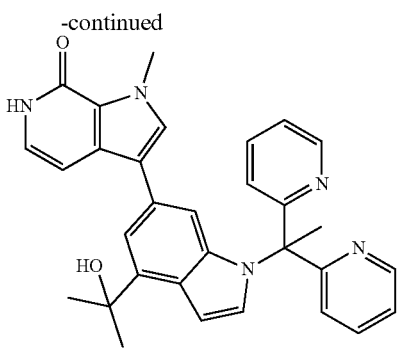

Methyl 6-bromo-1-(di(pyridin-2-yl)methyl)-1H-indole-4-carboxylate: 1) To a solution of methyl 6-bromo-1H-indole-4-carboxylate (660 mg, 1 eq) in DMF (8 mL) was added 60% NaH (125 mg, 1.2 eq) at 0° C. and stirred for 30 minutes. Then dipyridyl methyl bromide (780 mg, 1.2 eq) was added and the reaction was heated at 80° C. for 6 hours. TLC showed the reaction was complete. The mixture was concentrated and the residue was purified with silica gel column (EtOAc/petroleum ether=1/1) to give methyl 6-bromo-1-(di(pyridin-2-yl)methyl)-1H-indole-4-carboxylate (662 mg) as pale grey solid.

Methyl 6-bromo-1-(1,1-di(pyridin-2-yl)ethyl)-1H-indole-4-carboxylate: 2) To a solution of methyl 6-bromo-1-(di(pyridin-2-yl)methyl)-1H-indole-4-carboxylate (662 mg, 1 eq) in THF (6 mL) was added MeI (0.3 mL, 3 eq) and t-BuOK (444 mg, 2.3 eq) at RT and stirred for 2 hours. TLC showed the reaction was complete. The mixture was concentrated and the residue was purified with silica gel column (EtOAc/petroleum ether=1/1) to give methyl 6-bromo-1-(1,1-di(pyridin-2-yl)ethyl)-1H-indole-4-carboxylate (436 mg) as pale yellow solid.

Methyl 1-(1,1-di(pyridin-2-yl)ethyl)-6-(7-methoxy-1-methyl-1H-pyrrolo[2,3-c]pyridin-3-yl)-1H-indole-4-carboxylate: 3) A mixture of methyl 6-bromo-1-(1,1-di(pyridin-2-yl)ethyl)-1H-indole-4-carboxylate (130 mg, 1 eq), (S-2) (104 mg, 1.2 eq), K₂CO₃ (82 mg, 2 eq) and Pd(dppf)Cl₂ (49 mg, 0.2 eq) in dioxane/H₂O (4:1, 5 mL) was heated at 80° C. for 3 hours. TLC showed the reaction was complete. The mixture was concentrated and the residue was purified with silica gel column (EtOAc/petroleum ether=1/1) to give the target methyl 1-(1,1-di(pyridin-2-yl)ethyl)-6-(7-methoxy-1-methyl-1H-pyrrolo[2,3-c]pyridin-3-yl)-1H-indole-4-carboxylate (90 mg) as a pale yellow solid.

Methyl 1-(1,1-di(pyridin-2-yl)ethyl)-6-(1-methyl-7-oxo-6,7-dihydro-1H-pyrrolo[2,3-c]pyridin-3-yl)-1H-indole-4-carboxylate: 4) Compound methyl 1-(1,1-di(pyridin-2-yl)ethyl)-6-(7-methoxy-1-methyl-1H-pyrrolo[2,3-c]pyridin-3-yl)-H-indole-4-carboxylate (56 mg, 1 eq) dissolved in acetonitrile (1.0 M), Sodium iodide (1.6 eq) was then added to the solution followed by slow addition of trimethylsilyl chloride (1.6 eq) and dropwise addition of water (0.5 eq). The thick slurry was heated to 50° C. for 2 hours. The reaction mixture was cooled to room temperature and water was added to quench the reaction. The solution was concentrated and the residue was purified with silica gel column (EtOAc/petroleum ether=1/1) to give the product methyl 1-(1,1-di(pyridin-2-yl)ethyl)-6-(1-methyl-7-oxo-6,7-dihydro-1H-pyrrolo[2,3-c]pyridin-3-yl)-1H-indole-4-carboxylate (30 mg) as a pale yellow solid.

3-(1-(1,1-di(pyridin-2-yl)ethyl)-4-(2-hydroxypropan-2-yl)-1H-indol-6-yl)-1-methyl-1,6-dihydro-7H-pyrrolo[2,3-c]pyridin-7-one: 5) To a solution of methyl 1-(1,1-di(pyridin- 2-yl)ethyl)-6-(1-methyl-7-oxo-6,7-dihydro-1H-pyrrolo[2,3-c]pyridin-3-yl)-1H-indole-4-carboxylate (30 mg, 1 eq) in THF (2 mL) was added MeLi (1.6 M, 0.43 mL, 10 eq) at −78° C. and stirred for 1 hour, and then stirred for another 1 hour at RT. TLC showed the reaction was complete. The mixture was concentrated and the residue was purified with preparative TLC (DCM/MeOH=20:1) to give 3-(1-(1,1-di(pyridin-2-yl)ethyl)-4-(2-hydroxypropan-2-yl)-1H-indol-6-yl)-1-methyl-1,6-dihydro-7H-pyrrolo[2,3-c]pyridin-7-one) (7.3 mg) as pale yellow solid.

Example 2. Fulvestrant-Resistant Breast Cancer Cell Viability Assay

For the cell proliferation assay, the fulvestrant-resistant MCF7:5C-FR cells were seeded at about 2000 to about 2500/well in 96-well plates. The next day, compounds were add to the cells at desired serial concentrations form 3 nM to 10 uM. A final 0.1% (v/v) DMSO was used as vehicle control and 1 uM JQ1 was used as positive. The cell were grown in the normal culture condition for 120 hrs. Then the Hoechst 33342 dye were add to each well at a final concentration of 5 μg/ml, and put back to the incubator at 37° C. for 90 min. The plates were scanned immediately after the incubation with Celigo (Nexcelcom Bioscense) for the fluorescence of the nuclear using DAPI channel, and the cell number was counted thought the analysis function of the Celigo software. The normalized cell number to the vehicle control was used to represent the cell proliferation. Results are demonstrated in Table 2. N.D.=Not determined.

Figure 2:
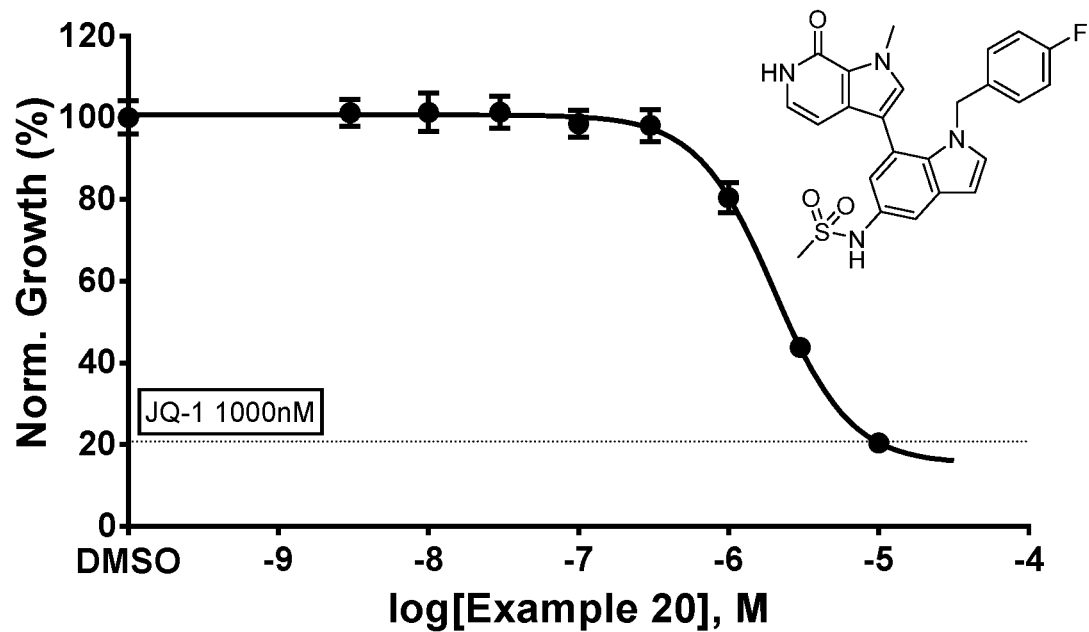
FIG. 2 shows a graph that can demonstrate growth inhibition of Compound (20) in fulvestrant-resistant MCF-7:CFR breast cancer cell model.
Figure 3:
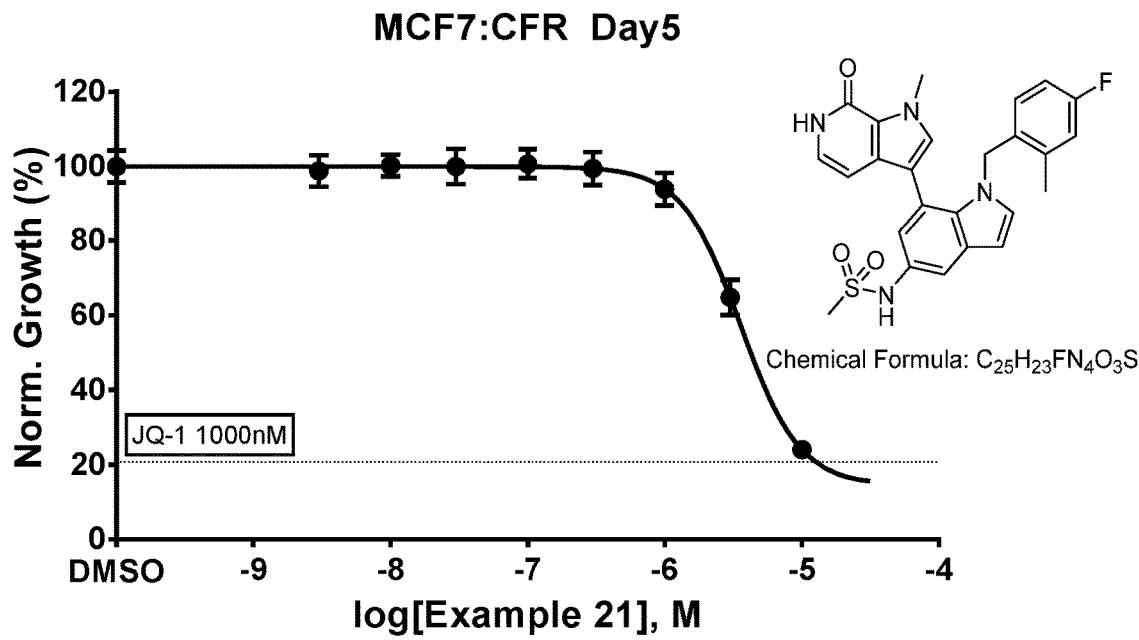
FIG. 3 shows a graph that can demonstrate growth inhibition of Compound (21) in fulvestrant-resistant MCF-7:CFR breast cancer cell model.
Figure 4:
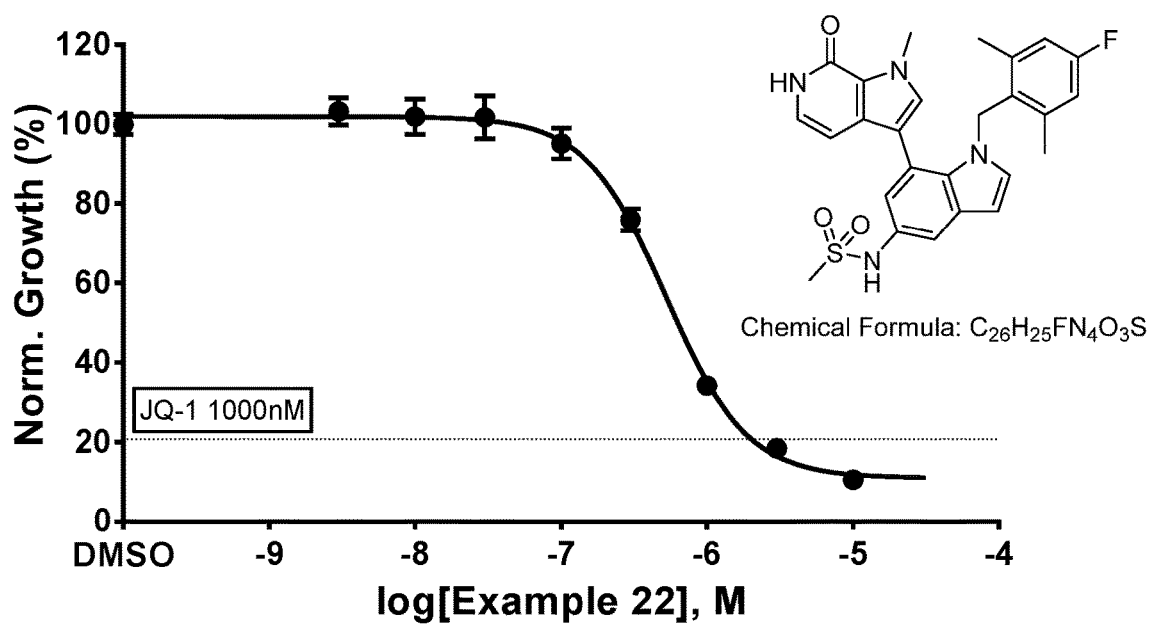
FIG. 4 shows a graph that can demonstrate growth inhibition of Compound (22) in fulvestrant-resistant MCF-7:CFR breast cancer cell model.
Figure 5:
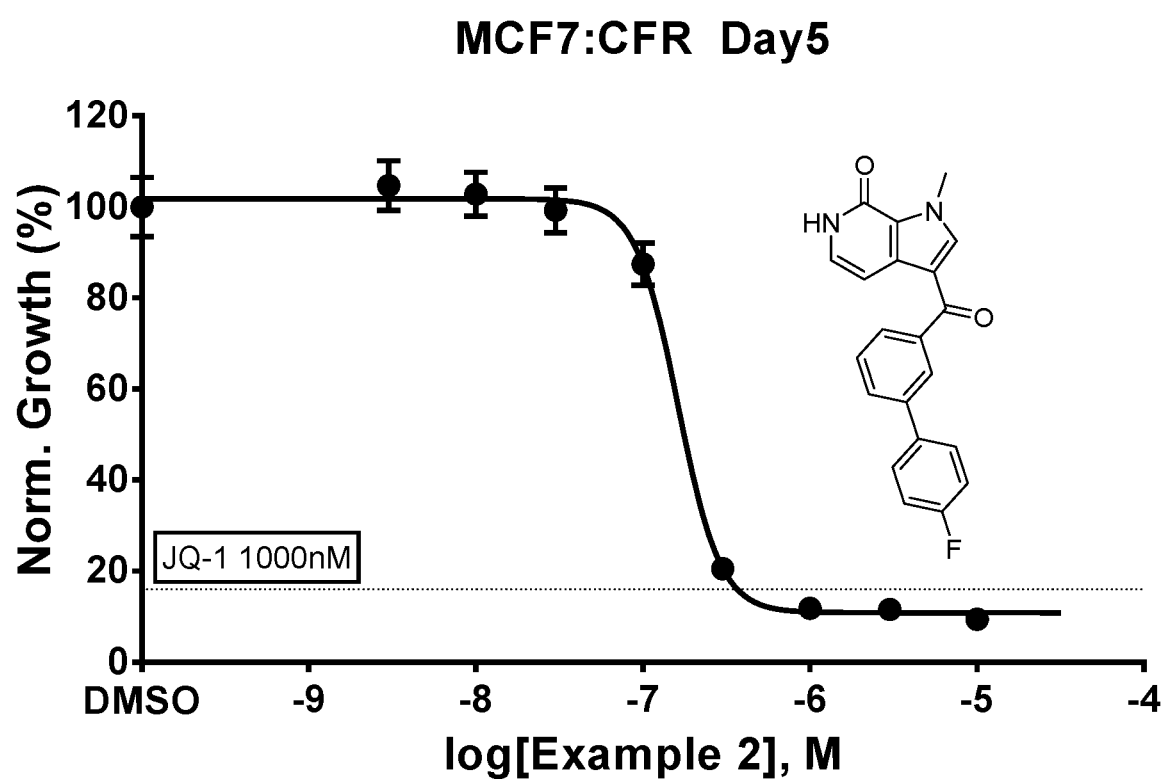
FIG. 5 shows a graph that can demonstrate growth inhibition of Compound (2) in fulvestrant-resistant MCF-7:CFR breast cancer cell model.
Figure 7:
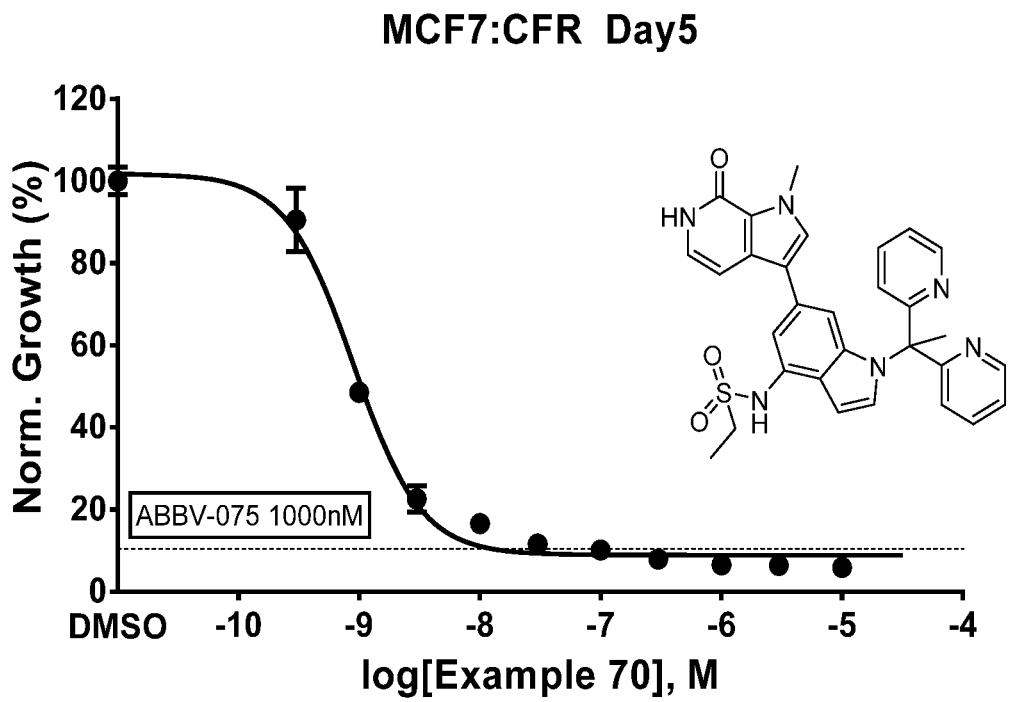
FIG. 7 shows a graph that can demonstrate growth inhibition of Compound (70) in fulvestrant-resistant MCF-7:CFR breast cancer cell mod el.
Figure 8:
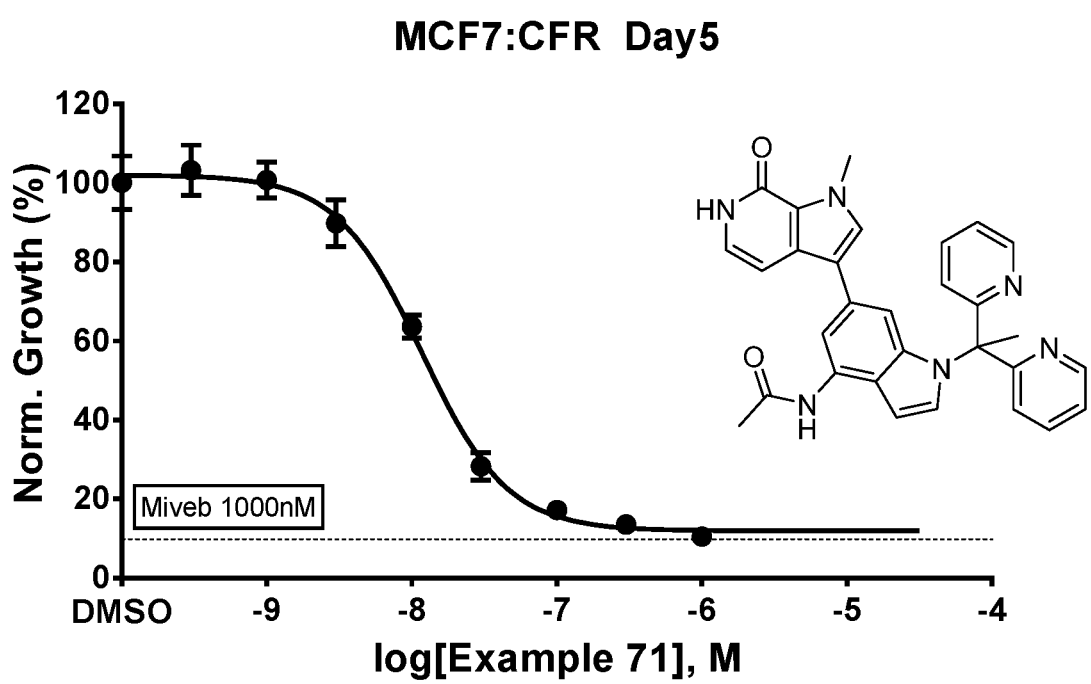
FIG. 8 shows a graph that can demonstrate growth inhibition of Compound (71) in fulvestrant-resistant MCF-7:CFR breast cancer cell mod el.
Figure 9:
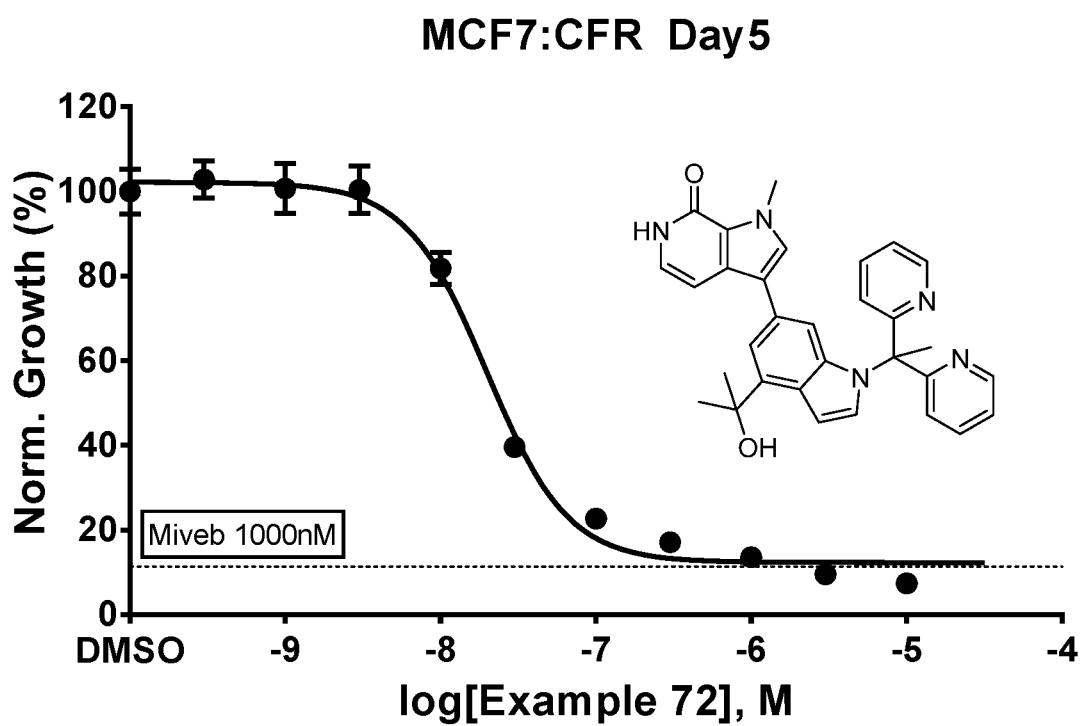
FIG. 9 shows a graph that can demonstrate growth inhibition of Compound (72) in fulvestrant-resistant MCF-7:CFR breast cancer cell mod el.
Figure 10:
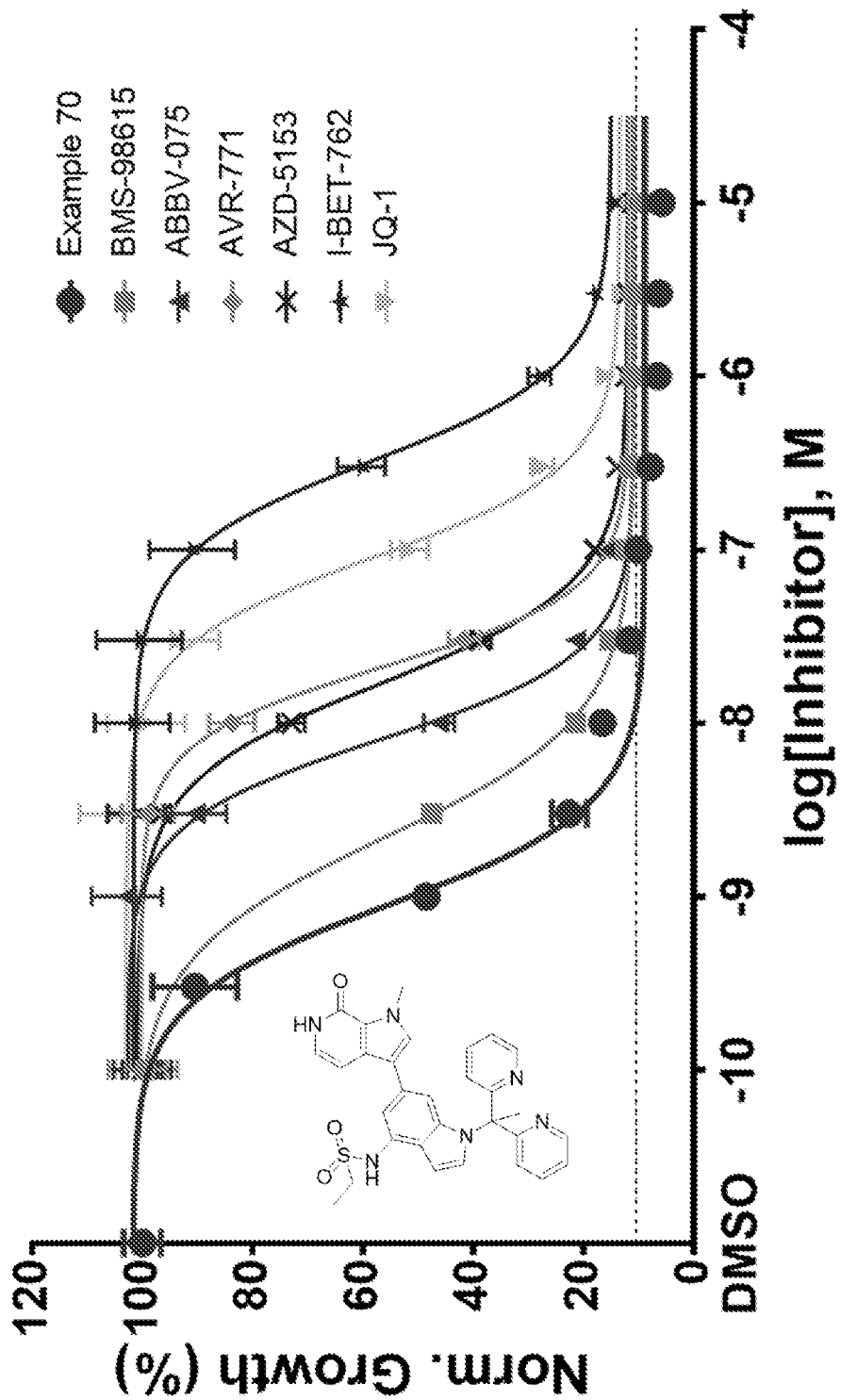
FIG. 10 shows a graph that can demonstrate growth inhibition of Compound (70) in comparison with other clinical benchmark BET inhibitors, including BMS-98615, ABBV-075, AVR-771, AZD-5153, I-BET-762 and JQ1, in fulvestrant-resistant MCF-7:CFR breast cancer cell model, showing the superior potency of Compound (70).
Figure 11:
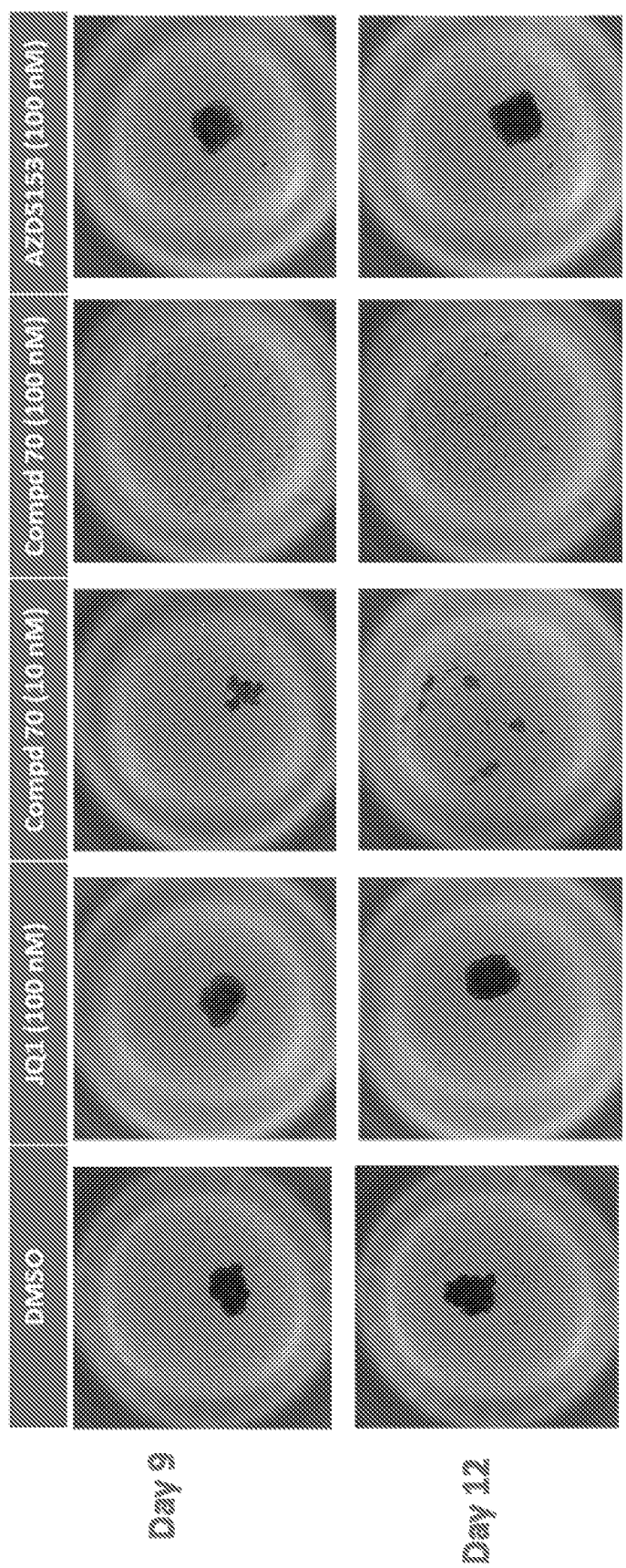
FIG. 11 shows a panel of photographic images that can demonstrate the efficacy of Compound (70) in inhibiting the growth of 3D spheroids of fulvestrant-resistant MCF-7:CFR; Compound (70) is more efficacious than JQ1 and AZD-5153 in this assay.

FIG. 1 shows a graph that can demonstrate growth inhibition of Compound (23) in fulvestrant-resistant MCF-7:CFR breast cancer cell model. FIG. 2 shows a graph that can demonstrate growth inhibition of Compound (20) in fulvestrant-resistant MCF-7:CFR breast cancer cell model. FIG. 3 shows a graph that can demonstrate growth inhibition of Compound (21) in fulvestrant-resistant MCF-7:CFR breast cancer cell model. FIG. 4 shows a graph that can demonstrate growth inhibition of Compound (22) in fulvestrant-resistant MCF-7:CFR breast cancer cell model. FIG. 5 shows a graph that can demonstrate growth inhibition of Compound (2) in fulvestrant-resistant MCF-7:CFR breast cancer cell model. FIG. 7 shows a graph that can demonstrate growth inhibition of Compound (70) in fulvestrant-resistant MCF-7:CFR breast cancer cell model. FIG. 8 shows a graph that can demonstrate growth inhibition of Compound (71) in fulvestrant-resistant MCF-7:CFR breast cancer cell model. FIG. 9 shows a graph that can demonstrate growth inhibition of Compound (72) in fulvestrant-resistant MCF-7:CFR breast cancer cell model. FIG. 10 shows a graph that can demonstrate growth inhibition of Compound (70) in comparison with other clinical benchmark BET inhibitors, including BMS-98615, ABBV-075, AVR-771, AZD-5153, I-BET-762 and JQ1, in fulvestrant-resistant MCF-7:CFR breast cancer cell model, showing the superior potency of Compound (70). FIG. 11 shows a panel of photographic images that can demonstrate the efficacy of Compound (70) in inhibiting the growth of 3D spheroids of fulvestrant-resistant MCF-7:CFR; Compound (70) is more efficacious than JQ1 and AZD-5153 in this assay.

TABLE 2

Example growth inhibition in fulvestrant-resistant MCF-7: CFR cells

| Compound | Structure | Chemical name | MCF-7: 5C-FR IC$_{50}$ (uM) |
|---|---|---|---|
| 1 | 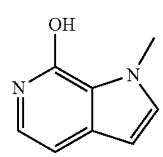 | 1-methyl-1H-pyrrolo[2,3-c]pyridin-7-ol | >5 |
| 2 | 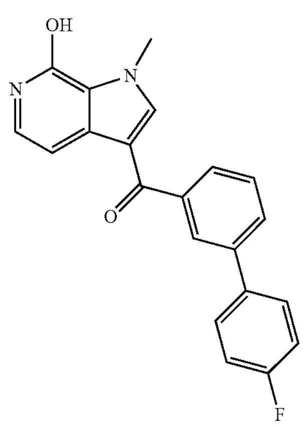 [SMILES: Cn1cc(C(=O)c2cccc(-c3ccc(F)cc3)c2)c2ccnc(O)c21] | (4'-fluoro-[1,1'-biphenyl]-3-yl)(7-hydroxy-1-methyl-1H-pyrrolo[2,3-c]pyridin-3-yl)methanone | 0.157 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 3 | 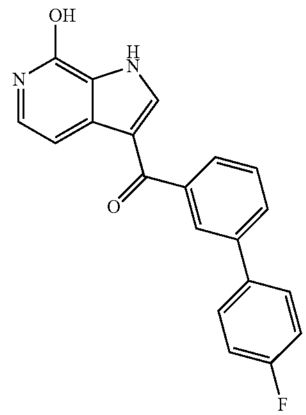 [SMILES: O=C(c1cccc(-c2ccc(F)cc2)c1)c1c[nH]c2c(O)nccc12] | (4'-fluoro-[1,1'-biphenyl]-3-yl)(7-hydroxy-1H-pyrrolo[2,3-c]pyridin-3-yl)methanone | >1 |
| 4 | 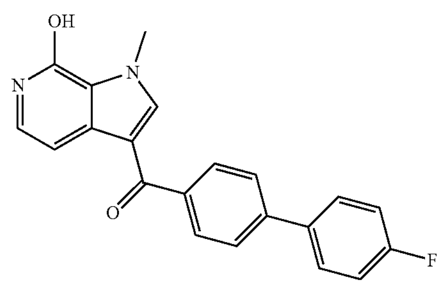 [SMILES: Cn1cc(C(=O)c2ccc(-c3ccc(F)cc3)cc2)c2ccnc(O)c21] | (4'-fluoro-[1,1'-biphenyl]-4-yl)(7-hydroxy-1-methyl-1H-pyrrolo[2,3-c]pyridin-3-yl)methanone | >5 |
| 5 | 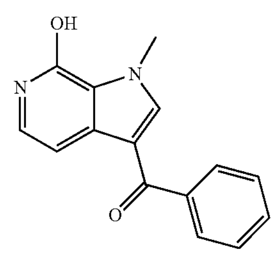 [SMILES: Cn1cc(C(=O)c2ccccc2)c2ccnc(O)c21] | (7-hydroxy-1-methyl-1H-pyrrolo[2,3-c]pyridin-3-yl)(phenyl)methanone | >5 |
| 6 | 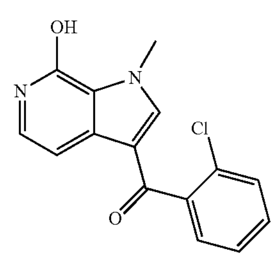 [SMILES: Cn1cc(C(=O)c2ccccc2Cl)c2ccnc(O)c21] | (2-chlorophenyl)(7-hydroxy-1-methyl-1H-pyrrolo[2,3-c]pyridin-3-yl)methanone | >5 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 7 | 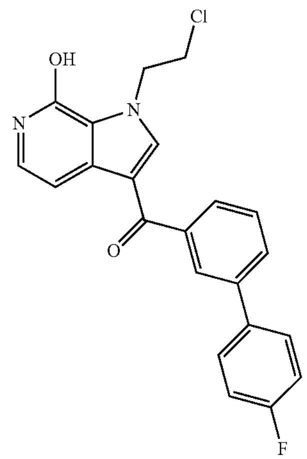 [SMILES: O=C(c1cccc(-c2ccc(F)cc2)c1)c1cn(CCCl)c2c(O)nccc12] | (1-(2-chloroethyl)-7-hydroxy-1H-pyrrolo[2,3-c]pyridin-3-yl)(4'-fluoro-[1,1'-biphenyl]-3-yl)methanone | 1.5 |
| 8 | 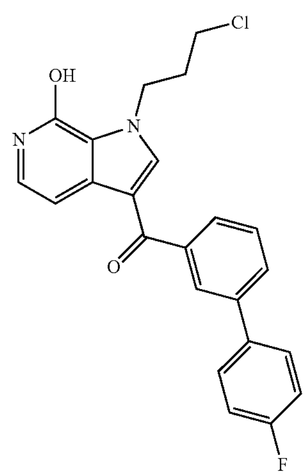 [SMILES: O=C(c1cccc(-c2ccc(F)cc2)c1)c1cn(CCCCl)c2c(O)nccc12] | (1-(3-chloropropyl)-7-hydroxy-1H-pyrrolo[2,3-c]pyridin-3-yl)(4'-fluoro-[1,1'-biphenyl]-3-yl)methanone | >5 |
| 9 | 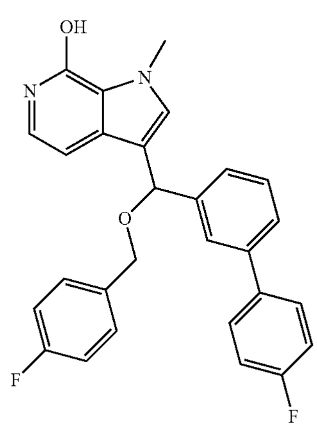 [SMILES: Cn1cc(C(OCc2ccc(F)cc2)c2cccc(-c3ccc(F)cc3)c2)c2ccnc(O)c21] | 3-((4'-fluoro-[1,1'-biphenyl]-3-yl)((4-fluorobenzyl)oxy)methyl)-1-methyl-1H-pyrrolo[2,3-c]pyridin-7-ol | >5 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 10 | 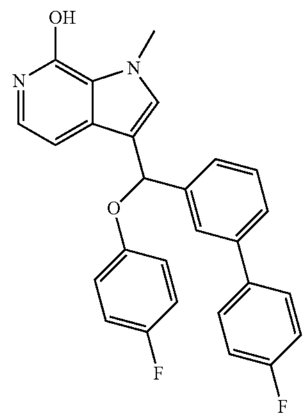 [SMILES: Cn1cc(C(Oc2ccc(F)cc2)c2cccc(-c3ccc(F)cc3)c2)c2ccnc(O)c21] | 3-((4'-fluoro-[1,1'-biphenyl]-3-yl)(4-fluorophenoxy)methyl)-1-methyl-1H-pyrrolo[2,3-c]pyridin-7-ol | 0.3 |
| 11 | 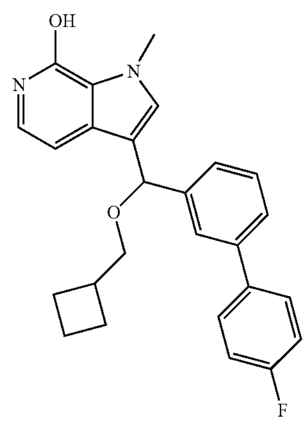 [SMILES: Cn1cc(C(OCC2CCC2)c2cccc(-c3ccc(F)cc3)c2)c2ccnc(O)c21] | 3-((cyclobutylmethoxy)(4'-fluoro-[1,1'-biphenyl]-3-yl)methyl)-1-methyl-1H-pyrrolo[2,3-c]pyridin-7-ol | >5 |
| 12 | 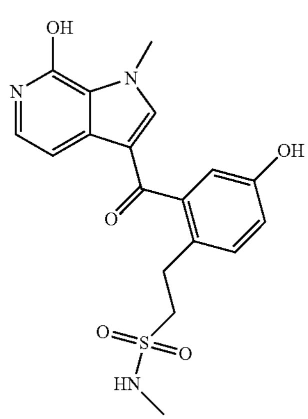 [SMILES: CNS(=O)(=O)CCc1ccc(O)cc1C(=O)c1cn(C)c2c(O)nccc12] | 2-(4-hydroxy-2-(7-hydroxy-1-methyl-1H-pyrrolo[2,3-c]pyridine-3-carbonyl)phenyl)-N-methylethane-1-sulfonamide | >1 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 13 | 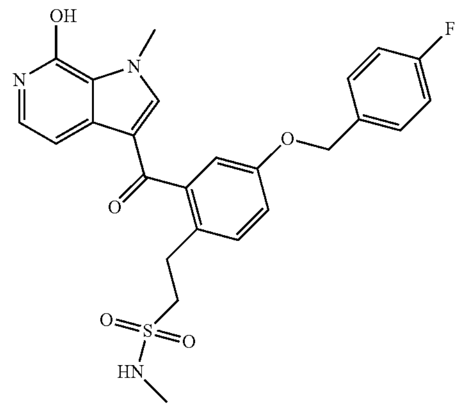 [SMILES: CNS(=O)(=O)CCc1ccc(OCc2ccc(F)cc2)cc1C(=O)c1cn(C)c2c(O)nccc12] | 2-(4-((4-fluorobenzyl)oxy)-2-(7-hydroxy-1-methyl-1H-pyrrolo[2,3-c]pyridine-3-carbonyl)phenyl)-N-methylethane-1-sulfonamide | >1 |
| 14 | 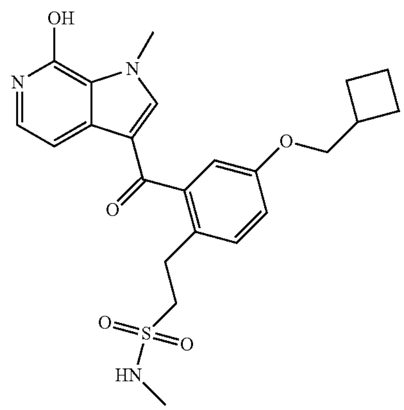 [SMILES: CNS(=O)(=O)CCc1ccc(OCC2CCC2)cc1C(=O)c1cn(C)c2c(O)nccc12] | 2-(4-(cyclobutylmethoxy)-2-(7-hydroxy-1-methyl-1H-pyrrolo[2,3-c]pyridine-3-carbonyl)phenyl)-N-methylethane-1-sulfonamide | >1 |
| 15 | 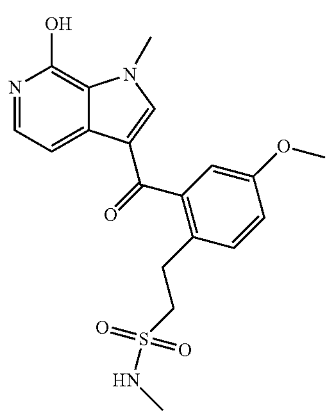 [SMILES: CNS(=O)(=O)CCc1ccc(OC)cc1C(=O)c1cn(C)c2c(O)nccc12] | 2-(2-(7-hydroxy-1-methyl-1H-pyrrolo[2,3-c]pyridine-3-carbonyl)-4-methoxyphenyl)-N-methylethane-1-sulfonamide | >1 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 16 | 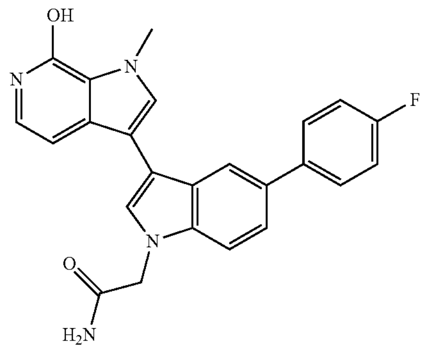 [SMILES: Cn1cc(-c2cn(CC(N)=O)c3ccc(-c4ccc(F)cc4)cc23)c2ccnc(O)c21] | 2-(5-(4-fluorophenyl)-3-(7-hydroxy-1-methyl-1H-pyrrolo[2,3-c]pyridin-3-yl)-1H-indol-1-yl)acetamide | >1 |
| 17 | 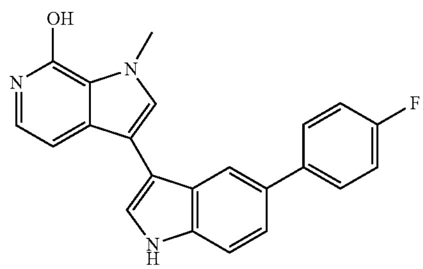 [SMILES: Cn1cc(-c2c[nH]c3ccc(-c4ccc(F)cc4)cc23)c2ccnc(O)c21] | 3-(5-(4-fluorophenyl)-1H-indol-3-yl)-1-methyl-1H-pyrrolo[2,3-c]pyridin-7-ol | >1 |
| 18 | 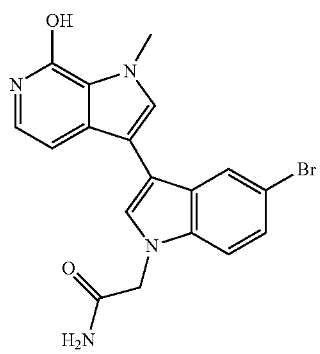 [SMILES: Cn1cc(-c2cn(CC(N)=O)c3ccc(Br)cc23)c2ccnc(O)c21] | 2-(5-bromo-3-(7-hydroxy-1-methyl-1H-pyrrolo[2,3-c]pyridin-3-yl)-1H-indole-1-yl)acetamide | >1 |
| 19 | 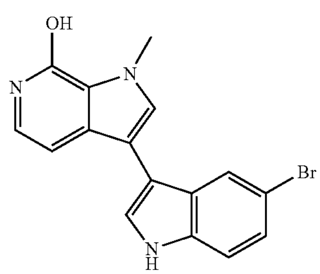 [SMILES: Cn1cc(-c2c[nH]c3ccc(Br)cc23)c2ccnc(O)c21] | 3-(5-bromo-1H-indol-3-yl)-1-methyl-1H-pyrrolo[2,3-c]pyridin-7-ol | >1 |
| 20 | 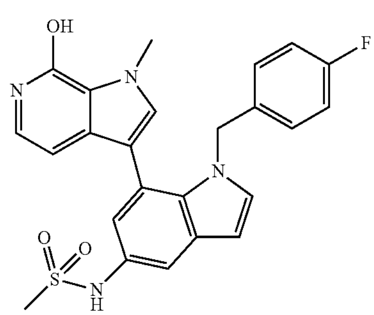 [SMILES: Cn1cc(-c2cc(NS(C)(=O)=O)cc3ccn(Cc4ccc(F)cc4)c23)c2ccnc(O)c21] | N-(1-(4-fluorobenzyl)-7-(7-hydroxy-1-methyl-1H-pyrrolo[2,3-c]pyridin-3-yl)-1H-indol-5-yl)methanesulfonamide | 1.99 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 21 | 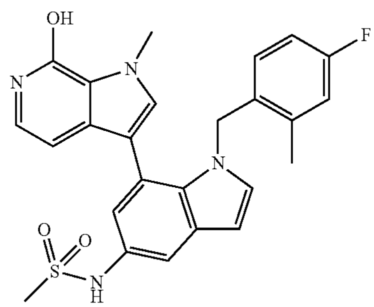 [SMILES: Cc1cc(F)ccc1Cn1ccc2cc(NS(C)(=O)=O)cc(-c3cn(C)c4c(O)nccc34)c21] | N-(1-(4-fluoro-2-methylbenzyl)-7-(7-hydroxy-1-methyl-1H-pyrrolo[2,3-c]pyridin-3-yl)-1H-indol-5-yl)methanesulfonamide | 3.5 |
| 22 | 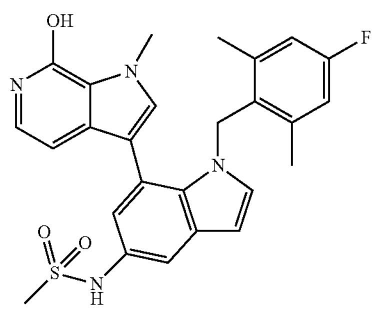 [SMILES: Cc1cc(F)cc(C)c1Cn1ccc2cc(NS(C)(=O)=O)cc(-c3cn(C)c4c(O)nccc34)c21] | N-(1-(4-fluoro-2,6-dimethylbenzyl)-7-(7-hydroxy-1-methyl-1H-pyrrolo[2,3-c]pyridin-3-yl)-1H-indol-5-yl)methanesulfonamide | 0.526 |
| 23 | 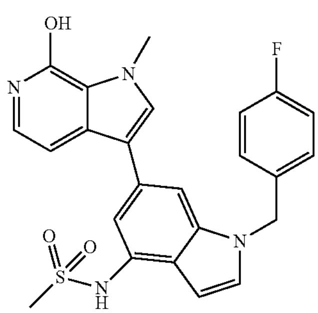 [SMILES: Cn1cc(-c2cc(NS(C)(=O)=O)c3ccn(Cc4ccc(F)cc4)c3c2)c2ccnc(O)c21] | N-(1-(4-fluorobenzyl)-6-(7-hydroxy-1-methyl-1H-pyrrolo[2,3-c]pyridin-3-yl)-1H-indol-4-yl)methanesulfonamide | 0.017 |
| 24 | 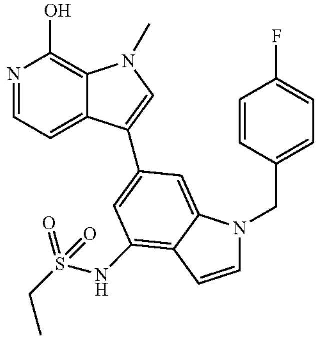 [SMILES: CCS(=O)(=O)Nc1cc(-c2cn(C)c3c(O)nccc23)cc2c1ccn2Cc1ccc(F)cc1] | N-(1-(4-fluorobenzyl)-6-(7-hydroxy-1-methyl-1H-pyrrolo[2,3-c]pyridin-3-yl)-1H-indol-4-yl)ethanesulfonamide | <0.2 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 25 | 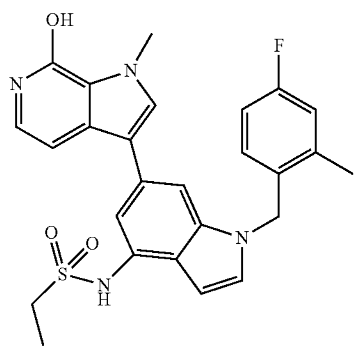 [SMILES: CCS(=O)(=O)Nc1cc(-c2cn(C)c3c(O)nccc23)cc2c1ccn2Cc1ccc(F)cc1C] | N-(1-(4-fluoro-2-methylbenzyl)-6-(7-hydroxy-1-methyl-1H-pyrrolo[2,3-c]pyridin-3-yl)-1H-indol-4-yl)ethanesulfonamide | <0.2 |
| 26 | 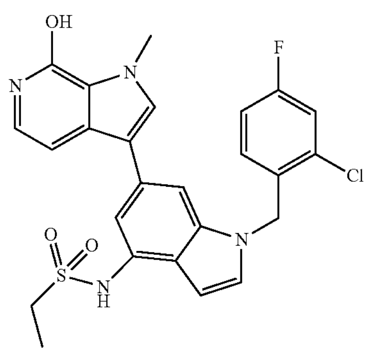 [SMILES: CCS(=O)(=O)Nc1cc(-c2cn(C)c3c(O)nccc23)cc2c1ccn2Cc1ccc(F)cc1Cl] | N-(1-(2-chloro-4-fluorobenzyl)-6-(7-hydroxy-1-methyl-1H-pyrrolo[2,3-c]pyridin-3-yl)-1H-indol-4-yl)ethanesulfonamide | <0.2 |
| 27 | 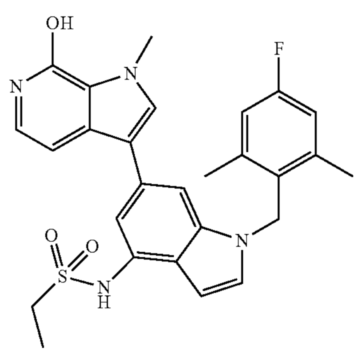 [SMILES: CCS(=O)(=O)Nc1cc(-c2cn(C)c3c(O)nccc23)cc2c1ccn2Cc1c(C)cc(F)cc1C] | N-(1-(4-fluoro-2,6-dimethylbenzyl)-6-(7-hydroxy-1-methyl-1H-pyrrolo[2,3-c]pyridin-3-yl)-1H-indol-4-yl)ethanesulfonamide | <1 |
| 28 | 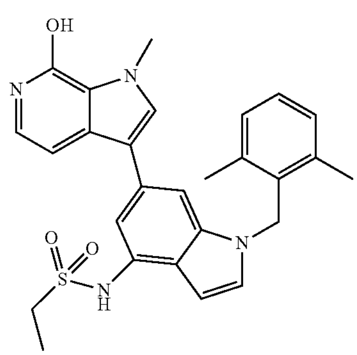 [SMILES: CCS(=O)(=O)Nc1cc(-c2cn(C)c3c(O)nccc23)cc2c1ccn2Cc1c(C)cccc1C] | N-(1-(2,6-dimethylbenzyl)-6-(7-hydroxy-1-methyl-1H-pyrrolo[2,3-c]pyridin-3-yl)-1H-indol-4-yl)ethanesulfonamide | <1 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 29 | 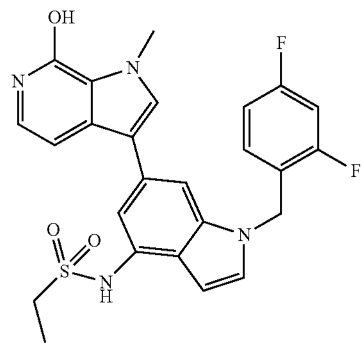 [SMILES: CCS(=O)(=O)Nc1cc(-c2cn(C)c3c(O)nccc23)cc2c1ccn2Cc1ccc(F)cc1F] | N-(1-(2,4-difluorobenzyl)-6-(7-hydroxy-1-methyl-1H-pyrrolo[2,3-c]pyridin-3-yl)-1H-indol-4-yl)ethanesulfonamide | <0.5 |
| 30 | 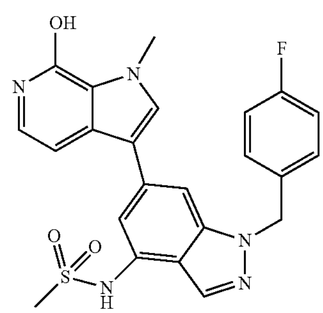 [SMILES: Cn1cc(-c2cc(NS(C)(=O)=O)c3cnn(Cc4ccc(F)cc4)c3c2)c2ccnc(O)c21] | N-(1-(4-fluorobenzyl)-6-(7-hydroxy-1-methyl-1H-pyrrolo[2,3-c]pyridin-3-yl)-1H-indazol-4-yl)methanesulfonamide | 0.04 |
| 31 | 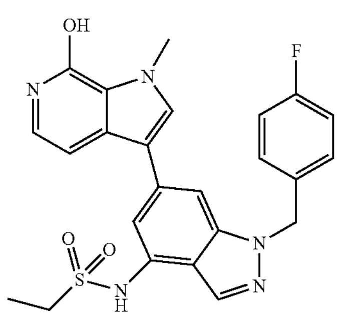 [SMILES: CCS(=O)(=O)Nc1cc(-c2cn(C)c3c(O)nccc23)cc2c1cnn2Cc1ccc(F)cc1] | N-(1-(4-fluorobenzyl)-6-(7-hydroxy-1-methyl-1H-pyrrolo[2,3-c]pyridin-3-yl)-1H-indazol-4-yl)ethanesulfonamide | 0.015 |
| 32 | 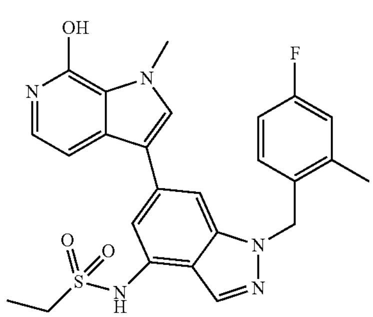 [SMILES: CCS(=O)(=O)Nc1cc(-c2cn(C)c3c(O)nccc23)cc2c1cnn2Cc1ccc(F)cc1C] | N-(1-(4-fluoro-2-methylbenzyl)-6-(7-hydroxy-1-methyl-1H-pyrrolo[2,3-c]pyridin-3-yl)-1H-indazol-4-yl)ethanesulfonamide | <0.2 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 33 | 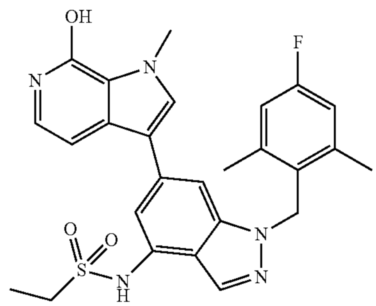 [SMILES: CCS(=O)(=O)Nc1cc(-c2cn(C)c3c(O)nccc23)cc2c1cnn2Cc1c(C)cc(F)cc1C] | N-(1-(4-fluoro-2,6-dimethylbenzyl)-6-(7-hydroxy-1-methyl-1H-pyrrolo[2,3-c]pyridin-3-yl)-1H-indazol-4-yl)ethanesulfonamide | <1 |
| 34 | 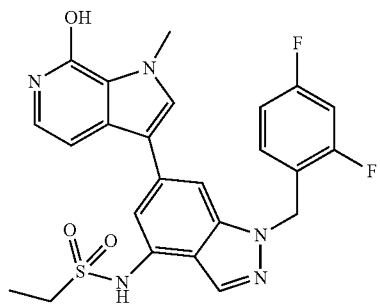 [SMILES: CCS(=O)(=O)Nc1cc(-c2cn(C)c3c(O)nccc23)cc2c1cnn2Cc1ccc(F)cc1F] | N-(1-(2,4-difluorobenzyl)-6-(7-hydroxy-1-methyl-1H-pyrrolo[2,3-c]pyridin-3-yl)-1H-indazol-4-yl)ethanesulfonamide | <0.5 |
| 35 | 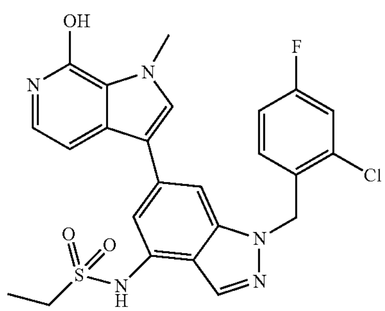 [SMILES: CCS(=O)(=O)Nc1cc(-c2cn(C)c3c(O)nccc23)cc2c1cnn2Cc1ccc(F)cc1Cl] | N-(1-(2-chloro-4-fluorobenzyl)-6-(7-hydroxy-1-methyl-1H-pyrrolo[2,3-c]pyridin-3-yl)-1H-indazol-4-yl)ethanesulfonamide | <0.5 |
| 36 | 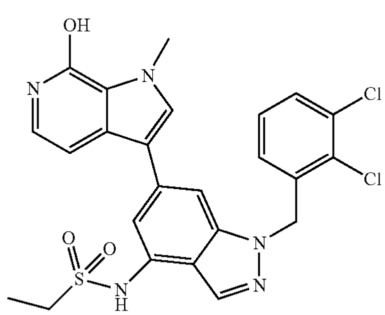 [SMILES: CCS(=O)(=O)Nc1cc(-c2cn(C)c3c(O)nccc23)cc2c1cnn2Cc1cccc(Cl)c1Cl] | N-(1-(2,3-dichlorobenzyl)-6-(7-hydroxy-1-methyl-1H-pyrrolo[2,3-c]pyridin-3-yl)-1H-indazol-4-yl)ethanesulfonamide | <1 |
| 37 | 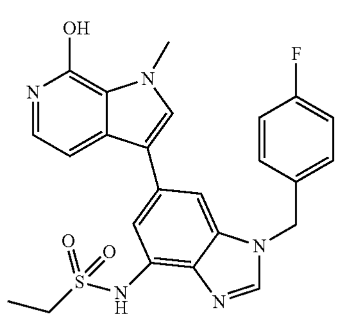 [SMILES: CCS(=O)(=O)Nc1cc(-c2cn(C)c3c(O)nccc23)cc2c1ncn2Cc1ccc(F)cc1] | N-(1-(4-fluorobenzyl)-6-(7-hydroxy-1-methyl-1H-pyrrolo[2,3-c]pyridin-3-yl)-1H-benzo[d]imidazol-4-yl)ethanesulfonamide | <1 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 38 | 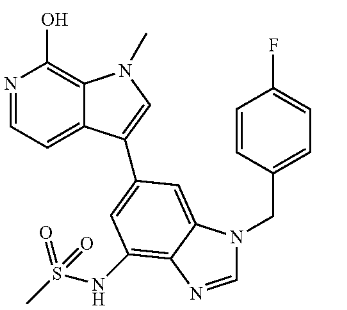 [SMILES: Cn1cc(-c2cc(NS(C)(=O)=O)c3ncn(Cc4ccc(F)cc4)c3c2)c2ccnc(O)c21] | N-(1-(4-fluorobenzyl)-6-(7-hydroxy-1-methyl-1H-pyrrolo[2,3-c]pyridin-3-yl)-1H-benzo[d]imidazol-4-yl)methanesulfonamide | <0.2 |
| 39 | 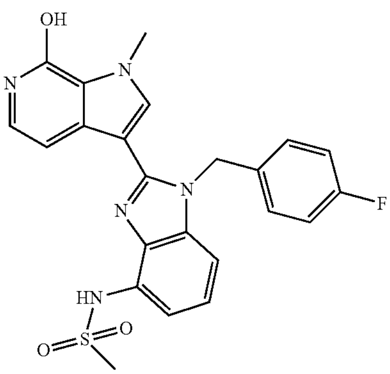 [SMILES: Cn1cc(-c2nc3c(NS(C)(=O)=O)cccc3n2Cc2ccc(F)cc2)c2ccnc(O)c21] | N-(1-(4-fluorobenzyl)-2-(7-hydroxy-1-methyl-1H-pyrrolo[2,3-c]pyridin-3-yl)-1H-benzo[d]imidazol-4-yl)methanesulfonamide | <1 |
| 40 | 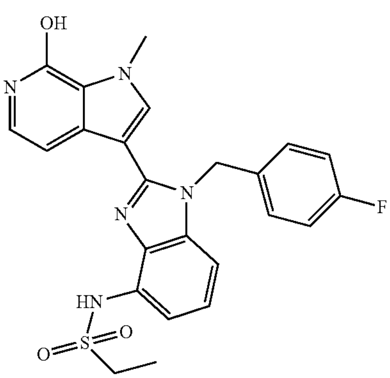 [SMILES: CCS(=O)(=O)Nc1cccc2c1nc(-c1cn(C)c3c(O)nccc13)n2Cc1ccc(F)cc1] | N-(1-(4-fluorobenzyl)-2-(7-hydroxy-1-methyl-1H-pyrrolo[2,3-c]pyridin-3-yl)-1H-benzo[d]imidazol-4-yl)ethanesulfonamide | <1 |
| 41 | 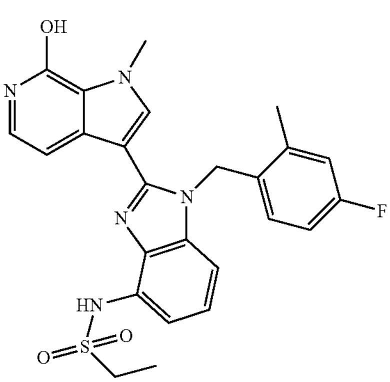 [SMILES: CCS(=O)(=O)Nc1cccc2c1nc(-c1cn(C)c3c(O)nccc13)n2Cc1ccc(F)cc1C] | N-(1-(4-fluoro-2-methylbenzyl)-2-(7-hydroxy-1-methyl-1H-pyrrolo[2,3-c]pyridin-3-yl)-1H-benzo[d]imidazol-4-yl)ethanesulfonamide | <1 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 42 | 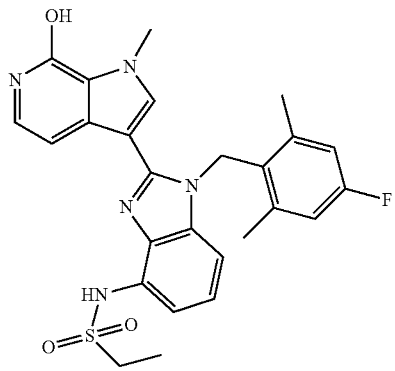 [SMILES: CCS(=O)(=O)Nc1cccc2c1nc(-c1cn(C)c3c(O)nccc13)n2Cc1c(C)cc(F)cc1C] | N-(1-(4-fluoro-2,6-dimethylbenzyl)-2-(7-hydroxy-1-methyl-1H-pyrrolo[2,3-c]pyridin-3-yl)-1H-benzo[d]imidazol-4-yl)ethanesulfonamide | <1 |
| 43 | 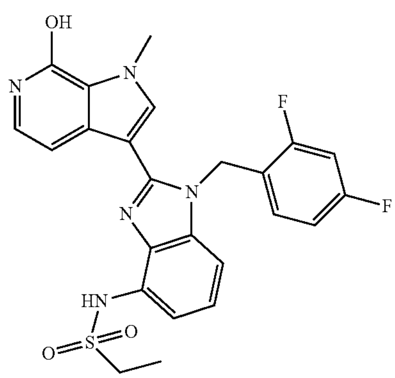 [SMILES: CCS(=O)(=O)Nc1cccc2c1nc(-c1cn(C)c3c(O)nccc13)n2Cc1ccc(F)cc1F] | N-(1-(2,4-difluorobenzyl)-2-(7-hydroxy-1-methyl-1H-pyrrolo[2,3-c]pyridin-3-yl)-1H-benzo[d]imidazol-4-yl)ethanesulfonamide | <1 |
| 44 | 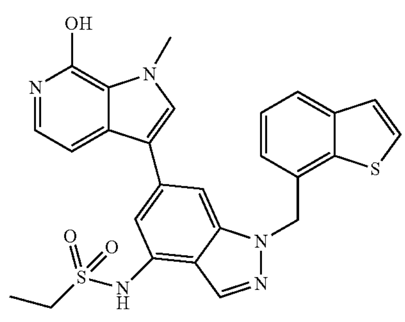 [SMILES: CCS(=O)(=O)Nc1cc(-c2cn(C)c3c(O)nccc23)cc2c1cnn2Cc1cccc2ccsc12] | N-(1-(benzo[b]thiophen-7-ylmethyl)-6-(7-hydroxy-1-methyl-1H-pyrrolo[2,3-c]pyridin-3-yl)-1H-indazol-4-yl)ethanesulfonamide | >0.1 |
| 45 | 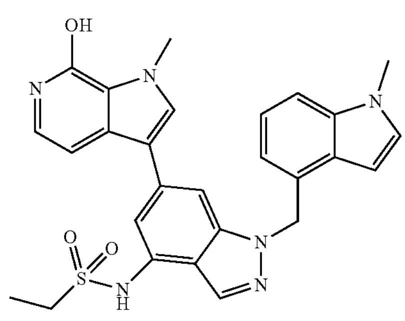 [SMILES: CCS(=O)(=O)Nc1cc(-c2cn(C)c3c(O)nccc23)cc2c1cnn2Cc1cccc2c1ccn2C] | N-(6-(7-hydroxy-1-methyl-1H-pyrrolo[2,3-c]pyridin-3-yl)-1-((1-methyl-1H-indol-4-yl)methyl)-1H-indazol-4-yl)ethanesulfonamide | >0.1 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 46 | 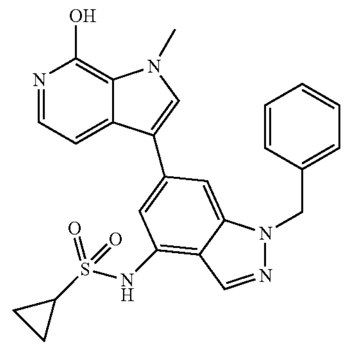 [SMILES: Cn1cc(-c2cc(NS(=O)(=O)C3CC3)c3cnn(Cc4ccccc4)c3c2)c2ccnc(O)c21] | N-(1-benzyl-6-(7-hydroxy-1-methyl-1H-pyrrolo[2,3-c]pyridin-3-yl)-1H-indazol-4-yl)cyclopropane-sulfonamide | <1 |
| 47 | 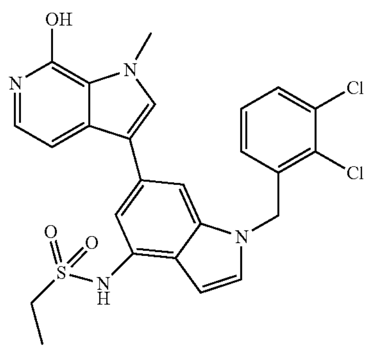 [SMILES: CCS(=O)(=O)Nc1cc(-c2cn(C)c3c(O)nccc23)cc2c1ccn2Cc1cccc(Cl)c1Cl] | N-(1-(2,3-dichlorobenzyl)-6-(7-hydroxy-1-methyl-1H-pyrrolo[2,3-c]pyridin-3-yl)-1H-indol-4-yl)ethanesulfonamide | <1 |
| 48 | 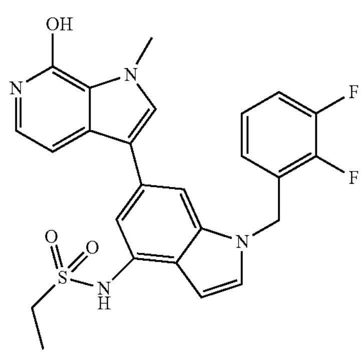 [SMILES: CCS(=O)(=O)Nc1cc(-c2cn(C)c3c(O)nccc23)cc2c1ccn2Cc1cccc(F)c1F] | N-(1-(2,3-difluorobenzyl)-6-(7-hydroxy-1-methyl-1H-pyrrolo[2,3-c]pyridin-3-yl)-1H-indol-4-yl)ethanesulfonamide | <1 |
| 49 | 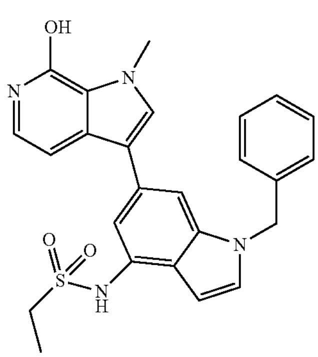 [SMILES: CCS(=O)(=O)Nc1cc(-c2cn(C)c3c(O)nccc23)cc2c1ccn2Cc1ccccc1] | N-(1-benzyl-6-(7-hydroxy-1-methyl-1H-pyrrolo[2,3-c]pyridin-3-yl)-1H-indol-4-yl)ethanesulfonamide | <1 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 50 | 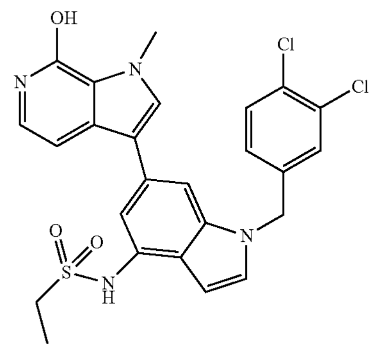 [SMILES: CCS(=O)(=O)Nc1cc(-c2cn(C)c3c(O)nccc23)cc2c1ccn2Cc1ccc(Cl)c(Cl)c1] | N-(1-(3,4-dichlorobenzyl)-6-(7-hydroxy-1-methyl-1H-pyrrolo[2,3-c]pyridin-3-yl)-1H-indol-4-yl)ethanesulfonamide | <1 |
| 51 | 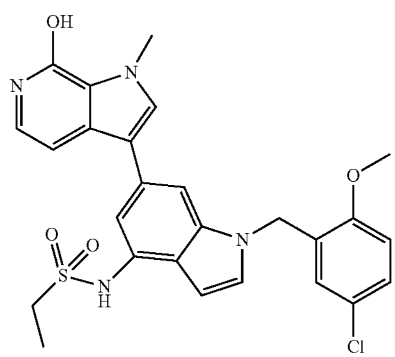 [SMILES: CCS(=O)(=O)Nc1cc(-c2cn(C)c3c(O)nccc23)cc2c1ccn2Cc1cc(Cl)ccc1OC] | N-(1-(5-chloro-2-methoxybenzyl)-6-(7-hydroxy-1-methyl-1H-pyrrolo[2,3-c]pyridin-3-yl)-1H-indol-4-yl)ethanesulfonamide | <1 |
| 52 | 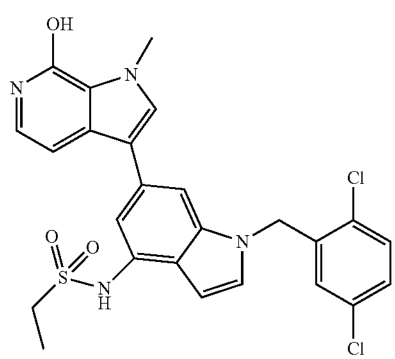 [SMILES: CCS(=O)(=O)Nc1cc(-c2cn(C)c3c(O)nccc23)cc2c1ccn2Cc1cc(Cl)ccc1Cl] | N-(1-(2,5-dichlorobenzyl)-6-(7-hydroxy-1-methyl-1H-pyrrolo[2,3-c]pyridin-3-yl)-1H-indol-4-yl)ethanesulfonamide | <1 |
| 53 | 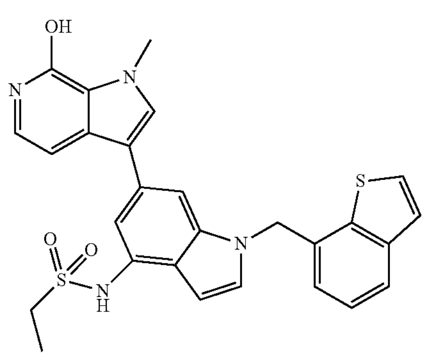 [SMILES: CCS(=O)(=O)Nc1cc(-c2cn(C)c3c(O)nccc23)cc2c1ccn2Cc1cccc2ccsc12] | N-(1-(benzo[b]thiophen-7-ylmethyl)-6-(7-hydroxy-1-methyl-1H-pyrrolo[2,3-c]pyridin-3-yl)-1H-indol-4-yl)ethanesulfonamide | <1 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 54 | 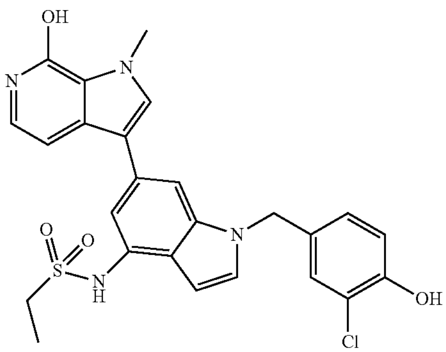 [SMILES: CCS(=O)(=O)Nc1cc(-c2cn(C)c3c(O)nccc23)cc2c1ccn2Cc1ccc(O)c(Cl)c1] | N-(1-(3-chloro-4-hydroxybenzyl)-6-(7-hydroxy-1-methyl-1H-pyrrolo[2,3-c]pyridin-3-yl)-1H-indol-4-yl)ethanesulfonamide | >0.1 |
| 55 | 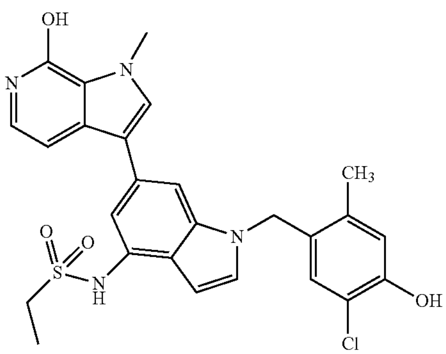 [SMILES: CCS(=O)(=O)Nc1cc(-c2cn(C)c3c(O)nccc23)cc2c1ccn2Cc1cc(Cl)c(O)cc1C] | N-(1-(5-chloro-4-hydroxy-2-methylbenzyl)-6-(7-hydroxy-1-methyl-1H-pyrrolo[2,3-c]pyridin-3-yl)-1H-indol-4-yl)ethanesulfonamide | >0.1 |
| 56 | 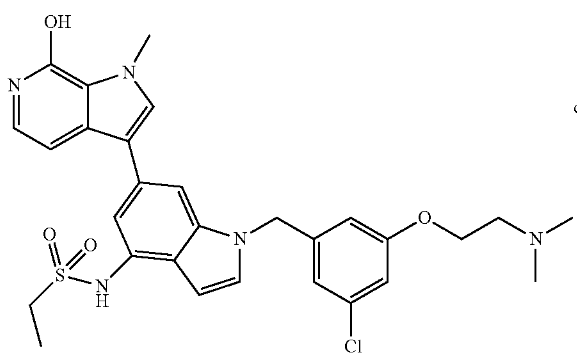 [SMILES: CCS(=O)(=O)Nc1cc(-c2cn(C)c3c(O)nccc23)cc2c1ccn2Cc1cc(Cl)cc(OCCN(C)C)c1] | N-(1-(3-chloro-5-(2-(dimethylamino)ethoxy)benzyl)-6-(7-hydroxy-1-methyl-1H-pyrrolo[2,3-c]pyridin-3-yl)-1H-indol-4-yl)ethanesulfonamide | >0.1 |
| 57 | 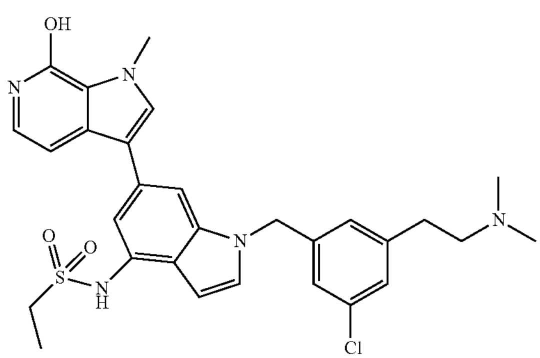 [SMILES: CCS(=O)(=O)Nc1cc(-c2cn(C)c3c(O)nccc23)cc2c1ccn2Cc1cc(Cl)cc(CCN(C)C)c1] | N-(1-(3-chloro-5-(2-(dimethylamino)ethyl)benzyl)-6-(7-hydroxy-1-methyl-1H-pyrrolo[2,3-c]pyridin-3-yl)-1H-indol-4-yl)ethanesulfonamide | >0.1 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 58 | 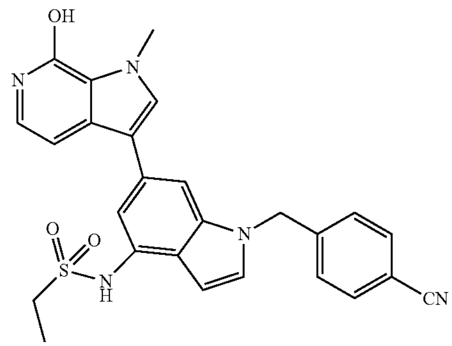 [SMILES: CCS(=O)(=O)Nc1cc(-c2cn(C)c3c(O)nccc23)cc2c1ccn2Cc1ccc(C#N)cc1] | N-(1-(4-cyanobenzyl)-6-(7-hydroxy-1-methyl-1H-pyrrolo[2,3-c]pyridin-3-yl)-1H-indol-4-yl)ethanesulfonamide | <1 |
| 59 | 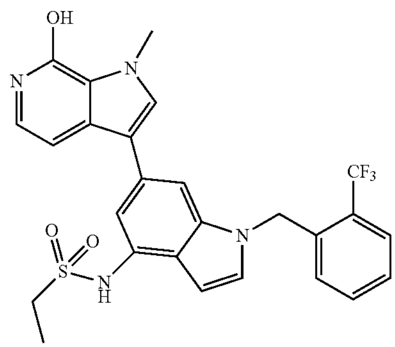 [SMILES: CCS(=O)(=O)Nc1cc(-c2cn(C)c3c(O)nccc23)cc2c1ccn2Cc1ccccc1C(F)(F)F] | N-(6-(7-hydroxy-1-methyl-1H-pyrrolo[2,3-c]pyridin-3-yl)-1-(2-(trifluoromethyl)benzyl)-1H-indol-4-yl)ethanesulfonamide | >0.1 |
| 60 | 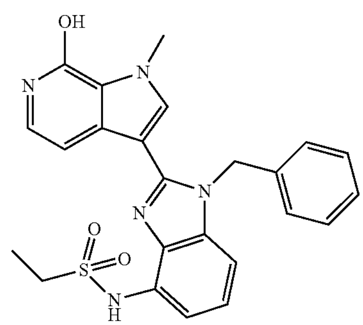 [SMILES: CCS(=O)(=O)Nc1cccc2c1nc(-c1cn(C)c3c(O)nccc13)n2Cc1ccccc1] | N-(1-benzyl-2-(7-hydroxy-1-methyl-1H-pyrrolo[2,3-c]pyridin-3-yl)-1H-benzo[d]imidazol-4-yl)ethanesulfonamide | >0.1 |
| 61 | 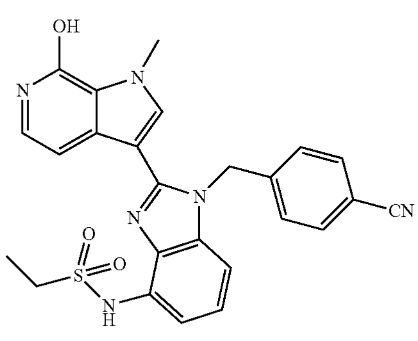 [SMILES: CCS(=O)(=O)Nc1cccc2c1nc(-c1cn(C)c3c(O)nccc13)n2Cc1ccc(C#N)cc1] | N-(1-benzyl-2-(7-hydroxy-1-methyl-1H-pyrrolo[2,3-c]pyridin-3-yl)-1H-benzo[d]imidazol-4-yl)ethanesulfonamide | N.D. |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 62 | 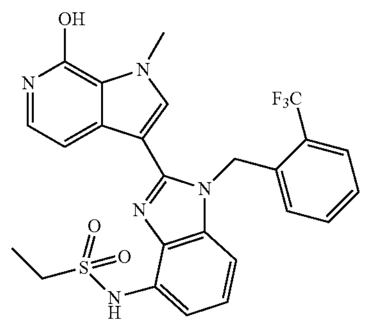 [SMILES: CCS(=O)(=O)Nc1cccc2c1nc(-c1cn(C)c3c(O)nccc13)n2Cc1ccccc1C(F)(F)F] | N-(2-(7-hydroxy-1-methyl-1H-pyrrolo[2,3-c]pyridin-3-yl)-1-(2-(trifluoromethyl)benzyl)-1H-benzo[d]imidazol-4-yl)ethanesulfonamide | >0.1 |
| 63 | 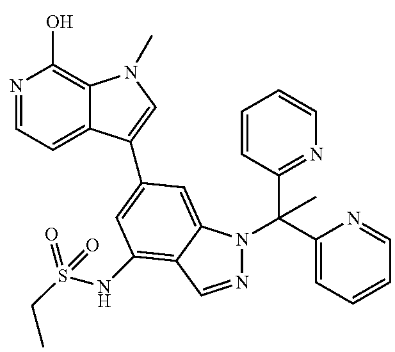 [SMILES: CCS(=O)(=O)Nc1cc(-c2cn(C)c3c(O)nccc23)cc2c1cnn2C(C)(c1ccccn1)c1ccccn1] | N-(1-(1,1-di(pyridin-2-yl)ethyl)-6-(7-hydroxy-1-methyl-1H-pyrrolo[2,3-c]pyridin-3-yl)-1H-indazol-4-yl)ethanesulfonamide | <1 |
| 64 | 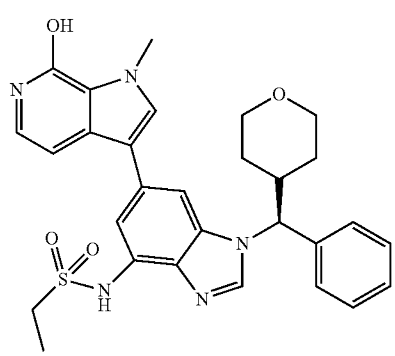 [SMILES: CCS(=O)(=O)Nc1cc(-c2cn(C)c3c(O)nccc23)cc2c1ncn2[C@H](c1ccccc1)C1CCOCC1] | (S)-N-(6-(7-hydroxy-1-methyl-1H-pyrrolo[2,3-c]pyridin-3-yl)-1-(phenyl(tetrahydro-2H-pyran-4-yl)methyl)-1H-benzo[d]imidazol-4-yl)ethanesulfonamide | <1 |
| 65 | 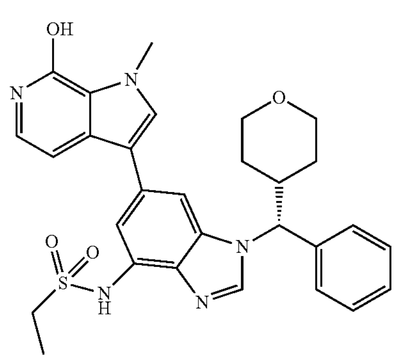 [SMILES: CCS(=O)(=O)Nc1cc(-c2cn(C)c3c(O)nccc23)cc2c1ncn2[C@@H](c1ccccc1)C1CCOCC1] | (S)-N-(6-(7-hydroxy-1-methyl-1H-pyrrolo[2,3-c]pyridin-3-yl)-1-(phenyl(tetrahydro-2H-pyran-4-yl)methyl)-1H-indol-4-yl)ethanesulfonamide | <1 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 66 | 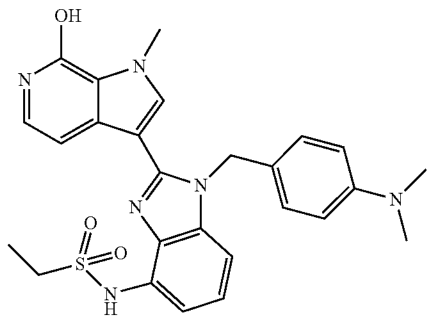 [SMILES: CCS(=O)(=O)Nc1cccc2c1nc(-c1cn(C)c3c(O)nccc13)n2Cc1ccc(N(C)C)cc1] | N-(1-(4-(dimethylamino)benzyl)-2-(7-hydroxy-1-methyl-1H-pyrrolo[2,3-c]pyridin-3-yl)-1H-benzo[d]imidazol-4-yl)ethanesulfonamide | >0.1 |
| 67 | 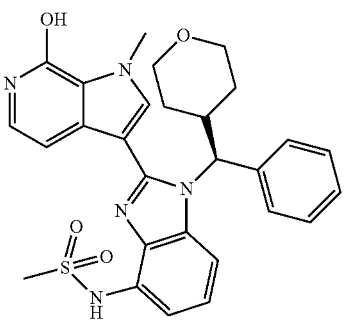 [SMILES: Cn1cc(-c2nc3c(NS(C)(=O)=O)cccc3n2[C@H](c2ccccc2)C2CCOCC2)c2ccnc(O)c21] | (S)-N-(2-(7-hydroxy-1-methyl-1H-pyrrolo[2,3-c]pyridin-3-yl)-1-(phenyl(tetrahydro-2H-pyran-4-yl)methyl)-1H-benzo[d]imidazol-4-yl)methanesulfonamide | <1 |
| 68 | 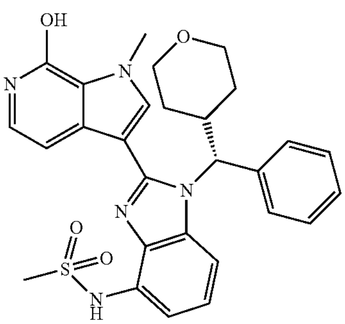 [SMILES: Cn1cc(-c2nc3c(NS(C)(=O)=O)cccc3n2[C@@H](c2ccccc2)C2CCOCC2)c2ccnc(O)c21] | (R)-N-(2-(7-hydroxy-1-methyl-1H-pyrrolo[2,3-c]pyridin-3-yl)-1-(phenyl(tetrahydro-2H-pyran-4-yl)methyl)-1H-benzo[d]imidazol-4-yl)methanesulfonamide | <1 |
| 69 | 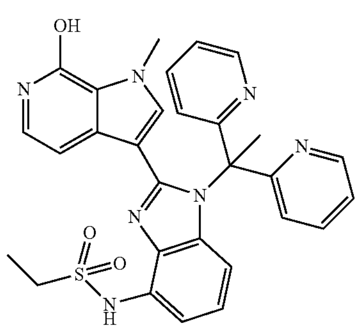 [SMILES: CCS(=O)(=O)Nc1cccc2c1nc(-c1cn(C)c3c(O)nccc13)n2C(C)(c1ccccn1)c1ccccn1] | N-(1-(1,1-di(pyridin-2-yl)ethyl)-2-(7-hydroxy-1-methyl-1H-pyrrolo[2,3-c]pyridin-3-yl)-1H-benzo[d]imidazol-4-yl)ethanesulfonamide | <1 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 70 | 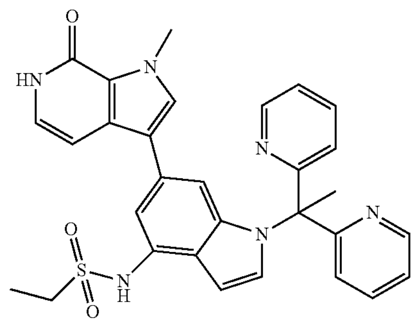 [SMILES: CCS(=O)(=O)Nc1cc(-c2cn(C)c3c(=O)[nH]ccc23)cc2c1ccn2C(C)(c1ccccn1)c1ccccn1] | N-(1-(1,1-di(pyridin-2-yl)ethyl)-2-(7-hydroxy-1-methyl-1H-pyrrolo[2,3-c]pyridin-3-yl)-1H-benzo[d]imidazol-4-yl)ethanesulfonamide | 0.0009 |
| 71 | 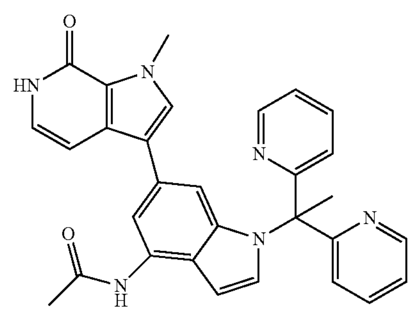 [SMILES: CC(=O)Nc1cc(-c2cn(C)c3c(=O)[nH]ccc23)cc2c1ccn2C(C)(c1ccccn1)c1ccccn1] | N-(1-(1,1-di(pyridin-2-yl)ethyl)-6-(1-methyl-7-oxo-6,7-dihydro-1H-pyrrolo[2,3-c]pyridin-3-yl)-1H-indol-4-yl)acetamide | 0.010 |
| 72 | 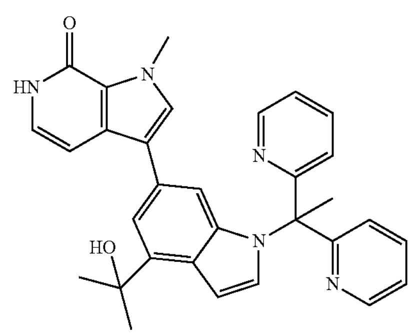 [SMILES: Cn1cc(-c2cc(C(C)(C)O)c3ccn(C(C)(c4ccccn4)c4ccccn4)c3c2)c2cc[nH]c(=O)c21] | (3-(1-(1,1-di(pyridin-2-yl)ethyl)-4-(2-hydroxypropan-2-yl)-1H-indol-6-yl)-1-methyl-1H-pyrrolo[2,3-c]pyridin-7(6H)-one | 0.020 |
| 73 | 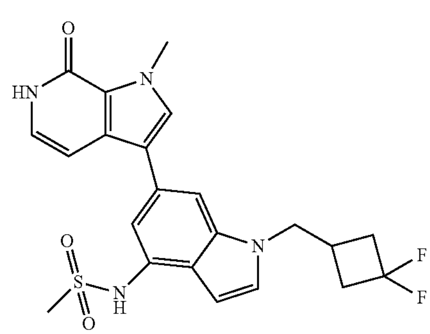 [SMILES: Cn1cc(-c2cc(NS(C)(=O)=O)c3ccn(CC4CC(F)(F)C4)c3c2)c2cc[nH]c(=O)c21] | N-(1-((3,3-difluorocyclobutyl)methyl)-6-(1-methyl-7-oxo-6,7-dihydro-1H-pyrrolo[2,3-c]pyridin-3-yl)-1H-indol-4-yl)methanesulfonamide | 0.062 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 74 | 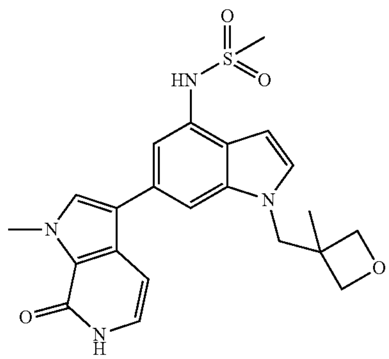 [SMILES: Cn1cc(-c2cc(NS(C)(=O)=O)c3ccn(CC4(C)COC4)c3c2)c2cc[nH]c(=O)c21] | N-(6-(1-methyl-7-oxo-6,7-dihydro-1H-pyrrolo[2,3-c]pyridin-3-yl)-1-((3-methyloxetan-3-yl)methyl)-1H-indol-4-yl)methanesulfonamide | 0.134 |
| 75 | 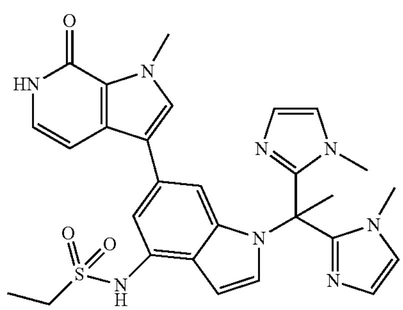 [SMILES: CCS(=O)(=O)Nc1cc(-c2cn(C)c3c(=O)[nH]ccc23)cc2c1ccn2C(C)(c1nccn1C)c1nccn1C] | N-(1-(1,1-bis(1-methyl-1H-imidazol-2-yl)ethyl)-6-(7-hydroxy-1-methyl-1H-pyrazolo[2,3-c]pyridin-3-yl)-1H-indol-4-yl)ethanesulfonamide | <1 |
| 76 | 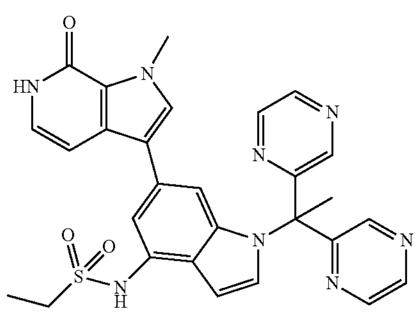 [SMILES: CCS(=O)(=O)Nc1cc(-c2cn(C)c3c(=O)[nH]ccc23)cc2c1ccn2C(C)(c1cnccn1)c1cnccn1] | N-(1-(1,1-di(pyrazin-2-yl)ethyl)-6-(7-hydroxy-1-methyl-1H-pyrrolo[2,3-c]pyridin-3-yl)-1H-indol-4-yl)ethnaesulfonamide | <1 |
| 77 | 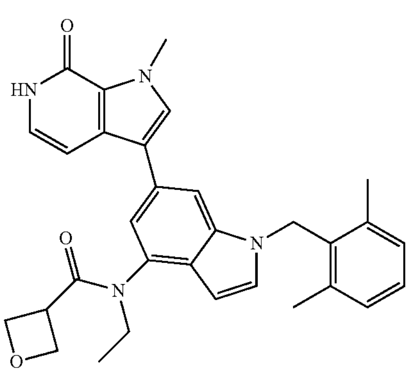 [SMILES: CCN(C(=O)C1COC1)c1cc(-c2cn(C)c3c(=O)[nH]ccc23)cc2c1ccn2Cc1c(C)cccc1C] | N-(1-(2,6-dimethylbenzyl)-6-(7-hydroxy-1-methyl-1H-pyrrolo[2,3-c]pyridin-3-yl)-1H-indol-4-yl)-N-ethyloxetane-3-carboxamide | >0.1 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 78 | 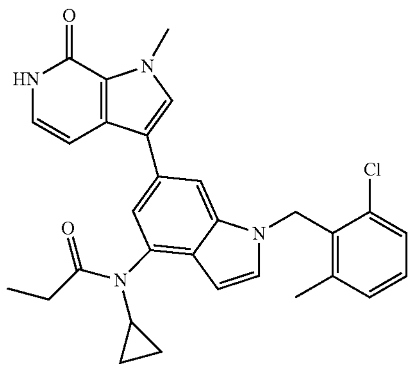 [SMILES: CCC(=O)N(c1cc(-c2cn(C)c3c(=O)[nH]ccc23)cc2c1ccn2Cc1c(C)cccc1Cl)C1CC1] | N-(1-(2-chloro-6-methylbenzyl)-6-(7-hydroxy-1-methyl-1H-pyrrolo[2,3-c]pyridin-3-yl)-1H-indol-4-yl)-N-cyclopropylpropionamide | >0.1 |
| 79 | 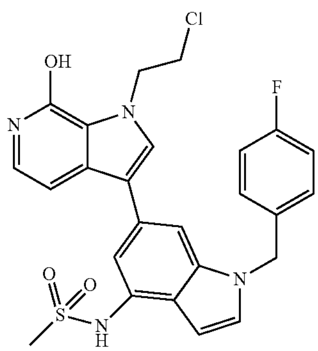 [SMILES: CS(=O)(=O)Nc1cc(-c2cn(CCCl)c3c(O)nccc23)cc2c1ccn2Cc1ccc(F)cc1] | N-(6-(1-(2-chloroethyl)-7-hydroxy-1H-pyrrolo[2,3-c]pyridin-3-yl)-1-(4-fluorobenzyl)-1H-indol-4-yl)methanesulfonamide | >0.1 |
| 80 | 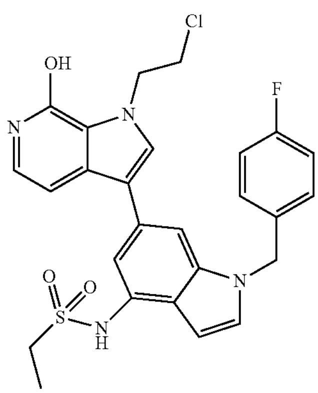 [SMILES: CCS(=O)(=O)Nc1cc(-c2cn(CCCl)c3c(O)nccc23)cc2c1ccn2Cc1ccc(F)cc1] | N-(6-(1-(2-chloroethyl)-7-hydroxy-1H-pyrrolo[2,3-c]pyridin-3-yl)-1-(4-fluorobenzyl)-1H-indol-4-yl)ethanesulfonamide | >0.1 |
| 81 | 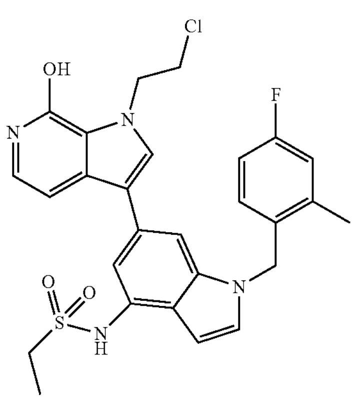 [SMILES: CCS(=O)(=O)Nc1cc(-c2cn(CCCl)c3c(O)nccc23)cc2c1ccn2Cc1ccc(F)cc1C] | N-(6-(1-(2-chloroethyl)-7-hydroxy-1H-pyrrolo[2,3-c]pyridin-3-yl)-1-(4-fluoro-2-methylbenzyl)-1H-indol-4-yl)ethanesulfonamide | >0.1 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 82 | 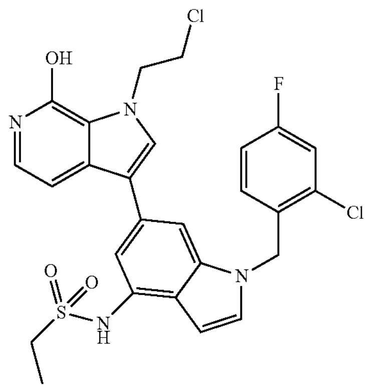 [SMILES: CCS(=O)(=O)Nc1cc(-c2cn(CCCl)c3c(O)nccc23)cc2c1ccn2Cc1ccc(F)cc1Cl] | N-(1-(2-chloro-4-fluorobenzyl)-6-(1-(2-chloroethyl)-7-hydroxy-1H-pyrrolo[2,3-c]pyridin-3-yl)-1H-indol-4-yl)ethanesulfonamide | >1 |
| 83 | 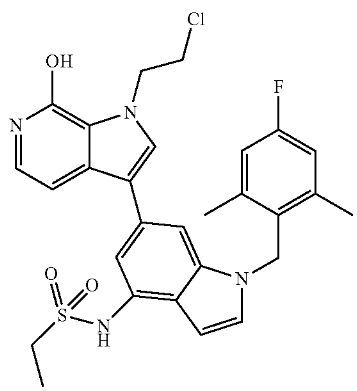 [SMILES: CCS(=O)(=O)Nc1cc(-c2cn(CCCl)c3c(O)nccc23)cc2c1ccn2Cc1c(C)cc(F)cc1C] | N-(6-(1-(2-chloroethyl)-7-hydroxy-1H-pyrrolo[2,3-c]pyridin-3-yl)-1-(4-fluoro-2,6-dimethylbenzyl)-1H-indol-4-yl)ethanesulfonamide | >1 |
| 84 | 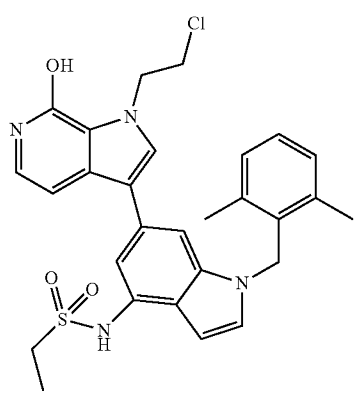 [SMILES: CCS(=O)(=O)Nc1cc(-c2cn(CCCl)c3c(O)nccc23)cc2c1ccn2Cc1c(C)cccc1C] | N-(6-(1-(2-chloroethyl)-7-hydroxy-1H-pyrrolo[2,3-c]pyridin-3-yl)-1-(2,6-dimethylbenzyl)-1H-indol-4-yl)ethanesulfonamide | <1 |
| 85 | 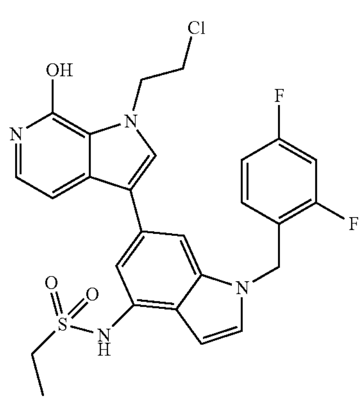 [SMILES: CCS(=O)(=O)Nc1cc(-c2cn(CCCl)c3c(O)nccc23)cc2c1ccn2Cc1ccc(F)cc1F] | N-(6-(1-(2-chloroethyl)-7-hydroxy-1H-pyrrolo[2,3-c]pyridin-3-yl)-1-(2,4-difluorobenzyl)-1H-indol-4-yl)ethanesulfonamide | <1 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 86 | 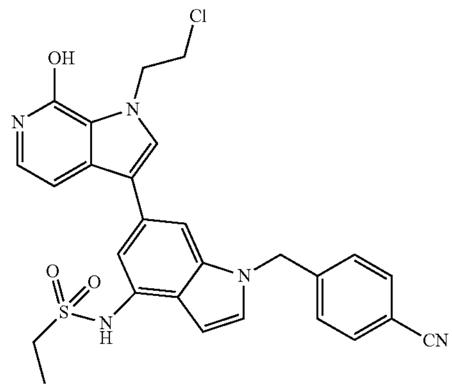 [SMILES: CCS(=O)(=O)Nc1cc(-c2cn(CCCl)c3c(O)nccc23)cc2c1ccn2Cc1ccc(C#N)cc1] | N-(6-(1-(2-chloroethyl)-7-hydroxy-1H-pyrrolo[2,3-c]pyridin-3-yl)-1-(4-cyanobenzyl)-1H-indol-4-yl)ethanesulfonamide | <1 |
| 87 | 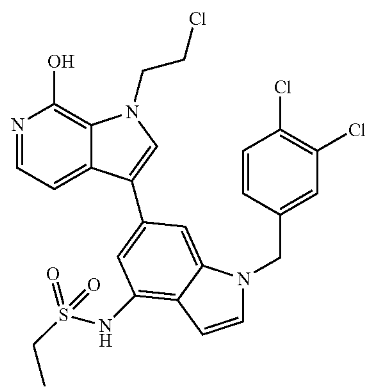 [SMILES: CCS(=O)(=O)Nc1cc(-c2cn(CCCl)c3c(O)nccc23)cc2c1ccn2Cc1ccc(Cl)c(Cl)c1] | N-(6-(1-(2-chloroethyl)-7-hydroxy-1H-pyrrolo[2,3-c]pyridin-3-yl)-1-(3,4-dichlorobenzyl)-1H-indol-4-yl)ethanesulfonamide | <1 |
| 88 | 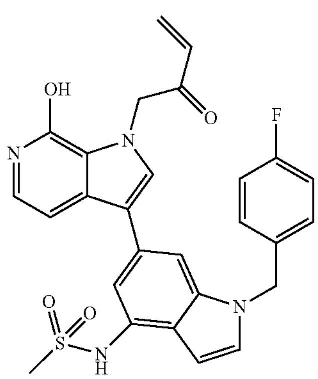 [SMILES: C=CC(=O)Cn1cc(-c2cc(NS(C)(=O)=O)c3ccn(Cc4ccc(F)cc4)c3c2)c2ccnc(O)c21] | N-(1-(4-fluorobenzyl)-6-(7-hydroxy-1-(2-oxobut-3-en-1-yl)-1H-pyrrolo[2,3-c]pyridin-3-yl)-1H-indol-4-yl)-methanesulfonamide | <1 |
| 89 | 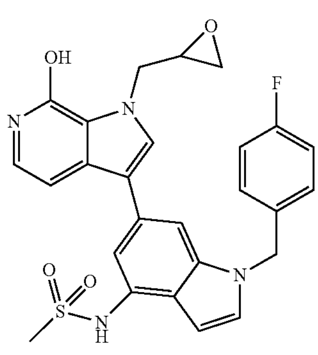 [SMILES: CS(=O)(=O)Nc1cc(-c2cn(CC3CO3)c3c(O)nccc23)cc2c1ccn2Cc1ccc(F)cc1] | N-(1-(4-fluorobenzyl)-6-(7-hydroxy-1-(oxiran-2-ylmethyl)-1H-pyrrolo[2,3-c]pyridin-3-yl)-1H-indol-4-yl)methanesulfonamide | <1 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 90 | 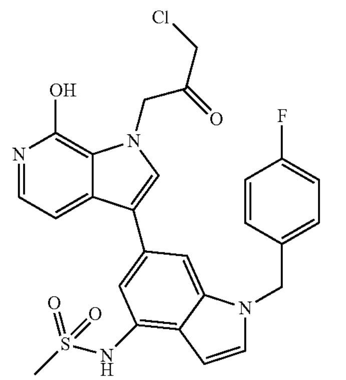 [SMILES: CS(=O)(=O)Nc1cc(-c2cn(CC(=O)CCl)c3c(O)nccc23)cc2c1ccn2Cc1ccc(F)cc1] | N-(6-(1-(3-chloro-2-oxopropyl)-7-hydroxy-1H-pyrrolo[2,3-c]pyridin-3-yl)-1-(4-fluorobenzyl)-1H-indol-4-yl)methanesulfonamide | <1 |
| 91 | 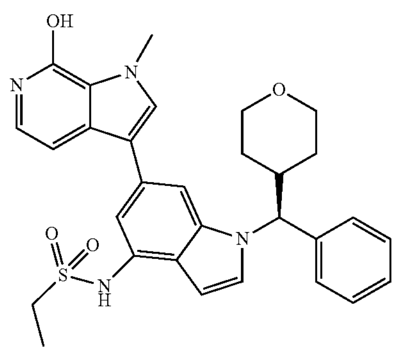 [SMILES: CCS(=O)(=O)Nc1cc(-c2cn(C)c3c(O)nccc23)cc2c1ccn2[C@H](c1ccccc1)C1CCOCC1] | (S)-N-(6-(7-hydroxy-1-methyl-1H-pyrrolo[2,3-c]pyridin-3-yl)-1-(phenyl(tetrahydro-2H-pyran-4-yl)methyl)-1H-indol-4-yl)ethanesulfonamide | <1 |
| 92 | 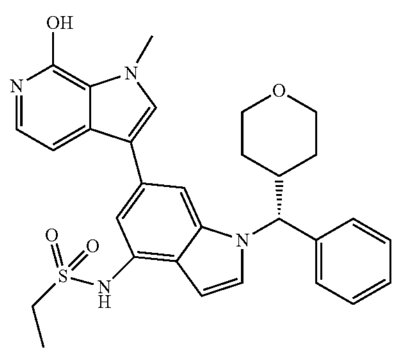 [SMILES: CCS(=O)(=O)Nc1cc(-c2cn(C)c3c(O)nccc23)cc2c1ccn2[C@@H](c1ccccc1)C1CCOCC1] | (R)-N-(6-(7-hydroxy-1-methyl-1H-pyrrolo[2,3-c]pyridin-3-yl)-1-(phenyl(tetrahydro-2H-pyran-4-yl)methyl)-1H-indol-4-yl)ethanesulfonamide | <1 |
| 93 | 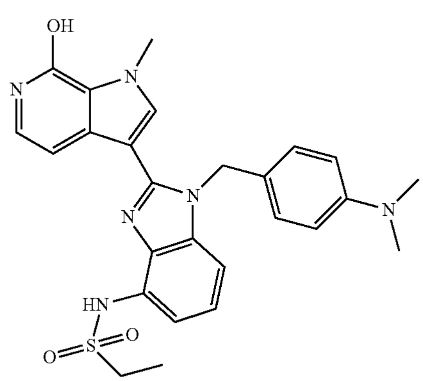 [SMILES: CCS(=O)(=O)Nc1cccc2c1nc(-c1cn(C)c3c(O)nccc13)n2Cc1ccc(N(C)C)cc1] | N-(1-(4-(dimethylamino)benzyl)-2-(7-hydroxy-1-methyl-1H-pyrrolo[2,3-c]pyridin-3-yl)-1H-benzo[d]imidazol-4-yl)ethanesulfonamide | >0.1 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 94 | 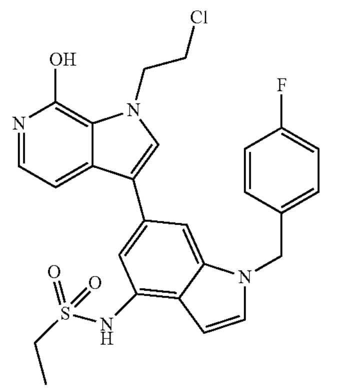 [SMILES: CCS(=O)(=O)Nc1cc(-c2cn(CCCl)c3c(O)nccc23)cc2c1ccn2Cc1ccc(F)cc1] | N-(6-(1-(2-chloroethyl)-7-hydroxy-1H-pyrrolo[2,3-c]pyridin-3-yl)-1-(4-fluorobenzyl)-1H-indol-4-yl)ethanesulfonamide | >0.1 |
| 95 | 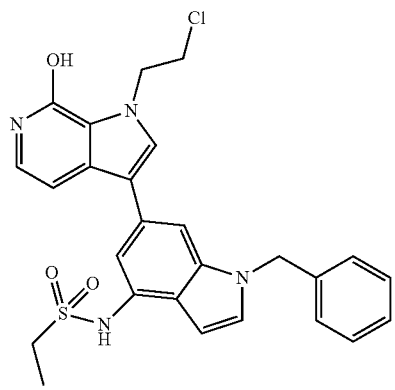 [SMILES: CCS(=O)(=O)Nc1cc(-c2cn(CCCl)c3c(O)nccc23)cc2c1ccn2Cc1ccccc1] | N-(1-benzyl-6-(1-(2-chloroethyl)-7-hydroxy-1H-pyrrolo[2,3-c]pyridin-3-yl)-1H-indol-4-yl)ethanesulfonamide | >0.1 |
| 96 | 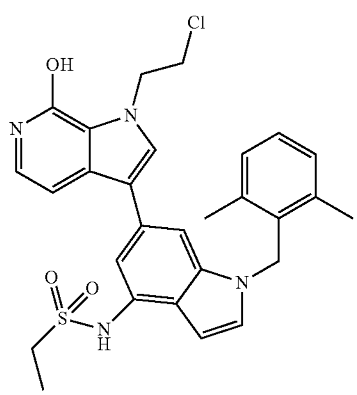 [SMILES: CCS(=O)(=O)Nc1cc(-c2cn(CCCl)c3c(O)nccc23)cc2c1ccn2Cc1c(C)cccc1C] | N-(6-(1-(2-chloroethyl)-7-hydroxy-1H-pyrrolo[2,3-c]pyridin-3-yl)-1-(2,6-dimethylbenzyl)-1H-indol-4-yl)ethanesulfonamide | >0.1 |
| 97 | 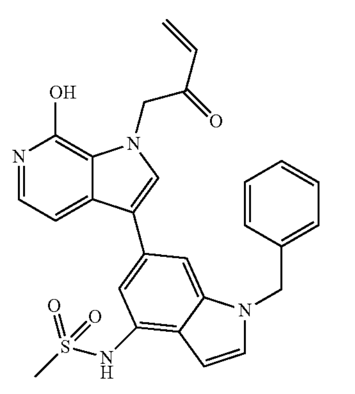 [SMILES: C=CC(=O)Cn1cc(-c2cc(NS(C)(=O)=O)c3ccn(Cc4ccccc4)c3c2)c2ccnc(O)c21] | N-(1-benzyl-6-(7-hydroxy-1-(2-oxobut-3-en-1-yl)-1H-pyrrolo[2,3-c]pyridin-3-yl)-1H-indol-4-yl)methanesulfonamide | >0.1 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 98 | 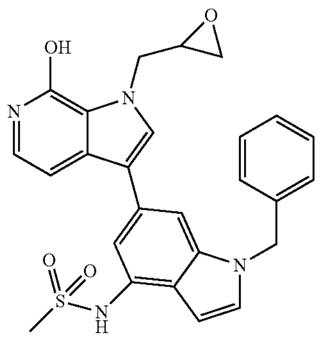 [SMILES: CS(=O)(=O)Nc1cc(-c2cn(CC3CO3)c3c(O)nccc23)cc2c1ccn2Cc1ccccc1] | N-(1-benzyl-6-(7-hydroxy-1-(oxiran-2-ylmethyl)-1H-pyrrolo[2,3-c]pyridin-3-yl)-1H-indol-4-yl)methanesulfonamide | <1 |
| 99 | 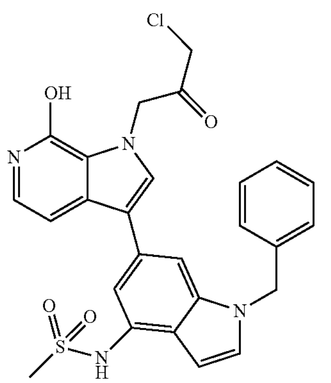 [SMILES: CS(=O)(=O)Nc1cc(-c2cn(CC(=O)CCl)c3c(O)nccc23)cc2c1ccn2Cc1ccccc1] | N-(1-benzyl-6-(1-(3-chloro-2-oxopropyl)-7-hydroxy-1H-pyrrolo[2,3-c]pyridin-3-yl)-1H-indol-4-yl)methanesulfonamide | <1 |
| 100 | 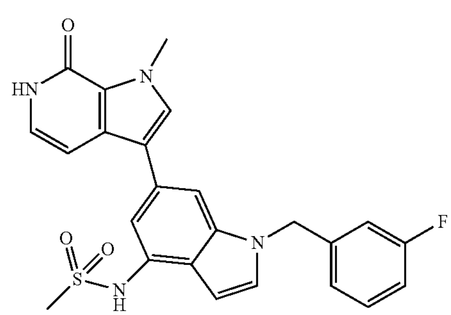 [SMILES: Cn1cc(-c2cc(NS(C)(=O)=O)c3ccn(Cc4cccc(F)c4)c3c2)c2cc[nH]c(=O)c21] | N-(1-(3-fluorobenzyl)-6-(1-methyl-7-oxo-6,7-dihydro-1H-pyrrolo[2,3-c]pyridin-3-yl)-1H-indol-4-yl)methanesulfonamide | <1 |
| 101 | 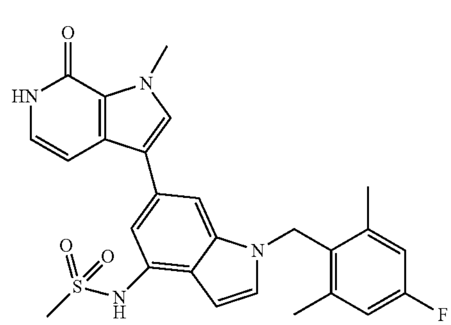 [SMILES: Cc1cc(F)cc(C)c1Cn1ccc2c(NS(C)(=O)=O)cc(-c3cn(C)c4c(=O)[nH]ccc34)cc21] | N-(1-(4-fluoro-2,6-dimethylbenzyl)-6-(1-methyl-7-oxo-6,7-dihydro-1H-pyrrolo[2,3-c]pyridin-3-yl)-1H-indol-4-yl)methanesulfonamide | <1 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 102 | 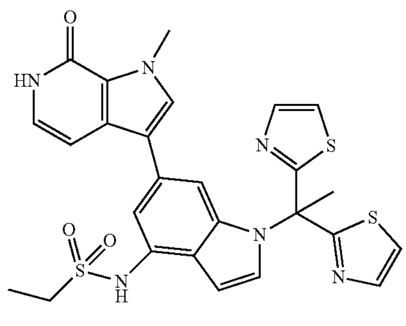 [SMILES: CCS(=O)(=O)Nc1cc(-c2cn(C)c3c(=O)[nH]ccc23)cc2c1ccn2C(C)(c1nccs1)c1nccs1] | N-(1-(1,1-di(thiazol-2-yl)ethyl)-6-(1-methyl-7-oxo-6,7-dihydro-1H-pyrrolo[2,3-c]pyridin-3-yl)-1H-indol-4-yl)ethanesulfonamide | <1 |
| 103 | 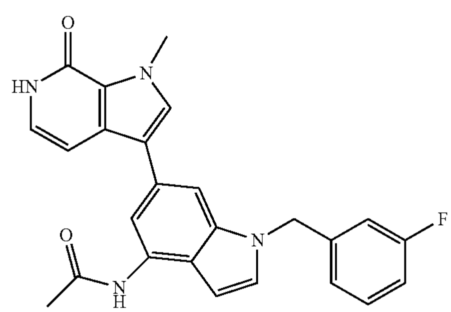 [SMILES: CC(=O)Nc1cc(-c2cn(C)c3c(=O)[nH]ccc23)cc2c1ccn2Cc1cccc(F)c1] | N-(1-(3-fluorobenzyl)-6-(1-methyl-7-oxo-6,7-dihydro-1H-pyrrolo[2,3-c]pyridin-3-yl)-1H-indol-4-yl)acetamide | <1 |
| 104 | 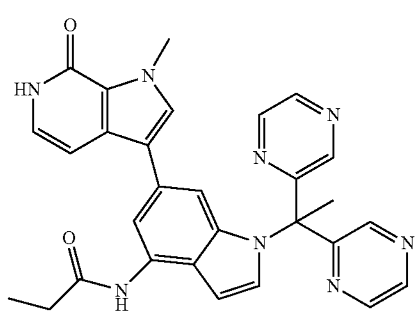 [SMILES: CCC(=O)Nc1cc(-c2cn(C)c3c(=O)[nH]ccc23)cc2c1ccn2C(C)(c1cnccn1)c1cnccn1] | N-(1-(1,1-di(pyrazin-2-yl)ethyl)-6-(1-methyl-7-oxo-6,7-dihydro-1H-pyrrolo[2,3-c]pyridin-3-yl)-1H-indol-4-yl)propionamide | <1 |
| 105 | 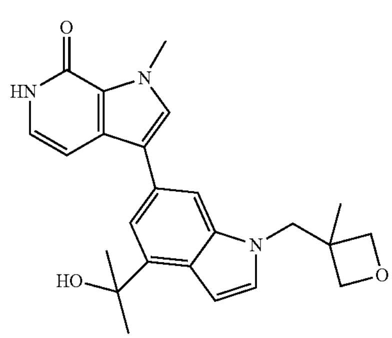 [SMILES: Cn1cc(-c2cc(C(C)(C)O)c3ccn(CC4(C)COC4)c3c2)c2cc[nH]c(=O)c21] | 3-(4-(2-hydroxypropan-2-yl)-1-((3-methyloxetan-3-yl)methyl)-1H-inidol-6-yl)-1-methyl-1,6-dihydro-7H-pyrrolo[2,3-c]pyridin-7-one | <1 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 106 | 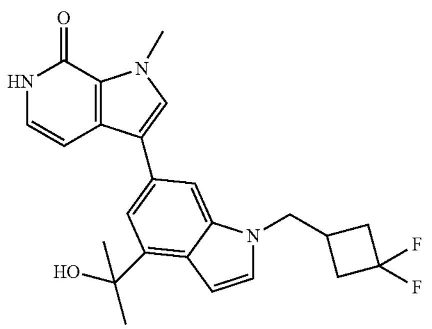 [SMILES: Cn1cc(-c2cc(C(C)(C)O)c3ccn(CC4CC(F)(F)C4)c3c2)c2cc[nH]c(=O)c21] | 3-(1-((3,3-difluorocyclobutyl)methyl)-4-(2-hydroxypropan-2-yl)-1H-indol-6-yl)-1-methyl-1,6-dihydro-7H-pyrrolo[2,3-c]pyridin-7-one | <1 |
| 107 | 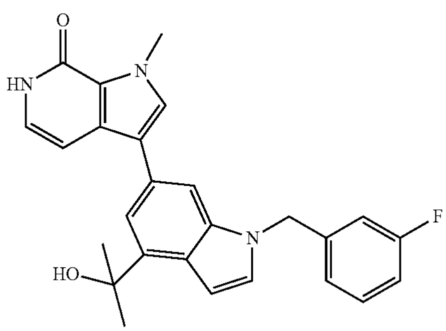 [SMILES: Cn1cc(-c2cc(C(C)(C)O)c3ccn(Cc4cccc(F)c4)c3c2)c2cc[nH]c(=O)c21] | 3-(1-(3-fluorobenzyl)-4-(2-hydroxypropan-2-yl)-1H-indol-6-yl)-1-methyl-1,6-dihydro-7H-pyrrolo[2,3-c]pyridin-7-one | <1 |
| 108 | 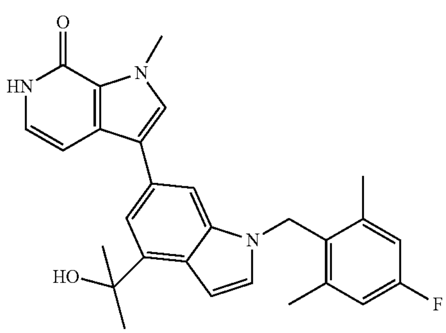 [SMILES: Cc1cc(F)cc(C)c1Cn1ccc2c(C(C)(C)O)cc(-c3cn(C)c4c(=O)[nH]ccc34)cc21] | 3-(1-(4-fluoro-2,6-dimethylbenzyl)-4-(2-hydroxypropan-2-yl)-1H-indol-6-yl)-1-methyl-1,6-dihydro-7H-pyrrolo[2,3-c]pyridin-7-one | <1 |
| 109 | 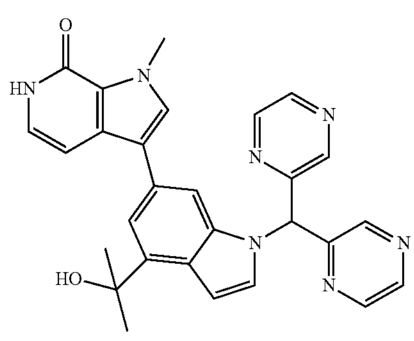 [SMILES: Cn1cc(-c2cc(C(C)(C)O)c3ccn(C(c4cnccn4)c4cnccn4)c3c2)c2cc[nH]c(=O)c21] | 3-(1-(1,1-di(pyrazin-2-yl)ethyl)-4-(2-hydroxypropan-2-yl)-1H-indol-6-yl)-1-methyl-1,6-dihydro-7H-pyrrolo[2,3-c]pyridin-7-one | <1 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 110 | 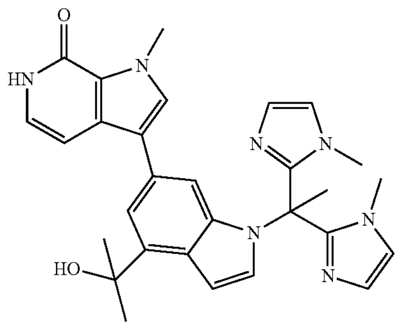 [SMILES: Cn1ccnc1C(C)(c1nccn1C)n1ccc2c(C(C)(C)O)cc(-c3cn(C)c4c(=O)[nH]ccc34)cc21] | 3-(1-(1,1-bis(1-methyl-1H-imidazol-2-yl)ethyl)-4-(2-hydroxypropan-2-yl)-1H-indol-6-yl)-1-methyl-1,6-dihydro-7H-pyrrolo[2,3-c]pyridin-7-one | <1 |
| 111 | 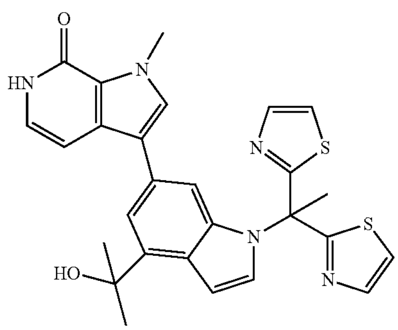 [SMILES: Cn1cc(-c2cc(C(C)(C)O)c3ccn(C(C)(c4nccs4)c4nccs4)c3c2)c2cc[nH]c(=O)c21] | 3-(1-(1,1-di(thiazol-2-yl)ethyl)-4-(2-hydroxypropan-2-yl)-1H-indol-6-yl)-1-methyl-1,6-dihydro-7H-pyrrolo[2,3-c]pyridin-7-one | <1 |
| 112 | 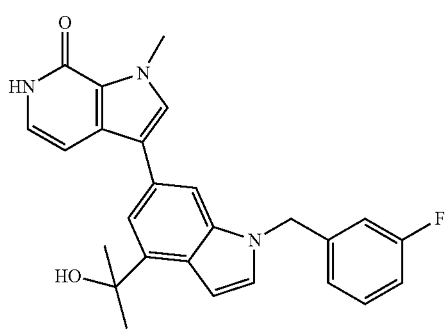 [SMILES: Cn1cc(-c2cc(C(C)(C)O)c3ccn(Cc4cccc(F)c4)c3c2)c2cc[nH]c(=O)c21] | 3-(1-(3-fluorobenzyl)-4-(2-hydroxypropan-2-yl)-1H-indol-6-yl)-1-methyl-1,6-dihydro-7H-pyrrollo[2,3-c]pyridin-7-one | <1 |
| 113 | 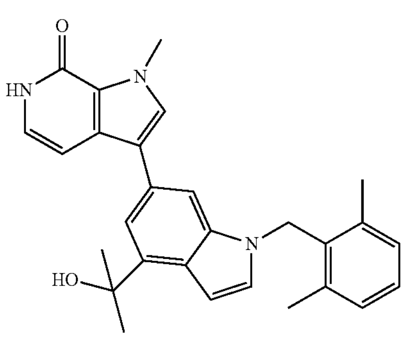 [SMILES: Cc1cccc(C)c1Cn1ccc2c(C(C)(C)O)cc(-c3cn(C)c4c(=O)[nH]ccc34)cc21] | 3-(1-(2,6-dimethylbenzyl)-4-(2-hydroxypropan-2-yl)-1H-indol-6-yl)-1-methyl-1,6-dihydro-7H-pyrrolo[2,3-c]pyridin-7-one | <1 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 114 | 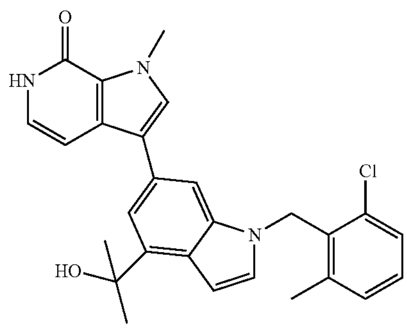 [SMILES: Cc1cccc(Cl)c1Cn1ccc2c(C(C)(C)O)cc(-c3cn(C)c4c(=O)[nH]ccc34)cc21] | 3-(1-(2-chloro-6-methylbenzyl)-4-(2-hydroxypropan-2-yl)-1H-indol-6-yl)-1-methyl-1,6-dihydro-7H-pyrrolo[2,3-c]pyridin-7-one | <1 |
| 115 | 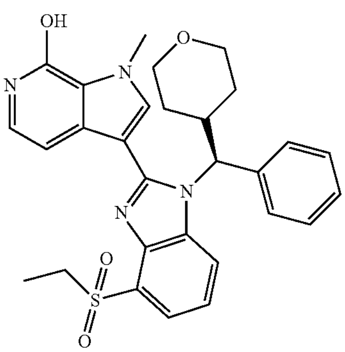 [SMILES: CCS(=O)(=O)c1cccc2c1nc(-c1cn(C)c3c(O)nccc13)n2[C@H](c1ccccc1)C1CCOCC1] | (S)-3-(4-(ethylsulfonyl)-1-(phenyl(tetrahydro-2H-pyran-4-yl)methyl)-1H-benzo[d]imidazol-2-yl)-1-methyl-1H-pyrrolo[2,3-c]pyridin-7-ol | <1 |
| 116 | 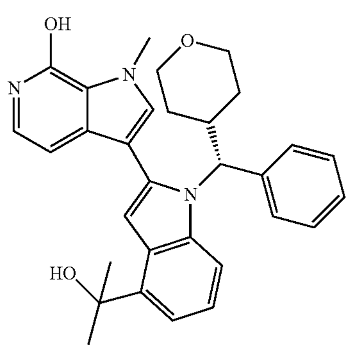 [SMILES: Cn1cc(-c2cc3c(C(C)(C)O)cccc3n2[C@@H](c2ccccc2)C2CCOCC2)c2ccnc(O)c21] | (R)-3-(4-(2-hydroxypropan-2-yl)-1-(phenyl(tetrahydro-2H-pyran-4-yl)methyl)-1H-indol-2-yl)-1-methyl-1H-pyrrolo[2,3-c]pyridin-7-ol | <1 |
| 117 | 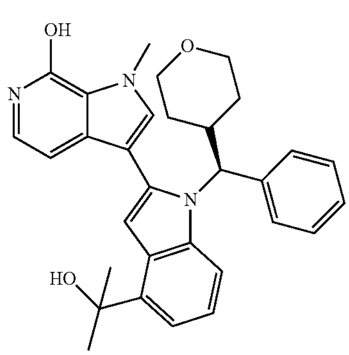 [SMILES: Cn1cc(-c2cc3c(C(C)(C)O)cccc3n2[C@H](c2ccccc2)C2CCOCC2)c2ccnc(O)c21] | (S)-3-(4-(2-hydroxypropan-2-yl)-1-(phenyl(tetrahydro-2H-pyran-4-yl)methyl)-1H-indol-2-yl)-1-methyl-1H-pyrrolo[2,3-c]pyridin-7-ol | <1 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 118 | 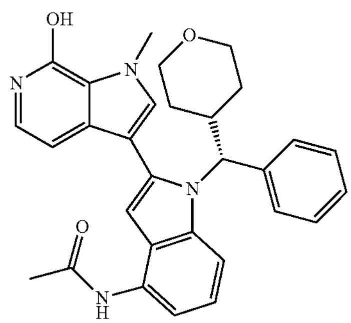 [SMILES: CC(=O)Nc1cccc2c1cc(-c1cn(C)c3c(O)nccc13)n2[C@@H](c1ccccc1)C1CCOCC1] | (R)-N-(2-(7-hydroxy-1-methyl-1H-pyrrolo[2,3-c]pyridin-3-yl)-1-(phenyl(tetrahydro-2H-pyran-4-yl)methyl)-1H-indol-4-yl)acetamide | <1 |
| 119 | 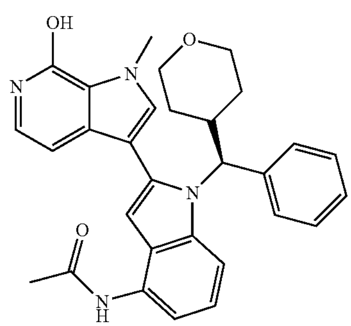 [SMILES: CC(=O)Nc1cccc2c1cc(-c1cn(C)c3c(O)nccc13)n2[C@H](c1ccccc1)C1CCOCC1] | (S)-N-(2-(7-hydroxy-1-methyl-1H-pyrrolo[2,3-c]pyridin-3-yl)-1-(phenyl(tetrahydro-2H-pyran-4-yl)methyl)-1H-indol-4-yl)acetamide | <1 |
| 120 | 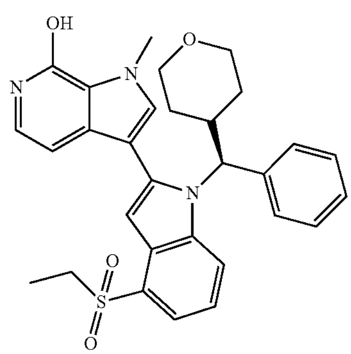 [SMILES: CCS(=O)(=O)c1cccc2c1cc(-c1cn(C)c3c(O)nccc13)n2[C@H](c1ccccc1)C1CCOCC1] | (S)-3-(4-(ethylsulfonyl)-1-(phenyl(tetrahydro-2H-pyran-4-yl)methyl)-1H-indol-2-yl)-1-methyl-1H-pyrrolo[2,3-c]pyridin-7-ol | <1 |
| 121 | 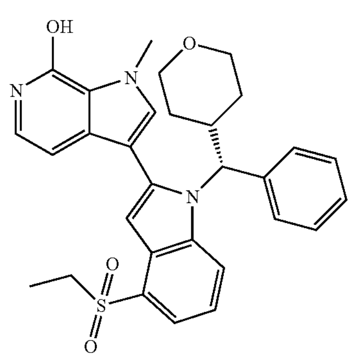 [SMILES: CCS(=O)(=O)c1cccc2c1cc(-c1cn(C)c3c(O)nccc13)n2[C@@H](c1ccccc1)C1CCOCC1] | (R)-3-(4-(ethylsulfonyl)-1-(phenyl(tetrahydro-2H-pyran-4-yl)methyl)-1H-indol-2-yl)-1-methyl-1H-pyrrolo[2,3-c]pyridin-7-ol | <1 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 122 | 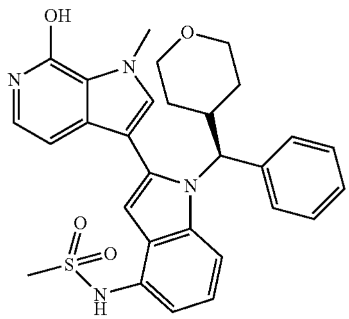 [SMILES: Cn1cc(-c2cc3c(NS(C)(=O)=O)cccc3n2[C@H](c2ccccc2)C2CCOCC2)c2ccnc(O)c21] | (S)-N-(2-(7-hydroxy-1-methyl-1H-pyrrolo[2,3-c]pyridin-3-yl)-1-(phenyl(tetrahydro-2H-pyran-4-yl)methyl)-1H-indol-4-yl)methanesulfonamide | <1 |
| 123 | 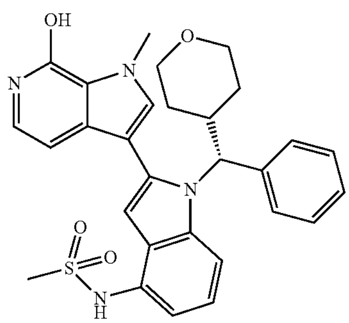 [SMILES: Cn1cc(-c2cc3c(NS(C)(=O)=O)cccc3n2[C@@H](c2ccccc2)C2CCOCC2)c2ccnc(O)c21] | (R)-N-(2-(7-hydroxy-1-methyl-1H-pyrrolo[2,3-c]pyridin-3-yl)-1-(phenyl(tetrahydro-2H-pyran-4-yl)methyl)-1H-indol-4-yl)methanesulfonamide | <1 |
| 124 | 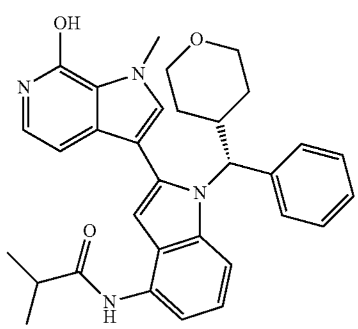 [SMILES: CC(C)C(=O)Nc1cccc2c1cc(-c1cn(C)c3c(O)nccc13)n2[C@@H](c1ccccc1)C1CCOCC1] | (R)-N-(2-(7-hydroxy-1-methyl-1H-pyrrolo[2,3-c]pyridin-3-yl)-1-(phenyl(tetrahydro-2H-pyran-4-yl)methyl)-1H-indol-4-yl)isobutyramide | <1 |
| 125 | 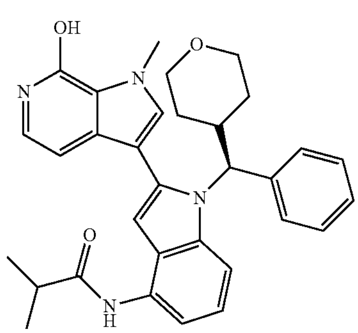 [SMILES: CC(C)C(=O)Nc1cccc2c1cc(-c1cn(C)c3c(O)nccc13)n2[C@H](c1ccccc1)C1CCOCC1] | (S)-N-(2-(7-hydroxy-1-methyl-1H-pyrrolo[2,3-c]pyridin-3-yl)-1-(phenyl(tetrahydro-2H-pyran-4-yl)methyl)-1H-indol-4-yl)isobutyramide | <1 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 126 | 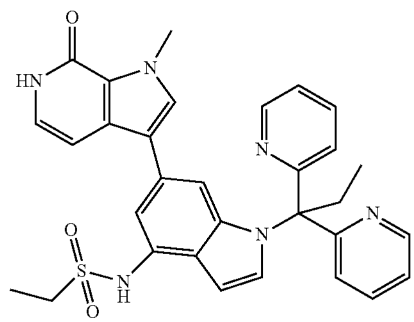 [SMILES: CCC(c1ccccn1)(c1ccccn1)n1ccc2c(NS(=O)(=O)CC)cc(-c3cn(C)c4c(=O)[nH]ccc34)cc21] | N-(1-(1,1-di(pyridin-2-yl)propyl)-6-(1-methyl-7-oxo-6,7-dihydro-1H-pyrrolo[2,3-c]pyridin-3-yl)-1H-indol-4-yl)ethanesulfonamide | <0.01 |
| 127 | 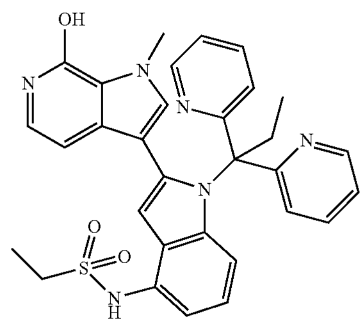 [SMILES: CCC(c1ccccn1)(c1ccccn1)n1c(-c2cn(C)c3c(O)nccc23)cc2c(NS(=O)(=O)CC)cccc21] | N-(1-(1,1-di(pyridin-2-yl)propyl)-2-(7-hydroxy-1-methyl-1H-pyrrolo[2,3-c]pyridin-3-yl)-1H-benzo[d]imidazol-4-yl)ethanesulfonamide | <1 |
| 128 | 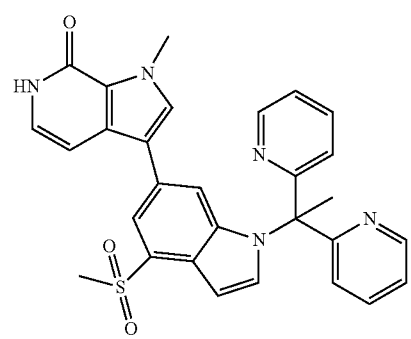 [SMILES: Cn1cc(-c2cc(S(C)(=O)=O)c3ccn(C(C)(c4ccccn4)c4ccccn4)c3c2)c2cc[nH]c(=O)c21] | 3-(1-(1,1-di(pyridin-2-yl)ethyl)-4-(methylsulfonyl)-1H-indol-6-yl)-1-methyl-1,6-dihydro-7H-pyrrolo[2,3-c]pyridin-7-one | <1 |
| 129 | 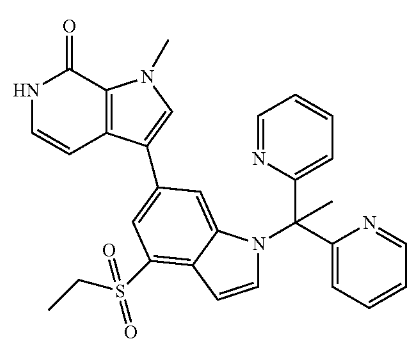 [SMILES: CCS(=O)(=O)c1cc(-c2cn(C)c3c(=O)[nH]ccc23)cc2c1ccn2C(C)(c1ccccn1)c1ccccn1] | 3-(1-(1,1-di(pyridin-2-yl)ethyl)-4-(ethylsulfonyl)-1H-indol-6-yl)-1-methyl-1,6-dihydro-7H-pyrrolo[2,3-c]pyridin-7-one | <1 |

TABLE 2-continued

Example growth inhibition in fulvestrant-resistant MCF-7: CFR cells

| Compound | Structure | Chemical name | MCF-7: 5C-FR IC$_{50}$ (uM) |
|---|---|---|---|
| 130 | [structure] | N-(1-benzhydryl-6-(1-methyl-7-oxo-6,7-dihydro-1H-pyrrolo[2,3-c]pyridin-3-yl)-1H-indol-4-yl)ethanesulfonamide | <0.1 |
| 131 | [structure] | N-(1-(1,1-di(pyridin-2-yl)ethyl)-6-(1-methyl-7-oxo-6,7-dihydro-1H-pyrrolo[2,3-c]pyridin-3-yl)-1H-indol-4-yl)isobutyramide | <0.1 |
| 132 | [structure] | N-(1-(1,1-di(pyridin-2-yl)ethyl)-6-(1-methyl-7-oxo-6,7-dihydro-1H-pyrrolo[2,3-c]pyridin-3-yl)-1H-indol-4-yl)methanesulfonamide | 0.013 |

Example 3. TR-FRET BRD4 Binding Assay

The BRD4 bromodomain 1 and/or 2 binding activity were measured by using the Cayman BRD4 bromodomain 1 or 2 TR-FRET Assay Kit (Item. No. 600520, 600530, MI, USA) respectively, according to the manufacturer's instructions. Briefly, compounds were serial diluted into the 1×TR-FRET Assay Buffer with no more than 8% DMSO, and the final concentration tested was distributed from 1 nM to 10 uM with no more than 2% DMSO. (+)JQ-1 was used as positive control. Pre-incubate the control or compounds with the bromodomain (1 or 2) Europium Chelate in the 384-well plate for 15 min at room temperature (Protect from light). Then the reconstituted BRD4 bromodomain ligand/APC Acceptor Mixture were added to every well and incubate for 1 hr at room temperature. The plate was sealed with adhesive aluminum seal to prevent photobleaching. Then the plate was read in time-resolved format by exiting the well at 340 nm and reading emmission at 620 and 670 nm, using 100 us delay and 500 us read window. Data analysis was performed using the TR-FRET ratio which is the 670 nm emission/620 nm emission. Results are demonstrated in Table 3.

TABLE 3

| Compound ID | TR-FRET BRD4-BD1 Ki (uM) | TR-FRET BRD4-BD2 Ki (uM) |
|---|---|---|
| 23 | <0.1 | <0.1 |
| 30 | <0.1 | <0.1 |
| 31 | <0.1 | <0.1 |
| 70 | <0.01 | <0.01 |
| 71 | <0.01 | <0.01 |
| 72 | <0.01 | <0.01 |

Example 4. Bromoscan Assay of Compound 70

Figure 6:
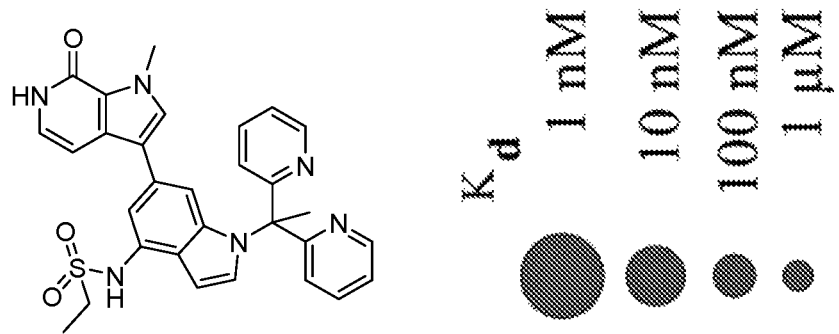
FIG. 6 shows the BromoScan of Compound (70) that measures the binding affinity across all bromodomain proteins, showing Compound (70) is selectively BET family with subnanomolar potency.
Figure 6:
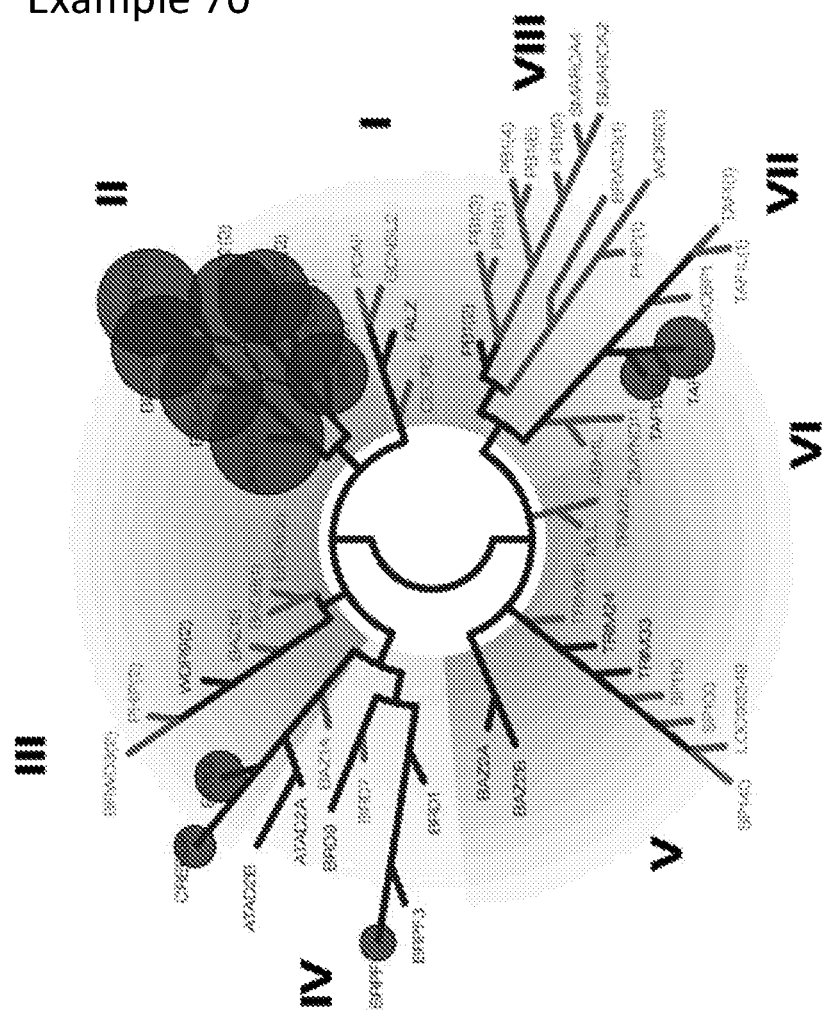

BROMOscan is a bromodomain inhibitor binding platform provided by DiscoverX that measures the interactions between compounds and a panel of bromodomain proteins. Compound (70) was tested in the bromoscan, which showed the strong binding selectivity towards BET family proteins. The data is summarized in FIG. 6 and the $K_d$s are shown in Table 4.

TABLE 4

Bromoscan Assay of Compound (70)

| DiscoveRx Gene Symbol | EntrezGene Symbol | Modifier | $K_d$ (nM) |
|---|---|---|---|
| ATAD2A | ATAD2 | > | 10000 |
| ATAD2B | ATAD2B | > | 10000 |
| BAZ2A | BAZ2A | = | 3500 |
| BAZ2B | BAZ2B | > | 10000 |
| BRD1 | BRD1 | = | 7700 |
| BRD2(1) | BRD2 | = | 0.27 |
| BRD2(1, 2) | BRD2 | = | 0.57 |
| BRD2(2) | BRD2 | = | 0.77 |
| BRD3(1) | BRD3 | = | 0.34 |
| BRD3(1, 2) | BRD3 | = | 0.27 |
| BRD3(2) | BRD3 | = | 0.61 |
| BRD4(1) | BRD4 | = | 0.29 |
| BRD4(1, 2) | BRD4 | = | 0.29 |
| BRD4(2) | BRD4 | = | 0.33 |
| BRD4(full-length, short-iso.) | BRD4 | = | 0.1 |
| BRD7 | BRD7 | > | 10000 |
| BRD8(1) | BRD8 | = | 4900 |
| BRD8(2) | BRD8 | > | 10000 |
| BRD9 | BRD9 | = | 3500 |
| BRDT(1) | BRDT | = | 0.14 |
| BRDT(1, 2) | BRDT | = | 0.23 |
| BRDT(2) | BRDT | = | 1.4 |
| BRPF1 | BRPF1 | = | 360 |
| BRPF3 | BRPF3 | > | 10000 |
| CECR2 | CECR2 | = | 6000 |
| CREBBP | CREBBP | = | 110 |
| EP300 | EP300 | = | 37 |
| FALZ | BPTF | > | 10000 |
| GCN5L2 | KAT2A | > | 10000 |
| PBRM1(2) | PBRM1 | > | 10000 |
| PBRM1(5) | PBRM1 | = | 6100 |
| PCAF | KAT2B | > | 10000 |
| SMARCA2 | SMARCA2 | > | 10000 |
| SMARCA4 | SMARCA4 | > | 10000 |
| TAF1(2) | TAF1 | = | 9.1 |
| TAF1L(2) | TAF1L | = | 44 |
| TRIM24(Bromo.) | TRIM24 | = | 4400 |
| TRIM24(PHD, Bromo.) | TRIM24 | > | 10000 |
| TRIM33(PHD, Bromo.) | TRIM33 | > | 10000 |
| WDR9(2) | BRWD1 | > | 10000 |

We claim:

1. A compound according to Formula XXVI

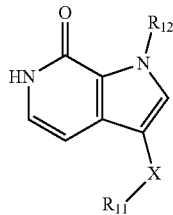

Formula XXVI wherein $R_{12}$ is a $C_1$-$C_3$ alkyl, a $C_1$-$C_3$ haloalkyl, propylenyl, —$CH_2(CO)CH=CH_2$, oxiran-2-ylmethyl, or $CH_2(CO)CH_2Cl$, wherein $R_{11}$ is a nitrogen-containing bicyclic or tricyclic heteroaryl, an aryl, or a biaryl, each of which is optionally substituted with 1, 2, or 3 substituents each independently selected from the group consisting of: —$N(R^a)S(O)_2R^b$, —$S(O)_2NR^aR^b$, —$C(O)NR^aR^b$ —$N(R^a)C(O)R^b$, —$NR^aR^b$, —($C_1$-$C_6$ alkylenyl)$R^c$, —($C_1$-$C_3$ cycloalkylenyl)$R^c$, an aryl, a heteroaryl, and —($C_1$-$C_6$ alkylenyl)$R^cR^{c'}$, —H, a halogen, —CN, a propylenyl, a $C_1$-$C_3$ alkyl, a $C_1$-$C_3$ haloalkyl, —$OR_{70}$, —$NR_{70}R_{70}$, —$C(O)OR_{70}$, —$C(O)NR_{70}R_{70}$, —$S(O)_2R_{70}$, —$S(O)_2NR_{70}R_{70}$, —$CH_2(CO)CH=CH_2$, oxiran-2-ylmethyl, and $CH_2(CO)CH_2Cl$, and $R_{70}$, wherein X is optionally present, and when present, is selected from —O—, —C(O)—, —$N(R_{77})$—, and —$CH(R_{70})$—, $R_{77}$ is selected from the group consisting of: —H, a halogen, —CN, a $C_1$-$C_3$ haloalkyl, —$OR_{70}$, —$NR_{70}R_{70}$, —$C(O)OR_{70}$, —$C(O)NR_{70}R_{70}$, —$S(O)_2R_{70}$, —$S(O)_2NR_{70}R_{70}$, and $R_{70}$, wherein $R_{70}$, at each occurrence, are each independently selected from the group consisting of: a $C_1$-$C_6$ alkyl, a $C_2$-$C_6$ alkenyl, a $C_2$-$C_6$ alkynyl, a halogen, a $C_1$-$C_6$ haloalkyl, —CN, $NO_2$, —$OR^e$, —$S(O)_2NR^eR^f$, —$C(O)R^e$, —$C(O)NR^eR^f$, —$NR^eR^f$, —$N(R^e)C(O)R^f$, a —($C_1$-$C_6$ alkylenyl)-$OR^e$, a —($C_1$-$C_6$ alkylenyl)-$C(O)NR^eR^f$, a —($C_1$-$C_6$ alkylenyl)-$NR^eR^f$, and a —($C_1$-$C_6$ alkylenyl)-$N(R^e)C(O)R^f$, wherein $R^a$ and $R^b$, at each occurrence, are independently selected from the group consisting of: H, a $C_1$-$C_6$ alkenyl, a $C_1$-$C_6$ alkynyl, a $C_1$-$C_6$ haloalkyl, $R^c$, and a $C_1$-$C_6$ alkyl, wherein the $C_1$-$C_6$ alkyl is optionally substituted with one substituent selected from the group consisting of: —$OR^e$, —$NR^eR^f$, —$C(O)OR^e$, —$C(O)NR^eR^f$, —$S(O)_2R^e$, —$S(O)_2NR^eR^f$, and $R^c$, wherein $R^c$ and $R^{c'}$, at each occurrence, are each independently selected from the group consisting of: an aryl, a heteroaryl, a heterocycle, a cycloalkyl, and a cycloalkenyl, and wherein each $R^c$ group is optionally substituted with 1, 2, 3, 4, or 5 $R^d$ groups, wherein $R^d$, at each occurrence, are each independently selected from the group consisting of: a $C_1$-$C_6$ alkyl, a $C_2$-$C_6$ alkenyl, a $C_2$-$C_6$ alkynyl, a halogen, a $C_1$-$C_6$ haloalkyl, —CN, $NO_2$, —$OR^e$, —$S(O)_2NR^eR^f$, —$C(O)R^e$, —$C(O)NR^eR^f$, —$NR^eR^f$, —$N(R^e)C(O)R^f$, , a —($C_1$-$C_6$ alkylenyl)-$OR^e$, a —($C_1$-$C_6$ alkylenyl)-$C(O)NR^eR^f$, a —($C_1$-$C_6$ alkylenyl)-$NR^eR^f$, and a —($C_1$-$C_6$ alkylenyl)-$N(R^e)C(O)R^f$, and wherein $R^e$ and $R^f$, at each occurrence, are each independently selected from the group consisting of: H, a $C_1$-$C_6$ alkyl, a $C_1$-$C_6$ cycloalkyl, a aryl, a heteroaryl and a $C_1$-$C_6$ haloalkyl.

2. A compound according claim 1 of Formula XXV

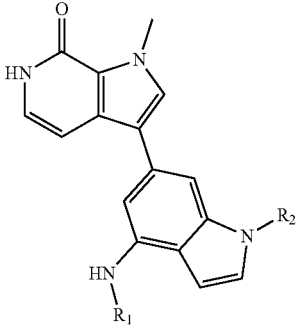

Formula XXV wherein R₁ is

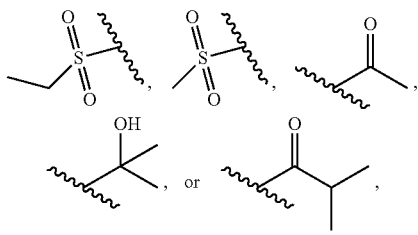

wherein R₂ is

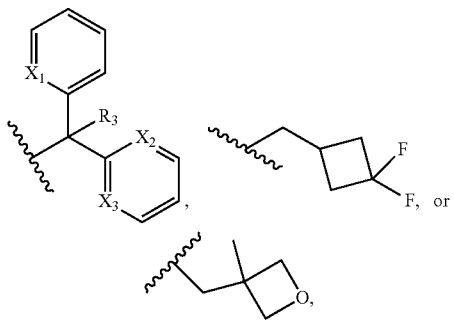

wherein R₃ is H, CH₃, or CH₂CH₃, and
wherein X₁, X₂, and X₃, are each independently selected from the group consisting of: C or N.

3. A compound according to claim 1 Formula I

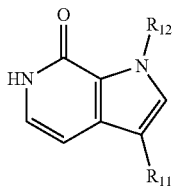

Formula I wherein $R_{12}$ is a $C_1$-$C_3$ alkyl, a $C_1$-$C_3$ haloalkyl, propylenyl, —CH₂(CO)CH=CH₂, oxiran-2-ylmethyl, or CH₂(CO)CH₂Cl, wherein $R_{11}$ is a nitrogen-containing bicyclic or tricyclic heteroaryl, each of which is optionally substituted with 1, 2, or 3 substituents each independently selected from the group consisting of: —N($R^a$)S(O)₂$R^b$, —S(O)₂NR$^a$R$^b$, —C(O)NR$^a$R$^b$ —N($R^a$)C(O)$R^b$ —NR$^a$R$^b$, —(C₁-C₆ alkylenyl)$R^c$, —(C₁-C₃ cycloalkylenyl)$R^c$, an aryl, a heteroaryl, and —(C₁-C₆ alkylenyl)$R^c R^{c'}$, wherein $R^a$ and $R^b$, at each occurrence, are each independently selected from the group consisting of: H, a C₁-C₆ alkenyl, a C₁-C₆ alkynyl, a C₁-C₆ haloalkyl, $R^c$, and a C₁-C₆ alkyl, wherein the C₁-C₆ alkyl is optionally substituted with one substituent selected from the group consisting of: —OR$^e$, —NR$^e$R$^f$, —C(O)OR$^e$, —C(O)NR$^e$R$^f$, —S(O)₂R$^e$, —S(O)₂NR$^e$R$^f$, and $R^c$, wherein $R^c$ and $R^{c'}$, at each occurrence, are each independently selected from the group consisting of: an aryl, a heteroaryl, a heterocycle, a cycloalkyl, and a cycloalkenyl, and wherein each $R^c$ group is optionally substituted with 1, 2, 3, 4, or 5 $R^d$ groups, wherein $R^d$, at each occurrence, are each independently selected from the group consisting of: a C₁-C₆ alkyl, a C₂-C₆ alkenyl, a C₂-C₆ alkynyl, a halogen, a C₁-C₆ haloalkyl, —CN, NO₂, —OR$^e$, —S(O)₂NR$^e$R$^f$, —C(O)R$^e$, —C(O)NR$^e$R$^f$, —NR$^e$R$^f$, —N(R$^e$)C(O)R$^f$, a —(C₁-C₆ alkylenyl)-OR$^e$, a —(C₁-C₆ alkylenyl)-C(O)NR$^e$R$^f$, a —(C₁-C₆ alkylenyl)-NR$^e$R$^f$, and a —(C₁-C₆ alkylenyl)-N(R$^e$)C(O)R$^f$, and wherein $R^e$ and $R^f$, at each occurrence, are each independently selected from the group consisting of: H, a C₁-C₆ alkyl, a C₁-C₆ cycloalkyl, a aryl, a heteroaryl and a C₁-C₆ haloalkyl.

4. A compound according to claim 1 of Formula II

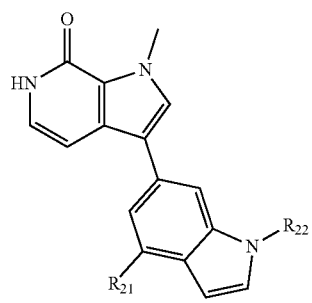

Formula II wherein $R^{21}$ is —N($R^a$)S(O)₂$R^b$, —S(O)₂NR$^a$R$^b$, S(O)₂R$^a$, —C(O)NR$^a$R$^b$ —N($R^a$)C(O)$R^b$ —NR$^a$R$^b$, or a —(C₁-C₆ alkylenyl) $R^c$, wherein $R^a$ and $R^b$, at each occurrence, are each independently selected from the group consisting of: H, a C₁-C₆ alkyl, a C₁-C₆ alkenyl, a C₁-C₆ alkynyl, a C₁-C₆ haloalkyl, $R^c$, and a C₁-C₆ alkyl, wherein the C₁-C₆ alkyl is optionally substituted with one substituent selected from the group consisting of: —OR$^{y1}$, —NR$^{y3}$R$^{y4}$, —C(O)OR$^{y2}$, —C(O)NR$^{y3}$R$^{y4}$, —S(O)₂R$^{y1}$, —S(O)₂NR$^{y3}$R$^{y4}$, and $R^c$, wherein $R^{y1}$, at each occurrence, are each independently selected from the group consisting of: H, a C₁-C₆ alkyl, a C₁-C₆ cycloalkyl, a aryl, a heteroaryl and a C₁-C₆ haloalkyl, wherein $R^{y2}$, at each occurrence, are each independently selected from the group consisting of: H, a C₁-C₆ alkyl, a C₁-C₆ cycloalkyl, a aryl, a heteroaryl and a C₁-C₆ haloalkyl, wherein $R^{y3}$, at each occurrence, are each independently selected from the group consisting of: H, a C₁-C₆ alkyl, a C₁-C₆ cycloalkyl, a aryl, a heteroaryl and a C₁-C₆ haloalkyl, wherein $R^{y4}$, at each occurrence, are each independently selected from the group consisting of: H, a C₁-C₆ alkyl, a C₁-C₆ cycloalkyl, a aryl, a heteroaryl and a C₁-C₆ haloalkyl, wherein $R^{22}$ is selected from the group consisting of: a —(C₁-C₆ alkylenyl)$R^c$, a —(C₁-C₃ cycloalkylenyl)$R^c$, and a —(C₁-C₆ alkylenyl)$R^c R^{c'}$, wherein $R^c$ and $R^{c'}$, at each occurrence, are each independently selected from the group consisting of: an aryl, a heteroaryl, a heterocycle, a cycloalkyl, and a cycloalkenyl; and each $R^c$ group is optionally substituted with 1, 2, 3, 4, or 5 $R^d$ groups, where $R^d$, at each occurrence, are each independently selected from the group consisting of: a C₁-C₆ alkyl, a C₂-C₆ alkenyl, a C₂-C₆ alkynyl, a halogen, a C₁-C₆ haloalkyl, —CN, NO$_2$, —OR$^e$, —S(O)$_2$NR$^e$R$^f$, —C(O)R$^e$, —C(O)NR$^e$R$^f$, —NR$^e$R$^f$, —N(R$^e$)C(O)R$^f$, a —(C$_1$-C$_6$ alkylenyl)-OR$^e$, —(C$_1$-C$_6$ alkylenyl)-C(O)NR$^e$R$^f$, a —(C$_1$-C$_6$ alkylenyl)-NR$^e$R$^f$, and a —(C$_1$-C$_6$ alkylenyl)-N(R$^e$)C(O)R$^f$, and wherein R$^e$ and R$^f$, at each occurrence, are each independently selected from the group consisting of: H, a C$_1$-C$_6$ alkyl, and a C$_1$-C$_6$ haloalkyl.

5. A compound according to claim 1 of Formula III

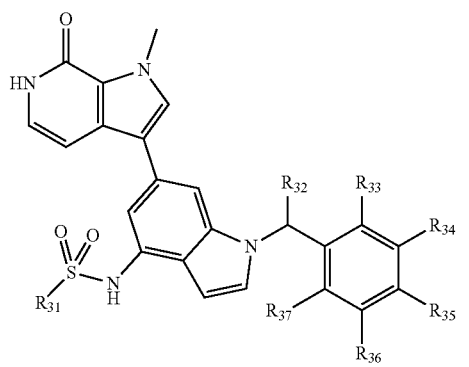

Formula III wherein R$_{31}$ is selected from the group consisting of: a C$_1$-C$_6$ alkenyl, a C$_1$-C$_6$ cycloalkyl, and a C$_1$-C$_6$ haloalkyl, wherein R$_{32}$ is selected from the group consisting of: a C$_1$-C$_6$ alkenyl, a C$_1$-C$_8$ cycloalkyl, —H, -D, a C$_1$-C$_8$ substituted cycloalkylenyl, a substituted aryl, and a substituted heteroaryl, and wherein R$_{33}$, R$_{34}$, R$_{35}$, R$_{36}$, and R$_{37}$ are each independently selected from the group consisting of: —H, a halogen, —CN, and a C$_1$-C$_3$ haloalkyl.

6. A compound according to claim 1 of Formula XVI

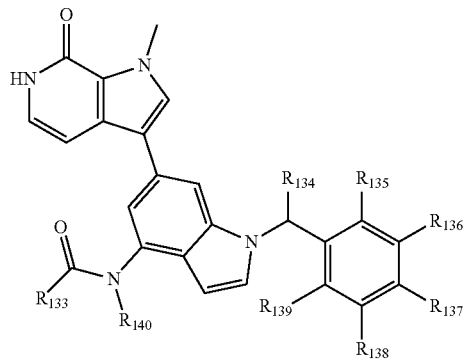

Formula XVI wherein R$_{133}$ is selected from the group consisting of: a C$_1$-C$_6$ alkenyl, a C$_1$-C$_6$ cycloalkyl, and a C$_1$-C$_6$ haloalkyl, wherein R$_{134}$ is selected from the group consisting of: a C$_1$-C$_6$ alkenyl, C$_1$-C$_8$ cycloalkyl, —H, -D, a C$_1$-C$_8$ substituted cycloalkylenyl, a substituted aryl, and a substituted heteroaryl, wherein R$_{135}$, R$_{136}$, R$_{137}$, R$_{138}$, and R$_{139}$ are each independently selected from the group consisting of: —H, a halogen, —CN, and a C$_1$-C$_3$ haloalkyl.

7. A compound according to claim 1 of Formula XVII

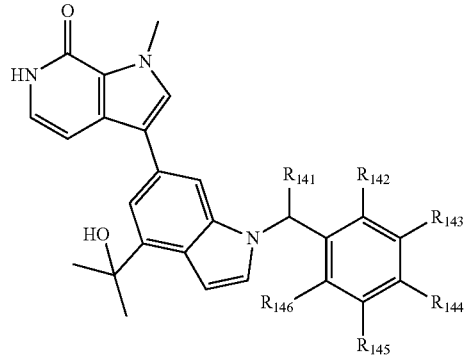

Formula XVII wherein R$_{141}$ is selected from the group consisting of: a C$_1$-C$_6$ alkenyl, a C$_1$-C$_8$ cycloalkyl, —H, -D, a C$_1$-C$_8$ substituted cycloalkylenyl, a substituted aryl, and a substituted heteroaryl, and wherein R$_{142}$, R$_{143}$, R$_{144}$, R$_{145}$, and R$_{146}$ are each independently selected from the group consisting of: —H, a halogen, —CN, and a C$_1$-C$_3$ haloalkyl, and wherein R$_{140}$ is selected from the group consisting of: a C$_1$-C$_6$ alkenyl, a C$_1$-C$_8$ cycloalkyl, —H, -D, a C$_1$-C$_8$ substituted cycloalkylenyl, a substituted aryl, and a substituted heteroaryl.

8. A compound according to claim 1 of Formula XIX

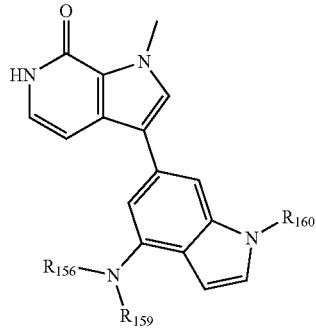

Formula XIX wherein R$_{156}$ is

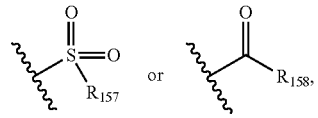

wherein R$_{157}$ is Me or CH$_2$CH$_3$,
wherein R$_{158}$ is Me, CH$_2$CH$_3$, or

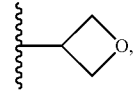

wherein $R_{159}$ is H, $CH_2CH_3$, or

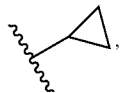, wherein $R_{160}$ is

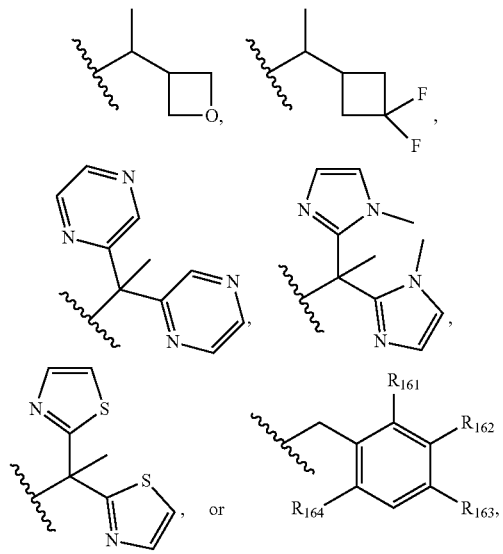

wherein $R_{161}$ is H, Me, or Cl,
wherein $R_{162}$ is H or F,
wherein $R_{163}$ is H or F,
and wherein $R_{164}$ is H or Me.

9. A compound according to claim 1 of Formula XX

Formula XX

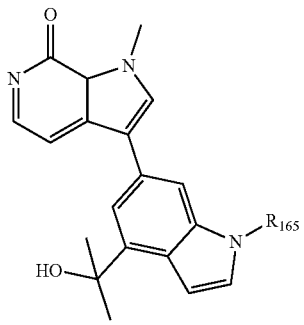

wherein $R_{165}$ is

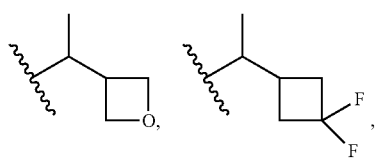

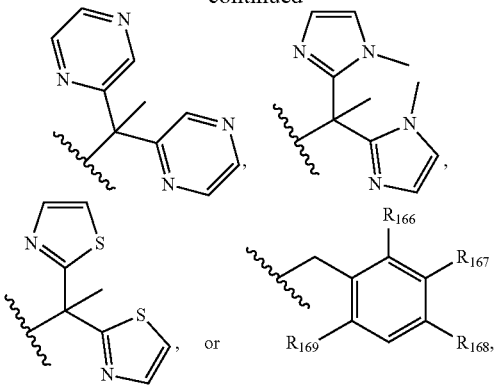

wherein $R_{166}$ is H, Me, or Cl,
wherein $R_{167}$ is H or F,
wherein $R_{168}$ is H or F,
and wherein $R_{169}$ is H or Me.

10. A compound according to claim 1 of Formula XXI

Formula XXI

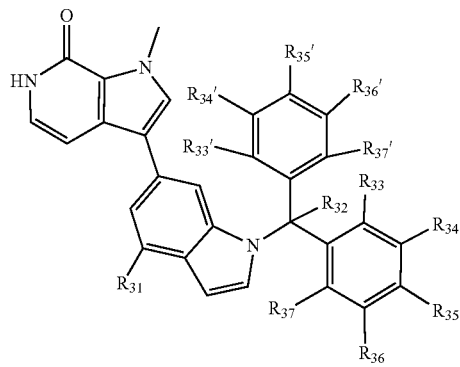

wherein $R_{31}$ is

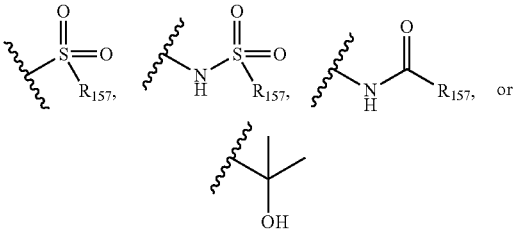

wherein $R_{157}$ is Me or $CH_2CH_3$, $CH(CH3)_2$ where $R_{158}$ can be Me, $CH_2CH_3$, $CH(CH3)_2$ or

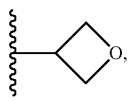, wherein $R_{31}$ is selected from the group consisting of: a $C_1$-$C_6$ alkyl, a $C_1$-$C_6$ alkenyl, a $C_1$-$C_6$ cycloalkyl, and a $C_1$-$C_6$ haloalkyl,
wherein $R_{32}$ is selected from the group consisting of: a $C_1$-$C_6$ alkyl, a $C_1$-$C_6$ alkenyl, a $C_1$-$C_8$ cycloalkyl, —H, -D, a $C_1$-$C_8$ substituted cycloalkylenyl, a substituted aryl, and a substituted heteroaryl, and wherein $R_{33}$, $R_{34}$, $R_{35}$, $R_{36}$, $R_{37}$, $R_{33}'$, $R_{34}'$, $R_{35}'$, $R_{36}'$, and $R_{37}'$ are each independently selected from the group consisting of: —H, a halogen, —CN, a $C_1$-$C_3$ haloalkyl, a $C_1$-C6 cycloalkyl, a $C_1$-$C_6$ alkylamine, a $C_1$-$C_6$ cycloalkylamine, a $C_1$-$C_6$ alkylester and a $C_1$-$C_6$ alkylamide.

11. A compound according to claim 1 of Formula XXII,

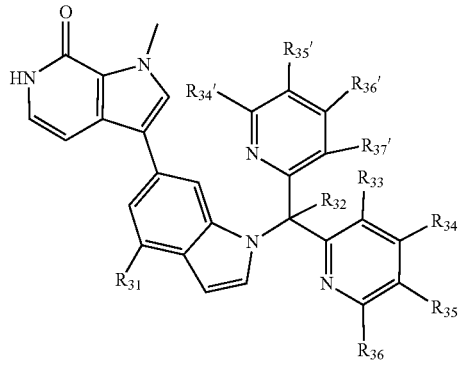

wherein $R_{31}$ is

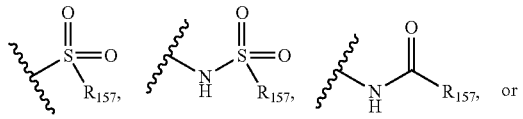

-continued

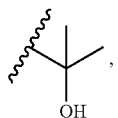

wherein $R_{157}$ is Me, $CH_2CH_3$, or $CH(CH3)_2$ wherein $R_{32}$ is selected from the group consisting of: a $C_1$-$C_6$ alkyl, a $C_1$-$C_6$ alkenyl, a $C_1$-$C_8$ cycloalkyl, —H, -D, a $C_1$-$C_8$ substituted cycloalkylenyl, a substituted aryl, and a substituted heteroaryl, and wherein $R_{33}$, $R_{34}$, $R_{35}$, $R_{36}$, $R_{37}$, R34', R35', R36' R37' are each independently selected from the group consisting of: —H, a halogen, —CN, $C_1$-$C_3$ haloalkyl, a $C_1$-$C_6$ cycloalkyl, a $C_1$-a $C_6$ alkylamine, a $C_1$-$C_6$ cycloalkylamine, a $C_1$-$C_6$ alkylester and a $C_1$-$C_6$ alkylamides.

12. A pharmaceutical formulation comprising: a compound according to claim 1 and a pharmaceutically acceptable carrier.

13. A method of treating a disease or disorder in a subject in need thereof, the method comprising:

administering a compound according to claim 1 to the subject in need thereof and wherein the disease or disorder is breast cancer.

* * * * *